United States Patent [19]
Shamovsky et al.

[11] Patent Number: 6,029,114
[45] Date of Patent: Feb. 22, 2000

[54] MOLECULAR MODELLING OF NEUROTROPHIN-RECEPTOR BINDING

[75] Inventors: Igor L. Shamovsky; Gregory M. Ross; Richard J. Riopelle; Donald F. Weaver, all of Kingston, Canada

[73] Assignee: Queen's University at Kingston, Kingston, Canada

[21] Appl. No.: 08/904,446

[22] Filed: Jul. 31, 1997

[30]   Foreign Application Priority Data

Jul. 31, 1996 [GB] United Kingdom ............... 96161054

[51] Int. Cl.$^7$ ............... G06F 19/00; G06F 17/00; C07K 14/00
[52] U.S. Cl. ............... 702/22; 702/19; 702/20; 364/528.01; 530/350
[58] Field of Search ............... 702/19, 20; 364/528.01; 530/350, 300

[56]   References Cited

U.S. PATENT DOCUMENTS 5,241,470   8/1993   Lee et al. ............... 364/413.15

FOREIGN PATENT DOCUMENTS 335637   10/1989   European Pat. Off. .

OTHER PUBLICATIONS

The Use of Hybrid Molecules in a Study of the Equilibrium between Nerve Growth Factor Monomers and Dimers, Moore et al. Neurobiology (1975) 5: 369–381.

NGF Binding to the trk Tyrosine Kinase Receptor Requires the Extracellular Immunoglobulin–like Domains, Perez et al. Mol Cell Neurosci (1995) 5: 97–105.

Baldwin et al., "Zone Mapping of the Binding Domain of the Rat Low Affinity Nerve Growth Factor Receptor by the Introduction of Novel N–Glycosylation Sites" *J. Biol. Chem.* 270: 4594–4602 (1995).

Banner et al., "Crystal Structure of the Soluble Human 55 kd TNF Receptor–Human TNFβ Complex: Implications for TNF Receptor Activation", *Cell* 73:431–445 (1993).

Burton et al., "Activity and Biospecificity of Proteolyzed Forms and Dimeric Combinations of Recombinant Human and Murine Nerve Growth Factor", *J. Neurochem.* 59: 1937–1945 (1992).

Burton et al., "Functional importance of the amino termini of neurotrophins", Abstract *Soc. for Neuroscience*, vol. 21 Abstract No. 422.10 (1995).

Cherfils, et al., "Rigid–Body Docking With Mutant Constraints of Influenza Hemagglutinin With Antibody HC19", *Proteins: Structure, Function, and Genetics* 18:8–18 (1994).

Drinkwater et al., "The carboxyl terminus of nerve growth factor is required for biological activity", *J. Biol. Chem.* 268(31): 23202–23207 (1993).

Gabb et al., "Modelling Protein Docking using Shape Complementarity, Electrostatics and Biochemical Information" *J. Mol. Biol.* 272, 106–120 (1997).

Hruby et al., "Emerging approaches in the molecular design of receptor–selective peptide ligands: conformational, topographical and dynamic considerations", *Biochem. J.* 268: 249–262 (1990).

Ibáñez et al., "Chimeric molecules with multiple neurotrophic activities reveal structural elements determining the specificities of NGF and BDNF", *EMBO J.* 10: 2105–2110 (1991).

Ibáñez et al., "Disruption of the low affinity receptor–binding site in NGF allows neuronal survival and differentiation by binding to the trk gene product", *Cell* 69: 329–341 (1992).

Kahle et al., "The amino terminus of nerve growth factor is involved in the interaction with the receptor tyrosine kinase p140$^{trkA}$", *J. Biol. Chem.* 267: 22707–22710 (1992).

Kullander et al., "Neurotrophin–3 Acquires NGF–Like Activity After Exchange to Five NGF Amino Acid Residues: Molecular Analysis of the Sites in NGF Mediating the Specific Interaction With the NGF High Affinity Receptor", *J. Neurosci. Res.* 39: 195–210 (1994).

Lai et al., "Structural Determinants of Trk Receptor Specificities Using BDNF–Based Neurotrophin Chimeras", *J. Neurosci. Res.* 46: 618–629 (1996).

LeSauteur et al., "Small Peptide Mimics of Nerve Growth Factor Bind TrkA Receptors and Affect Biological Responses", *J. Biol. Chem.* 270: 6564–6569 (1995).

Longo et al., "The in vitro biological effect of nerve growth factor is inhibited by synthetic peptides", *Cell Regulation* 1: 189–195 (1990).

(List continued on next page.)

*Primary Examiner*—Elizabeth Kemmerer
*Assistant Examiner*—Nirmal S. Basi
*Attorney, Agent, or Firm*—Hill & Schumacher; Lynn C. Schumacher

[57]   ABSTRACT

The present invention relates to computational methods for identifying the bioactive conformations of peptide domains, in particular the geometries of complexes of neurotrophins and neurotrophin receptors, and the geometries of neurotrophin receptors and ligands. The invention includes a method for identifying and theoretically modelling a receptor binding site for neurotrophins, such as NGF, BDNF, NT-3 and NT4/5, of the common neurotrophin receptor p75$^{NTR}$. The principal residues of the p75$^{NTR}$ binding site are Asp$^{47p}$, Lys$^{56p}$, Asp$^{75p}$, Asp$^{76p}$, Asp$^{88p}$ and Glu$^{88p}$ of the second and third cysteine-rich domains. These residues interact with residues of variable loop regions I and V and other neighboring residues of each of the neurotrophins. The invention provides a method of designing a ligand for binding with common neurotrophin receptor p75$^{NTR}$ including computationally evolving a ligand having effective moieties located relative to each other in the ligand so that the moieties bind to at least two of p75$^{NTR}$ binding loop 2A including region Cys$^{39p}$ to Cys$^{58p}$, p75$^{NTR}$ binding loop 2B including region Cys$^{58p}$ to Cys$^{78p}$, and p75$^{NTR}$ binding loop 3A including region Cys$^{79p}$ to Cys$^{94p}$. The invention further provides a method of identifying such a ligand encoded in a data base containing molecules coded for spatial occupancy, relative atomic position, bond type and/or charge. The designed or identified ligand may be an agonist or antagonist of p75$^{NTR}$.

18 Claims, 29 Drawing Sheets

OTHER PUBLICATIONS

Luo et al., "The Unprocessed C–terminal Dipeptide of Recombinant β–Nerve Growth Factor Determines Three Stable Forms with Distinct Biological Activities", *J. Biol. Chem.* 267: 12275–12283 (1992).

MacDonald et al., "Deletions in the Extracellular Domain of Rat TrkA Lead to an Altered Differentiative Phenotype in Neurotrophin Responsive Cells", *Mol. Cell. Neurosci.* 7: 371–390 (1996).

McDonald et al., "New protein fold revealed by a 2,3–Å resolution crystal structure of nerve growth factor", *Nature* 354:411–414 (1991).

Moore et al., *Neurobiology* 5:369–381 (1975).

Pérez et al., *Mol. Cell Neurosci.* 6:97–105 (1995).

Radziejewski et al., "Dimeric Structure and Conformational Stability of Brain–Derived Neurotrophic Factor and Neurotrophin–3", *Biochemistry* 31: 4431–4436 (1992).

Robinson et al., "Structure of the Brain–Derived Neurotrophic Factor/Neurotrophin 3 Heterodimer", *Biochemistry* 34:4139–4146 (1995).

Rydén et al., "Functional analysis of mutant neurotrophins deficient in low–affinity binding reveals a role for p75$^{LNGFR}$ in NT–4 signalling", *EMBO J.* 14: 1979–1990 (1995).

Rydén et al., "Binding of Neurotrophin–3 to p75$^{LNGFR}$, TrkA, and TrkB Mediated by a Single Functional Epitope Distinct from That Recognized by TrkC", *J. Biol. Chem.* 271:5623–5627 (1996).

Schneider et al., "A novel modular mosaic of cell adhesion motifs in the extracellular domains of the neurogenic trk and trkB tyrosine kinase receptors", *Oncogene* 6: 1807–1811 (1991).

Shih et al., "Mutagenesis identifies amino–terminal residues of nerve growth factor necessary for Trk receptor binding and biological activity", *J. Biol. Chem.* 269:27679–27686 (1994).

Sobolev et al., "Molecular Docking Using Surface Complementarity", *Proteins: Structure, Function, and Genetics* 25: 120–129 (1996).

Suter et al., "NGF/BDNF Chimeric Proteins: Analysis of Neurotrophin Specificity by Homolog–scanning Mutagenesis", *J. Neurosci.* 12: 306–318 (1992).

Strynadka et al. "Molecular docking programs successfully determine the binding of a beta–lactamase inhibitory protein to TEM–1 beta–lactamase", *Nature Struct. Biol.* 3: 233–239 (1996).

Taylor et al., "NGF Bioactivity: Role of the Amino Terminus", Abstract *Soc. for Neuroscience*, vol. 17 Abstract No. 283.7 (1991).

Treanor et al., "Heterodimeric Neurotrophins Induce Phosphorylation of Trk Receptors and Promote Neuronal Differentiation in PC 12 Cells", *J. Biol. Chem.* 270: 23104–23110 (1995).

Urfer et al., "The binding epitopes of neurotrophin–3 to its receptors of trkC and gp75 and the design of a multifunctional human neurotrophin" *EMBO J.* 13:5896–5909 (1994).

von Szentpály et al., "A "slow–cooling" Monte Carlo conformational space study of 18–crown–6 and its alkali metal cation complexes", *J. Mol. Struct.* (Theochem.) 308:125–140 (1994).

Windisch et al., "Brain–derived neurotrophic factor, neurotrophin–3 and neurotrophin–4 bind to a single leucine–richmotifofTrkB",*Biochemistry* 34:11256–11263 (1995).

Windisch et al., "Specific neurotrophin binding to leucine–rich motif peptides of TrkA and TrkB", *FEBS Lett.* 374:125–129 (1995).

Windisch et al., "Nerve growth factor binding site on TrkA mapped to a single 24–amino acid leucine–rich motif", *J. Biol. Chem.* 270:28133–28138 (1995).

Strynadka et al., "Molecular Docking Programs Successfully Predict the Binding of a β–Lactamase Inhibitory Protein to TEM–1 β–Lactamase", Nat. Structural Biol., 3: 233–239.

First monomer: amino terminus

|  | 1 | | | | 5 | | | | | 10 | | | | | 15 |
|---|---|---|---|---|---|---|---|---|---|---|---|---|---|---|---|
| hNGF | S | S | S | H | P | I | F | H | R | G | E | F | S | V | C ... |
| mNGF | S | S | T | H | P | V | F | H | M | G | E | F | S | V | C ... |
| mNGFΔ3-9 | - | - | - | - | - | - | - | S | S | G | E | F | S | V | C ... |
| hNGF-H4D | S | S | S | D | P | I | F | H | R | G | E | F | S | V | C ... |
| mNGFΔ1-8 | - | - | - | - | - | - | - | - | M | G | E | F | S | V | C ... |
| BDNF | - | - | H | S | D | P | A | R | R | G | E | L | S | V | C ... |

Second monomer: carboxyl terminus

|  | | | 112' | | | | | | 118' | |
|---|---|---|---|---|---|---|---|---|---|---|
| hNGF | ... C | V | C | V | L | S | R | K | A | V | R |
| mNGF | ... C | V | C | V | L | S | R | K | A | T | R |
| mNGFΔ3-9 | ... C | V | C | V | L | S | R | K | A | T | R |
| hNGF-H4D | ... C | V | C | V | L | S | R | K | A | V | R |
| mNGFΔ1-8 | ... C | V | C | V | L | S | R | K | A | T | R |
| BDNF | ... C | V | C | T | L | T | I | K | R | G | R |

Figure 1

LRM:                I                    II                    III

```
          68tA              93tA              117tA              140tA
           |                 |                  |                  |
    ...    ┌─────────────────┬──────────────────┬─────────────────┐
           │     ▨           │       ▨          │      ▨          │    ...
           └─────────────────┴──────────────────┴─────────────────┘
              β  <- - - - -> β  <- - - - - -> β  <- - - - - ->
```

NGF binding

```
         72tA                                                143tA
B1:       └─────────────────────────────────────────────────────┘

97tA
B2:                        └──────────────────────────────────────

120tA
B3:      ─────────────────────────────────────┘

97tA                120tA
B4:                        └──────────────────┘
```

No NGF binding

First monomer: amino terminus

|  | 1 | | | | 5 | | | | | 10 | | | | | 15 | |
|---|---|---|---|---|---|---|---|---|---|---|---|---|---|---|---|---|
| hNGF | S | S | S | H | P | I | F | H | R | G | E | F | S | V | C | D... |
| mNGF | S | S | T | H | P | V | F | H | M | G | E | F | S | V | C | D... |
| mNGFΔ3-9 | S | - | - | - | - | - | - | F | H | R | G | E | F | S | V | C | D... |
| hNGF:NT-4/5 | S | S | S | H | P | I | F | H | R | G | E | F | S | V | C | D... |

Second monomer: carboxyl terminus

|  | 75' | | | | 110' | | | | 115' | | | | | | 118' | |
|---|---|---|---|---|---|---|---|---|---|---|---|---|---|---|---|---|
| hNGF | ...K | H | W | N | ...C | V | C | V | L | S | R | K | A | V | R |
| mNGF | ...K | H | W | N | ...C | V | C | V | L | S | R | K | A | T | R |
| mNGFΔ3-9 | ...K | H | W | N | ...C | V | C | V | L | S | R | K | A | T | R |
| hNGF:NT-4/5 | ...R | H | W | V | ...C | V | C | T | L | L | S | R | T | G | R |

Figure 9

| | | | | | | Amino terminus | | | | | | | | | | |
|---|---|---|---|---|---|---|---|---|---|---|---|---|---|---|---|---|
| | 1 | | | | 5 | | | | | 10 | | | | | 15 | |
| hNGF sequence | S | S | S | H | P | I | F | H | R | G | E | F | S | V | C | D .... |
| Conserved in NGF | | | | X | X | X | | X | X | X | X | | X | X | X | X |
| Determine structure | | | | X | X | X | | X | X | X | X | X | X | X | X | X |
| Interact with LRM | | | | | | | | X | X | | | | | | | |
| LRM binding sites | | | | | | | | | | | | | | | X | |
| | | | | E | B | E | | E | D | E | D | | | | | D |

| | | | | | | Carboxyl terminus | | | | | | | | | |
|---|---|---|---|---|---|---|---|---|---|---|---|---|---|---|---|
| | 75' | | | | | | | 110' | | | | | | 115' | |
| hNGF sequence | ....K | H | W | N .... | C | V | C | V | L | S | R | K | A | V | R |
| Conserved in NGF | | | X | X | X | X | X | X | X | X | X | X | X | | X |
| Determine structure | | | X | X | X | X | X | X | X | X | X | | | | |
| Interact with LRM | | | X | | | | | | | | X | X | | | |
| LRM binding sites | | | | | | | | | | | | | | | |
| | | | A | | | | | | | | | C | C | | |

| | 93tA | 95tA | | | | | | 100tA | | | | | 105tA | | | | | 110tA | | | | | 115tA | | |
|---|---|---|---|---|---|---|---|---|---|---|---|---|---|---|---|---|---|---|---|---|---|---|---|---|---|
| LRM sequence | L | R | N | L | T | I | V | K | S | G | L | R | F | V | A | P | D | A | F | H | F | T | P | R | L |
| Specific for trkA | - | - | - | - | - | - | - | X | - | - | - | - | X | - | - | X | X | - | - | X | X | X | X | - | - |
| Consensus | X | - | - | X | - | X | - | - | - | - | X | - | - | X | - | - | - | - | X | - | - | - | - | - | X |
| Interact with NGF | - | - | - | X | - | - | - | X | X | - | - | - | X | X | - | X | - | - | X | - | X | X | X | X | - |
| Form binding site | | | | <--E--> | | | | D | | | | | A C | | | | C | | | | B C B B C | | | | |

Second Cysteine-Rich Domain

| | | |
|---|---|---|
| p75$^{NTR}$(h) | 39 | C L D S V T F S D V V S A T E P C K P C T |
| p75$^{NTR}$(r) | 39 | C L D N V T F S D V V S A T E P C K P C T |
| p75$^{NTR}$(c) | 40 | C L D S V T Y S D T V S A T E P C K P C T |
| p55$^{TNFR}$ | 41 | C - E S G S F T A S E N H L R H C L S C S |

| | | |
|---|---|---|
| p75$^{NTR}$(h) | 60 | E C V G L Q S M S A - - P C V E A D D A V C |
| p75$^{NTR}$(r) | 60 | E C L G L Q S M S A - - P C V E A D D A V C |
| p75$^{NTR}$(c) | 61 | Q C V G L H S M S A - - P C V E S D D A V C |
| p55$^{TNFR}$ | 61 | K C R K E M G Q V E I S S C T V D R D T V C |

Third Cysteine-Rich Domain

| | | |
|---|---|---|
| p75$^{NTR}$(h) | 80 | R C A Y G Y Y Q D E - - - T T G R C E A |
| p75$^{NTR}$(r) | 80 | R C A Y G Y Y Q D E - - - E T G H C E A |
| p75$^{NTR}$(c) | 81 | R C A Y G Y F Q D E - - - L S G S C K E |
| p55$^{TNFR}$ | 83 | G C R K N Q Y R H Y W S E N L F Q C F N |

Figure 17

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..16
        (D) OTHER INFORMATION:/note= "N-terminal residues 1-16 of
            human NGF"

(xi) SEQUENCE DESCRIPTION: SEQ ID NO: 1:

Ser Ser Ser His Pro Ile Phe His Arg Gly Glu Phe Ser Val Cys Asp
1               5                   10                  15

(2) INFORMATION FOR SEQ ID NO: 2:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..16
        (D) OTHER INFORMATION:/note= "N-terminal residues 1-16 of
            mouse NGF"

(xi) SEQUENCE DESCRIPTION: SEQ ID NO: 2:

Ser Ser Thr His Pro Val Phe His Met Gly Glu Phe Ser Val Cys Asp
1               5                   10                  15

(2) INFORMATION FOR SEQ ID NO: 3:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..9
        (D) OTHER INFORMATION:/note= "N-terminus of deletion
            mutant delta 3-9 of mouse NGF"

(xi) SEQUENCE DESCRIPTION: SEQ ID NO: 3:

Ser Ser Gly Glu Phe Ser Val Cys Asp
1               5

(2) INFORMATION FOR SEQ ID NO: 4:

(i) SEQUENCE CHARACTERISTICS:
        (A) LENGTH: 15 amino acids
        (B) TYPE: amino acid

```
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..15
        (D) OTHER INFORMATION:/note= "N-terminal residues 1-15 of
            mutant H4D of human NGF"

(xi) SEQUENCE DESCRIPTION: SEQ ID NO: 4:

Ser Ser Ser Asp Pro Ile Phe His Arg Gly Glu Phe Ser Val Cys
1               5                   10                  15

(2) INFORMATION FOR SEQ ID NO: 5:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..13
        (D) OTHER INFORMATION:/note= "N-terminal residues 1-13 of
            BDNF"

(xi) SEQUENCE DESCRIPTION: SEQ ID NO: 5:

His Ser Asp Pro Ala Arg Arg Gly Glu Leu Ser Val Cys
1               5                   10

(2) INFORMATION FOR SEQ ID NO: 6:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..11
        (D) OTHER INFORMATION:/note= "C-terminal residues 108-118
            of human NGF"

(xi) SEQUENCE DESCRIPTION: SEQ ID NO: 6:

Cys Val Cys Val Leu Ser Arg Lys Ala Val Arg
1               5                   10

(2) INFORMATION FOR SEQ ID NO: 7:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..11
        (D) OTHER INFORMATION:/note= "C-terminal residues 108-118
            of mouse NGF"

(xi) SEQUENCE DESCRIPTION: SEQ ID NO: 7:
```

```
Cys Val Cys Val Leu Ser Arg Lys Ala Thr Arg
  1               5                   10
```

(2) INFORMATION FOR SEQ ID NO: 8:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..11
        (D) OTHER INFORMATION:/note= "C-terminal residues 108-118
            of BDNF"

(xi) SEQUENCE DESCRIPTION: SEQ ID NO: 8:

```
Cys Val Cys Thr Leu Thr Ile Lys Arg Gly Arg
  1               5                   10
```

(2) INFORMATION FOR SEQ ID NO: 9:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..11
        (D) OTHER INFORMATION:/note= "C-terminal residues 108-118
            of NT-4/5"

(xi) SEQUENCE DESCRIPTION: SEQ ID NO: 9:

```
Cys Val Cys Thr Leu Leu Ser Arg Thr Gly Arg
  1               5                   10
```

(2) INFORMATION FOR SEQ ID NO: 10:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..4
        (D) OTHER INFORMATION:/note= "Residues 74-77 of human
            NGF, mouse NGF or delta 3-9 mutant of mouse NGF"

(xi) SEQUENCE DESCRIPTION: SEQ ID NO: 10:

```
Lys His Trp Asn
  1
```

(2) INFORMATION FOR SEQ ID NO: 11:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide

```
    (ix) FEATURE:
          (A) NAME/KEY: Peptide
          (B) LOCATION:1..4
          (D) OTHER INFORMATION:/note= "Residues 74-77 of NT-4/5"

(xi) SEQUENCE DESCRIPTION: SEQ ID NO: 11:

Arg His Trp Val
1

(2) INFORMATION FOR SEQ ID NO: 12:

(i) SEQUENCE CHARACTERISTICS:
          (A) LENGTH: 25 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION:1..25
          (D) OTHER INFORMATION:/note= "Second leucine rich motif
              (LRM)of TrkA, residues 93 to 117"

(xi) SEQUENCE DESCRIPTION: SEQ ID NO: 12:

Leu Arg Asn Leu Thr Ile Val Lys Ser Gly Leu Arg Phe Val Ala Pro
1               5                   10                  15

Asp Ala Phe His Phe Thr Pro Arg Leu
            20                  25

(2) INFORMATION FOR SEQ ID NO: 13:

(i) SEQUENCE CHARACTERISTICS:
          (A) LENGTH: 24 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION:1..24
          (D) OTHER INFORMATION:/note= "Second Leucine rich motif (LRM)
              of TrkB, residues 93 to 117"

(xi) SEQUENCE DESCRIPTION: SEQ ID NO: 13:

Leu Arg Asn Leu Thr Ile Val Asp Ser Gly Leu Lys Phe Val Ala Tyr
1               5                   10                  15

Lys Ala Glu Leu Lys Asn Ser Asn
            20

(2) INFORMATION FOR SEQ ID NO: 14:

(i) SEQUENCE CHARACTERISTICS:
          (A) LENGTH: 58 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION:1..58
          (D) OTHER INFORMATION:/note= "Identified neurotrophin
              binding site of human p75NTR, residues 39-96"

(ix) FEATURE:
```

(A) NAME/KEY: Peptide
             (B) LOCATION:1..2
             (D) OTHER INFORMATION:/note= "cysteine 39 forms a
                 disulfide bond with cysteine 55"

(ix) FEATURE:
             (A) NAME/KEY: Peptide
             (B) LOCATION:17..18
             (D) OTHER INFORMATION:/note= "cysteine 55 forms a
                 disulfide bond with cysteine 39"

(ix) FEATURE:
             (A) NAME/KEY: Peptide
             (B) LOCATION:20..21
             (D) OTHER INFORMATION:/note= "cysteine 58 forms a
                 disulfide bond with cysteine 71"

(ix) FEATURE:
             (A) NAME/KEY: Peptide
             (B) LOCATION:33..34
             (D) OTHER INFORMATION:/note= "cysteine 71 forms a
                 disulfide bond with cysteine 58"

(ix) FEATURE:
             (A) NAME/KEY: Peptide
             (B) LOCATION:23..24
             (D) OTHER INFORMATION:/note= "cysteine 61 forms a
                 disulfide bond with cysteine 79"

(ix) FEATURE:
             (A) NAME/KEY: Peptide
             (B) LOCATION:41..42
             (D) OTHER INFORMATION:/note= "cysteine 79 forms a
                 disulfide bond with cysteine 61"

(ix) FEATURE:
             (A) NAME/KEY: Peptide
             (B) LOCATION:43..44
             (D) OTHER INFORMATION:/note= "cysteine 81 forms a
                 disulfide bond with cysteine 94"

(ix) FEATURE:
             (A) NAME/KEY: Peptide
             (B) LOCATION:56..57
             (D) OTHER INFORMATION:/note= "cysteine 94 forms a
                 disulfide bond with cysteine 81"

(xi) SEQUENCE DESCRIPTION: SEQ ID NO: 14:

Cys Leu Asp Ser Val Thr Phe Ser Asp Val Val Ser Ala Thr Glu Pro
 1               5                  10                  15

Cys Lys Pro Cys Thr Glu Cys Val Gly Leu Gln Ser Met Ser Ala Pro
                20                  25                  30

Cys Val Glu Ala Asp Asp Ala Val Cys Arg Cys Ala Tyr Gly Tyr Tyr
            35                  40                  45

Gln Asp Glu Thr Thr Gly Arg Cys Glu Ala
        50                  55

(2) INFORMATION FOR SEQ ID NO: 15:

(i) SEQUENCE CHARACTERISTICS:
             (A) LENGTH: 58 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Peptide
             (B) LOCATION:1..58
             (D) OTHER INFORMATION:/note= "Identified neurotrophin
                 binding site of rat p75NTR, residues 39-96"

(ix) FEATURE:

(A) NAME/KEY: Peptide
            (B) LOCATION:1..2
            (D) OTHER INFORMATION:/note= "cysteine 39 forms a
                disulfide bond with cysteine 55"

(ix) FEATURE:
            (A) NAME/KEY: Peptide
            (B) LOCATION:17..18
            (D) OTHER INFORMATION:/note= "cysteine 55 forms a
                disulfide bond with cysteine 39"

(ix) FEATURE:
            (A) NAME/KEY: Peptide
            (B) LOCATION:20..21
            (D) OTHER INFORMATION:/note= "cysteine 58 forms a
                disulfide bond with cysteine 71"

(ix) FEATURE:
            (A) NAME/KEY: Peptide
            (B) LOCATION:33..34
            (D) OTHER INFORMATION:/note= "cysteine 71 forms a
                disulfide bond with cysteine 58"

(ix) FEATURE:
            (A) NAME/KEY: Peptide
            (B) LOCATION:23..24
            (D) OTHER INFORMATION:/note= "cysteine 61 forms a
                disulfide bond with cysteine 79"

(ix) FEATURE:
            (A) NAME/KEY: Peptide
            (B) LOCATION:41..42
            (D) OTHER INFORMATION:/note= "cysteine 79 forms a
                disulfide bond with cysteine 61"

(ix) FEATURE:
            (A) NAME/KEY: Peptide
            (B) LOCATION:43..44
            (D) OTHER INFORMATION:/note= "cysteine 81 forms a
                disulfide bond with cysteine 94"

(ix) FEATURE:
            (A) NAME/KEY: Peptide
            (B) LOCATION:56..57
            (D) OTHER INFORMATION:/note= "cysteine 94 forms a
                disulfide bond with cysteine 81"

(xi) SEQUENCE DESCRIPTION: SEQ ID NO: 15:

Cys Leu Asp Asn Val Thr Phe Ser Asp Val Val Ser Ala Thr Glu Pro
 1               5                  10                  15

Cys Lys Pro Cys Thr Glu Cys Leu Gly Leu Gln Ser Met Ser Ala Pro
                20                  25                  30

Cys Val Glu Ala Asp Asp Ala Val Cys Arg Cys Ala Tyr Gly Tyr Tyr
            35                  40                  45

Gln Asp Glu Glu Thr Gly His Cys Glu Ala
    50                  55

(2) INFORMATION FOR SEQ ID NO: 16:

(i) SEQUENCE CHARACTERISTICS:
            (A) LENGTH: 58 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1..58
            (D) OTHER INFORMATION:/note= "Identified neurotrophin
                binding site of chicken p75NTR, residues 40-97."

(ix) FEATURE:

(A) NAME/KEY: Peptide
                (B) LOCATION:1..2
                (D) OTHER INFORMATION:/note= "cysteine 40 forms a
                    disulfide bond with cysteine 56"

(ix) FEATURE:
                (A) NAME/KEY: Peptide
                (B) LOCATION:17..18
                (D) OTHER INFORMATION:/note= "cysteine 56 forms a
                    disulfide bond with cysteine 40"

(ix) FEATURE:
                (A) NAME/KEY: Peptide
                (B) LOCATION:20..21
                (D) OTHER INFORMATION:/note= "cysteine 59 forms a
                    disulfide bond with cysteine 72"

(ix) FEATURE:
                (A) NAME/KEY: Peptide
                (B) LOCATION:33..34
                (D) OTHER INFORMATION:/note= "cysteine 72 forms a
                    disulfide bond with cysteine 59"

(ix) FEATURE:
                (A) NAME/KEY: Peptide
                (B) LOCATION:23..24
                (D) OTHER INFORMATION:/note= "cysteine 62 forms a
                    disulfide bond with cysteine 80"

(ix) FEATURE:
                (A) NAME/KEY: Peptide
                (B) LOCATION:41..42
                (D) OTHER INFORMATION:/note= "cysteine 80 forms a
                    disulfide bond with cysteine 62"

(ix) FEATURE:
                (A) NAME/KEY: Peptide
                (B) LOCATION:43..44
                (D) OTHER INFORMATION:/note= "cysteine 82 forms a
                    disulfide bond with cysteine 95"

(ix) FEATURE:
                (A) NAME/KEY: Peptide
                (B) LOCATION:56..57
                (D) OTHER INFORMATION:/note= "cysteine 95 forms a
                    disulfide bond with cysteine 82"

(xi) SEQUENCE DESCRIPTION: SEQ ID NO: 16:

Cys Leu Asp Ser Val Thr Tyr Ser Asp Thr Val Ser Ala Thr Glu Pro
 1               5                  10                  15

Cys Lys Pro Cys Thr Gln Cys Val Gly Leu His Ser Met Ser Ala Pro
                20                  25                  30

Cys Val Glu Ser Asp Asp Ala Val Cys Arg Cys Ala Tyr Gly Tyr Phe
                35                  40                  45

Gln Asp Glu Leu Ser Gly Ser Cys Lys Glu
        50                  55

(2) INFORMATION FOR SEQ ID NO: 17:

(i) SEQUENCE CHARACTERISTICS:
                (A) LENGTH: 62 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Peptide
                (B) LOCATION:1..62
                (D) OTHER INFORMATION:/note= "Region of P55TNFR
                    homologous to identified neurotrophin binding site of
                    p75NTR, residues 41-102"

```
    (ix) FEATURE:
         (A) NAME/KEY: Peptide
         (B) LOCATION:1..2
         (D) OTHER INFORMATION:/note= "cysteine 41 forms a
             disulfide bond with cysteine 56"

(ix) FEATURE:
         (A) NAME/KEY: Peptide
         (B) LOCATION:17..18
         (D) OTHER INFORMATION:/note= "cysteine 56 forms a
             disulfide bond with cysteine 41"

(ix) FEATURE:
         (A) NAME/KEY: Peptide
         (B) LOCATION:20..21
         (D) OTHER INFORMATION:/note= "cysteine 59 forms a
             disulfide bond with cysteine 74"

(ix) FEATURE:
         (A) NAME/KEY: Peptide
         (B) LOCATION:33..34
         (D) OTHER INFORMATION:/note= "cysteine 74 forms a
             disulfide bond with cysteine 59"

(ix) FEATURE:
         (A) NAME/KEY: Peptide
         (B) LOCATION:23..24
         (D) OTHER INFORMATION:/note= "cysteine 62 forms a
             disulfide bond with cysteine 82"

(ix) FEATURE:
         (A) NAME/KEY: Peptide
         (B) LOCATION:41..42
         (D) OTHER INFORMATION:/note= "cysteine 82 forms a
             disulfide bond with cysteine 62"

(ix) FEATURE:
         (A) NAME/KEY: Peptide
         (B) LOCATION:44..45
         (D) OTHER INFORMATION:/note= "cysteine 84 forms a disulfide
             bond with cysteine 100"

(ix) FEATURE:
         (A) NAME/KEY: Peptide
         (B) LOCATION:56..57
         (D) OTHER INFORMATION:/note= "cysteine 100 forms a
             disulfide bond with cysteine 84"

(xi) SEQUENCE DESCRIPTION: SEQ ID NO: 17:

Cys Glu Ser Gly Ser Phe Thr Ala Ser Glu Asn His Leu Arg His Cys
 1               5                  10                  15

Leu Ser Cys Ser Lys Cys Arg Lys Glu Met Gly Gln Val Glu Ile Ser
            20                  25                  30

Ser Cys Thr Val Asp Arg Asp Thr Val Cys Gly Cys Arg Lys Asn Gln
        35                  40                  45

Tyr Arg His Tyr Trp Ser Glu Asn Leu Phe Gln Cys Phe Asn
 50                  55                  60
```

MOLECULAR MODELLING OF NEUROTROPHIN-RECEPTOR BINDING

FIELD OF THE INVENTION

The present invention relates to a computational method for identifying minimum-energy struct and van der Waals interactions between their three antiparallel pairs of β-strands; consequently, the amino terminus of one NGF monomer and the carboxyl terminus of the other are spatially juxtaposed (McDonald et al., 1991). Furthermore, although a dimer has 2 pairs of termini, only one pair of termini is required for TrkA receptor recognition (Treanor et al., 1995; Burton et al., 1995). Accordingly, solving the conformation of the complex formed by the amino terminus of one monomer and the carboxyl terminus of the other in dimeric NGF is of fundamental relevance to understanding the interaction of NGF with TrkA.

The X-ray crystallographic 3-dimensional structure of a dimeric mouse NGF (mNGF) has been reported recently (McDonald et al., 1991). However, within this structure, the amino terminus (residues 1–11) and the carboxyl terminus (residues 112–118) remain unresolved for both pairs of termini. High flexibility of the NGF termini makes it difficult to experimentally determine their bioactive conformations, particularly since transition metal ions commonly used in X-ray crystallography (McDonald et al., 1991) have high affinity for His residues (Gregory et al., 1993) which are present in the NGF amino terminus (Bradshaw et al., 1994). Indeed, conformational alterations in the receptor binding domains of NGF caused by $Zn^{2+}$ cations leading to its inactivation have been described recently (Ross et al., 1997). Since the amino and carboxyl termini are crucial for NGF bioactivity as mediated via TrkA and because of the significance of NGF in multiple neurologic disease processes, the determination of the biologically active conformation of these termini is an important and challenging problem for computational chemistry.

In contrast with NGF, little is known about the BDNF binding determinant for TrkB activation. Although there were several attempts to identify structural elements of BDNF that determine its receptor specificity (Ibáñez et al.,1991, 1993,1995; Suter et al., 1992; Ilag et al., 1994; Kullander and Ebendal., 1994; Urfer et al., 1994; Lai et al., 1996), the results of mutational experiments are still controversial. Thus, the reported importance of residues 40–49 (variable loop region 11) for TrkB related activity of BDNF (Ibáñez et al., 1991; Ilag et al., 1994) has not been confirmed by recent studies (Lai et al., 1996), in which it has also been shown that the key residues of the TrkB receptor binding domain of BDNF are situated between residues 80 and 109. The latter result is consistent with earlier observations that the BDNF termini are not involved in TrkB binding and that the key residues of the BDNF binding epitope are $Arg^{81}$ and $Gln^{84}$ (Ibáñez et al., 1993). In addition, it has been found that receptor binding domains of BDNF and NT-3 are located in the same regions of the molecules, i.e. in their "waist" parts (Ibáñez et al., 1993; Urfer et al., 1994). As far as the NT-3 receptor binding domain is concerned, detailed mutational studies carried out by Urfer et al. (1994) revealed that it comprises a surface that includes major parts of the central β-strand stem, with the most important residues being $Arg^{103}$, $Thr^{22}$, $Glu^{54}$, $Arg^{56}$, $Lys^{80}$ and $Gln^{83}$. These residues correspond to $Arg^{104}$, $Thr^{21}$, $Glu^{55}$, $Lys^{57}$, $Arg^{81}$ and $Gln^{84}$ of BDNF, respectively (McDonald et al., 1991).

The location of the neurotrophin binding sites within the Trk receptors is the subject of debate (MacDonald and Meakin, 1996). Published data indicate the existence of two putative neurotrophin binding sites of Trk proteins: the "second immunoglobulin-like domain" (residues $Trp^{299t}$-$Asn^{365t}$, denoted IgC2) and the "second leucine-rich motif" (LRM-2A and LRM-2B, residues $Thr^{97}$-$Leu^{120}$ of TrkA and TrkB, respectively) (Schneider and Schweiger, 1991; Kullander and Ebendal, 1994; Pérez et al., 1995; Urfer et al., 1995; Windisch et al., 1995a, 1995b, 1995c; MacDonald and Meakin, 1996; Rydén and Ibáñez, 1996).

$p75^{NTR}$ belongs to a family of cell surface proteins that share a common pattern of four repeated cysteine-rich domains (CRDs) in the extracellular portion (Yan and Chao, 1991; Baldwin and Shooter, 1994). X-ray crystallographic studies on the extracellular portion of the related protein $p55^{TNFR}$ revealed that CRDs fold independently of each other, and three conserved disulfide bonds maintain a specific geometry of each CRD which consists of two loops (Banner et al., 1993) (loops A and B, FIG. 1a). Very little is known about the $p75^{NTR}$ receptor functional epitope and, particularly, about residues directly participating in molecular recognition processes. All four CRD repeats of $p75^{NTR}$ are found to be required for binding, with the second CRD being most important (Baldwin and Shooter, 1995). Residue $Ser^{50}$ of $p75^{NTR}$ seems to be essential for NGF binding (Baldwin and Shooter, 1995).

The results of site-directed mutagenesis suggest that the $p75^{NTR}$ receptor binding domains within neurotrophins are juxtaposed positively charged residues located in two adjacent hairpin loops which represent variable region I (residues 23–35) and V (residues 93–98) (Ibáñez et al., 1992; Rydén et al., 1995; Ibáñez, 1994; Ibáñez, 1995; Rydén and Ibáñez, 1996) (FIG. 1c). In NGF, residues $Lys^{32}$, $Lys^{34}$, and $Lys^{95}$ have been found to be involved in $p75^{NTR}$ receptor binding, with $Lys^{32}$ making the strongest contact, followed by $Lys^{34}$ and $Lys^{95}$. In addition, some role of $Asp^{30}$, $Glu^{35}$, $Arg^{103}$, $Arg^{100}$, $Lys^{88}$, and $Ile^{31}$ in $p75^{NTR}$ binding and biological activity has been demonstrated (Ibáñez et a., 1992; Ibáñez, 1994). Two residues of variable region I, namely $Arg^{31}$ and $His^{33}$, have been demonstrated to be essential for binding of NT-3 to $p75^{NTR}$, whereas similarly located $Arg^{34}$ and $Arg^{36}$ mediate binding of NT-4/5 (Rydén et al., 1995). In contrast to NGF, a positively charged residue in variable region V is not critical for binding of NT-3 or NT-4/5 to $p55^{NTR}$ (Rydén et al., 1995). In BDNF, however, only residues of variable region V, $Lys^{95}$, $Lys^{96}$ and $Arg^{97}$, bind to $p75^{NTR}$ and compensate for the lack of positively charged residues in variable loop region I (Rydén et al., 1995).

Therefore, it is an object of the invention to establish explicit atom-level models of the Trk and $p75^{NTR}$ recognition sites for neurotrophins.

It is a further object of the invention to provide atom-level models of the mechanism of interaction of neurotrophins and their receptors.

SUMMARY OF THE INVENTION

The inventors describe a method of characterizing the interaction between non-contiguous domains of a ligand and its receptor. The specific examples of the method described in detail below concern the interaction of nerve growth factor (NGF) with its TrkA receptor binding site, brain-derived neurotrophic factor (BDNF) with its TrkB receptor binding site, and the interaction of the neurotrophins (e.g., NGF, BDNF, NT-3, and NT-4/5) with the neurotrophin binding site of the common neurotrophin receptor $p75^{NTR}$.

In one aspect of the invention there is provided a variable basis Monte-Carlo (VBMC) simulated annealing method for identifying an optimal structure in a molecular system. The method comprises:

(a) providing a Markov chain with an initial basis set of N configurational variables which define a structure for said molecular system;

(b) translating the N configurational variables simultaneously along a basis vector to produce a new structure for the molecular system, wherein magnitude of translation is chosen randomly within a preselected range;

(c) calculating potential energy of the new state of the molecular system;

(d) deciding whether to accept or reject the new structure using an effective temperature dependent transition function, and if the new structure is accepted, replacing the current structure with the accepted structure;

(e) repeating steps (b) to (d), each repetition having a new basis vector, for a preselected first number of repetitions at a preselected upper temperature; then (f) decreasing temperature according to a preselected cooling schedule;

(g) repeating steps (b) to (d) and (f), each repetition having a new basis vector, for a preselected second number of repetitions; then (h) storing current structure of the molecular system;

(i) repeating steps (g) and (h) until a preselected number of stored structures have been accumulated; then (j) rotating the basis set of configurational variables according to an effective distribution of the accumulated structures so that basis vectors are directed along low-energy valleys of a potential energy hypersurface thereby accelerating conformational motions and structural transitions of the molecular system, and erasing accumulated structures from steps (h) and (i);

(k) repeating steps (i) and (j) until, after an effective third number of repetitions, a preselected lower temperature limit is reached, thereby producing an unrefined global minimum structure; and (l) refining the global energy minimum structure so that at least one local minimum on the potential energy hypersurface is identified.

The present invention also provides a method of identifying structures of a peptide domain of a neurotrophin to bind with a binding site of a receptor. The method comprises providing a plurality of neurotrophin analogues wherein at least one of neurotrophin analogue binds the receptor, identifying an optimal or near-optimal structure for respective peptide domains of the neurotrophin analogues that bind the receptor by applying a preselected number of the variable basis Monte-Carlo (VBMC) annealing simulations described above to each of the respective peptide domains to identify minimum or near-minimum energy structures for the peptide domains, and comparing said minimum or near-minimum energy structures to identify common structural features shared by neurotrophin analogues exhibiting receptor mediated activity.

The step of providing neurotrophin analogues may include providing wild-type neurotrophin analogues or mutants thereof.

The present invention also provides a method of identifying structures of a domain of a ligand to bind with a binding site of a receptor, comprising providing a plurality of ligand analogues wherein at least one ligand analogue binds the receptor, identifying an optimal or near-optimal structure for respective domains of the ligand analogues that bind the receptor by applying a preselected number of the variable basis Monte-Carlo (VBMC) annealing simulations described above to each of the respective domains to identify minimum or near-minimum energy structures for the domains; and comparing said minimum or near-minimum energy structures to identify common structural features shared by ligands exhibiting receptor mediated activity.

As would be apparent to a person skilled in the art, methods of the present invention are not limited to neurotrophin-receptor interactions, but are applicable to the characterization of other ligand-receptor interactions. That is, an array of ligands that are either known to interact with a specific receptor or are candidate ligands that may potentially interact with this receptor may be computationally analyzed to identify optimal or near-optimal structures that provide the desired interaction. In some embodiments of the invention, the ligand may have a peptide domain, e.g., the ligand may be a peptide hormone, such as insulin, prolactin, or growth hormone. In some embodiments, the ligands or candidate ligands under study may be native ligands, mutants of native ligands, or isosteres of native ligands. They may be structurally different but have similar binding activity or functional effect(s). The optimal or near-optimal structure identified may act as an agonist or antagonist. "Isosteric" is an art-recognized term and, for purposes of this disclosure, a first moiety is "isosteric" to a second when they have similar molecular topography and functionality. This term should not, therefore, be restricted to mere similarity in chemical bond configuration. Two compounds may have different chemical bond configurations but nonetheless be isosteric due their 3-dimensional similarity of form and chemical nature, e.g. relevant centers such as heteroatoms are located in the same position, charges and/or dipoles are comparable, and the like.

The present invention provides a ligand for binding with TrkA, wherein TrkA comprises a leucine rich motif (LRM) comprising amino acid residues 93 to 117, the coordinates of the residues of said LRM given in Appendix 1, said LRM motif having five binding areas, area A comprising amino acid residue $Phe^{105tA}$ capable of hydrophobic bonding, area B comprising residues $Phe^{111tA}$, $Phe^{113tA}$, and $Thr^{114tA}$ capable of hydrophobic bonding, area C comprising residues $Asp^{109tA}$ and $His^{112tA}$ capable of ionic interaction, area D comprising residue $Lys^{100tA}$ capable of ionic interaction, and area E comprising residues $Asn^{95tA}$ to $Ile^{98tA}$ capable of multiple parallel N-strand type hydrogen bonding. The ligand includes at least three moieties each comprising effective atomic elements having spatial occupancy, relative atomic position, bond type and charge to define a three dimensional conformation of said ligand so that a first moiety can bind with a first binding area, a second moiety can bind with a second binding area, and a third moiety can bind with a third binding area.

Put another way, the ligand comprises at least three moieties effectively spaced relative to each other so that a first moiety can bind with a first binding area, a second moiety can bind with a second binding area, and a third moiety can bind with a third binding area. More specifically, the ligand comprises at least one moiety being capable of hydrophobic bonding and being present in an effective position in the ligand to hydrophobically bind to area A, at least one positively charged moiety being present in an effective position in said ligand to ionically bind to area C, and at least one negatively charged moiety being present in an effective position in said ligand to tonically bind to area D.

The present invention also provides a method of designing a ligand to bind with an LRM of TrkA. The method comprises providing a template of said LRM of TrkA, said LRM comprising amino acid residue sequence 93 to 117 inclusive, said amino acid residues having spatial Cartesian coordinates given in Appendix 1 wherein binding area A in the sequence comprises residue $Phe^{105tA}$ capable of hydrophobic bonding, binding area B comprises residues $Phe^{111tA}$, Phe$^{113tA}$, Thr$^{114tA}$ capable of hydrophobic bonding, binding area comprises residues Asp$^{109tA}$ and His$^{121tA}$ capable of ionic interaction, binding area D comprises Lys$^{100tA}$ capable of ionic interactions, and binding area E comprises residues Asn$^{95tA}$ to Ile$^{98tA}$ capable of multiple parallel β-strand type hydrogen bonding and computationally evolving a chemical ligand using any effective algorithm with preselected spatial constraints so that said evolved ligand comprises at least three effective moieties of suitable identity and spatially located relative to each other in the ligand so that a first of the moieties hydrophobically interacts with binding area A, a second of the moieties ionically interacts with binding area C, and a third of the moieties tonically interacts with binding area D of the LRM of TrkA. The algorithm may be a genetic algorithm and the LRM may be the second LRM of a plurality of LRMs.

The invention further provides a method of designing a ligand to bind with an LRM of TrkA, comprising providing a template of said LRM of TrkA, said LRM comprising amino acid residue sequence 93 to 117 inclusive, the amino acid residues having spatial Cartesian coordinates given in Appendix 1 wherein binding area A comprises Phe$^{105tA}$ capable of hydrophobic bonding, binding area B comprises Phe$^{111tA}$, Phe$^{113tA}$, Thr$^{114tA}$ capable of hydrophobic bonding, binding area C comprises Asp$^{109tA}$ and His$^{112tA}$ capable of ionic interaction, binding area D comprises Lys$^{100tA}$ capable of ionic interaction, and binding area E comprises Asn$^{95tA}$ to Ile$^{98tA}$ capable of hydrogen bonding. The method comprises computationally evolving a ligand using an effective algorithm so that said evolved ligand comprises at least three effective moieties located relative to each other in the ligand so that a first moiety can bind with a first of the five binding areas, a second moiety can bind with a second of the five binding areas, and a third moiety can bind with a third of the binding areas.

In another aspect the invention provides a ligand for binding with TrkB, wherein TrkB comprises a leucine-rich motif (LRM) comprising amino acid residues 93 to 117, the coordinates of the residues of said LRM given in Appendix 2, said LRM having five binding areas, binding area F comprising amino acid residue Asp$^{100tB}$ capable of ionic interaction, binding area G comprising amino acid residue Lys$^{109tB}$ capable of ionic interaction, binding area H comprising amino acid residues Lys$^{113tB}$ capable of ionic interaction, binding area I comprising amino acid residue Arg$^{94tB}$ capable of ionic interaction, and binding area K comprising amino acid residue Lys$^{104tB}$ capable of hydrogen bonding or ionic interaction. The ligand comprises at least three moieties effectively spaced relative to each other so that a first moiety can bind with a first binding area, a second moiety can bind with a second binding area, and a third moiety can bind with a third binding area.

The present invention provides a method of designing a ligand to bind with TrkB, wherein TrkB comprises a leucine-rich motif (LRM) comprising amino acid residues 93 to 117, the coordinates of the residues of said LRM given in Appendix 2, said LRM having five binding areas, binding area F comprising amino acid residue Asp$^{100tB}$ capable of ionic interaction, binding area G comprising amino acid residue Lys$^{109tB}$ capable of ionic interaction, binding area H comprising amino acid residue Lys$^{113tB}$ capable of ionic interaction, binding area I comprising amino acid residue Arg$^{94tB}$ capable of ionic interaction, and binding area K comprising amino acid residue Lys$^{104tB}$ capable of hydrogen bonding or ionic interaction. The method comprises computationally evolving a ligand using an effective algorithm so that the evolved ligand comprises at least three effective moieties located relative to each other in the ligand so that a first moiety can bind with a first of said five binding areas, a second moiety can bind with a second of said five binding areas, and a third moiety can bind with a third of the binding areas. The algorithm may be a genetic algorithm.

The invention also provides a ligand for binding with the common neurotrophin receptor p75$^{NTR}$, wherein p75$^{NTR}$ comprises a binding site including amino acid residues Cys$^{39p}$ to Cys$^{94p}$ inclusive, said residues of said binding site having spatial coordinates given in Appendix 3, said binding site having three binding areas including binding loop 2A comprising region Cys$^{39p}$ to Cys$^{58p}$ capable of attractive electrostatic interactions, binding loop 2B comprising region Cys$^{58p}$ to Cys$^{79p}$ capable of attractive electrostatic interactions, and binding loop 3A comprising region Cys$^{79p}$ to Cys$^{94p}$ capable of attractive electrostatic interactions. The ligand comprises at least two moieties effectively spaced relative to each other so that a first moiety can bind to a first loop and a second moiety can bind to a second loop.

The present invention also provides a method of designing a ligand for binding with the common neurotrophin receptor p75$^{NTR}$, wherein p75$^{NTR}$ comprises a binding site including amino acid residues Cys$^{39p}$ to Cys$^{94p}$ inclusive. The residues of the binding site have spatial coordinates given in Appendix 3. The binding site has three binding areas including binding loop 2A comprising region Cys$^{39p}$ to Cys$^{58p}$ capable of attractive electrostatic interaction, binding loop 2B comprising region Cys$^{58p}$ to Cys$^{79p}$ capable of attractive electrostatic interaction, and binding loop 3A comprising region Cys$^{79p}$ to Cys$^{94p}$ capable of attractive electrostatic interaction. The method comprises computationally evolving a ligand using an effective algorithm so that the evolved ligand comprises at least two effective moieties located relative to each other in the ligand so that a first moiety can bind to a first of the three loops and a second moiety can bind to a second loop of the three loops.

The invention provides a method of identifying a ligand to bind with a leucine rich motif (LRM) of TrkA. The method comprises providing a three dimensional conformation for the LRM. The LRM comprises amino acid residue sequence 93 to 117 inclusive, the amino acid residues having spatial Cartesian coordinates given in Appendix 1. The LRM has five binding areas, area A comprising amino acid residue Phe$^{105tA}$ capable of hydrophobic interaction, area B comprising amino acid residues Phe$^{111tA}$, Phe$^{113tA}$, and Thr$^{114tA}$ capable of hydrophobic interaction, area C comprising amino acid residues Asp$^{109tA}$ and His$^{112tA}$ capable of ionic interaction, area D comprising amino acid residue Lys$^{100tA}$ capable of ionic interaction, and area E comprising Asn$^{95tA}$ to Ile$^{98tA}$ capable of multiple parallel β-strand type hydrogen bonding. The method includes providing a data base containing molecules coded for spatial occupancy, relative atomic position, bond type and/or charge; and screening the data base to select those molecules comprising moieties having a three dimensional conformation and effective charge that can bind with at least three of the five binding areas.

The invention provides a method of identifying a ligand to bind with a leucine rich motif (LRM) of TrkB. The method comprises providing a three dimensional conformation for the LRM. The LRM comprises amino acid residues 93 to 117, the coordinates of the residues of the LRM are given in Appendix 2, the LRM having five binding areas, binding area F comprising amino acid residue Asp$^{100tB}$ capable of ionic interaction, binding area G comprising amino acid residue Lys$^{109tB}$ capable of ionic interaction, binding area H comprising amino acid residue Lys$^{113tB}$ capable of ionic interaction, binding area I comprising amino acid residue $Arg^{94tB}$ capable of ionic interaction, and binding area K comprising amino acid residue $Lys^{104tB}$ capable of hydrogen bonding or ionic interaction. The method includes providing a data base containing molecules coded for spatial occupancy, relative atomic position, bond type and/or charge; and screening the data base to select those molecules comprising moieties having a three dimensional conformation and effective charge that can bind with at least three of the five binding areas.

The present invention also provides a method of identifying a ligand to bind with common neurotrophin receptor $p75^{NTR}$. The method comprises providing a three dimensional conformation for the common neurotrophin receptor $p75^{NTR}$, wherein $p75^{NTR}$ comprises a binding site including amino acid residues $Cys^{39p}$ to $Cys^{94p}$ inclusive. The residues of the binding site have spatial coordinates given in Appendix 3, the binding site having three binding areas including binding loop 2A comprising region $Cys^{39p}$ to $Cys^{58p}$ capable of attractive electrostatic interaction, binding loop 2B comprising region $Cys^{58p}$ to $Cys^{79p}$ capable of attractive electrostatic interaction, and binding loop 3A comprising region $Cys^{79p}$ to $Cys^{94p}$ capable of attractive electrostatic interaction. The method includes providing a data base containing molecules coded for spatial occupancy, relative atomic position, bond type and/or charge; and screening the data base to select those molecules comprising moieties that can bind with at least two of the three binding loops.

In one aspect of the invention, a ligand (e.g., small molecule) designed to interact with a receptor such as Trk or $p75^{NTR}$ may be bifunctional, such that a first portion of the ligand binds to one receptor monomer and a second portion of the ligand binds to a second receptor monomer. Thus, a receptor dimer is effectively cross-linked by the interaction of ligand with both receptor monomers.

According to the invention, detailed information is provided regarding those amino acid residues of neurotrophins and of neurotrophin receptors which are involved in neurotrophin-receptor binding. Such information includes the bioactive conformations of the respective peptide domains of the neurotrophins and receptors. This in turn permits the design of small molecules which interact with said amino acid residues or domains. Where such interaction block the residues or changes the conformation of the domain, the small molecule can inhibit neurotrophin-receptor binding, in certain cases abolishing it completely. As would be appreciated by a person skilled in the art, small molecule design according to this aspect of the invention is applicable to other ligand-receptor interactions in addition to neurotrophins, according to the methods disclosed herein.

As a person skilled in the art would appreciate, the invention not only provides molecules (ligands) that interact with receptors, but also molecules which, in their mimicry of a receptor's bioactive conformation, can bind to the receptor binding site of a ligand such as, for example, a neurotrophin. Such molecules, whether they interact with ligand or with receptor, can block native ligand-receptor interaction. In some embodiments of the invention, a small molecule which binds to a receptor may even trigger signal transduction similar to that of the native ligand, i.e., act as an agonist.

BRIEF DESCRIPTION OF THE DRAWINGS

The invention will be described, by example only, reference being had to the accompanying drawings, in which:

FIG. 1 shows the amino acid sequences of the conformationally variable termini of the dimeric NGF analogues under study. (First monomer, amino terminus: residues 1–15 of SEQ ID NO:1; residues 1–15 of SEQ ID NO:2; residues 1–8 of SEQ ID NO: 3; SEQ ID NO: 4; residues 9–15 of SEQ ID NO: 2; SEQ ID NO: 5. Second monomer, carboxyl terminus: SEQ ID NO: 6; SEQ ID NO: 7; SEQ ID NO: 8.) The residues are numbered from 1 to 118 for the first monomer, and from 1' to 118' for the second monomer. The fixed parts of the proteins simulated by the X-ray geometry of mouse NGF (McDonald et al., 1991) are underlined.

FIG. 2 shows the structure of the complex of the amino and carboxyl termini of (1–118)hNGF homodimer. The carboxyl terminus is shown in grey (residues 5–11 of SEQ ID NO: 6), the amino terminus in white, (residues 1–12 of SEQ ID NO: 1) and the interacting conservative region $His^{75'}$-$Asn^{77'}$ of the "south" part of the NGF dimer, in black (residues 2–4 of SEQ ID NO: 10).

FIG. 3 shows the structure of the complex of the amino and carboxyl termini of (1–118)mNGF homodimer (grey: residues 5–11 of SEQ ID NO: 7, white: residues 1–12 of SEQ ID NO: 2, black: residues 2–4 of SEQ ID NO: 10).

FIG. 4 shows the structure of the complex of the amino and carboxyl termini of dimeric mNGFΔ3–9 molecule grey: residues 5–11 of SEQ ID NO: 7, white: residues 1–5 of SEQ ID No: 3, black: residues 2–4 of SEQ ID NO: 10).

FIG. 5 shows the structure of the complex of the amino and carboxyl termini of dimeric hNGF-H4D molecule. (grey: residues 5–11 of SEQ ID NO: 6, white: residues 1–12 of SEQ ID NO: 4, black: residues 2–4 of SEQ ID NO: 10).

FIG. 6 shows the structure of the complex of the amino and carboxyl termini of dimeric mNGFΔ1–8 molecule (grey: residues 5–11 of SEQ ID NO: 7, white: residues 9–12 of SEQ ID NO: 2, black: residues 2–4 of SEQ ID NO: 10).

FIG. 7 shows the structure of the complex of the amino and carboxyl termini of BDNF homodimer (grey: residues 5–11 of SEQ ID NO: 8, white: residues 1–10 of SEQ ID NO: 5, black: residues 2–4 of SEQ ID NO: 10).

FIG. 8 illustrates the TrkA leucine-rich motifs. Locations of parallel β-strands are illustrated by the shaded areas designated by symbol β. Fragments B1–B4 demonstrate NGF binding affinity, while N1–N4 do not (Windisch et al., 1995a, 1995b).

FIG. 9 shows sequences of the amino and carboxyl termini of fully active NGF analogues. Regions with rigid structures are underlined. (First monomer, amino terminus: SEQ ID NO: 1; SEQ ID NO: 2; SEQ ID NO: 3. Second monomer, carboxyl terminus: SEQ ID NO: 10; SEQ ID NO: 6; SEQ ID NO: 7; SEQ ID NO: 11; SEQ ID NO: 9).

FIG. 10 shows the predicted bioactive conformation of the NGF binding domain (a) and the structures of the NGF/LRM-2A complexes of hNGF (b), mNGF (c), mNGFΔ3–9 (d), and hNGF:NT-4/5 (e). Only residues essential for discussion are designated. A, B, C, D and E represent specific NGF/LRM-2A binding areas. The LRM-2A is illustrated in grey, NGF in white.

FIG. 11 shows the TrkB receptor binding site of BDNF (a), predicted features of the BDNFILRM-2B complex (b), and geometry of the "improper" NGF/LRM-2B complex (c). Only residues essential for discussion are designated. F, G, H, I and K represent specific BDNF/LRM-2B binding areas. The LRM-2B is illustrated in grey, BDNF and NGF in white.

FIG. 12 is a detail of the LRM-2A (SEQ ID NO:12) conformation when bound to hNGF. The three groups of the β-strand involved in H-bonding with the parallel N-strand motif of the NGF analogues are designated by NH or CO. Hydrophobic residues are illustrated as light, polar uncharged as dark, charged as black.

FIG. 13 presents principal residues of the NGF binding domain essential for TrkA receptor recognition. (Amino terminus: SEQ ID NO: 1; carboxyl terminus: SEQ ID NO: 10; SEQ ID NO: 6). Conserved residues of NGF molecules among all characterized species (McDonald et al., 1991) are designated by X, whereas those which are substituted in NGF molecules derived from different species by similar amino acids and NGF residues maintaining the bioactive conformation or interacting with specific binding areas A–E of the LRM-2A are indicated by X.

FIG. 14 presents principal residues of the LRM-2A (SEQ ID NO: 12). The residues which are specific for TrkA (Windisch et al., 1995a, 1995b) and critical for the present model are designated by X and X̲, respectively.

FIG. 15 is a schematic representation of the second leucine-rich motif of TrkA (residues 93tA to 116tA) (a: residues 1–24 of SEQ ID NO:12) and TrkB (residues 93tB to 116tB) (b: SEQ ID NO:12) as specific binding sites for NGF and BDNF, respectively. General consensus residues are shaded. Arrows designate distinct positions essential for molecular recognition processes.

FIG. 16 represents the X-ray crystallography-derived geometry of the α-carbon trace of the two loops (2A and 2B) of the second cysteine-rich domain (white bonds) and the first loop (3A) of the third cysteine-rich domain (grey bonds) of $p55^{TNFR}$ (Banner et al., 1993) (a), the preferred geometry of the α-carbon trace of the corresponding fragment of $p75^{NTR}$ (b), and the predicted bioactive conformation of mouse NGF (McDonald et al., 1991); (c). White and grey bonds in panel (c) illustrate different protomers. The $p75^{NTR}$ binding determinant of NGF (loops I and V) is denoted. Disulfide bonds are shown in black.

FIG. 17 shows the sequence of a putative binding site for neurotrophins within $p75^{NTR}$ aligned with the corresponding sequence of homologous $p55^{TNFR}$ (SEQ ID NO: 14; SEQ ID NO: 15; SEQ ID NO: 16; SEQ ID NO: 17). Conserved pattern of disulfide bonds is illustrated. Abbreviation (h) stands for human (Johnson et al., 1986), (r) for rat (Radeke et al., 1987), and (c) for chicken (Large et al., 1989) $p75^{NTR}$.

FIG. 18 illustrates the most stable geometries of the complexes of the neurotrophins with the common neurotrophin receptor $p75^{NTR}$: with NGF (a); with BDNF (b); with NT-3 (c); with NT-4/5 (d). The α-carbon traces of the neurotrophins are shown in white, while that of the $p75^{NTR}$ binding site is shown in grey. Disulfide bonds are illustrated in black. Only residues mentioned in the text are denoted.

FIG. 19 demonstrates geometric compatibility of the van der Waals surfaces of BDNF (light) and the $p75^{NTR}$ binding site (dark).

FIG. 20 illustrates conformational changes of the $p75^{NTR}$ binding site upon BDNF binding. Conformation of the $p75^{NTR}$ receptor binding site before binding is illustrated in white, after binding in grey. The two conformations have been superimposed using the equilibrium positions of the reference a-carbon atoms located in loops 2A and 3A. Straight lines denote linear approximations of the conformations of the a.-carbon traces of loop 2B in both structures.

DETAILED DESCRIPTION OF THE INVENTION

PART A

Theoretical Studies of the Bioactive Conformation of Nerve Growth Factor Using VBMC—A Novel Variable Basis Monte-Carlo Simulated Annealing Algorithm for Peptides Background of the VBMC Algorithm The structural optimization of the peptide domains under study required a rigorous search of conformational space. As with other theoretical peptide studies, such calculations are plagued by a multiple-minima problem (Gibson and Scheraga, 1988) which traditionally is addressed using either molecular dynamics, Monte Carlo approaches or other algorithms. The Monte Carlo method, although exceedingly powerful, is limited by the excessive CPU time requirements on existing computers. To remedy this problem, we have devised a novel Variable Basis Monte Carlo simulated annealing algorithm for peptides (VBMC).

The potential energy hypersurface of a peptide has an enormous number of local minima (Gibson and Scheraga, 1988; Piela et al., 1989, 1994), but usually only the global energy minimum structure is required. Despite efforts to elaborate an efficient method of global energy minimization (Gibson and Scheraga, 1988; Judson et al., 1994), the multiple-minima problem is far from being solved. Although simulated annealing (Kirkpatrick et al., 1983; Vanderbilt et al., 1984) is mathematically correct and guarantees convergence to the global minimum in principle, the suggested "cooling" schedule appears to be far too slow for practical purposes, and faster "cooling" has to be used (Gidas, 1985; Kushner, 1987). Within the simulated annealing approach, thermal molecular motion can be simulated either by Monte Carlo (Kirkpatrick et al., 1983; Nayeem et al., 1991; Wilson et al., 1988; Snow, 1992; Shamovsky et al., 1992) or molecular dynamics (Lelj et al., 1991; Villani and Tamburro, 1994) methods.

The major problem of the Monte Carlo technique is that motion of a molecular system along a Markov chain is very slow (Piela et al., 1994; Scheraga, 1989; Nayeem et al., 1991). On the other hand, the Monte Carlo technique has several considerable advantages over molecular dynamics. First, it does not require calculating forces. Second, potential energy functions do not have to be continuous. Third, much larger steps in conformational space can be utilized (Li and Scheraga, 1988; Kincaid and Scheraga, 1982). Fourth, the additional iterative self-consistent SHAKE routine (Ryckaert et al., 1977), which is used in molecular dynamics simulations to deal with holonomic constraints (Brooks III and Case, 1993), is not required in the Monte Carlo method. This has led to efforts to accelerate configurational motion within the Monte Carlo approach (Raj et al., 1994; Snow, 1992; Kincaid and Scheraga, 1982; Rao et al., 1979; Rossky et al., 1978). The main reason for inefficiency with the conventional Monte Carlo method (Metropolis et al., 1953) is a slow and cumbersome sequential change of configurational variables.

To overcome these problems, lessons can be learned from molecular dynamics. In molecular dynamics (Allen and Tildesley, 1987) configurational variables move simultaneously, and the soft modes of the system explicitly direct these motions. Soft modes are defined as low-energy valleys on the potential energy hypersurface. Although there have been attempts to direct Monte Carlo configurational motion along the soft modes (Raj et al., 1994; Rao et al., 1979; Rossky et al., 1978), these improvements require calculating forces and, consequently, result in losing the main advantages of the Monte Carlo approach. An algorithm which would retain the advantages of the Monte Carlo method and direct configurational changes along the soft modes is thus required. One possible solution has recently been suggested (Szentpaly et al., 1994).

The classical Monte Carlo-Metropolis method (Metropolis et al., 1953) consists of modelling a Markov chain containing subsequent conformations of the molecule under study: $x_0, x_1, x_2, \ldots, x_i, \ldots$, where $x$ ($x_i = \{x_i^1 \ldots x_i^m \ldots x_i^N\}$) is the vector of independent structural parameters. Each vector $x_{i+1}$, is derived from the preceding one, $x_i$, by means of a random change of one randomly chosen variable:

$$x_{i+1}^m = x_i^m + \lambda_m \cdot \xi \qquad (1)$$

where $\xi$ is a random quantity from the interval $(-1,1)$ and $\lambda_m$ is a maximal allowed increment of the given variable. N moves of the Markov chain (where N is the number of independent parameters) represent a Monte Carlo step. Whether the new state $x_{i+1}$ is accepted or rejected is decided according to a transition probability function. The following functional form of transition probability is used in the present expression (2) (Gunningham and Meijer, 1976):

$$W(x_i \rightarrow x_{i+1}) = 1/[1 + \exp(\Delta E_i / kT)] \qquad (2)$$

where $\Delta E_i$ is the difference between conformational energies of the states $x_{i+1}$ and $x_i$, k is the Boltzmann constant and T is absolute temperature.

Those skilled in the art will appreciate that other functional forms of transition functions may be used to screen state a new state $x_{i+1}$. For example, another effective temperature dependent transition function for screening a new state $x_{i+1}$ derived from a previous state $x_i$ is given by:

$$W(x_i \rightarrow x_{i+1}) = 1. \qquad \text{if } E(x_{i+1}) \leq E(W(x_i)$$
$$= \exp(-\Delta E_i / kT), \text{ if } E(x_{i+1}) \geq E(W(x_i)$$

where $\Delta E_i$ is the difference between conformational energies of the states $x_{i+1}$ and $x_i$, k is the Boltzmann constant and T is absolute temperature.

The direct application of this conventional Monte Carlo technique to the conformational space study of protein structure is not efficient because the conformational variables of peptide chains appear to be mutually dependent, i.e., low-energy conformational motions involve several conformational variables. When applied to molecular systems such as protein secondary, tertiary or quaternary structure, equation (1), in which structural parameters are sequentially changed one after another, results in very small values of $\xi$ and, consequently, in a very slow conformational motion (Piela et al., 1994; Scheraga, 1989; Nayeem et al., 1991). In order to model a simultaneous change of the structural parameters, we have used Eq.(3) (instead of the conventional (1)), $$x_{i+1} = x_i + \lambda_m \cdot \xi \cdot g^m \qquad (3)$$

where $g^m$ is a randomly or sequentially chosen basis vector from a basis $G = \{g^m\}$, $\xi$ is a random quantity from an interval $(-1,1)$ and $\lambda_m$ is a maximal acceptable move in direction $g^m$. In this study $\lambda_m$ was constant and equal to $10°$.

A basis G is formed from linear combinations of independent conformational parameters x for their change to be realized along the soft modes of the molecule. These modes are revealed by dispersion analysis of the distribution of the sequential configurational points of the Markov chain. The soft modes of the molecular system are to be directed along the axes of the dispersion ellipsoid because they should correspond to the directions of maximal deviations made by the independent variables during a certain period of simulation. Initially, basis G coincides with a unit matrix, i.e., G=I, and Eq.(3) is equivalent to (1). The rotation of basis G is carried out after every 150 Monte Carlo steps based on the particular scattering of the previous 150 configurations x. Basis vectors $g^m$ are made equal to the eigenvectors of the covariant matrix D which has the following elements:

$$d_{ij}(1/M) \cdot \sum_{n=1}^{m} \left( x_n^j - (1/M) \cdot \sum_{n=1}^{m} x_n^j \right) \cdot \left( x_n^j - (1/M) \cdot \sum_{n=1}^{m} x_n^j \right) \qquad (4)$$

where M is the number of points in the distributions (M=150), and $x_n^1$ is the i-th structural parameter at the n-th Monte Carlo step. Vectors $g^m$ form the orthonormalized basis and are used in the Markov chain instead of independent conformational parameters. Periodic rotations of basis G in Monte Carlo simulations result in a simultaneous change of all the conformational variables along the valleys of a potential energy surface, which considerably accelerates conformational motions and transitions (Szentpaly et al., 1994).

The method disclosed herein is highly advantageous over known processes for several reasons. In the present process the preselected range from which the magnitude of translation is chosen is constant and does not depend on the basis set. Thus the present method is much more efficient than previous methods in part because the magnitude of translation along the basis vector is limited by a preselected range. The present method is also more efficient because rotation of the basis set of configurational variables is avoided at the upper temperatures and is implemented only at the lower temperatures.

Implementation of the VBMC Algorithm

VBMC was written in Fortran-77. The algorithm was then interfaced with the CHARMM force field (Brooks et al., 1983; The force field parameters are extracted from CHARMM release 23.1, Molecular Simulations, Inc., Waltham, Mass.). Torsional distortion, van der Waals and electrostatic interactions, and hydrogen bonding were thus explicitly considered. The united atom approach was used for all carbons with non-polar hydrogens. Point atomic charges of Weiner et al. (Weiner et al., 1984) were used. A dielectric constant equal to the interatomic separation in angstroms was utilized to implicitly simulate solvation effects (Weiner et al., 1984). All calculations were performed on an 8-node IBM Scalable POWERparallel 2 [SP2] high performance computer at Queen's University, Kingston, Canada. Each Monte Carlo simulated annealing computation required up to 120 hours of CPU time.

Appendix 4 is attached. Appendix 4 is a computer program written in Fortran-77 and is a non-limiting example of a program used to perform the VBMC simulated annealing method in accordance with the present invention.

Each run of the VBMC algorithm provides a unique final structure which would represent the global energy minimum structure, regardless of the initial geometry, if the "cooling" was performed infinitely slowly. However, since this is impossible, several Monte Carlo simulated annealing computations must be performed from different starting points $x_0$, using different initial temperatures $T_0$, "cooling" schedules and random sequences. An initial temperature of 1000° K. is sufficient. The Markov chain is kept at a constant temperature $T_0$ for $10^4$ Monte Carlo steps before the initiation of "cooling". The temperature T is then decreased at every Monte Carlo move (3) by a small increment such that after $2 \cdot 10^4$ Monte Carlo steps it reaches 120° K. producing an unrefined global energy minimum structure.

The global energy minimum structure is then refined to identify the nearest local minimum or stationary point on the potential energy hypersurface. Refinement may be accomplished using any one of several non-linear minimization routines to identify the local minimum on the potential energy hypersurface. For example, gradient descent minimization and conjugate gradient minimization may be used. Quasi-Newton minimization methods such as the Newton-Raphson method may also be used. Other non-linear methods include the Marquardt method, the Powell method and a variable metric method. Those skilled in the art will be aware of the various non-linear routines which may be used for refinement and those mentioned herein are more fully described in *Nonlinear Programming: Theory, Algorithms, and Applications*. 1983. New York: John Wiley & Sons.

Applying VBMC to NGF

The aim of this computational study was to ascertain the biologically active conformation of the TrkA receptor binding determinant of NGF. A comprehensive review of the literature identified an initial study set of 17 proteins which have been assessed for TrkA mediated activity using comparable experimental methods. From these 17 analogues, a subset of six (three active and three inactive) which reflects the range of structural diversity was selected for preliminary study. Accordingly, in the present invention the low-energy conformations of the amino and carboxyl termini of six NGF analogues were obtained by means of Monte Carlo simulated annealing calculations. Three of these analogues retain full TrkA mediated activity: human NGF (hNGF; Shih et al., 1994; Burton et al., 1992), mouse NGF (mNGF; Burton et al., 1992; Drinkwater et al., 1993), and mNGFΔ3–9 (deletion 3–9 of mNGF; Drinkwater et a., 1993). The other three analogues are biologically inactive: hNGF-H4D (a point mutation of hNGF in which His [H] in position 4 is replaced by Asp [D]; Shih et al., 1994), mNGF&1-8 (Burton et al., 1992; Drinkwater et al., 1993; Taylor et al., 1991) and BDNF (Suter et al., 1992). The results and conclusions obtained from these six analogues were then validated by being applied to the remaining 11 analogues of the initial study set.

The amino acid sequences of the termini of the neurotrophin molecules under study are presented in FIG. 1. Residues are numbered from 1 to 118 for the first monomer, and from 1' to 118' for the second monomer. The mutual orientation of the termini of the different monomers is determined by the disulfide bonds $Cys^{15}-Cys^{80}$ and $Cys^{68'}-Cys^{110'}$ and hydrophobic interactions $Val^{14}:Val^{14'}$ and $Val^{109}:Val^{109'}$, which are absolutely conserved in all neurotrophins (McDonald et al., 1991). The conformational space of the peptide molecules consists of flexible torsional angles determining geometry of the amino terminus of one monomer and the carboxyl terminus of the other, while keeping the rest of the dimer fixed in the known geometry of mNGF (McDonald et al., 1991). Covalent bond lengths and bond angles of the termini are kept fixed. The geometry of each residue is determined only by flexible torsional angles of the peptide backbone ($\phi$ and $\psi$) and the side chain ($x_1, x_2, \ldots$). All torsional angles of amino acid Pro except for $\psi$ are fixed. Torsional angles describing structural motifs with the essentially planar geometry (such as peptide bonds or conjugated regions in side chains) are kept fixed. Likewise, the configurations of the $sp^3$-carbons are fixed. With these constraints, the total conformational space of the flexible termini of hNGF, mNGF and BDNF consists of 74, 73 and 67 variables, respectively.

Results and Discussion

By diagonalizing the covariant matrix in the framework of the VBMC algorithm, rigid modes of a molecular system, which should slow down conformational changes, are supposed to be revealed simultaneously with soft modes of the system. To test the efficiency of the VBMC algorithm, its performance was compared with the conventional Monte-Carlo method at the equilibrium parts of the Markov chains generated at different constant temperatures. These comparisons showed that at high temperatures (700°–1000° K.) the basis variability results in decreasing acceptance rates. On the other hand, the temperature decrease reinforces the advantage of the VBMC approach, and at temperatures below 600° acceptance rates of the VBMC Markov chains were significantly higher. Thus, at T=300° K. the acceptance rate of the conventional Markov chain was found to be 0.22, which is very close to that recommended by Kincaid and Scheraga (1982) as optimal (0.20). The acceptance rate of the VBMC algorithm obtained at the same conditions was 0.26, i.e. 18% higher. These evaluations are in agreement with what one would expect. Indeed, at low temperatures only soft modes of molecules are involved in thermal motions, hence, they are especially populated in corresponding Monte-Carlo generated conformational ensembles and can be revealed from them. Higher acceptance rates of the low temperature VBMC Markov chains over conventional Markov chains mean that the average increase of the sizes of the Monte-Carlo moves along soft modes of the system are higher than their decrease along the rigid modes. Thus, the VBMC disclosed herein for evaluating peptide conformations not only changes directions of the Monte-Carlo moves, but also accelerates conformational changes by directing them along the soft -modes of the molecule. Consequently, the present VBMC algorithm is more efficient than conventional Monte-Carlo method only at moderate and low temperatures, when thermal motions tend to take place along the valleys of the potential energy surface. This particular temperature region causes serious problems in known simulated annealing algorithms, and the VBMC method disclosed herein provides a solution to these problems.

Seven independent VBMC simulations for each of the six molecular systems under study were performed. Simultaneously, local energy refinements were periodically carried out from a number of points generated during the "slow cooling" stage. All local minimizations resulted in higher energy stationary points on the potential energy surface than those produced by VBMC computations. This means that the VBMC technique as an approach to global minimization cannot be replaced by relatively inexpensive periodic energy refinements from the high-temperature conformational space; at high temperatures only high-energy conformers are sufficiently populated. Although VBMC runs did not converge to the same conformation, the final structures differed insignificantly; i.e., the peptide backbone conformation remained unchanged but there were limited differences in the side chain torsional angles. Multiple VBMC simulations identified rigid and flexible parts of the molecules. Minimum energy structures of all molecules are displayed in FIGS. 2–7 while Table 1 presents optimized conformational parameters of the amino and carboxyl termini of the considered NGF analogues.

Geometric Similarity of Bioactive NGF Conformers

Rigid regions of hNGF and mNGF which maintain the same conformation in all independent VBMC simulations are formed by residues 9–11 and 112'–118', creating a richly hydrogen bonded (H-bonded) 3-dimensional complex. Conformational variability within this rigid zone is primarily restricted to side chains and does not affect the geometry of the backbone. An interesting example of such side chain mobility occurs with $Arg^{114'}$, which is H-bonded to the carbonyl oxygen of the ninth amino acid of the amino terminus and which is therefore expected to have a fixed conformation. Nevertheless, $Arg^{114'}$ has two distinct conformers in which the H-bonding is realized by the hydrogen atoms attached to the different $NH_2$ groups, with the energy difference being about 1 kcal/mol. In addition to local conformational variability, hNGF and mNGF have a region of "cooperative" flexibility which is made up of residues 1–8. Several distinct conformations exist within this region, with its conformational variability being caused by a number of possibilities for the H-bond network formed by residues 1–3.

Comparison of the most stable conformers of hNGF (FIG. 2) and mNGF (FIG. 3) reveals striking conformational similarity between their rigid regions in spite of several differences in the primary structure of the amino and carboxyl termini (FIG. 1). As shown in Table 1, both termini have the same conformation, except for the variable region consisting of residues 1–3. The most stable H-bond networks in this area differ considerably because of the mT3hS substitution.

The essential difference between the amino acid sequences of the termini of hNGF and mNGF is the mM9hR substitution, which does not change the geometry of the rigid region. Residues Met and Arg have different side chain types, i.e., the former is non-polar while the latter is polar and positively charged under physiological conditions. It is surprising that this substitution does not affect geometry since it introduces the positive charge of $Arg^9$ which is located in an electrostatic field created by at least five neighbouring charged functional groups. Conformational stability of the rigid region of hNGF is maintained by the exact fit of the $Arg^9$ side chain into a "hollow" in the rigid region, which is occupied by the $Met^9$ side chain in mNGF. Furthermore, the $Arg^9$ side chain, being in this "hollow", forms two additional interchain H-bonds with carbonyl oxygens of residues $Val^{117'}$ and $Arg^{118'}$. This further stabilizes the rigid region of hNGF.

The physical reason for the geometric similarity of the rigid regions of hNGF and mNGF is that the structural features of these two complexes are determined by similar H-bonding and electrostatic interactions. The major stabilizing factor is the H-bonding and electrostatic interaction of charged side chains of residues $Glu^{11}$ and $Arg^{118'}$. In addition, these side chains are involved in other H-bonding: the carboxyl oxygens of $Glu^{11}$ are bonded to the δ-NH group of $His^8$, the hydroxyl group of $Ser^{113'}$ and the backbone NH group of $Lys^{115'}$; the side chain NH and $NH_2$ groups of $Arg^{118'}$ are bonded to the backbone $Phe^7$ and $Lys^{115'}$ carbonyl groups. There are some other common interchain H-bonds in hNGF and mNGF. The ε-amino group of the $Lys^{115'}$ side chain forms a H-bond with the δ-carbonyl oxygen of the $Asn^{77'}$ residue, situated at the "south" part of NGF structure (McDonald et al., 1991).

In addition to H-bonding, the particular geometry of the rigid region in both molecules is also maintained by electrostatic interactions of positively charged residues, specifically $His^4$, $His^8$, $Arg^{114'}$, $Arg^{118'}$ and $His^{75'}$. An electrostatic repulsion between $His^4$ and boundary residues $His^8$ and $Arg^{118'}$ of the rigid region forces $His^4$ to be located as far as possible from the rigid region, separating the 1–8 loop from the rest of the structure. This tendency is further reinforced in hNGF by the presence of a third positively charged boundary residue $Arg^9$. The $His^{75'}$ amino acid located in the "south" part of NGF also participates in maintaining the structure of the rigid region. An electrostatic repulsion between $His^{75'}$ and $Arg^{114'}$ prevents H-bonding of the amino group of $Arg^{114'}$ with the $Asn^{77'}$ side chain and the $Ser^{113'}$ backbone: indeed, removing the ε-proton from $His^{75'}$ results in two H-bond contacts which change the global energy minimum structure of the complex.

The separation of flexible loop 1–8 from the rigid region is also determined by residue $Pro^5$. This amino acid imposes restrictions on conformational motion of the loop, making it "bent" at this particular point, and thereby defining the location of the adjacent $His^4$ residue at the most distant point from the rigid region. Thus, residues $His^4$ and $Pro^5$ are primarily responsible for the separation of the flexible loop from the rigid region.

Although mNGFΔ3–9 does not have the flexible loop, the energy optimized geometric features of its termini are very similar to those of the hNGF and mNGF rigid regions (Table 1, FIGS. 2–4). There are only two structural elements which are specific for the rigid region of mNGFΔ3–9. First, although $Arg^{118'}$ has a different conformation, the result is functionally the same, namely both $NH_2$ groups of the $Arg^{118'}$ side chain are H-bonded to the $Glu^{11}$ side chain. In addition, the ε-NH group of $Arg^{118'}$, which is H-bonded to the $Phe^7$ carbonyl group of the flexible loop in both hNGF and mNGF, faces the carboxyl terminus in mNGFΔ3–9. Second, the "hollow", which is occupied by the ninth amino acid side chain in hNGF and mNGF, is now filled with the protein backbone of the remainder of the loop, i.e., residues 1–2. Functionally, the structure of the rigid region of mNGFΔ3–9 resembles that of hNGF because of the stabilizing interchain H-bond contacts of the moieties located in the "hollow".

Geometric Distinction of NGF Analogues Inactive of TrkA Binding

The energy minimum structures of the complexes formed by the amino and carboxyl termini of molecules, hNGF-H4D, mNGFΔ1–8 and BDNF, which are inactive with respect to TrkA binding, do not possess the common structural features found in active molecules. Point mutation H4D in hNGF incorporates negative instead of positive charge into the 1–8 loop. As a result of this mutation, the loop is no longer separated from the rigid region, forming a united complex instead (FIG. 5). In this complex the negatively charged carboxyl group of $Asp^4$ is surrounded by four positively charged $NH_2$ groups of $Arg^9$ and $Arg^{114'}$, and residue $His^8$ is not H-bonded to the $Glu^{11}$ carboxyl group. Thus, because of the H4D point mutation, the common structural features inherent in hNGF and mNGF are lost from hNGF-H4D.

Deletion 1–8 also changes dramatically the most stable structure of the rigid region of mNGF (FIG. 6). The newly created positively charged amino terminus is located between negatively charged carboxyl groups of $Glu^{11}$ and $Arg^{118'}$, with charged side chains of $Arg^{114'}$, $Lys^{118'}$ and $Arg^{118'}$ being substantially shifted from their preferred positions in active molecules. Thus, the electrostatic field caused by the positive charge of the new amino terminus in mNGFΔ1–8, located in the vicinity of the carboxyl group of $Glu^{11}$, is responsible for the destruction of the geometry of the rigid region inherent in the active molecules.

The complex formed by the amino and carboxyl termini of BDNF is also significantly different from those formed by the molecules active for TrkA binding (FIG. 7, Table 1). There are several reasons for the considerable conformational changes in BDNF. First, negatively charged residue Asp$^5$ eliminates the separation of the flexible loop from the rigid region, and interacts with the positively charged His$^3$, Arg$^9$ and amino terminus. Second, because of its long tail, Arg$^8$ is unable to form the H-bond contact with the Glu$^{11}$ side chain and forms bifurcated H-bonds with the carbonyl group of Gly$^{10}$. Third, Arg$^{116'}$ is H-bonded to Glu$^{66'}$ located in the "south" part of the molecule, which imposes a specific restriction on conformational possibilities of the carboxyl terminus of BDNF.

Explanation for The Observed Structure-Activity Relationships

The principal result of the molecular simulations presented is that the NGF molecules with full TrkA mediated activity considered in this study have regions with similar 3-dimensional structure, whereas in all inactive analogues, the geometry of this region is altered, mainly by novel electrostatic interactions. It is therefore reasonable to attribute the TrkA mediated activity to a specific conformation of this particular region. The amino and carboxyl terminal regions therefore represent a "functional epitope" which contains relatively few contact residues mediating high affinity binding. The ability of a small number of residues to cause high affinity binding has previously been demonstrated in other systems and may represent a general property of protein-protein interfaces. Some experimental data consistent with this concept are presented below.

The VBMC computations show that the following amino acids are critical in determining the structure of the complex in wild type NGF dimers: His$^4$, Pro$^5$, His$^8$, Arg$^9$, Glu$^{11}$, His$^{75'}$, Asn$^{77'}$, Lys$^{115'}$ and Arg$^{118'}$. This is significant since residues His$^4$, Pro$^5$, Glu$^{11}$, His$^{75'}$, Asn$^{77'}$ and Lys$^{115'}$ are conserved in NGF molecules across all species (McDonald et al., 1991). The overlap between these two sets reflects a tendency to maintain the particular geometry of the complex in natural NGF molecules. In addition, as demonstrated, the substitution of the important residue Arg$^9$ by the essentially different Met$^9$ does not result in geometric changes of the complex, which is consistent with equivalent bioactivity of hNGF and mNGF (Burton et al., 1992). Thus, because of multiple physical factors maintaining the geometry of the complex, some species variability observed in NGF termini (McDonald et al., 1991) is acceptable and does not cause geometric changes in the rigid region.

It is shown that each NGF terminus has several important residues, which determine the particular structure of the complex. This is consistent with high sensitivity of biological activity of NGF to the primary structure of both the amino and carboxyl termini (Klein et al., 1991; Shih et a., 1994; Burton et al., 1992, 1995; Kahle et al., 1992; Drinkwater et al., 1993; Treanor et a., 1995; Taylor et al., 1991). The lack of the TrkA mediated activity of the mNGFΔ3–11, mNGFΔ3–12, mNGFΔ3–13, mNGFΔ3–14, mNGFΔ9–14 and mNGFΔ112–118 deletion mutants (Drinkwater et al., 1993) is thus explained by the absence of the key residues Glu$^{11}$ and Arg$^{118'}$.

The separation of the flexible loop from the rest of the complex is crucial in permitting the rigid region to exist with definite geometric features. Residues His$^4$ and Pro$^5$ which cause this separation are absolutely conserved elements of the wild type NGF molecules derived from different species (McDonald et al., 1991), and their compulsory location in the middle of the flexible loop is well suited for facilitating the maximal separation. Point mutation P5A or H4D weakens or destroys the tendency of the loop to separate from the rigid region; accordingly, these mutations result in dramatic loss of TrkA related activity (Shih et al., 1994).

The flexible loop is not an essential structural element for TrkA activation since the mNGFΔ3–9 deletion mutant, which does not contain the loop (FIG. 4), is as active as wild type mNGF (Drinkwater et al., 1993). However, complete elimination of all loop residues results in almost inactive mutants mNGFΔ1–8 (Burton et al., 1992; Drinkwater et al., 1993; Taylor et al., 1991) and hNGFΔ1–9 (Shih et al., 1994; Burton et al., 1992, 1995; Kahle et al., 1992; Luo and Neet, 1992). Our molecular simulation studies enable the explanation for this apparent contradiction. It is demonstrated that the backbone of residues Ser$^8$–Ser$^9$ in the mNGFΔ3–9 mutant is naturally incorporated into the structure of the rigid region because it matches the geometry of the "hollow" occupied by either Met$^9$ or Arg$^9$ side chain in wild type NGF dimers. On the contrary, total truncation of the flexible loop in the mNGFΔ1–8 deletion mutant results in placing the positively charged amino end in the vicinity of the key H-bonded Glu$^{11}$ and Arg$^{118'}$ charged side chains (FIG. 3), which abolishes the desired geometry of the rigid region (FIG. 6). The same applies to the hNGFΔ1–9 deletion mutant which has neither the 1–8 loop nor the stabilizing Arg$^9$ residue (FIG. 2). This being the case, biological activity of amino terminus deletions of NGF should be determined by the length of the remainder of the terminus rather than its particular sequence. Indeed, available experimental data confirm this point. Deletion mutant mNGFΔ2–8 which has exactly the same number of residues in the amino terminus as the highly active mNGFΔ3–9 mutant is also very active (Drinkwater et al., 1993). Some decrease in biological activity of mNGFΔ2–8 is likely to be caused by unfavorable directing of the Met$^9$ hydrophobic side chain away from the complex whereas in the mNGFΔ3–9 deletion mutant this side chain is replaced by the hydrophilic hydroxyl group (FIG. 4). Deletion mutants mNGFΔ3–8 (Drinkwater et al., 1993) and hNGFΔ1–5 (Shih et al., 1994), which contain a greater number of amino terminus residues, are remarkably less active than wild type NGF because the remainder of the loop is too long to occupy the "hollow" but too short to separate from the rigid region. The present explanations for the observed structure-activity relationships enable the prediction that, for example, a S2G mutation in the mNGFΔ3–9 deletion mutant would retain high biological activity.

Although the bioactive conformation of the NGF binding determinant has been disclosed above, the question of which NGF residues are involved in NGF/TrkA recognition was not yet addressed. One would reason, most probably, those residues which are primarily responsible for maintaining the particular structure of the NGF termini do not directly interact with the receptor. Thus, side chains of His$^4$, Pro$^5$, His$^8$, Met$^9$, Arg$^9$, Glu$^{11}$ and Arg$^{118'}$ are not expected to play a crucial role in molecular recognition. On the other hand, charged residues Arg$^{114'}$ and Lys$^{115'}$ which are conserved in NGF molecules across all species (McDonald et al., 1991) but not involved in principal intramolecular electrostatic interactions are candidates for the centres of intramolecular electrostatic recognition. Although both Arg$^{114'}$ and Lys$^{115'}$ participate in stabilizing intramolecular H-bonding within the bioactive conformations of the NGF termini, their electrostatic properties as charged residues are not utilized for this purpose.

The other structural element of the termini with potential for stereochemical fit to the TrkA receptor is a short exposed β-sheet motif located between the α-carbons of residues 7 and 9 (FIGS. 2,3). On the one hand, H-bonding between β-pleated sheets is rather common for protein-protein interactions (Kobe and Deisenhofer, 1993, 1994, 1995; Yoder et al., 1993; Baumann et al., 1993). On the other hand, a short exposed β-sheet motif is generally inherent in the structure of a leucine-rich repeat (Kobe and Deisenhofer, 1993, 1994, 1995) which has been recently identified as the TrkA recognition site for NGF (Windisch et al., 1995a, 1995b). Other regions of NGF might also be involved in the NGF/TrkA recognition (Shih et al., 1994; Ibáñez et al., 1993). This will be discussed in depth below.

Conclusions

The Variable Basis Monte Carlo simulated annealing technique disclosed herein enables analysis of the low-energy conformational space of peptide molecules. Although multiple VBMC calculations do not consistently converge to the global energy minimum structure, they do permit the biologically active conformation to be evaluated. Definite physical factors maintain and distinguish the bioactive conformation of a molecule, and these factors can be understood by analyzing the low-energy conformational space. The precisely defined global energy minimum structure is unnecessary, especially considering that any empirical force field functions are not ideal. In biologically relevant molecular modelling, exploring the bioactive conformation is more important than determining the global energy minimum. VBMC is a useful tool for facilitating this exploration.

The present VBMC simulations predict that the amino (1–11) and carboxyl (112'–118') termini of dimeric (1–118) NGF form a complex comprised of a rigid region and a conformationally variable loop. The rigid region is formed by residues 9–11 and 112'–118' while the variable loop is formed by residues 1–8. The major stabilizing factor of the rigid region is the ionic contact of the $Glu^{11}$ and $Arg^{118'}$ side chains. The separation of the loop from the rigid region arises from the electrostatic repulsion between $His^4$ and boundary residues of the rigid region $His^8$, $Arg^9$ (in hNGF) and $Arg^{118'}$. The geometry of the complex explains observed structure-activity relationships. Accordingly, it is the conformation of the rigid region which is recognized by the TrkA receptor, defining the biologically active conformation of NGF for TrkA activation.

The split of the complex of the NGF termini into two distinct moieties could have important biological implications. Although only the structure of the rigid region is recognized by the TrkA receptor, the flexible loop is able to control conformational stability of the biologically active conformation of the rigid region and, consequently, NGF-induced TrkA phosphorylation.

PART B

Theoretical Modelling of Trk-Receptor Recognition Sites for NGF and BDNF

Introduction

As mentioned above, the location of the neurotrophin binding sites within the Trk receptors is the subject of debate (MacDonald and Meakin, 1996). Based upon published data, there is reason to believe that Trk proteins have two putative neurotrophin binding sites: the "second putative immunoglobulin-like domain" (IgC2, residues $Trp^{299}$-$Asn^{365}$) and the "second leucine-rich motif" (LRM-2A and LRM-2B, residues $Thr^{97}$-$Leu^{120}$ of TrkA and TrkB, respectively) (Schneider and Schweiger, 1991; Kullander and Ebendal, 1994; Pérez et al., 1995; Urfer et al., 1995; Windisch et al., 1995a, 1995b, 1995c; MacDonald and Meakin, 1996; Rydén and Ibáñez, 1996). LRM containing proteins are a diverse group with different functions and cellular locations, and are known to mediate strong and selective protein-protein interactions (Kobe and Deisenhofer, 1993,1994,1995). The amino acid sequence of an LRM is characterized by conserved hydrophobic consensus residues (Schneider et al., 1988; Schneider and Schweiger, 1991; Kobe and Deisenhofer, 1993, 1994, 1995). Typically, LRMs exist as repetitive cassettes, with an individual LRM representing a right-handed β-α hairpin unit (Kobe and Deisenhofer, 1993, 1994,1995). Recent crystallographic studies on porcine ribonuclease inhibitor indicate that the side chains of the consensus residues form the hydrophobic core of the LRM modules, thereby determining their geometric features (Kobe and Deisenhofer, 1993).

According to the invention, the inventors report explicit atom-level models of the receptor sites for NGF and BDNF based on the structures of the second LRMs of TrkA (LRM-2A) and of TrkB (LRM-2B), respectively. To deduce these models, we have investigated the interaction of the bioactive conformation of the NGF amino and carboxyl termini region with the LRM-2A and of the "waist" region of BDNF with the LRM-2B. A series of four active NGF analogues, namely human NGF (hNGF) (Burton et al., 1992; Shih et al., 1994), mouse NGF (mNGF) (Burton et al., 1992; Drinkwater et al., 1993), the 3–9 deletion of mNGF (mNGFΔ3–9) (Drinkwater et al., 1993) and the hNGF:NT-4/5 heterodimer (Treanor et al., 1995), have been docked to the LRM-2A of rat TrkA. For all four NGF molecules studied, a stereochemical fit of the LRM-2A to the amino and carboxyl region was achieved. These results indicate that the bioactive conformation of the NGF termini is a functional epitope which mediates high affinity binding via an interaction with the LRM-2A. This approach has also been applied to BDNF/LRM-2B docking, and their stereochemical fit, based mainly on electrostatic complementarity, has been identified and is described below.

Methods

A sequence of three logical steps has been used to deduce the models of the interactions of NGF and BDNF with their respective Trk receptor binding sites: Step 1: The bioactive conformations of the amino and carboxyl termini of NGF analogues were determined. Step 2: The residues of the Trk proteins which form potential binding sites for NGF and BDNF were identified. Step 3: The interaction of the bioactive conformation of the NGF amino and carboxyl termini with the TrkA binding site and the BDNF β-strand stem region with the TrkB binding site were modeled computationally. Finally, the predicted features of the NGF/TrkA and BDNF/TrkB interaction models were validated against available experimental data. Residues of the first monomer of a neurotrophin are designated 1 to 118, those of the second monomer are designated 1' to 118'. Residues of the TrkA LRM-2A and the TrkB LRM-2B binding sites are designated by abbreviations tA and tB, respectively. Residues of the BDNF monomer are designated 1 to 119.

Step 1: Revealing the Bioactive Conformative of the NGF Termini

The most energetically favored conformations of the amino and carboxyl termini of NGF analogues have been obtained by VBMC computations and are described above. Since the 3-dimensional structures of the termini of fully active NGF molecules were found to be different from those of TrkA-inactive analogues, the former conformations were predicted to be "bioactive" for TrkA-mediated activity of NGF. That is, those geometric features that are exclusively inherent to active NGF molecules are expected to be compatible with the structure of the TrkA binding site for NGF. Since the geometry of the central β-strand stem of BDNF is rigid and has been established by X-ray crystallography (Radziejewski and Robinson, 1993), this logical step is bypassed for BDNF. Instead, it is assumed that the X-ray crystallography deduced conformation of the amino acid backbone of the TrkB binding determinant of BDNF represents its "bioactive" conformation.

Step 2: Selection of The LRM-2 Boundaries Within The TRK Receptors

Since there is controversy in the literature regarding the actual boundaries of LRMs (Schneider et al., 1988; Schneider and Schweiger, 1991; Kobe and Deisenhofer, 1993, 1994, 1995; Windisch et al., 1995a, 1995b), the following experimental background (FIG. 8) was used to define boundaries for this computational study. According to Schneider and colleagues (1988, 1991), the LRM domains of TrkA begin with $Leu^{68tA}$, $Leu^{93tA}$ and $Leu^{117tA}$, whereas those boundaries are slightly shifted in the crystallographic studies of Kobe and Deisenhofer (1993). Furthermore, the boundaries of the "minimal" LRM module of TrkA (designated B4 in FIG. 8), which demonstrates the same NGF binding affinity as wild type TrkA, are substantially shifted towards the carboxyl terminus (Windisch et al., 1995a, 1995b) with respect to those suggested by Schneider and colleagues (1988, 1991). The same boundary shift has been suggested for the LRM-2B module (Windisch et al., 1995a, 1995b, 1995c). However, a comparison of active (B1 and B4) and inactive (N4) LRM domains indicates that the presence of the "minimal" amino acid sequence (B4) does not ensure NGF binding. Understanding those factors which maintain the essential features of the LRM geometry in segments B1 and B4, and those factors which destroy them in N4, is of fundamental relevance to the correct assignment of the LRM boundaries.

β-Strand motifs exist in proteins only if hydrogen bonded (H-bonded) to other β-strands; otherwise their structure is unstable (Kobe and Deisenhofer, 1994). Tandem repeats of LRMs represent a prominent example of H-bonded parallel β-strand motifs. The general location of the β-strand motifs in the LRM, according to X-ray data, is illustrated in FIG. 8; however, in a single LRM their particular geometry is destroyed (Kobe and Deisenhofer, 1993, 1994, 1995). Consequently, the only possible way to exclude dramatic conformational changes in a protein domain upon disruption of the inter-strand H-bonding between β-strand motifs is to avoid those motifs. Accordingly, both boundaries of segment B4 are located in the middle of the N-strand regions of the adjacent LRMs such that this segment appears to be free of any β-strand. Nevertheless, the β-strand motif is a characteristic structural unit of LRMs, and thus it is likely that this unit is involved in the NGF/TrkA recognition process. Additionally, a short exposed β-strand motif has been detected in the bioactive conformation of the NGF termini, as described above. The incorporation of the β-strand regions at both sides of the B4 segment (as in N4) results in cooperative H-bonding between these P-strands and a complete loss of NGF binding, which indicates that accessibility of the P-strand motif for intermolecular contacts is essential. On the other hand, the separation of the entire LRM segment from the adjacent LRMs within the B1 molecule as a result of conformational kinking is likely to be energetically more favorable, since the entire LRM module has the internal stabilizing factors. Moreover, kinking between adjacent LRMs does not disrupt the structure of their β-strand motifs (since they remain H-bonded with their opposite sides), but makes them accessible for molecular recognition processes.

Accordingly, in the modelling of the present invention we used the conventional boundaries of the LRMs of TrkA and TrkB (Schneider et al., 1988; Schneider and Schweiger, 1991), which keep the β-strand motif in the LRM, and we explicitly arranged H-bonding of this unit with the parallel β-strand motif of the NGF amino terminus to preserve it from conformational reorganizations. Thus, the segments between residues $Leu^{93tA}$ and $Leu^{117tA}$ in TrkA, and $Leu^{93tB}$ and $Leu^{117tB}$ in TrkB, were respectively designated the LRM-2A and the LRM-2B.

Step 3: Computational Simulation of The Neurotrophin/Receptor Interactions

Docking interactions NGF/LRM-2A and BDNF/LRM-2B were simulated using a combined VBMC/CHARMM approach. As described above, the VBMC algorithm permits conformational space search; CHARMM (Brooks et al., 1983) is a force field which defines conformational energy. The same approach was also used to study improper docking interactions of the central β-strand stem region of NGF with the LRM-2B, as a negative control.

The VBMC algorithm performs conformational and orientational space searches of a complicated molecular system with the aim of finding the structure which corresponds to the global minimum on the potential energy $E_{tot}$ surface.

$$E_{tot}=E_t+E_w+E_e+E_{hb}+E_{qq}+E_{hy}+E_c \quad (4)$$

The following potential energy terms have been considered in the framework of the united atom CHARMM force field (Brooks et al., 1983; The force field parameters are extracted from CHARMM version 23.1, Molecular Simulations, Inc., Waltham, Mass.): torsional distortion $E_t$, van der Waals interactions $E_w$, electrostatic interactions $E_e$, and hydrogen bonding $E_{hb}$. Since the united atom approach is not appropriate to treat rigorously the quadrupole-quadrupole interactions of benzene rings (which are important for determining their mutual orientations in proteins (Hunter and Sanders, 1990; Hunter et al., 1991), single quadrupoles have been placed at the centers of the benzene rings of phenylalanine, tryptophan and tyrosine, and the energy of the quadrupole-quadrupole interactions, $E_{qq}$, has been calculated as suggested by Schauer and Bernstein (1985). (The potential energy function of two interacting benzene molecules, comprising $E_{qq}$ and $E_w$ terms, has stationary points corresponding to both known electrostatically favorable "edge-to-face" and "offset stacked" orientations, with the dimerization energy of 1.94 kcal/mol agreeing well with ab initio quantum mechanical calculations (Hobza et al., 1994).) In addition, the conformationally dependent free energy of hydration, $E_{hy}$, has been calculated according to the hydration shell model including both non-specific and specific hydration terms (Hopfinger, 1973; Hodes et al., 1979). Point atomic charges of Weiner and colleagues (1984) have been used. A dielectric constant equal to the interatomic separation in angstroms has been used to implicitly simulate salvation effects (Weiner et al., 1984).

The $E_c$ term is used only for the NGF/LRM-2A complex and represents the distance constraints which restrain the H-bonding of residues $Glu^{11}$ and $Arg^{118'}$ within the bioactive conformation of the NGF termini, as described above. In addition, two intermolecular H-bonds, arising from the alignment of complementary parallel β-strand motifs of NGF and LRM-2A, are also constrained and contribute to $E_c$. In the Monte Carlo conformational space search, $E_c$ is defined as follows:

$$E_c = 10 \times \Sigma(d_{AB} - 1.8)^2, \quad (5)$$

where $d_{AB}$ is the distance in angstroms between atoms A and B which are to be H-bonded. The $E_c$ term is neglected when performing final energy minimization following the VBMC simulated annealing. In addition, this term has not been utilized when studying the mNGFΔ3–9/LRM-2A complex. Since, as described above, the mNGFΔ3–9 deletion mutant does not have a β-strand region, the geometry of its LRM-2A counterpart, namely $Leu^{93tA}$-$Ile^{98tA}$, has been kept fixed in the crystallographic conformation (Kobe and Deisenhofer, 1993) during Monte Carlo simulations. The $E_c$ term, being "soft", does not preclude conformational and orientational changes to occur during Monte Carlo simulations. This term increases rigidity of the bioactive conformation of the ligand, which allows us to utilize the knowledge obtained at Step 1, instead of explicit considerations of inactive NGF analogues, in Step 3. In addition, this term keeps conformations of the β-strands of both ligand and binding site from destruction, and thereby allows us to avoid an explicit consideration of the adjacent first LRM of TrkA. Furthermore, this term maintains the known orientation of the parallel β-strand motifs in the NGF/LRM-2A complex.

The amino acid sequences of the binding determinants of the NGF molecules studied are presented in FIG. 9. The conformational space of the NGF analogues consists of torsional angles determining geometry of the amino terminus of one monomer (residues 1–11) and the carboxyl terminus of the other (residues 112'–118'), while keeping the rest of the dimer in the experimental geometry of mNGF (McDonald et al., 1991). The conformational spaces of the LRM domains of TrkA and TrkB consist of torsional angles representing fragments $Arg^{94tA}$-$Leu^{117tA}$ and $Arg^{94tB}$-$Leu^{117tB}$, respectively. Covalent bond lengths and bond angles have been kept fixed. The geometry of each i-th residue is determined only by flexible torsional angles of the backbone ($\phi_i$ and $\psi_i$) and the side chain ($X_i1, X_i2, \ldots$). All torsional angles for prolines, except $\psi_i$ have been fixed. Torsional angles describing structural motifs with planar geometries (such as peptide bonds or conjugated regions in side chains) were fixed. Likewise, the configurations of the $sp^3$-carbons were fixed. The conformational space of BDNF consists only of torsional angles determining side-chain geometries of those residues which are located in the vicinity of its central β-strand stem and define a molecular surface (Table 2). In addition to the conformational variables of each complex, the six orientational variables (three Euler angles and three translations along the coordinate axes) were used to describe the ligand-receptor orientations.

In accordance generally with the simulated annealing approach (Kirkpatrick et al., 1983; Vanderbilt and Louie, 1984; Brünger, 1998; Nilges et al., 1988; Wilson et al, 1988; Wilson and Doniach, 1989), the molecular systems were kept at a constant temperature of 800° K. for $2 \times 10^6$ Monte Carlo moves before the initiation of "cooling". The temperature was then decreased at every Monte Carlo move by a small increment such that after $2 \times 10^6$ Monte Carlo moves it reached 120° K. At this time, a local energy refinement was performed to identify the nearest stationary point on the potential energy surface. According to the VBMC algorithm described above, the basis of independent structural parameters was recalculated after every $7 \times 10^4$ Monte Carlo moves to direct them along the valleys of the potential energy surface, thereby accelerating conformational and orientational changes.

All calculations were performed on an Indigo-2 Silicon Graphics Workstation and an 8-node IBM Scalable POWER parallel 2 [SP2] high performance computer.

Results and Discussion

Conformational Flexibility within Receptor Environments

Five independent VBMC simulations from different initial configurations were performed for each of the six molecular complexes under study. The elimination of the distance constraints $E_c$ in the complexes with the LRM-2A did not result in any noticeable conformational changes within the complexes. Although independent VBMC simulations did not always converge to the same geometry for the same molecule, the final structures differed insignificantly; i.e., the conformations of the peptide backbones remained unchanged with the exception of residues 1–3 of the NGF amino terminus and the terminal residue $Leu^{117tA}$ of the LRM-2A. The differences between the VBMC generated structures were located in side-chain conformations of a limited number of residues, specifically $Ser^1$, $Val^{117'}$ ($Thr^{117'}$ in mNGF), $Thr^{97tA}$ and $Ser^{101tA}$. These residues are not involved in intermolecular or intramolecular interactions, and do not affect the overall structures of the complexes. No considerable differences were identified in the independent VBMC-generated conformations of the BDNF/LRM-2B and the NGF/LRM-2B complexes.

A grid search of the internal space of the complexes using the water molecule radius 1.4 Å as a probe (Ponnuswamy and Manavalan, 1976) (as incorporated into the QUANTA program, Version 4.1, Molecular Simulations, Inc., Waltham, Mass.) showed that there is no internal cavity available for a solvent molecule in the hNGF/LRM-2A complex. This explains the rigidity of the complex and demonstrates the "perfect" stereochemical fit of the hNGF amino-carboxyl termini complex to the LRM-2A. Other complexes have some internal cavities, especially with the LRM-2B binding site.

Specific Binding Areas within Receptor Environments

The TrkA Receptor Binding Site

Comparison of the most stable structures of the different complexes with the LRM-2A binding site (FIG. 10) shows their striking conformational similarity. In all molecules, ligand-receptor binding is caused by similar hydrophobic, ionic, H-bonding and van der Waals interactions. There are five distinct areas (A–E) within the NGF/LRM-2A fit: areas A 30 and B have hydrophobic interactions, areas C and D have ionic H-bonding, and area E has cooperative H-bonding between parallel β-strand motifs.

Area A represents the hydrophobic region at which residue $Phe^{105tA}$ interacts with $Trp^{76'}$, which in turn forms hydrophobic contacts with $Phe^{12}$ and $Leu^{112'}$. The aromatic rings of $Phe^{12}$, $Trp^{76'}$ and $Phe^{105tA}$ are approximately perpendicular to each other, which is energetically favorable (Hunter and Sanders, 1990; Hunter et al., 1991; Hobza et al., 1994). This particular geometry would create a hole within the complex, if it was not filled by hydrophobic residue $Leu^{112'}$.

In area B, $Phe^7$ of NGF is placed within the hydrophobic core of the LRM-2A created by the consensus residues (Schneider et al., 1988; Schneider and Schweiger, 1991; Kobe and Deisenhofer, 1993, 1994, 1995). Similar to the favorable orientation of the aromatic residues in area A, the aromatic rings of $Phe^{111tA}$ and $Phe^{113tA}$ are perpendicular to that of $Phe^7$. On the other hand, residues $Phe^{111tA}$ and $Phe^{113tA}$ are not perpendicular to each other; their orientation instead resembles the favorable "offset stacked" geometry described by Hunter and others (Hunter and Sanders, 1990; Hunter et al., 1991; Hobza et al., 1994). As in area A, a hole created by the three neighboring favorably oriented aromatic rings is filled by a fourth residue, $Thr^{114tA}$. Interactions between aromatic rings in proteins is very common and represent an important conformational driving force (Warme and Morgan, 1978; Hunter et al., 1991). Consequently, the fact that all three phenylalanine residues of the LRM-2A find their counterparts within the NGF binding domain supports the calculated structure of the NGF/LRM-2A complex.

In ionic binding area C, the negatively charged residue $Asp^{109tA}$ exerts a central role. It is surrounded by the three positively charged amino acids $His^{112tA}$, $Arg^{114'}$ and $Lys^{115'}$ in hNGF, mNGF and mNGFΔ3–9, and by $His^{112tA}$, $Arg^{115'}$ and $Arg^9$ in hNGF:NT-4/5. Residue $His^{112tA}$ plays a secondary role: it creates the electrostatic dipole $Asp^{109tA} \rightarrow His^{112tA}$ in the LRM-2A, which imposes constraints on the spatial positions of the recognized positively charged residues of NGF, thereby reinforcing geometric selectivity in this area. Although the hNGF:NT-4/5 heterodimer has two substitutions in the C-area segment of the NT-4/5 carboxyl terminus, namely R114S and K115R, the geometry of the C area remains qualitatively the same, since residues $Arg^9$ and $Arg^{115'}$ of hNGF:NT-4/5 functionally replace the absent $Lys^{115'}$ and $Arg^{114'}$ amino acids, respectively. Although $Arg^9$ also exists in the hNGF homodimer, it is not involved in the ionic binding in this molecule, since it is separated from area C due to electrostatic repulsions. Similarly, the charged amino end of mNGFΔ3–9, which functionally replaces $Arg^9$, is also separated from area C. There is no place for the fourth positively charged residue in area C. Thus, in all molecules studied, the two positively charged amino acids of the ligand saturate the coordination possibilities of the receptor residue $Asp^{109tA}$.

Area C is partially isolated from its surrounding environment by flanking hydrophobic residues $Val^{106tA}$ and $Pro^{115tA}$. Similarly, the principal charged residues of NGF, namely $His^8$, $Glu^{11}$ and $Arg^{118'}$, are located between hydrophobic residues $Ile^6$ ($Val^6$ in mNGF), $Val^{111'}$ ($Leu^{113'}$ in hNGF:NT-4/5) and $Val^{99tA}$ within the complexes. Thus, residues $Val^{911tA}$, $Val^{106tA}$ and $Pro^{115tA}$ of the LRM-2A participate in "compartmentalization" of the principal ionic interactions of the complexes, thereby shielding them from the conformation destructive influence of salvation.

The organization of ionic binding area D is similar to that of area C. Positively charged residues $Arg^{59}$ and $Arg^{69}$ are located in the vicinity of negatively charged $Asp^{16}$ within the NGF structure (McDonald et al., 1991; Bradshaw et al., 1994), such that the coordination of the latter is not full. The third positively charged residue, $Lys^{100tA}$, comes from the LRM-2A to complete the $Asp^{16}$ coordination. In addition to the ionic binding, residue $Lys^{100tA}$ forms an H-bond with the $Ser^{13}$ side chain.

Area E consists of the H-bonded parallel β-strand motifs of the LRM-2A and NGF (FIG. 10b, 10c and 10e), each of the β-strands having three peptide bonds. The LRM-2A β-strand motif is located between the α-carbon atoms of $Asn^{95tA}$ and $Ile^{98tA}$, whereas the NGF β-strand is located between the α-carbons of the sixth and ninth residues. The locations of the β-strand regions in the uncomplexed LRM (Kobe and Deisenhofer, 1993) and NGF (see above) resemble those in the complexes considered. In the complexed LRM-2A, the β-strand motif is shortened by one peptide bond at its amino end to accommodate the $His^4$ side chain of NGF. On the other hand, the two peptide bond β-strand of the uncomplexed NGF is lengthened by one peptide bond at its amino end in the complexes.

The TrkB Receptor Binding Site

FIG. 11a illustrates the central N-strand stem region of BDNF, and FIG. 11b presents the VBMC-generated structure of the BDNF/LRM-2B complex. In this complex, ligand-receptor binding is based mainly on intermolecular electrostatic interactions of either ionic or hydrogen bonding origin. There are five distinct binding areas (F–K) within the TrkB receptor environment: four salt bridges (areas F, G, H and 1) and one H-bonding area K. In contrast with the NGF/LRM-2A binding pattern, there is no participation of the LRM-2B β-strand motif in cooperative H-bonding with the BDNF binding epitope.

In area F, the primary positively charged residue (Ibañez et al., 1993) of the BDNF binding domain, $Arg^{81}$, is bound to $Asp^{100tB}$, the only negatively charged residue of the LRM-2B. It should be noted that $Arg^{81}$ is exclusively inherent in BDNF molecules while being substituted by electrostatically neutral Thr in NGF or by Lys in NT-3 or NT-4/5 molecules (Bradshaw et al., 1994), which indicates the importance of this area in neurotrophin recognition processes (see also Urfer et al., 1994). On the contrary, residue $Gln^{84}$, identified by Ibañez and co-workers (1993) as important, is not directly involved in specific intermolecular interactions within the LRM-2B domain.

In binding area G, the negatively charged residue $Glu^{55}$, which is absolutely conserved in all neurotrophins (Bradshaw et al., 1994), exerts a central role. It is surrounded by the three positively charged amino acids, $Lys^{25}$, $Lys^{57}$ and $Lys^{109tB}$. Two of them, belonging to the neurotrophin, are also highly conserved (Bradshaw et al., 1994). The third one, $Lys^{109tB}$, is specific for the TrkB receptor site (Windisch et al., 1995a, 1995b, 1995c). All BDNF residues of the G binding area, namely $Lys^{25}$, $Lys^{57}$ and $Glu^{55}$, have been shown to be essential in NT-3 structure for TrkC receptor activation (Urfer et al., 1994), which is in agreement with observations that the TrkB and TrkC binding domains are located in the same region of these neurotrophins. This particular arrangement of the three positively charged residues around one with a negative charge seems to be very common in neurotrophin-receptor recognition processes, since the NGF/LRM-2A interaction also includes two binding areas of this type (C and D). Existence of the absolutely conserved negatively charged residue $Asp^{106}$ in direct proximity to area G increases binding affinity of $Lys^{109tB}$, thereby highlighting some importance of this area in the BDNF/TrkB recognition processes. Although detailed mutational experiments did not demonstrate importance of the equivalent residue $Asp^{105}$ in NT-3 for TrkC related activities (Urfer et al., 1994), its direct involvement in the $Zn^{2+}$ mediated regulation of neurotrophin bioactivities has been recently proven by multidisciplinary studies (Ross et al., 1997), and, therefore, its location within the binding determinants of BDNF and NT-3 is consistent with these observations.

In area H, conserved residue $Asp^{24}$ of BDNF forms a salt bridge with specific TrkB residue $Lys^{113tB}$. Although $Asp^{24}$ has not been demonstrated to be involved in direct neurotrophin-receptor interactions, either for TrkB or TrkC related activities, it is highly conserved in neurotrophins (Bradshaw et al., 1994) and located in direct proximity to $Thr^{22}$ in NT-3, which has been shown to be included in the TrkC receptor binding domain (Urfer et al., 1994). These observations are consistent with the present model of BDNF/TrkB binding, since substitution of the equivalent residue of BDNF, $Thr^{21}$, by bulky Gln (Urfer et al., 1994) would sterically hinder proper location of the LRM-2B domain (FIG. 11b), whereas mutation D24A, although lacking one specific ligand-receptor interaction, would not significantly alter the BDNF/LRM-2B orientation resulting from multiple-point electrostatic complementarity. In addition, the absence of negatively charged residue $Asp^{24}$ is shown to induce salt bridge interaction of $LyS^{113tB}$ with neighboring $Glu^{18}$, with only minor conformational alterations of the LRM-2B.

In area I, $Glu^{18}$, a specific residue of BDNF (Bradshaw et al., 1994), forms a salt bridge with the LRM-2B amino acid $Arg^{94tB}$. Residue $Glu^{18}$ is also involved in intramolecular electrostatic interactions with $Lys^{57}$.

Area K is the only region of the distinct BDNF/LRM-2B interactions which is not of ionic nature. The positively charged residue $Lys^{104tB}$ forms multiple H-bond contacts with the BDNF loop I backbone carbonyl groups and the neutral $Thr^{35}$ side chain. The energy of such H-bonding is much lower than that of salt bridge contact, and, therefore, a substitution of the uncharged amino acid $Thr^{35}$ by a negatively charged residue would stabilize the particular structure of the BDNF/LRM-2B complex. In accordance with the present model, the experimental substitution of BDNF residues 34–41 by the corresponding segment of NGF, which includes the substitution of negatively charged residue $Glu^{35}$ for $Thr^{35}$, resulted in a significant increase in bioactivity of the resulting chimeric molecule relative to wild type BDNF in TrkB mediated survival (Lai et al., 1996).

In addition to these five distinct binding areas of the BDNF/LRM-2B complex, there is one more area which reinforce binding specificity. The side chain of $Pro^{60}$, a specific residue of BDNF (Bradshaw et al., 1994), demonstrates a perfect geometric fit into the hollow in the "zigzag"-shaped β-strand region of the LRM-2B (FIG. 11b). This geometric complementarity indicates that $Pro^{60}$ "recognizes" the β-strand motif of the receptor binding site. This interaction, obviously, does not significantly contribute to the total energy of the complex in the case of a perfect fit, but does represent a steric hindrance when this fit cannot be readily achieved. Accordingly, BDNF is very selective and does not bind non-cognate Trk receptors.

FIG. 11c illustrates the VBMC-generated geometry of the "improper" NGF/LRM-2B complex. In this complex, specific binding areas F and I are absent due to lack of properly charged residues at positions 20 and 81, which would correspond to BDNF residues $Glu^{18}$ and $Arg^{81}$, respectively. In addition, residue $Pro^{60}$, determining the proper BDNF/LRM-2B orientation, is substituted in NGF molecules (Bradshaw et al., 1994). These substitutions cause dramatic conformational and orientational alterations in the complexed LRM-2B domain (compare FIG. 11b and 11c). Predicted Cartesian 3-dimensional coordinates of atoms of the TrkB LRM-2B binding site in the complex with BDNF are presented in Appendix 2.

Ligand-Receptor Interaction Energy
NGF/TrkA Interactions

Table 3 presents the components of the intermolecular energies of the NGF/TrkA complexes. Stability of the NGF/LRM-2A complexes results primarily from attractive electrostatic and van der Waals interactions, with intermolecular H-bonding playing a secondary role. It should be noted, however, that in the framework of the molecular mechanical approach, the H-bonding energy is partially incorporated into the electrostatic interaction energy term, so the tabulated $E_{hb}$ values reflect only part of the H-bonding energy. Accordingly, intermolecular H-bonding is more important for the NGF/LRM-2A interaction than it appears in Table 3. On the other hand, the intermolecular component of the $E_{qq}$ term seems to be insignificant. The reason for the latter is that the aromatic moieties of $Phe^7$, $Trp^{76'}$, $Phe^{105tA}$, $Phe^{111tA}$ and $Phe^{113tA}$ are "preorganized" for intermolecular contacts with their counterparts in the complexes in electrostatically attractive geometry in which the quadrupole-quadrupole interaction energy term is not significant. In addition, hydrophobic ligand-receptor interaction energy is presumably extremely important for NGF/LRM-2A complex formation, but rigorous quantitative evaluation is currently not possible.

Since neither electrostatic interactions nor hydrogen bonding can significantly stabilize a ligand-receptor complex in a water environment, the stability of the complex generally results from van der Waals and hydrophobic interactions (Clackson and Wells, 1995). Considerable contribution of intermolecular van der Waals interaction energy $E_w$ (Table 3) arises from the geometric complementarity of the NGF binding domain and the TrkA recognition site, such that the high value of the $E_w$ term is due to a large number of intermolecular van der Waals contacts. This complementarity is a consequence of the right-handed twists of both the NGF amino-carboxyl termini complex and the LRM-2A, this geometric feature being characteristic of each of these domains in both uncomplexed (Kobe and Deisenhofer, 1993; Shamovsky et al., 1996) and complexed conformations. Thus, purely geometric ligand-receptor compatibility together with distinct hydrophobic contacts play a crucial role in NGF/TrkA recognition, while attractive electrostatic interactions and H-bonding further reinforce specificity of binding, which is in agreement with generalizations made by Clackson and Wells (1995).

BDNF/TrkB and NGF/TrkB Interactions

Table 4 presents the components of the potential energies of the complexes of BDNF and NGF with the LRM-2B in their minimum-energy conformations. Data presented in section A of Table 4 indicate that the difference in total energies (92.0 kcal/mol) is almost exclusively a consequence of more favorable electrostatic interactions in the BDNF/LRM- 2B complex than in the NGFILRM-2B complex (negative control). Section B of Table 4 illustrates that the BDNF complex is also more favorable in terms of intermolecular electrostatic energy by 77.2 kcal/mol (85% of the difference in total electrostatic energies). On the contrary, intermolecular van der Waals interactions are more favorable in the "improper" NGF/LRM-2B complex. Furthermore, the value of intermolecular van der Waals energy is significantly lower for NGF/LRM-2B than for the NGF/LRM-2A complex, whereas electrostatic contribution is more than twice as high. Consequently, in contrast to the NGF/TrkA binding pattern, molecular recognition of BDNF by the TrkB receptor binding site is almost exclusively based on electrostatic complementarity, whereas the roles of van der Waals and hydrophobic interactions are insignificant. At the same time, such a perfect electrostatic fit could not be achieved without a purely geometric compatibility of the BDNF and the LRM-2B binding domains in size and shape (FIG. 11b).

Induced Conformational Changes
The NGF Amino and Carboxyl Termini

Conformations of the NGF amino and carboxyl termini remain almost the same after complexation with the LRM-2A (Table 5; compare FIG. 10a with 10b, 10c, 10d and 10e). A few local conformational changes occur in the $Arg^{114'}$ and the $Lys^{115'}$ side chains, and in the backbones of residues $Ser^2$ and $Phe^7$. As predicted above, conserved charged residues $Arg^{114'}$ and $Lys^{115'}$ do not participate in principal intermolecular interactions within the NGF termini but are expected to form ionic intermolecular contacts with the TrkA binding site. Indeed, these are the intermolecular ionic NGF/LRM- 2A interactions in area C, which change considerably the side-chain conformations of Arg$^{114'}$ and Lys$^{115'}$ while keeping their backbone geometry intact. The LRM-2A-induced conformational changes in residue Phe$^7$ are caused by the intermolecular H-bonding in area E while the geometry of Ser$^2$ is slightly changed to accommodate the LRM-2A residue Thr$^{114tA}$. The rest of the structure of the LRM-2A-complexed NGF termini retains the energy minimum conformation of the uncomplexed molecules because it is controlled by multiple intramolecular H-bonds. Consequently, the geometry of the NGF termini is "preorganized" for complexation with the LRM-2A, and only local conformational changes, primarily in residues Arg$^{114'}$ and Lys$^{115'}$, occur upon complexation. Geometric "preorganization" of the NGF termini as a ligand for binding to a leucine-rich motif is consistent with X-ray studies of Kobe and Deisenhofer (1995), who have demonstrated that ribonuclease A maintains a fixed geometry upon binding to the LRMs of ribonuclease inhibitor.

The LRM-2A Domain

FIG. 12 illustrates the isolated structure of the LRM-2A from the hNGF/LRM-2A complex. Table 6 presents the equilibrium torsional angles of the hNGF-bound LRM-2A. As seen, the side chains of the general consensus residues, Leu$^{93tA}$, Leu$^{96tA}$, Ile$^{98tA}$, Leu$^{103tA}$ and Phe$^{111tA}$ (Schneider et al., 1988; Schneider and Schweiger, 1991), form the hydrophobic core, similarly to their conformations in intact leucine-rich repeats (Kobe and Deisenhofer, 1993). Terminal consensus residue Leu$^{117tA}$ is solvent-exposed due to a boundary effect. Amino acids Ala$^{107tA}$, Pro$^{108tA}$, Ala$^{110tA}$ and Phe$^{113tA}$ are also incorporated into the LRM-2A hydrophobic core. On the other hand, residues Val$^{99tA}$, Phe$^{105tA}$, Val$^{106tA}$ and Pro$^{115tA}$ are not involved in hydrophobic interaction within the core, and apparently have specific roles in the recognition site of TrkA. The most hydrophilic residues of the LRM-2A, namely Arg$^{94tA}$, Lys$^{100tA}$, Arg$^{104tA}$, Asp$^{109tA}$, His$^{112tA}$ and Arg$^{116tA}$ are exposed from the hydrophobic core in the complexes. Amino acids Lys$^{100tA}$, Asp$^{109tA}$ and His$^{112tA}$ participate in specific intermolecular interactions, while the other three are solvent-exposed. The reasonable locations of the hydrophobic and hydrophilic residues of the LRM-2A within the NGF/LRM-2A complexes with respect to water environment supports the calculated structures.

NGF/LRM-2A binding spans almost the whole LRM-2A domain, i.e., an interval between residues Leu$^{93tA}$ and Pro$^{115tA}$ comprising three distinct regions: β-strand, α-helix, and loop connecting the carboxyl terminus of the β-strand and the amino terminus of the α-helix. This is in agreement with recent crystallographic studies on the ribonuclease A—porcine ribonuclease inhibitor complex (Kobe and Deisenhofer, 1995), in which these particular regions of leucine-rich repeats of ribonuclease inhibitor are also involved in the molecular recognition process. While the β-strand structure exists in the complexed LRM-2A, the α-helix motif is destroyed by intermolecular interactions with NGF. Accordingly, the LRM-2A β-strand determines the proper orientation of the ligand with respect to the recognition site of TrkA, but does not undergo noticeable conformational changes. Consequently, the cooperative ligand-receptor H-bonding in area E cannot directly mediate those changes in receptor conformation which trigger receptor phosphorylation processes. Available experimental data confirm this point. First, the mNGFΔ3–9 deletion mutant, which does not have the β-strand motif and, consequently, cannot specifically bind area E, is as active as wild type mNGF (Drinkwater et al., 1993). Second, the 24-residue LRM fragment Thr$^{97tA}$-Leu$^{120tA}$ lacking the β-strand region (Kobe and Deisenhofer, 1993), demonstrates the same kinetics of binding to NGF as wild type TrkA (Windisch et al., 1995a, 1995b).

The LRM-2B Domain

Table 7 presents the equilibrium torsional angles of the LRM-2B in the complex with BDNF. Side chains of all general consensus residues of the LRM-2B, except for Phe$^{111tB}$ and terminal amino acid Leu$^{117tB}$, form the hydrophobic core and thereby stabilize the characteristic hairpin shape of the LRM (FIG. 11b). In contrast with the LRM-2A, aromatic residues of the LRM-2B, namely Phe$^{105tB}$, Tyr$^{108tB}$ and Phe$^{111tB}$, do not seem to have any specific roles in BDNF/LRM-2B molecular recognition. They form a cluster in which their aromatic rings interact with each other and are about mutually perpendicular (FIG. 11b). On the contrary, all charged residues of the LRM-2B, namely Arg$^{94tB}$, Asp$^{100tB}$, Lys$^{104tB}$, Lys$^{109tB}$ and Lys$^{113tB}$, are involved in specific electrostatic interactions with BDNF.

Similar to the NGF/LRM-2A complex, almost the whole LRM-2B domain, from Leu$^{93tB}$ to Lys$^{113tB}$, fits to the BDNF binding determinant (FIG. 11b). On the other hand, there are significant differences of the neurotrophin-induced conformational alterations in the two LRM domains. First, since the BDNF binding domain does not have a β-strand motif which would fit to the β-strand of the LRM-2B, the characteristic geometric features of the latter are lost. Second, region Tyr$^{108tB}$ to Asn$^{116tB}$ retains its α-helical structure in the BDNF-bound LRM-2B domain. The reason of this conformational stability is that the spacer between the two BDNF-bound residues, Lys$^{109tB}$ and Lys$^{113tB}$ (3 residues), is consistent with the period of an α-helix (3.5 residues).

Principal Amino Acids Involved in Molecular Recognition

Principal NGF Residues

The amino acids of NGF which are primarily responsible for maintaining bioactive conformations (McDonald et al., 1991; Shamovsky et al., 1996) or which directly participate in NGF/TrkA recognition are specified in FIG. 13. Almost all residues of the amino and carboxyl termini of NGF as well as the His$^{75'}$-Asn$^{77'}$ region are involved in specific intra- or intermolecular interactions. Only five amino acids of the 30-residue binding domain of NGF do not seem to be essential for either maintaining its bioactive conformation or binding to the recognition site of TrkA. These include Ser$^1$, Ser$^2$, Ser$^3$, Ala$^{116'}$ and Val$^{117'}$.

The observation that the important amino acids of the NGF binding domain are conserved across all species while the apparently unimportant five residues are variable (FIG. 13) (McDonald et al., 1991) supports the particular structural features of the NGF/LRM-2A complexes calculated herein. There are, however, exceptions which require explanation. In most cases, principal amino acids of NGF molecules derived from different species appear to be substituted by similar residues, e.g. 16V, F7L, L112I, S113T or R114K. In some special cases, the substituted amino acid is quite different but the particular substitution is still consistent with the present model, e.g. R9M, R9L or RI 18Q (McDonald et al., 1991; Shamovsky et al., 1996); in the case of the H8N substitution (McDonald et al., 1991), histidine and asparagine have the same topology with respect to H-bonding to the Glu$^{11}$ carboxyl oxygen. The structure of snake NGF (sNGF) requires special consideration. Principal hydrophobic residues Phe$^7$ and Phe$^{12}$ are replaced by histidine residues in sNGF. Although these mutations could be accompanied by structural differences in snake TrkA, they are consistent with the present model. According to the survey of Warme and Morgan (1978), side-chain interactions of histidine with tryptophan or threonine are very common in natural proteins, which implies the existence of specific inter-residue affinities. This being the case, attractive interactions $His^7 \ldots Thr^{114tA}$ and $His^{12} \ldots Trp^{76'}$ in areas B and A, respectively, may replace corresponding hydrophobic interactions with $Phe^7$ and $Phe^{12}$.

Principal LRM-2A Residues

The principal residues of the LRM-2A are shown in FIG. 14. The general consensus residues (Schneider et al., 1988; Schneider and Schweiger, 1991) maintain the specific geometry of the LRM (Kobe and Deisenhofer, 1993, 1994, 1995). The amino acids which form the distinct binding areas are involved in specific intermolecular interactions with the NGF binding domain. Since NGF does not activate the TrkB receptor, those residues which are specific for the TrkA receptor have been postulated to be directly involved in NGF/LRM-2A recognition (Windisch et al., 1995a, 1995b). As shown, the LRM-2A segment has nine specific residues, seven of them directly participating in NGFILRM-2A recognition in the framework of the present model. Thus, $Lys^{100tA}$ binds $Asp^{16}$ in area D, $Pro^{108tA}$ is completely buried inside the NGF/LRM-2A complex, residues $ASp^{109tA}$, $His^{112tA}$ and $Pro^{115tA}$ form binding area C, and residues $Phe^{131tA}$ and $Thr^{114tA}$ are involved in forming area B. The other specific residues, $Arg^{104tA}$ and $Arg^{116tA}$, do not seem to be required for specific NGF/LRM-2A interactions. It is seen, furthermore, that binding areas A and E are not specific for the recognition site of TrkA, indicating that binding specificity of the LRM-2A is determined by $Lys^{100tA}$, $Asp^{109tA}$ and $Phe^{113tA}$. The fact that these particular amino acids are replaced in the recognition site of TrkB by residues of a different chemical nature, namely $Asp^{100tA}$, $Lys^{109tA}$ and $Lys^{113'}$, respectively (Windisch et al., 1995a, 1995b), making NGF/TrkB binding impossible, supports the herein predicted details of NGF/LRM-2A recognition. Principal residue $Phe^{105tA}$, although common to both the TrkA and TrkB recognition sites (Windisch et al., 1995a, 1995b), is also important for the NGF/TrkA recognition process, since oxidation of its counterpart, $Trp^{76'}$, results in a complete loss of receptor binding (Merrell et al., 1975).

Principal BDNF Residues

Since BDNF/TrkB molecular recognition is predicted to be primarily based on electrostatic complementarity, principal BDNF and LRM-2B residues are identified by analysing their contribution to the intermolecular electrostatic energy. Table 8 presents a comparison of individual contributions of residues of BDNF, NGF and the LRM-2B to the intermolecular electrostatic energy for the BDNF/LRM-2B and the NGF/LRM-2B complexes, with cutoff being ±10 kcal/mol. BDNF/TrkB molecular recognition is achieved by those residues that make significantly more favourable contacts with their counterparts than do corresponding residues in the "improper" NGF/LRM-2B interaction. Accordingly, in section A of Table 8, residues of BDNF that make more favourable contacts with the LRM-2B than do those of NGF by at least 10 kcal/mol, are highlighted. They are: $Glu^{18}$, $Asp^{24}$, $Glu^{55}$, $Arg^{81}$ and $Gln^{84}$. These residues make up the BDNF binding epitope for TrkB activation. Only two of them, $Arg^{81}$ and $Gln^{84}$, have been previously identified (Ibáñez et al., 1993). The most unusual case is residue $Gln^{84}$, which does not markedly participate in electrostatic interactions with the LRM-2B; however, its substitution by $His^{84}$ results in considerable repulsive interactions with positively charged residues of the receptor site. Therefore, $Gln^{84}$ cannot be referred to as a principal residue by itself in terms of the TrkB receptor binding, and its apparent importance (Ibáñez et al., 1993) comes from unfavorable substitution by a positively charged $His^{84}$. The only residue of NGF which binds to the TrkB receptor site significantly more strongly than does the corresponding residue of BDNF is $Glu^{35}$, in agreement with observations (Lai et al., 1996).

Principal LRM-2B Residues

Section B of Table 8 identifies the LRM-2B residues which significantly contribute to specificity of binding. Amino acids $Arg^{94tB}$, $Asp^{100tB}$, $Ser^{101tB}$, $Lys^{109tB}$ and $Lys^{113tB}$ make significantly more favorable contacts with their counterparts in BDNF than with those in NGF. Additionally, these residues are responsible for specific binding in areas F–K. The only residue of the LRM-2B that favours the NGF counterpart is $Lys^{104tB}$, which is caused by the abovementioned effect of $GIu^{35}$.

FIG. 15 illustrates schematically the geometry of the LRM-2A and the LRM-2B receptor sites. Those residues which are predicted to form specific bonds with their preferred ligand are shown by arrows. The similarity of the binding patterns of the two LRMs is striking, especially bearing in mind the differences pointed out in the nature of the intermolecular interactions, and that the binding patterns were identified in independent computations. Thus, binding specificity of TrkA and TrkB is determined by the residues located in distinct positions of their second LRMs, with their respective binding patterns being incompatible with each other.

It is shown that van der Waals and hydrophobic interactions play a more important role in TrkA than in TrkB recognition. As a part of this phenomenon, we have demonstrated that NGF/LRM-2A binding is characterized by greater geometric complementarity, such that the ligand-receptor complex does not contain marked internal cavities. A plausible explanation for these particular features of Trk receptor recognition is that the NGF binding determinant is flexible and, because of that, more is required to stabilize its bioactive conformation in solution. Accordingly, TrkA receptor binding involves physical factors that are more effective in an aqueous environment, namely van der Waals and hydrophobic interactions.

Explanation for Structure-Activity Relationships

TrkA mediated activity has been evaluated for 27 point and deletion mutants of the TrkA binding domain of NGF: hNGF (Burton et al., 1992; Shih et al., 1994), mNGF (Burton et al., 1992; Drinkwater et al., 1993), mNGFΔ3–9 (Drinkwater et al., 1993), (1–120)hNGF (Schmelzer et al., 1992), (1–120)mNGF (Luo and Neet, 1992), (1–117)hNGF (Schmelzeret al., 1992) and hNGF:NT-4/5 (Treanor et al., 1995) retain full activity; mNGFΔ2–8, mNGFΔ61–66 (Drinkwater et al., 1993), hNGF-R9A, hNGFΔ1–5 and hNGF-P5A (Shih et al., 1994) demonstrate intermediate potency; hNGFΔ1–9 (Burton et al., 1992; Kahle et al., 1992; Luo and Neet, 1992; Drinkwater et al., 1993; Shih et al., 1994; Burton et al., 1995), mNGFΔ1–8 (Taylor et al., 1991; Burton et al., 1992), mNGFΔ1–9, mNGFΔ9–13 (Woo et al., 1995), mNGFΔ3–8, mNGFΔ3–11, mNGFΔ3–12, mNGFΔ3–13, mNGFΔ3–14, mNGFΔ9–14, mNGFΔ112–118 (Drinkwater et al., 1993), hNGF-H4A, hNGF-H4D (Shih et al., 1994), BDNF (Suter et al., 1992), and NT-4/5 (Treanor et al., 1995) are almost or completely inactive. The present model of NGF/LRM-2A recognition enables a comprehensive explanation for the structure-activity relationships.

As demonstrated, fully active hNGF, mNGF and hNGF:NT-4/5 fit to the five binding areas A–E of the recognition site of TrkA, while the mNGFΔ3–9 deletion mutant fits only to A, C and D, without any specific binding taking place in areas B or E. Therefore, there are three common geometric features of the four fully active molecules which distinguish them from the less active analogues. First, conformations of the amino and carboxyl termini of these NGF analogues are "preorganized" for binding to the principal LRM-2A binding areas A, C and D. Second, there is no stereochemical incompatibility in the binding areas B and E. Third, There is no Hole Inside the NGF/LRM-2A Complexes The structures of the other three fully active NGF analogues, (1–120)hNGF, (1–120)mNGF and (1–117) hNGF, are consistent with the above criteria. Indeed, since the NGF carboxyl end is located on the surface of the NGF/LRM-2A complexes (FIG. 10) and does not directly participate in principal intermolecular interactions, the lengthening of the NGF carboxyl terminus by two amino acids does not explicitly affect NGFILRM-2A compatibility. As far as the (1–1 17)hNGF molecule is concerned, terminal residue $Arg^{118'}$ of NGF has been shown to form inter-chain ionic H-bonds with $Glu^{11}$ (see above) and, hence, seems to be important in maintaining the structure of the NGF bioactive conformation. On the other hand, there is a second factor stabilizing the bioactive conformation of the hNGF termini, namely inter-chain H-bonding of residue $Arg^9$. Because of the latter binding, the above criteria are still fulfilled for (1–117)hNGF.

The deletion of principal residue $Phe^{12}$, which participates in hydrophobic interactions in area A, results in a substantial loss of TrkA mediated activity of the mNGFΔ3–12, mNGFΔ3–13, mNGFΔ3–14 and mNGFΔ9–14 deletion mutants (Drinkwater et al., 1993). Likewise, the absence of principal residues $Arg^{114'}$ and $Lys^{115'}$, essential for the ionic binding in area C, results in dramatic loss of bioactivity of mNGFΔ112–118 (Drinkwater et al., 1993). Similarly, geometric perturbations of the essential residues $Arg^{59}$ and $Arg^{69}$ in the mNGFΔ61–66 deletion mutant result in incomplete NGF/LRM-2A compatibility in area D and, accordingly, a considerable loss of activity.

The specific location of the NGF ninth amino acid side chain in the "hollow" existing on the surface of the NGF rigid region has been predicted herein to be critical for high TrkA mediated activity. The present invention provides a detailed explanation for this prediction. That is, the "hollow" is buried inside the NGF/LRM-2A complex, and a moiety located in this "hollow" fills the cavity which otherwise would exist inside the complex and destroy NGF/LRM-2A compatibility. Since this moiety is located in the internal cavity of the complex (FIG. 10), severe limitations are imposed on its size. A short side chain does not fill this cavity; therefore, the hNGF-R9A mutant demonstrates noticeably diminished activity (Shih et al., 1994). The cavity preferably is filled either by a bulky amino acid side chain, such as arginine (e.g. hNGF), methionine (e.g. mNGF) or leucine (sNGF), or by the two residue peptide backbone (mNGFΔ3–9 or mNGFΔ2–8). A longer amino terminus tail (e.g. in mNGFΔ3–8, mNGFΔ9–13 or mNGFΔ1–5) cannot be accommodated in the internal cavity of the NGF/LRM-2A complex and, hence, interferes with binding areas B and E.

Most deletion or point mutations of the NGF amino terminus destroy the exposed β-strand motif $Phe^7$-$Arg^9$ and change the proper orientation of the $Phe^7$ side chain, thereby affecting NGF/LRM-2A compatibility in areas B and E. Thus, incorporation of a negatively charged residue into the relatively long NGF amino terminus, as in hNGF-H4D, BDNF, NT-3 and NT-4/5, or substitution H8R, which is characteristic for BDNF and NT-4/5, has each been demonstrated to cause dramatic conformational changes in the complex of the neurotrophin amino-carboxyl termini, making it incompatible with the LRM-2A. This stereochemical incompatibility of the geometry of the NGF amino terminus with binding areas B and E of the LRM-2A is the reason for the partial or complete loss of TrkA-related activity of mNGFΔ3–8, mNGFΔl-5, hNGF-P5A, hNGF-H4A, hNGF-H4D, mNGFΔ1–8, hNGFΔ1–9, mNGFΔ1–9, mNGFΔ9–13, mNGFΔ3–11, BDNF and NT-4/5.

As demonstrated, both NGF monomers are-directly involved in specific ligand-receptor interactions, i.e., the first monomer binds areas B, D and E, whereas the second one binds areas A and C. Consequently, the dimeric structure of NGF is necessary to retain high biological activity, which is also consistent with experimental data (Maness et al., 1994). On the contrary, only one BDNF protomer is essential for TrkB binding (FIGS. 11*a*, 11*b*).

In addition, recent reports of experiments have demonstrated the importance of residues $Phe^7$ (Kullander and Ebendal, 1996), $Leu^{112}$, $Arg^{114}$ and $Lys^{115}$ (Krüttgen et al., 1996) for TrkA mediated activity of NGF. This is consistent with their participation in the specific NGF/LRM-2A binding in the framework of the present model.

Conclusions

The complexes of the amino and carboxyl termini of the four fully active NGF analogues with the second leucine-rich motif of TrkA were obtained using Variable Basis Monte Carlo simulated annealing calculations. The same methodology was utilized to define the structure of the complex of the second leucine-rich motif of TrkB with the BDNF receptor binding determinant. The structural features of the resulting NGF/TrkA and BDNF/TrkB binding predictions are supported by the following: (i) geometric and electrostatic complementarity of the binding domains of NGF and BDNF to binding sites of TrkA and TrkB, respectively, without considerable conformational changes of the ligands; (ii) appropriate environments for hydrophobic and hydrophilic residues within the complexes; (iii) analysis of structural variability of both binding domains; and (iv) comprehensive explanation of currently published structure-activity relationships. Within these complexes, NGF/TrkA molecular recognition is based upon multiple-point intermolecular interactions of hydrophobic, van der Waals, ionic and hydrogen bonding type. Extensive intermolecular van der Waals contacts arise from complementarity of the NGF binding domain and the TrkA recognition site in size and shape. In addition, there are five specific binding areas within the receptor model: hydrophobic A and B, ionic C and D and cooperative hydrogen bonding E. The NGF/TrkA stereochemical compatibility in areas A, C and D is required for TrkA receptor activation, whereas areas B and E reinforce binding specificity, making the NGF molecule a very sophisticated key triggering the chain of biological events following receptor phosphorylation. The 3-dimensional structures of the binding domains of the fully active NGF analogues are "preorganized" for stereochemical fit to the second leucine-rich motif of TrkA. Five distinct binding areas F–K were also identified in the BDNF/TrkB complex, although, in contrast with NGF/TrkA binding, BDNF/TrkB recognition is based primarily on ionic and hydrogen bonding interactions. In spite of significant differences in the nature of ligand-receptor interactions involved in TrkA and TrkB recognition processes, binding patterns of their receptor binding sites for NGF and BDNF are almost identical. The predicted mechanism of high affinity NGF/TrkA and BDNF/TrkB binding is consistent with the conformational model of TrkA-$p75^{NTR}$ interactions (Chao and Hempstead, 1995).

PART C

Theoretical Modelling of the P75$^{NTR}$ Receptor Recognition Site for Neurotrophins Introduction As summarized above, the neurotrophins represent a family of structurally and functionally related proteins which play a crucial role in the development, survival and maintenance of the sympathetic and sensory neurons (Purves, 1988; Snider and Johnson, 1989; Barde, 1989; Thoenen, 1991; Korsching, 1993; Persson and Ibáñez, 1993; Davies, 1994; Ibáñez, 1995). The neurotrophin family consists of nerve growth factor (NGF), brain-derived neurotrophic factor (BDNF), neurotrophin-3 (NT-3), neurotrophin-4/5 (NT-4/5), and more recently discovered neurotrophin-6 (NT-6) (Berkmeier et al., 1991; Barde, 1991; Barbacid, 1993; Bradshaw et al., 1994; Chao, 1994; Gotz et al., 1994). Each neurotrophin is capable of binding independently with the common neurotrophin receptor p75$^{NTR}$, as opposed to specific Trk receptor interactions.

Methods

The geometric features of complexes of monomeric neurotrophins with the p75$^{NTR}$ receptor binding site have been obtained by multiple molecular dynamics runs of 200–300 ps at constant temperatures between 300 and 400° K., followed by local energy refinements. The QUANTA V4.1 molecular modelling program (Molecular Simulations Inc., Waltham, Mass.) with the united atom CHARMM potential energy terms (Brooks et al., 1983) has been used. Residues of p75$^{NTR}$ are designated by abbreviation p.

According to the invention, we superimposed the binding domains of NGF, BDNF, NT-3 and NT-4/5 with a putative binding site of p75$^{NTR}$ and carried out multiple molecular dynamics computations of the ligand-receptor complexes. These calculations revealed the 3-dimensional structures of the binding domains of the neurotrophins and p75$^{NTR}$, demonstrated their geometric and electrostatic complementarity, and identified principal residues involved in receptor recognition. All neurotrophins are believed to induce similar conformational changes in the p75$^{NTR}$ binding site, generally located in the orientation of the sequential loops within the cysteine-rich repeats.

Initial geometries of individual components of the complexes were based upon the X-ray crystallographic coordinates of neurotrophins NGF (McDonald et al., 1991), BDNF and NT-3 (Robinson et al., 1995) and the p55$^{TNFR}$ receptor extracellular domain (Banner et al., 1993) which is homologous to p75$^{NTR}$. Geometry of the NT-4/5 monomer was constructed from the X-ray derived structure of NT-3 (Robinson et al., 1995). Since NGF and other neurotrophins fold in similar rigid conformations, their molecular motions were restricted by imposing the following atom constraints. First, peptide backbones of the neurotrophins were fixed at their crystallographic coordinates. Further, conformations of the amino acid side chains of the neurotrophins were also fixed except for those located within and in the vicinity of the variable loop regions I and V (the p75$^{NTR}$ binding determinant). Thus, amino acid side-chain motions were allowed for residues 23–35 and 93–98 (NGF numbering) as well as for eight additional neighboring residues, namely His$^{84}$ (Gln in other neurotrophins), Phe$^{86}$ (Tyr in other neurotrophins), Lys$^{88}$ (Arg in other neurotrophins), Trp$^{99}$, Arg$^{100}$, Phe$^{101}$ (Trp in NT-3 and NT-4/5), Arg$^{103}$, and Asp$^{105}$. The flexible amino and carboxyl termini of the neurotrophins were excluded to avoid artifactual spacial hindrances for the receptor binding.

FIG. 16a represents a fragment of the crystallographically resolved structure of the p55$^{TNFR}$ extracellular domain (Banner et al., 1993), corresponding to the second CRD (loops 2A and 2B) and the first loop of the third CRD (loop 3A). FIG. 17 illustrates the sequence of this fragment and its alignment with the three known p75$^{NTR}$ peptides (Johnson et al., 1986; Radeke et al., 1987; Large et al., 1989). FIG. 16b presents the minimum energy conformation of the corresponding fragment of human p75$^{NTR}$. As is apparent, its size and shape are complementary to the exposed p75$^{NTR}$ binding determinant of NGF (FIG. 16c). Accordingly, this 58-amino acid fragment of p75$^{NTR}$, including the second and the beginning of the third CRDs (FIG. 17), has been considered as a putative binding site for neurotrophins. The artefactual charges on the terminal amino and carboxyl groups of the peptide representing the p75$^{NTR}$ binding site were neglected.

Once the most stable equilibrium 3-dimensional structures of the complexes being studied were obtained, the residues contributing the most to the energy of intermolecular interactions were identified. Point atomic charges of Weiner et al. (1984) and a dielectric constant equal to the interatomic separation in angstroms (to implicitly simulate solvation effects) (Weiner et al., 1984) were utilized to calculate the electrostatic intermolecular terms. The van der Waals intermolecular terms were evaluated by the united atom CHARMM force field (Brooks et al., 1983). The calculations were performed on a 200 MHz Indigo-2 SiliconGraphics Workstation.

Results and Discussion

The most stable structures of the complexes of the neurotrophins with the putative p75$^{NTR}$ receptor binding site obtained by the molecular dynamics computations described herein are illustrated in FIG. 18. Table 9 presents net values of the electrostatic and van der Waals terms of the ligand-receptor interaction energy. Tables 9 and 10 list individual residues of the neurotrophins and the p75$^{NTR}$ receptor which significantly contribute to the intermolecular electrostatic interaction energy. The highlighted residues represent the functional epitopes of the ligands (Table 9) and the receptor (Table 10), whereas the other listed residues, although being located within the binding interfaces, apparently do not participate in major ligand-receptor electrostatic interactions in the particular complex. Predicted Cartesian 3-dimensional coordinates of atoms of the p75$^{NTR}$ binding sites in the complexes with NGF and BDNF are presented in Appendix 3.

Significant contributions of electrostatic interactions to the ligand-receptor interaction energy (Table 9) result from opposite net charges of the binding domains of neurotrophins (positively charged) and the common neurotrophin receptor (negatively charged), which effect is consistent with published predictions (Rydén et al., 1995). Data presented in Tables 9 and 10 demonstrate that, on the average, the interaction between the functional epitopes is responsible for 94% of intermolecular electrostatic energy, but only 43% of van der Waals interaction energy. Consequently, residues participating in strong and specific ligand-receptor interactions represent only a part of a bigger binding interface in which significant van der Waals contribution is accumulated from a large number of weak contacts, which is possible only as a consequence of geometric complementarity of the binding domains. FIG. 19 presents the structure of the BDNF/p75$^{NTR}$ complex as atomic van der Waals spheres and demonstrates the geometric fit of the binding domains. The van der Waals energy and, therefore, geometric complementarity of the binding interfaces in the NGF/p75$^{NTR}$ complex is significantly lower than in the other neurotrophin/p75$^{NTR}$ complexes (Table 9), which is consistent with its fastest rate of dissociation (Ibáñez, 1995). However, the pure geometric factor cannot explain the slowest rate of dissociation observed for the BDNF/p75$^{NTR}$ complex (Ibáñez, 1995). Thus, stability of the complex arises from a combination of geometric and electrostatic complementarities of the binding interfaces, consistent with the generalizations of Clackson and Wells (1995). A specific feature of the neurotrophin/p75$^{NTR}$ binding interfaces is that they do not include substantially hydrophobic residues, so they do not have a hydrophobic core, which has been found in many other protein-protein complexes (Clackson and Wells, 1995; Livnah et al., 1996). The predominant interactions within the binding domains of the complexes under study are of the salt-bridge type.

Specificity of binding of the neurotrophins to the p75$^{NTR}$ receptor is determined by charged residues within the binding domains (Rydén et al., 1995). As seen in FIG. 18, they create 3-dimensional networks in which most of them are in contact with more than one residue of the opposite charge. Therefore, any missing charge would destroy more than just one bond, but a significant portion of, if not the whole, network. That is, the electrostatic complementarity of the binding interfaces would be altered, which is consistent with the experimentally observed sensitivity of binding to mutations of charged residues (Ibáñez et al., 1992; Rydén et al., 1995; Rydén and Ibáñez, 1996). Both ligand and receptor provide the network with positive and negative charges (Table 9 and 10, FIG. 18), even though negative charges dominate in the receptor, and positive in the ligands. This particular spatial arrangement of the charges increases specificity of binding and prevents electrostatic repulsions within the same binding domains. For example, in all the complexes, positively charged residue Lys$^{56p}$ of the receptor forms salt-bridges with negatively charged residues Asp$^{75p}$ and Asp$^{76p}$ of the receptor, thereby occupying one site of their coordination, such that only the opposite sides of the latter residues remain available for intermolecular ionic interactions (FIG. 18). Negatively charged residue Asp$^{93}$ of BDNF holds together positively charged residues Arg$^{97}$ and Arg$^{101}$ of BDNF, such that they are both able to interact with juxtaposed amino acids Asp$^{75p}$ and Asp$^{76p}$ of the receptor (FIG. 18b). Similarly, negatively charged residue Asp$^{30}$ of the neurotrophins forms a salt-bridge interaction with Arg$^{100}$, which directly interacts with p75$^{NTR}$.

In spite of the differences in the binding interfaces of the respective complexes, binding patterns of the p75$^{NTR}$ receptor are similar. All three loops of the receptor binding site (2A, 2B and 3A) are involved in binding (FIG. 18). The principal residues of loop 2A are Asp$^{47p}$ and Lys$^{56p}$; those of loop 2B are Asp$^{75p}$ and Asp$^{76p}$; and those of loop 3A are Asp$^{88p}$ and Glu$^{89p}$. As is seen in Table 10, loop 2B forms the strongest contacts. In addition to the principal binding pattern, the p75$^{NTR}$ binding domain comprises specific residues for ionic interactions with particular neurotrophins (Table 10, FIG. 18). Thus, Arg$^{80p}$ interacts only with Glu$^{35}$ of NGF; residue Glu$^{53p}$ interacts only with Lys$^{96}$ of BDNF, and Glu$^{60p}$ and Glu$^{73p}$ interact only with residues of NT-3 and NT-4/5.

Site-directed mutagenesis studies of the p75$^{NTR}$ binding site have suggested that mutation of any one of the residues Asp$^{75p}$, Asp$^{76p}$ or Glu$^{89p}$ to Ala does not affect NGF binding, whereas mutation of Ser$^{50p}$, which does not participate in major ionic interactions, results in the complete abolishment of binding (Baldwin and Shooter, 1995). The apparent discrepancy with the present theoretical studies can be explained, since the cited experimental observations are still controversial. Indeed, although both Asp$^{75p}$ and Asp$^{76p}$ are involved in ionic interactions in the loop 2B region with positively charged residues of neurotrophins, one of them might be enough to maintain binding to NGF. Likewise, the functional role of the missing residue Glu$^{89p}$ in loop 3A might be fulfilled by adjacent Asp$^{88p}$. Residue Ser$^{50p}$ of p75$^{NTR}$ is predicted to be hydrogen bonded to Gln$^{96}$ of NGF (FIG. 18a), and its mutation to Asn, Ala or Thr, which abolishes receptor binding (Baldwin and Shooter, 1995), may create steric hindrances in the NGF/p75$^{NTR}$ interface. The present molecular modelling studies suggest that Ser$^{50p}$ is not important for binding of any other neurotrophin (FIG. 18, b–d).

In contrast to the p75$^{NTR}$ receptor binding pattern, there are only two common residues of the binding interfaces of neurotrophins which directly interact with the receptor site, Arg$^{100}$ and Arg$^{103}$. Contribution of Arg$^{103}$ is significant in all the complexes, while Arg$^{100}$ seems to be less important for the NGF/p75$^{NTR}$ binding.

As is seen in Table 9, most important residues of the NGF binding domain are (in order of decreasing significance) Lys$^{32}$, Lys$^{34}$, Arg$^{103}$, Lys$^{95}$, and His$^{84}$, all of them forming specific ionic contacts with negatively charged residues of p75$^{NTR}$ (FIG. 18a). Involvement of Lys$^{32}$, Lys$^{34}$, and Lys$^{95}$ in p75$^{NTR}$ binding has been very well established experimentally, with the same order of significance being observed (Ibáñez, 1994). The most important residues of NGF, Lys$^{32}$ and Lys$^{34}$, bind to the loop 2B residues of p75$^{NTR}$ (FIG. 18a). Here we demonstrate that residue Lys$^{88}$ is not critical for p75$^{NTR}$ binding, whereas residues Arg$^{103}$ and His$^{84}$ make direct ionic contacts with the receptor binding site. Importance of the latter residue has not been previously reported in the context of p75$^{NTR}$ binding. The roles of Asp$^{30}$, Glu$^{35}$ and Arg$^{100}$ seem to be secondary, since their contributions are relatively small. Hydrophobic residue Ile$^{31}$ is not directly involved in ligand-receptor interactions.

In BDNF, all three positively charged residues of variable region V, Lys$^{95}$, Lys$^{96}$ and Arg$^{97}$ (Rydén et al., 1995), bind to negatively charged residues of the p75$^{NTR}$ binding site, namely Asp$^{47p}$, Glu$^{53p}$ and Asp$^{75p}$, respectively (FIG. 18b). In addition, the residues Arg$^{88}$ and Arg$^{101}$ play a more important role than in the NGF case (Table 9); they bind to the loop 2B residues Asp$^{75p}$ and Asp$^{76p}$ of p75$^{NTR}$, thereby fulfilling the function of missing positively charged residues of loop 1. The increased importance of residue Arg$^{88}$ in BDNF and other neurotrophins relative to that of Lys$^{88}$ in NGF (Table 9) is permitted by a longer side chain of Arg, which results in a decrease of the separation between opposite charges (FIG. 18). Because of missing residue His$^{84}$, only the positively charged residue Arg$^{104}$ binds to the loop 3A residues Asp$^{88p}$ and Glu$^{89p}$ of p75$^{NTR}$.

In NT-3, the loop 2B residues of the receptor Glu$^{73p}$, Asp$^{75p}$, and Asp$^{76p}$ bind to Arg$^{31}$, His$^{33}$, Arg$^{100}$, and Arg$^{87}$. Residue Asp$^{47p}$ of loop 2A of the receptor also binds to Arg$^{100}$. Residue Lys$^{95}$ of variable region V does not form any salt-bridge contact with the receptor, consistent with its reported insignificance for NT-3 binding (Rydén et al., 1995). Thus, the present results agree well with the established roles of Arg$^{31}$ and His$^{33}$ of NT-3 (Rydén et al., 1995; Rydén and Ibáñez, 1996) and predict the increased importance of residue Arg$^{100}$ in NT-3 for p75$^{NTR}$ binding (Table 9). The binding pattern of NT-4/5 is similar to that of NT-3 (FIG. 18, c,d). The increased electrostatic contribution of Arg$^{36}$ with respect to corresponding NT-3 residue His$^{33}$ (Table 9) is caused by the longer side chain of the former, which results in formation of a salt-bridge contact with residue Glu$^{60p}$ of the receptor (FIG. 18d).

Binding of a neurotrophin induces conformational changes in the p75$^{NTR}$ binding site. The conformational space of the three loops (2A, 2B and 3A) is limited by eight disulfide bonds; therefore, the most significant changes occur in the junction areas of those loops. FIG. 20 illustrates the superimposed equilibrium geometries of the free and the BDNF-complexed p75$^{NTR}$ binding site. The superimposition is performed by a least-square minimization technique using the a-carbon reference atoms of loops 2A and 3A. As is apparent, the orientation of loop 2B with respect to the two flanking loops is considerably changed upon binding. Because of striking similarities between the binding patterns of the p75$^{NTR}$ receptor with the different neurotrophins, a similar conformational change takes place in all four complexes under investigation. The driving force behind this particular conformational transition is ionic interactions of the principal residues of loop 2B, Asp$^{75P}$ and Asp$^{76P}$, with positively charged residues of the neurotrophins, taking into account that spacial positions of the flanking loops 2A and 3A are fixed by ionic interactions of residues Asp$^{47P}$, Lys$^{56P}$, Asp$^{88P}$, and Glu$^{89P}$ with corresponding residues of the neurotrophins (FIG. 18). Thus, structural variability between the neurotrophins does not preclude them from inducing similar conformational change in the common neurotrophin receptor.

The binding pattern of neurotrophins to the p75$^{NTR}$ receptor predicted by the present molecular modelling studies can be additionally verified by checking conservation of the identified principal residues. The sequences of the binding site of the p75$^{NTR}$ receptor from different species (FIG. 17) demonstrate that principal residues forming its common binding pattern, namely Asp$^{47P}$, Lys$^{56P}$, Asp$^{75P}$, Asp$^{76P}$, Asp$^{88P}$, and Glu$^{89P}$, are conserved in p75$^{NTR}$. The known variability of regions I and V among neurotrophins (Rydén et al., 1995) implies that conservation of the principal residues of the p75$^{NTR}$ binding determinants may be checked only within the same neurotrophin derived from different species. Study of a recent sequence alignment of neurotrophins (Bradshaw et al., 1994) allowed us to conclude that the functional epitope of the neurotrophins (Table 9) is generally conserved within the same neurotrophin even though there are some exceptions, often represented by the substitution by a similar amino acid. Arg$^{100}$ and Arg$^{103}$ are the only two residues of the binding epitopes which are conserved throughout all neurotrophins (Bradshaw et al., 1994). Other residues within the functional epitopes maintain specificity of binding of different neurotrophins.

The present model also represents a key to understanding the conservation of residues which do not directly participate in receptor binding. For example, Gly$^{33}$ is absolutely conserved in all neurotrophins, yet is not involved in any specific interactions with the receptor binding site. However, within the present model, its conservation can be understood, since it is located very close to loop 3A of the receptor and forms van der Waals contacts with it (FIG. 18), such that any other residue would impose steric hindrance which would alter or destroy the ligand-receptor geometric complementarity.

The principal NGF/TrkA binding areas necessary to trigger TrkA phosphorylation and subsequent biological events have been discovered by the inventors. Specifically, the inventors have discovered that essentially the full binding site of the second leucine rich motif (LRM) of TrkA, amino acid residues 93 to 117, forms the binding site for NGF, and comprises five distinct binding areas, A, B, C, D and E. Appendix 1 provides the Cartesian coordinates of the LRM-2A residues defining the areas A to E in PDB format. Binding areas A and B bind hydrophobically to ligands, areas C and D form ionic bonds with charged portions on ligands and area E forms hydrogen bonds with ligands.

The stereochemical fit to at least three of these binding sites, A, C and D by a ligand is necessary to activate TrkA receptor. Binding areas B and E reinforce stereoselectivity of the TrkA binding site by selecting an NGF analogue with a stereochemically compatible amino terminus.

Binding area A of the second LRM comprises hydrophobic interaction of residue Phe$^{105tA}$. Binding area B comprises hydrophobic interaction of residues Phe$^{111tA}$, Phe$^{113tA}$ and Thr$^{114tA}$. Binding area C comprises attractive ionic interaction between a suitable portion on the ligand and Asp$^{109tA}$. Binding area D comprises attractive ionic interaction between a suitable portion on the ligand and residue Lys$^{100tA}$. Binding area E comprises multiple parallel β-strand type hydrogen bonding with region Asn$^{95tA}$-Ile$^{98tA}$.

Main structural features of the bioactive conformation of NGF include: 1) ionic hydrogen bonding between Glu$^{11}$ in the amino terminus and Arg$^{118'}$ in the carboxyl terminus; 2) separation of the flexible loop 1–8 from the rigid region (9–11 and 112' to 118') because of electrostatic repulsions caused by His$^4$ and conformational restrictions imposed by Pro$^5$; 3) packing the side chain of Arg$^9$ or Met$^9$ in the "hollow" of the rigid region, this "hollow" being an indentation in the protein structure by residues Lys$^{115'}$-Arg$^{118'}$; and 4) an embryonic β-sheet structure present between the a-carbons of the 7th and 9th residues.

Within NGF, residues Trp$^{76'}$, Arg$^{114'}$, Lys$^{115'}$ and Asp$^{16}$ comprise the pharmacophore which binds TrkA. Any synthetic molecule, whether peptide or non-peptide, which fits into binding areas A, C and D is contemplated to elicit a biological response (agonist) or block biological response (antagonist).

The present invention provides a ligand for binding with TrkA, wherein TrkA comprises a second leucine rich motif (LRM) region comprising amino acid residues 93 to 117, the coordinates of the residues of said LRM given in Appendix 1, said LRM motif having five binding areas, area A comprising hydrophobic interaction of amino acid residue Phe$^{105tA}$, area B comprising hydrophobic interaction of amino acid residues Phe$^{111tA}$, Phe$^{113tA}$, and Thr$^{114tA}$, area C comprising ionic interaction of amino acid residues Asp$^{109tA}$ and His$^{112tA}$, area D comprising ionic interaction of amino acid residue Lys$^{100tA}$, and area E comprising multiple parallel β-strand type hydrogen bonding of region Asn$^{95tA}$ to Ile$^{98tA}$. The ligand comprises at least one functional group being capable of hydrophobic bonding and being present in an effective position in the ligand to hydrophobically bind to area A, at least one positively charged functional group being present in an effective position in the ligand to ionically bind to area C, and at least one negatively charged functional group being present in an effective position in the ligand to tonically bind to area D.

Secondary features of the ligand include at least one effective functional group present in a position in the ligand to hydrophobically bind to area B of TrkA, and a functional group present in an effective position in the ligand to hydrogen bind to area E of TrkA.

The invention further provides the ligand comprising amino acid residues, at least one of the residues being capable of hydrophobic bonding and being present in an effective position in the ligand to hydrophobically bind to Phe$^{105tA}$ in area A on the TrkA receptor, at least one of the residues being a positively charged residue present in an effective position in the ligand to tonically interact with Asp$^{109tA}$ and His$^{112tA}$ forming area C on the TrkA receptor, and one of the residues being a negatively charged residue present in an effective position in the ligand to tonically bind to Lys$^{100tA}$ in area D on the TrkA receptor.

The present invention also provides a method of designing a ligand to bind with an LRM binding site on TrkA. The method includes computationally evolving a chemical ligand using an effective genetic algorithm with preselected spatial constraints so that the evolved ligand comprises at least three effective functional groups of suitable identity and spatially located relative to each other in the ligand so that a first of the functional groups hydrophobically interacts with binding area A, a second of the functional groups ionically interacts with binding area C, and a third one of the functional groups ionically interacts with binding area D of the second LRM of TrkA. Those skilled in the art will be aware of the various techniques which may be used for de novo ligand design. For example, packages such as Quanta, Discover and Insight provide computational methodologies for generating ligands.

Some ligands according to the present invention may be peptides or peptidomimetics. Morgan and co-workers (Morgan et al., 1989) define peptide mimetics as "structures which serve as appropriate substitutes for peptides in interactions with receptors and enzymes". The mimetic must possess not only affinity but also efficacy and substrate function. For purposes of this disclosure, the terms "peptide mimetic" and "peptidomimetic" are used interchangeably according to the above excerpted definition. That is, a peptidomimetic exhibits function(s) of a particular peptide, without restriction of structure. Peptidomimetics of the invention, e.g., analogues of the neurotrophin and receptor binding sites described herein, may include amino acid residues or other chemical moieties which provide functional characteristics described herein. "Isosteric" is an art-recognized term and, for purposes of this disclosure, a first moiety is "isosteric" to a second when they have similar molecular topography and functionality. This term should not, therefore, be restricted to mere similarity in chemical bond configuration. Two compounds may have different chemical bond configurations but nonetheless be isosteric due their 3-dimensional similarity of form and chemical nature, e.g. relevant centers such as heteroatoms are located in the same position, charges and/or dipoles are comparable, and the like.

Known compounds may also be screened to determine if they satisfy the spatial and functional requirements for binding with the second LRM of TrkA. The molecules in the data bases are screened to determine if they contain effective moieties spaced relative to each other so that a first moiety hydrophobically interacts with binding area A, a second of moiety ionically interacts with binding area C, and a third moiety ionically interacts with binding area D of the second LRM of TrkA.

The contents of all references and appendices (see Appendices 1, 2, 3, and 4) cited throughout this application are hereby expressly incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

TABLE 1

Equilibrium variable torsional angles (in degrees) of the amino and carboxyl termini of the most stable conformations of the NGF dimers and analogues.*

| | | Active structures | | | | | | Inactive structures | | | | | |
|---|---|---|---|---|---|---|---|---|---|---|---|---|---|
| No. | | hNGF | | mNGF | | mNGFD3-9 | | hNGF-H4D | | mNGFDI-8 | | BDNF | |
| | | | | | | Amino terminus | | | | | | | |
| 11 | ψ | E | 82.9 | E | 85.9 | E | 89.2 | E | 80.9 | E | 63.7 | E | 68.2 |
| | φ | | 55.7 | | 56.3 | | 57.8 | | 57.2 | | 47.9 | | 56.3 |
| | $X^1$ | | −69.8 | | −72.0 | | −72.1 | | −75.0 | | −66.2 | | −76.9 |
| | $X^2$ | | 72.7 | | 71.7 | | 66.0 | | 72.6 | | 71.2 | | 70.1 |
| | $X^3$ | | −120.4 | | −111.7 | | −107.0 | | −104.8 | | −102.8 | | −97.7 |
| 10 | ψ | G | −89.1 | G | −95.1 | G | −88.0 | G | −129.5 | G | −81.6 | G | −134.1 |
| | φ | | −172.5 | | −178.6 | | −177.5 | | 104.7 | | −80.8 | | 155.0 |
| 9 | ψ | R | −36.1 | M | −21.1 | S | 146.5 | R | −46.5 | M | −66.6 | R | 71.4 |
| | φ | | −92.8 | | −91.4 | | −103.6 | | −80.9 | | 157.5 | | −128.5 |
| | $X^1$ | | −77.2 | | −75.2 | | −66.7 | | −115.0 | | −142.4 | | −73.5 |
| | $X^2$ | | −173.9 | | −179.7 | | 64.0 | | 69.5 | | −69.7 | | −179.8 |
| | $X^3$ | | −175.5 | | 179.9 | | — | | −141.9 | | 178.3 | | −71.4 |
| | $X^4$ | | 134.3 | | — | | — | | 98.1 | | — | | −109.8 |
| 8 | ψ | H | 118.6 | H | 110.4 | S | 106.1 | H | 151.6 | | — | R | 105.2 |
| | φ | | −116.5 | | −110.4 | | 52.8 | | −53.7 | | — | | −100.1 |
| | $X^1$ | | −89.7 | | −90.9 | | −45.9 | | −62.0 | | — | | 179.6 |
| | $X^2$ | | −73.8 | | −71.5 | | −172.3 | | −72.5 | | — | | −105.5 |
| | $X^3$ | | — | | — | | — | | — | | — | | 162.1 |
| | $X^4$ | | — | | — | | — | | — | | — | | 133.7 |
| 7 | ψ | F | 135.7 | F | 129.4 | | — | F | 142.3 | | — | A | 161.6 |
| | φ | | −68.8 | | −89.0 | | — | | −114.8 | | — | | −166.6 |
| | $X^1$ | | −171.6 | | −163.9 | | — | | −170.7 | | — | | — |
| | $X^2$ | | −96.3 | | −91.5 | | — | | −100.2 | | — | | — |
| 6 | ψ | I | 40.3 | V | 61.7 | | — | I | 40.0 | | — | P | 114.4 |
| | φ | | 40.4 | | 47.7 | | — | | 39.9 | | — | | — |
| | $X^1$ | | −159.7 | | −177.3 | | — | | −159.7 | | — | | — |

TABLE 1-continued Equilibrium variable torsional angles (in degrees) of the amino and carboxyl termini of the most stable conformations of the NGF dimers and analogues.*

| | | | Active structures | | | | | | Inactive structures | | | | |
|---|---|---|---|---|---|---|---|---|---|---|---|---|---|
| No. | | | hNGF | | mNGF | | mNGFD3-9 | | hNGF-H4D | | mNGFDI-8 | | BDNF |
| | $X^2$ | | 87.1 | | — | | — | | 88.6 | | — | | — |
| 5 | $\psi$ | P | 156.0 | P | 149.8 | | — | P | 105.5 | | — | D | 82.8 |
| | $\phi$ | | — | | — | | — | | — | | — | | 56.5 |
| | $X^1$ | | — | | — | | — | | — | | — | | −176.9 |
| | $X^2$ | | — | | — | | — | | — | | — | | −112.8 |
| 4 | $\psi$ | H | 121.4 | H | 122.1 | | — | D | 117.9 | | — | S | 136.2 |
| | $\phi$ | | −129.2 | | −129.8 | | — | | −102.8 | | — | | −53.4 |
| | $X^1$ | | −162.5 | | −163.3 | | — | | −66.4 | | — | | −172.9 |
| | $X^2$ | | −69.1 | | −69.2 | | — | | −97.5 | | — | | −178.3 |
| 3 | $\psi$ | S | 2.1 | T | −1.9 | | — | S | −25.0 | | — | H | 153.8 |
| | $\phi$ | | −91.9 | | −84.5 | | — | | −68.2 | | — | | 48.2 |
| | $X^1$ | | −171.8 | | −174.9 | | — | | 39.3 | | — | | 82.1 |
| | $X^2$ | | −53.2 | | −51.2 | | — | | −120.5 | | — | | 69.8 |
| 2 | $\psi$ | S | 138.5 | S | 139.4 | | — | S | 38.5 | | — | | — |
| | $\phi$ | | −128.9 | | −114.1 | | — | | 50.8 | | — | | — |
| | $X^1$ | | 173.3 | | 169.7 | | — | | −173.2 | | — | | — |
| | $X^2$ | | −141.9 | | −139.8 | | — | | −120.6 | | — | | — |
| 1 | $\psi$ | S | 133.0 | S | 127.9 | | — | S | 131.9 | | — | | — |
| | $\phi$ | | 48.6 | | 49.4 | | — | | −133.8 | | — | | — |
| | $X^1$ | | −43.2 | | −44.1 | | — | | −43.5 | | — | | — |
| | $X^2$ | | −171.5 | | −172.4 | | — | | −173.6 | | — | | — |
| | | | | | | Carboxyl terminus | | | | | | | |
| 112' | $\phi$ | L | −113.3 | L | −113.0 | L | −112.4 | L | −112.0 | L | −111.5 | L | −110.6 |
| | $\psi$ | | 98.8 | | 98.7 | | 99.2 | | 97.7 | | 89.9 | | 100.1 |
| | $X^1$ | | −72.3 | | −71.6 | | −71.6 | | −71.7 | | −71.8 | | −72.1 |
| | $X^2$ | | 163.7 | | 163.0 | | 162.6 | | 162.2 | | 161.9 | | 161.1 |
| 113' | $\phi$ | S | −83.4 | S | −77.2 | S | −77.4 | S | −76.8 | S | −91.9 | T | −89.5 |
| | $\psi$ | | 136.1 | | 146.0 | | 143.5 | | 141.7 | | 149.4 | | 134.0 |
| | $X^1$ | | 177.0 | | 179.4 | | 176.3 | | 175.6 | | 169.6 | | 57.4 |
| | $X^2$ | | 65.2 | | 60.6 | | 59.0 | | 57.5 | | 73.2 | | −179.7 |
| 114' | $\phi$ | R | −66.7 | R | −71.5 | R | −78.0 | R | −75.1 | R | −117.0 | I | −57.9 |
| | $\psi$ | | −47.0 | | −53.7 | | −59.3 | | −57.1 | | −31.9 | | −32.2 |
| | $X^1$ | | −99.1 | | −145.6 | | −93.4 | | 177.5 | | −168.1 | | −162.1 |
| | $X^2$ | | −173.1 | | −179.8 | | −171.5 | | −159.7 | | 86.5 | | 87.9 |
| | $X^3$ | | 170.4 | | −173.6 | | −172.9 | | 58.1 | | −73.8 | | — |
| | $X^4$ | | 138.4 | | 140.3 | | 141.5 | | 124.7 | | 173.4 | | — |
| 115' | $\phi$ | K | −163.2 | K | −162.1 | K | −167.1 | K | −163.0 | K | −133.4 | K | −167.7 |
| | $\psi$ | | 110.6 | | 132.0 | | 153.3 | | 157.6 | | 141.7 | | 126.1 |
| | $X^1$ | | −139.8 | | −143.3 | | −140.1 | | −137.8 | | −164.0 | | −142.2 |
| | $X^2$ | | 78.7 | | 81.7 | | 85.0 | | 79.3 | | 172.4 | | 83.5 |
| | $X^3$ | | −96.4 | | −97.9 | | −95.8 | | −97.4 | | 133.9 | | −100.4 |
| | $X^4$ | | 129.5 | | 120.9 | | 131.0 | | 133.6 | | −73.6 | | 109.2 |
| | $X^5$ | | −39.1 | | −35.6 | | −47.7 | | −44.1 | | 9.6 | | −9.5 |
| 116' | $\phi$ | A | −60.5 | A | −69.6 | A | −58.2 | A | −63.9 | A | −51.6 | R | −61.4 |
| | $\psi$ | | −47.5 | | −40.7 | | −47.5 | | −42.4 | | −45.3 | | −39.3 |
| | $X^1$ | | — | | — | | — | | — | | — | | −80.9 |
| | $X^2$ | | — | | — | | — | | — | | — | | −173.4 |
| | $X^3$ | | — | | — | | — | | — | | — | | 174.3 |
| | $X^4$ | | — | | — | | — | | — | | — | | 129.6 |
| 117' | $\phi$ | V | −71.8 | T | −85.5 | T | −64.6 | V | −41.0 | T | −114.6 | G | −73.3 |
| | $\psi$ | | 112.0 | | 116.4 | | 108.2 | | 130.2 | | 168.4 | | 77.3 |
| | $X^1$ | | −74.3 | | 53.4 | | 50.9 | | −66.2 | | 57.2 | | — |
| | $X^2$ | | — | | 60.5 | | 58.0 | | — | | −170.5 | | — |
| 118' | $\phi$ | R | −93.8 | R | −118.2 | R | −58.5 | R | −125.2 | R | −−51.5 | R | −49.0 |
| | $\psi$ | | −57.9 | | −48.4 | | −37.6 | | 141.3 | | −56.3 | | −40.3 |
| | $X^1$ | | −104.3 | | −80.9 | | −109.5 | | −126.2 | | −153.8 | | −125.9 |
| | $X^2$ | | 79.1 | | 109.1 | | 73.3 | | 106.7 | | 88.0 | | 98.0 |
| | $X^3$ | | 147.7 | | 116.1 | | −76.3 | | −78.8 | | −74.9 | | −76.6 |
| | $X^4$ | | 147.0 | | 116.1 | | −87.2 | | −98.5 | | −125.9 | | −111.5 |

*Torsional angles are designated according to the IUPAC-IUB rules (1970).

TABLE 2

Residues of BDNF and NGF defining the surfaces of their central β-strand stems, the side-chain thermal motion of which is taken into account when optimizing the structures of the complexes with the LRM-2B.

| BDNF | | NGF | |
|---|---|---|---|
| Ile$^{16}$ | Lys$^{57}$ | — | Lys$^{57}$ |
| Glu$^{18}$ | Asn$^{59}$ | Val$^{18}$ | Arg$^{59}$ |
| Val$^{20}$ | Met$^{61}$ | Val$^{20}$ | Ser$^{61}$ |
| Thr$^{21}$ | Lys$^{65}$ | Val$^{22}$ | — |
| Asp$^{24}$ | Gln$^{79}$ | Asp$^{24}$ | Tyr$^{79}$ |
| Lys$^{25}$ | Arg$^{81}$ | Lys$^{25}$ | Thr$^{81}$ |
| Lys$^{26}$ | Thr$^{82}$ | Thr$^{26}$ | Thr$^{82}$ |
| Thr$^{27}$ | Gln$^{84}$ | Thr$^{27}$ | His$^{84}$ |
| Val$^{29}$ | Tyr$^{86}$ | Thr$^{29}$ | Phe$^{86}$ |
| Thr$^{35}$ | Arg$^{104}$ | Glu$^{35}$ | Arg$^{103}$ |
| Glu$^{55}$ | Asp$^{106}$ | Glu$^{55}$ | Asp$^{105}$ |

TABLE 3

Components of the molecular mechanical potential energy of the intermolecular NGF/LRM-2A interactions (in kcal/mol)

| Term | hNGF | mNGF | mNGFΔ3-9 | hNGF:NT-4/5 |
|---|---|---|---|---|
| $E_w$ | −61.2 | −57.9 | −39.3 | −65.1 |
| $E_e$ | −96.2 | −87.9 | −99.0 | −65.2 |
| $E_{hb}$ | −7.4 | −5.9 −3.1 | −4.6 | |
| $E_{qq}$ | −0.3 | −0.3 −0.1 | −0.1 | |
| Total | −165.1 | −152.0 | −141.5 | −135.1 |

TABLE 4

Components of the molecular mechanical potential energy of the BDNF/LRM-2B and the NGF/LRM-2B complexes (in kcal/mol)

| | BDNF/LRM-2B | NGF/LRM-2B | Difference* |
|---|---|---|---|
| A. Components of the potential energy | | | |
| $E_w$ | 89.3 | 82.3 | −7.0 |
| $E_{el}$ | −183.8 | −93.1 | 90.7 |
| $E_{hb}$ | −31.0 | −21.5 | 9.5 |
| Et | 114.9 | 114.0 | −0.9 |
| $E_{qq}$ | 0.4 | 0.0 | −0.4 |
| Total | −10.2 | 81.8 | 92.0 |
| B. Components of the intermolecular interactions energy | | | |
| $E_w$ | −48.0 | −64.9 | −16.9 |
| $E_{el}$ | −221.4 | −144.2 | 77.2 |
| $E_{hb}$ | −5.6 | −4.3 | 1.3 |
| Total | −275.0 | −213.5 | 61.5 |

*Difference of the energy terms within the minimum-energy structures of the NGF/LRM-2B and the BDNF/LRM-2B complexes. Underlined values demonstrate that the difference in intermolecular electrostatic interactions dominates in the differences in potential energies of the complexes.

TABLE 5

Equilibrium variable torsional angles (in degrees) of the amino and carboxyl termini of the most stable conformations of the uncomplexed (UC) and complexed (C) NGF analogues.*

| | | | hNGF | | | mNGF | | | mNGFΔ3-9 | |
|---|---|---|---|---|---|---|---|---|---|---|
| No. | | | UC | C | | UC | C | | UC | C |
| | | | Amino terminus | | | | | | | |
| 11 | ψ | E | 82.9 | 78.2 | E | 85.9 | 85.4 | E | 89.2 | 96.6 |
| | φ | | 55.7 | 60.3 | | 56.3 | 56.3 | | 57.8 | 60.3 |
| | χ$^1$ | | −69.8 | −69.3 | | −72.0 | −69.4 | | −72.1 | −73.7 |
| | χ$^2$ | | 72.7 | 70.2 | | 71.7 | 71.3 | | 66.0 | 67.0 |
| | χ$^3$ | | −120.4 | −117.6 | | −111.7 | −117.1 | | −107.0 | −109.2 |
| 10 | ψ | G | −89.1 | −122.1 | G | −95.1 | −103.2 | G | −88.0 | −94.8 |
| | φ | | −172.5 | −166.5 | | −178.6 | 174.1 | | −177.5 | 168.7 |
| 9 | ψ | R | −36.1 | −25.7 | M | −21.1 | −14.3 | S | 146.5 | 166.1 |
| | φ | | −92.8 | −84.2 | | −91.4 | −77.3 | | −103.6 | −132.1 |
| | χ$^1$ | | −77.2 | −92.9 | | −75.2 | −84.9 | | −66.7 | −179.1 |
| | χ$^2$ | | −173.9 | −174.1 | | −179.7 | 179.0 | | 64.0 | 122.2 |
| | χ$^3$ | | −175.5 | 158.1 | | 179.9 | 171.5 | | — | — |
| | χ$^4$ | | 134.3 | 136.4 | | — | — | | — | — |
| 8 | ψ | H | 118.6 | 98.3 | H | 110.4 | 96.1 | S | 106.1 | 156.1 |
| | φ | | −116.5 | −127.3 | | −110.4 | −121.8 | | 52.8 | 46.0 |
| | χ$^1$ | | −89.7 | −108.0 | | −90.9 | −104.1 | | −45.9 | −35.5 |
| | χ$^2$ | | −73.8 | −87.9 | | −71.5 | −65.8 | | −172.3 | −174.1 |
| 7 | ψ | F | 135.7 | 113.6 | F | 129.4 | 106.7 | | — | — |
| | φ | | −68.8 | −122.4 | | −89.0 | −130.8 | | — | — |
| | χ$^1$ | | −171.6 | −147.2 | | −163.9 | −143.9 | | — | — |
| | χ$^2$ | | −96.3 | −85.8 | | −91.5 | −87.5 | | — | — |
| 6 | ψ | I | 40.3 | 57.9 | V | 61.7 | 67.9 | | — | — |
| | φ | | 40.4 | 38.5 | | 47.7 | 48.3 | | — | — |
| | χ$^1$ | | −159.7 | −165.7 | | −177.3 | −177.3 | | — | — |
| | χ$^2$ | | 87.1 | 88.3 | | — | — | | — | — |
| 5 | ψ | P | 156.0 | 164.8 | P | 149.8 | 153.3 | | — | — |
| 4 | ψ | H | 121.4 | 125.4 | H | 122.1 | 122.9 | | — | — |

TABLE 5-continued

Equilibrium variable torsional angles (in degrees) of the amino and carboxyl termini of the most stable conformations of the uncomplexed (UC) and complexed (C) NGF analogues.*

| No. | | | hNGF UC | hNGF C | | mNGF UC | mNGF C | | mNGFΔ3-9 UC | mNGFΔ3-9 C |
|---|---|---|---|---|---|---|---|---|---|---|
| | $\phi$ | | −129.2 | −133.8 | | −129.8 | −125.9 | | — | — |
| | $\chi^1$ | | −162.5 | −163.2 | | −163.3 | −161.8 | | — | — |
| | $\chi^2$ | | −69.1 | −71.9 | | −69.2 | −69.9 | | — | — |
| 3 | $\psi$ | S | 2.1 | −4.9 | T | −1.9 | −5.1 | | — | — |
| | $\phi$ | | −91.9 | −78.9 | | −84.5 | −82.3 | | — | — |
| | $\chi^1$ | | −171.8 | −172.3 | | −174.9 | −171.4 | | — | — |
| | $\chi^2$ | | −53.2 | −51.2 | | −51.2 | −52.3 | | — | — |
| 2 | $\psi$ | S | 138.5 | 135.7 | S | 139.4 | 139.4 | | — | — |
| | $\phi$ | | −128.9 | −157.5 | | −114.1 | −160.3 | | — | — |
| | $\chi^1$ | | 173.3 | 173.4 | | 169.7 | 170.3 | | — | — |
| | $\chi^2$ | | −141.9 | −133.0 | | −139.8 | −134.5 | | — | — |
| 1 | $\psi$ | S | 133.0 | 129.5 | S | 127.9 | 128.6 | | — | — |
| | $\phi$ | | 48.6 | 46.6 | | 49.4 | 53.8 | | — | — |
| | $\chi^1$ | | −43.2 | −41.9 | | −44.1 | −44.0 | | — | — |
| | $\chi^2$ | | −171.5 | −171.0 | | −172.4 | −170.9 | | — | — |
| Carboxyl terminus | | | | | | | | | | |
| 112' | $\phi$ | L | −113.3 | −113.1 | L | −113.0 | −114.1 | L | −112.4 | −113.7 |
| | $\psi$ | | 98.8 | 95.5 | | 98.7 | 99.3 | | 99.2 | 103.9 |
| | $\chi^1$ | | −72.3 | −72.1 | | −71.6 | −72.1 | | −71.6 | −72.1 |
| | $\chi^2$ | | 163.7 | 163.2 | | 163.0 | 164.1 | | 162.6 | 163.8 |
| 113' | $\phi$ | S | −83.4 | −72.5 | S | −77.2 | −70.5 | S | −77.4 | −63.0 |
| | $\psi$ | | 136.1 | 147.9 | | 146.0 | 148.6 | | 143.5 | 145.8 |
| | $\chi^1$ | | 177.0 | 179.1 | | 179.4 | −177.9 | | 176.3 | −177.0 |
| | $\chi^2$ | | 65.2 | 56.0 | | 60.6 | 56.3 | | 59.0 | 52.4 |
| 114' | $\phi$ | R | −66.7 | −101.6 | R | −71.5 | −92.5 | R | −78.0 | −92.3 |
| | $\psi$ | | −47.0 | −41.9 | | −53.7 | −43.8 | | −59.3 | −50.4 |
| | $\chi^1$ | | −99.1 | −175.3 | | −145.6 | −173.2 | | −93.4 | −167.4 |
| | $\chi^2$ | | −173.1 | −130.0 | | −179.8 | −114.8 | | −171.5 | −101.4 |
| | $\chi^3$ | | 170.4 | 159.9 | | −173.6 | 151.4 | | −172.9 | 172.3 |
| | $\chi^4$ | | 138.4 | −117.4 | | 140.3 | −139.0 | | 141.5 | −130.9 |
| 115' | $\phi$ | K | −163.2 | −155.3 | K | −162.1 | −152.2 | K | −167.1 | −161.4 |
| | $\psi$ | | 110.6 | 111.2 | | 132.0 | 111.0 | | 153.3 | 132.6 |
| | $\chi^1$ | | −139.8 | −150.7 | | −143.3 | −156.2 | | −140.1 | −144.6 |
| | $\chi^2$ | | 78.7 | −170.9 | | 81.7 | −170.0 | | 85.0 | −177.7 |
| | $\chi^3$ | | −96.4 | 177.2 | | −97.9 | −174.3 | | −95.8 | −169.3 |
| | $\chi^4$ | | 129.5 | −165.4 | | 120.9 | −173.7 | | 131.0 | 175.4 |
| | $\chi^5$ | | −39.1 | −63.2 | | −35.6 | −61.4 | | −47.7 | −53.3 |
| 116' | $\phi$ | A | −60.5 | −62.3 | A | −69.6 | −61.7 | A | −58.2 | −67.9 |
| | $\psi$ | | 47.5 | −43.9 | | −40.7 | −47.8 | | −47.5 | −40.4 |
| 117' | $\phi$ | V | −71.8 | −106.1 | T | −85.5 | −106.0 | T | −64.6 | −74.3 |
| | $\psi$ | | 112.0 | 107.0 | | 116.4 | 98.5 | | 108.2 | 107.7 |
| | $\chi^1$ | | −74.3 | −75.0 | | 53.4 | 55.1 | | 50.9 | 56.6 |
| | $\chi^2$ | | — | — | | 60.5 | 63.2 | | 58.0 | 54.0 |
| 118' | $\phi$ | R | −93.8 | −58.0 | R | −118.2 | −58.4 | R | −58.5 | −79.4 |
| | $\psi$ | | −57.9 | −53.7 | | −48.4 | −59.7 | | −37.6 | −49.6 |
| | $\chi^1$ | | −104.3 | −88.5 | | −80.9 | −84.7 | | −109.5 | −135.3 |
| | $\chi^2$ | | 79.1 | 74.4 | | 109.1 | 79.7 | | 73.3 | 108.0 |
| | $\chi^3$ | | 147.7 | 161.4 | | 116.1 | 147.5 | | −76.3 | −70.1 |
| | $\chi^4$ | | 147.0 | 119.7 | | 116.1 | 118.7 | | −87.2 | −135.3 |

*Torsional angles are designated according to the IUPAC-IUB rules (1970). Torsional angles undergoing considerable changes upon LRM-2A binding are shown in bold.

TABLE 6

Optimized conformational variables (in degrees) of hNGF-complexed LRM-2A.*

| No. | Type | $\phi$ | $\psi$ | $\chi^1$ | $\chi^2$ | $\chi^3$ | $\chi^4$ | $\chi^5$ |
|---|---|---|---|---|---|---|---|---|
| 94tA | Arg | −161.6 | −62.5 | −169.2 | −164.9 | 66.8 | 172.2 | |
| 95tA | Asn | −114.1 | 132.0 | 33.0 | −111.6 | | | |
| 96tA | Leu | −131.9 | 114.2 | −161.2 | 141.1 | | | |
| 97tA | Thr | −145.0 | 125.0 | −179.9 | −176.6 | | | |
| 98tA | Ile | −123.1 | 21.6 | 61.3 | 105.7 | | | |
| 99tA | Val | −61.2 | 107.3 | 175.7 | | | | |
| 100tA | Lys | 54.4 | 40.8 | −75.6 | 161.7 | −174.8 | 166.2 | −41.3 |
| 101tA | Ser | −97.4 | −40.0 | −176.4 | 167.7 | | | |
| 102tA | Gly | 144.4 | 46.5 | | | | | |
| 103tA | Leu | −135.6 | 155.5 | −85.0 | 90.0 | | | |
| 104tA | Arg | −81.7 | 179.3 | −33.6 | 165.0 | −52.8 | −144.7 | |
| 105tA | Phe | −68.6 | −40.8 | −159.4 | 93.3 | | | |
| 106tA | Val | −106.1 | 94.3 | 176.1 | | | | |
| 107tA | Ala | −173.5 | −54.8 | | | | | |

TABLE 6-continued

Optimized conformational variables (in degrees) of hNGF-complexed LRM-2A.*

| No. | Type | φ | ψ | $\chi^1$ | $\chi^2$ | $\chi^3$ | $\chi^4$ | $\chi^5$ |
|---|---|---|---|---|---|---|---|---|
| 108tA | Pro | | -26.2 | | | | | |
| 109tA | Asp | -85.5 | 64.7 | -116.1 | 102.8 | | | |
| 110tA | Ala | -117.5 | -57.2 | | | | | |
| 111tA | Phe | -79.4 | 135.3 | 38.4 | 89.8 | | | |
| 112tA | His | -132.1 | 78.5 | -67.1 | 89.9 | | | |
| 113tA | Phe | -120.8 | -29.0 | 54.6 | 95.4 | | | |
| 114tA | Thr | -59.9 | -56.0 | -23.4 | -176.5 | | | |
| 115tA | Pro | | -47.9 | | | | | |
| 116tA | Arg | -150.8 | 142.7 | 46.8 | 98.5 | -100.4 | 155.7 | |
| 117tA | Leu | -76.3 | -39.4 | 57.0 | 117.9 | | | |

*Torsional angles are designated according to the IUPAC-IUB rules (1970).

TABLE 7

Optimized conformational variables (in degrees) of BDNF-complexed LRM-2B.*

| No. | Type | φ | ψ | $\chi^1$ | $\chi^2$ | $\chi^3$ | $\chi^4$ | $\chi^5$ |
|---|---|---|---|---|---|---|---|---|
| 94tB | Arg | -109.3 | -54.2 | -69.7 | 169.4 | -171.6 | 119.4 | |
| 95tB | Asn | -163.6 | 141.0 | -129.4 | -109.4 | | | |
| 96tB | Leu | -81.9 | 86.5 | -92.9 | -58.2 | | | |
| 97tB | Thr | -138.3 | 143.5 | -177.9 | 169.6 | | | |
| 98tB | Ile | -136.4 | 136.6 | -164.6 | 86.9 | | | |
| 99tB | Val | -107.6 | 151.8 | -70.1 | | | | |
| 100tB | Asp | -68.8 | -72.2 | 23.6 | 95.2 | | | |
| 101tB | Ser | 36.4 | 36.0 | -156.1 | 157.6 | | | |
| 102tB | Gly | 42.0 | 44.4 | | | | | |
| 103tB | Leu | -118.2 | 149.0 | 49.9 | 87.1 | | | |
| 104tB | Lys | -92.9 | 68.5 | -147.2 | 173.5 | 91.3 | -169.5 | 45.1 |
| 105tB | Phe | 73.7 | -78.5 | -160.5 | -111.0 | | | |
| 106tB | Val | 52.6 | 19.9 | -174.2 | | | | |
| 107tB | Ala | -113.9 | 26.4 | | | | | |
| 108tB | Tyr | -58.7 | -20.3 | -46.5 | 102.7 | -74.2 | | |
| 109tB | Lys | -71.4 | -27.6 | 62.1 | -113.2 | 176.6 | 176.6 | -55.9 |
| 110tB | Ala | -91.7 | -32.6 | | | | | |
| 111tB | Phe | -63.5 | -37.4 | -168.3 | 83.6 | | | |
| 112tB | Leu | -60.3 | -43.2 | -169.7 | 91.0 | | | |
| 113tB | Lys | -61.5 | -48.0 | -78.9 | 152.7 | -167.9 | 63.2 | 22.9 |
| 114tB | Asn | -59.4 | -36.6 | -70.9 | -107.4 | | | |
| 115tB | Ser | -68.6 | -32.9 | -60.0 | 68.6 | | | |
| 116tB | Asn | -80.7 | -45.4 | -83.4 | -96.8 | | | |
| 117tB | Leu | -127.8 | -58.8 | -75.6 | 105.5 | | | |

*Torsional angles are designated according to the IUPAC-IUB rules (1970).

TABLE 8

Contributions of individual residues to intermolecular electrostatic interaction energies of the complexes BDNF/LRM-2B and NGF/LRM-2B (in kcal/mol)*.

| BDNF/LRM-2B | | NGF/LRM-2B | | Difference‡ |
|---|---|---|---|---|
| A. Binding epitopes of neurotrophins | | | | |
| $Glu^{18}$ | -61.6 | $Val^{18}$ | 0.3 | 61.9 |
| $Asp^{24}$ | -65.1 | $Asp^{24}$ | -44.9 | 20.2 |
| $Lys^{25}$ | 25.3 | Lys25 | 15.5 | -9.8 |
| $Gly^{33}$ | -11.9 | $Gly^{33}$ | -13.4 | -1.5 |
| $Thr^{35}$ | -11.4 | $Glu^{35}$ | -50.5 | -39.1 |
| $Glu^{55}$ | -50.2 | $Glu^{55}$ | -18.9 | 31.3 |
| $Lys^{57}$ | 27.1 | $Lys^{57}$ | 22.5 | -4.6 |
| $Arg^{81}$ | -32.2 | $Thr^{81}$ | 0.1 | 32.3 |
| $Gln^{81}$ | 1.2 | $His^{84}$ | 11.5 | 10.3 |
| $Arg^{104}$ | -14.3 | $Arg^{103}$ | -9.5 | 4.8 |
| $Asp^{106}$ | -39.7 | $Asp^{105}$ | -46.4 | -6.7 |
| Total | -232.8 | | -133.7 | 99.1 |
| B. Binding epitopes of the LRM-2B | | | | |
| $Arg^{94tB}$ | -40.9 | | 4.2 | 45.1 |
| $Asn^{95tB}$ | 0.2 | | -12.8 | -13.0 |
| $Asp^{100tB}$ | -42.1 | | -9.3 | 32.8 |
| $Ser^{101tB}$ | -17.9 | | -0.1 | 17.8 |
| $Gly^{102tB}$ | -1.3 | | -12.0 | -10.7 |
| $Lys^{104tB}$ | -18.5 | | -48.1 | -29.6 |
| $Lys^{109tB}$ | -46.4 | | -21.5 | 24.9 |
| $Lys^{113tB}$ | -54.6 | | -37.2 | 17.4 |
| Total | -221.5 | | -136.8 | 84.7 |

*The ±10 kcal/mol cutoff of intermolecular electrostatic interaction energy has been used to identify binding epitopes within the complexes.

‡Difference of the intermolecular electrostatic interaction energies of the given residue within the minimum-energy structures of the NGF/LRM-2B and the BDNF/LRM-2B complexes. Residues within the binding epitopes of BDNF and the LRM-2B which cause their binding specificity are bolded.

TABLE 9

Contributions of individual residues of the neurotrophins to the intermolecular interaction energy of their complexes with the common neurotrophin receptor p75$^{NTR}$ (kcal/mol)*

| NGF Res. | EL | VDW | BDNF Res. | EL | VDW | NT-3 Res. | * EL | VDW | NT-4/5 Res. | EL | VDW |
|---|---|---|---|---|---|---|---|---|---|---|---|
| D-30 | 17.9 | -0.9 | D-30 | 25.0 | -1.8 | D-29 | 24.6 | -2.6 | D-32 | 19.8 | -1.8 |
| K-32 | -94.9 | -6.0 | S-32 | 0.5 | -4.5 | R-31 | -48.2 | -8.0 | R-34 | -42.6 | -9.3 |
| K-34 | -88.8 | -3.3 | G-34 | -1.8 | -3.1 | H-33 | -35.0 | -7.1 | R-36 | -57.2 | -7.7 |
| E-35 | -10.0 | -2.2 | T-35 | 1.7 | -1.4 | Q-34 | 0.5 | -2.3 | D-37 | -0.8 | -1.7 |
| H-84 | -30.9 | -1.0 | Q-84 | 1.19 | -2.4 | Q-83 | 0.8 | -0.7 | Q-83 | 0.6 | -1.0 |
| F-86 | -0.2 | -0.3 | Y-86 | -0.5 | -0.5 | Y-85 | -13.4 | 0.3 | Y-96 | -9.2 | -0.3 |
| K-88 | -8.5 | -0.1 | R-88 | -12.7 | -0.2 | R-87 | -20.0 | -0.3 | R-98 | -16.2 | -0.2 |

TABLE 9-continued

Contributions of individual residues of the neurotrophins to the intermolecular interaction energy of their complexes with the common neurotrophin receptor p75$^{NTR}$ (kcal/mol)*

| NGF Res. | EL | BDNF VDW | Res. | EL | NT-3 VDW | Res. | EL | NT-4/5 VDW | Res. | EL | VDW |
|---|---|---|---|---|---|---|---|---|---|---|---|
| D-93 | −9.0 | −1.3 | D-93 | 13.7 | −2.2 | E-92 | 24.1 | −2.8 | D-103 | 9.0 | −2.1 |
| K-95 | −63.7 | −5.6 | K-95 | −82.9 | −7.6 | N-94 | −0.1 | −0.2 | Q-105 | −0.3 | −0.2 |
| Q-96 | −0.3 | −3.7 | K-96 | −58.2 | 2.0 | K-95 | −49.6 | −2.6 | G-106 | −0.6 | −0.6 |
| A-97 | 0.2 | −0.2 | R-97 | −79.3 | −5.7 | L-96 | −0.5 | −6.7 | R-107 | −28.0 | −11.2 |
| R-100 | −11.8 | −0.7 | R-101 | −59.2 | −1.1 | R-100 | −79.3 | 1.7 | R-111 | −57.8 | −1.9 |
| R-103 | −64.5 | 0.0 | R-104 | −64.2 | −1.6 | R-103 | −51.5 | 0.6 | R-114 | −55.3 | −2.9 |
| D-105 | 10.6 | −0.2 | D-106 | 8.3 | −0.2 | D-105 | 5.5 | −0.1 | D-116 | 4.8 | −0.1 |
| Total | −336.1 | −15.6 | | −317.8 | −18.2 | | −248.3 | −15.6 | | −237.3 | −35.0 |
| | 100% | 55% | | 99% | 39% | | 97% | 32% | | 102% | 61% |
| Net | −337.3 | −32.3 | | −321.4 | −46.7 | | −254.8 | −48.9 | | −233.0 | −57.5 |

*EL and VDW denote electrostatic and van der Waals terms of the ligand-receptor interaction energy, respectively. The ±10 kcal/mol cutoff of the intermolecular electrostatic interaction energy has been used to identify the functional epitopes (bolded). "Total" electrostatic and van der Waals contributions of the functional epitopes to the "net" values of the intermolecular interaction energy calculated over the whole binding interface are presented. Residue numbering corresponds to the general alignment of neurotrophins (Bradshaw et al, 1994).

TABLE 10

Contributions of individual residues of p75$^{NTR}$ to the intermolecular interaction energy of their complexes with neurotrophins (kcal/mol)*.

| NGF Res. | EL | BDNF VDW | Res. | EL | NT-3 VDW | Res. | EL | NT-4/5 VDW | Res. | EL | VDW |
|---|---|---|---|---|---|---|---|---|---|---|---|
| D-47 | −46.0 | 0.2 | D-47 | −67.1 | 0.1 | D-47 | −50.5 | −0.3 | D-47 | −26.7 | −4.1 |
| E-53 | −2.6 | −0.2 | E-53 | −55.4 | 1.6 | E-53 | −6.6 | −0.2 | E-53 | −3.6 | −0.1 |
| P-54 | −12.4 | −2.8 | P-54 | −13.5 | −2.5 | P-54 | −15.1 | 0.2 | P-54 | −5.3 | −0.8 |
| C-55 | −1.4 | −0.9 | C-55 | −8.4 | −1.3 | C-55 | −14.9 | −1.0 | C-55 | −3.0 | −1.2 |
| K-56 | 21.8 | −4.5 | K-56 | 13.2 | −4.8 | K-56 | 32.9 | −5.0 | K-56 | 14.8 | −5.8 |
| E-60 | −6.2 | −0.3 | E-60 | −3.0 | −0.1 | E-60 | −10.0 | −0.2 | E-60 | −10.4 | −0.4 |
| E-73 | −4.2 | 0.0 | E-73 | −9.7 | −0.2 | E-73 | −12.5 | −0.3 | E-73 | −11.2 | −0.3 |
| D-75 | −56.5 | 0.6 | D-75 | −77.1 | 0.4 | D-75 | −65.5 | −1.1 | D-75 | −59.4 | −2.7 |
| D-76 | −91.6 | −2.0 | D-76 | −22.3 | −8.4 | D-76 | −39.9 | −3.7 | D-76 | −39.3 | −5.1 |
| R-80 | −18.5 | −3.9 | R-80 | 2.9 | −2.1 | R-80 | 5.3 | −4.0 | R-80 | 3.1 | −4.3 |
| D-88 | −49.1 | 0.4 | D-88 | −39.8 | −0.4 | D-88 | −34.4 | 0.4 | D-88 | −33.1 | −1.2 |
| E-89 | −32.5 | −1.6 | E-89 | −25.2 | −6.2 | E-89 | −33.8 | −3.8 | E-89 | −33.0 | −5.9 |
| Total | −285.4 | −13.6 | | −287.2 | −20.2 | | −243.7 | −14.8 | | −198.3 | −25.5 |
| | 84% | 42% | | 89% | 43% | | 96% | 30% | | 85% | 44% |

*See footnote to Table 9.

REFERENCES

Allen, M. P., and D. J. Tildesley. 1987. Computer Simulation of Liquids. Claredon Press: Oxford.

Baldwin, A. N., and E. M. Shooter. 1994. *J. Biol. Chem.* 269:11456–11461.

Baldwin, A. N., and E. M. Shooter. 1995. *J. Biol. Chem.* 270:4594–4602.

Banner, D. W., A. D'Arcy, W. Janes, R. Gentz, H.-J. Schoenfeld, C. Broger, H. Loetscher, and W. Lesslauer. 1993. *Cell* 73:431–445.

Barbacid, M. 1993. *Oncogene* 8:2033–2042.

Barbacid, M. 1994. *J. Neurobiol.* 25:1386–1403.

Barde, Y.-A. 1989. *Neuron* 2:1525–1534.

Barker, P. A., and E. M. Shooter. 1994. *Neuron* 13:203–215.

Baumann, U.; Wu, S.; Flaherty, K. M.; McKay, D. B. 1993. *EMBO J.* 12: 3357–3364.

Ben Ari, Y.; Represa, A. 1990. *TINS* 13: 312–318.

Benedetti, M., A. Levi, and M. V. Chao. 1993. *Proc. Natl. Acad. Sci. U.S.A.* 90:7859–7863.

Berkemeier, L., J. Winslow, D. Kaplan, K. Nicolics, D. Goeddel, and A. Rosenthal. 1991. *Neuron* 7:857–866.

Bothwell, M. A. 1991. *Cell* 65:915–918.

Bothwell, M. A., Shooter, E. M. 1977. *J. Biol. Chem.* 23: 8532–8536.

Bradshaw, R. A., J. Murray-Rust, C. F. Ibáñez, N. Q. McDonald, R. Lapatto, and T. L. Blundell. 1994. *Protein Science* 3:1901–1913.

Brooks, B. R., R. E. Bruccoleri, B. D. Olason, D. J. States, S. Swaminathan, and M. Karplus. 1983. *J. Comput. Chem.* 4:187–217.

Brooks III, C. L., and D. A. Case, 1993. *Chem. Rev.* 93:2487–2502.

Brünger, A. T. 1988. *J. Mol. Biol.* 203:803–816.

Burton, L. E., C. H. Schmelzer, E. Szönyi, C. Yedinak, and A. Gorrell. 1992. *J. Neurochem.* 59:1937–1945.

Burton, G., C. Schmelzer, M. Sadic, F. Hefti, and J. Treanor. 1995. *Soc. Neurosci. Abs.* 21:1061.

Carter, B. D., C. Kaltschmidt, B. Kaltschmidt, N. Offenhäuser, R. Böhm-Matthaei, P. A. Baeuerle, and Y.-A. Barde. 1996. *Science* 272:542–545.

Cassacia-Bonnefil, P., B. D. Carter, R. T. Dobrowsky, and M. V. Chao. 1996. *Nature* 383:716–719.

Chang, G., W. C. Guida, and W. C. Still. 1989. *J. Am. Chem. Soc.* 111:4379–4386.

Chao, M. V. 1992a. *Cell* 68:995–997.

Chao, M. V. 1992b. *Neuron* 9:583–593.

Chao, M. 1994. *J. Neurobiol.* 25:1373–1385.

Chao, M. V., and B. L. Hempstead. 1995. *Trends Neurosci.* 18:321–326.

Clackson, T., and J. A. Wells. 1995. *Science* 267:383–386.

Clary, D. O., and L. F. Reichardt. 1994. *Proc. Natl. Acad. Sci. U.S.A.* 91:11133–11137.

Davies, A. M. 1994. *J. Neurobiol.* 25:1334–1348.

Dobrowsky, R., M. H. Werner, A. M. Castellino, M. V. Chao, and Y. A. Hannun. 1994. *Science* 265:1596–1599.

Drinkwater, C. C., P. A. Barker, U. Suter, and E. M. Shooter. 1993. *J. Biol. Chem.* 268:23202–23207.

Escandon, E., L. E. Burton, E. Szonyi, and K. J. Nikolics. 1993. *Neurosci. Res.* 34:601–613.

Frade, J. M., A. Rodrigues-Tebar, Y.-A. Barde. 1996. *Nature* 383:166–168.

Gibson, K. D., and H. A Scheraga. 1988. *In Structure and Expression: Vol.* 1. *From Proteins to Ribosomes;* Sarma, M. H., Sarma, R. H., Eds.; Adenine Press: Guilderland, N.Y., pp. 67–94.

Gidas, B. 1985. *J. Stat. Phys.* 39: 73–131.

Glass, D.; Nye, S.; Hantzopoulos, P.; Macchi, M.; Squinto, S.; Goldfarb, M.; Yancopoulos, G. 1991. *Cell* 66: 405–413.

Gotz, R.; Koster, R.; Winkler, C.; Raulf, F.; Lottspeich, F.; Schard, M.; Thoenen, H. 1994. *Nature* 372: 266–269.

Gregory, D. S., A. C. R. Martin, J. C. Cheetham, and A. R. Rees. 1993. *Protein Engineenng* 6:29–35.

Gunningham, G. W.; Meijer, P. H. E. 1976. *J. Comp. Phys.* 20: 50–63.

Hallböök, F., C. F. Ibáñez, and H. Persson. 1991. *Neuron* 6:845–858.

Hefti, F. H. 1986. *J. Neurosci.* 6:2155–2162.

Hefti, F. H., and Weiner, W. J. 1986. *Annals of Neurology* 20:275–281.

Heldin, C. H., A. Emlund, C. Rorsman, and L. Rönnstrand. 1989. *J. Biol. Chem.* 264:8905–8912.

Hempstead, B. L., D. Martin-Zanca, D. L. Kaplan, L. F. Parada, and M. V. Chao. 1991. *Nature* 350:678–683.

Herrmann, J. L., D. G. Menter, J. Hamada, D. Marchetti, M. Nakajima, and G. L. Nicolson. 1993. *Mol. Biol.* 4:1205–1216.

Hobza, P., H. L. Selzle, and E. W. Schlag. 1994. *J. Am. Chem. Soc.* 116:3500–3506.

Hodes, Z. I., G. Némethy, and H. A. Scheraga. 1979. *Biopolymers* 18:1565–1610.

Hohn, A.; Leibrock, J.; Bailey, K.; Barde, Y.-A. 1990. *Nature* 344: 339–341.

Hopfinger, A. J. 1973. Conformational Properties of Macromolecules. Academic Press, New York-London. pp. 70–85.

Hunter, C. A., and J. K. M. Sanders. 1990. *J. Am. Chem. Soc.* 112:5525–5534.

Hunter, C. A., J. Singh, and J. M. Thornton. 1991. *J. Mol. Biol.* 218:837–846.

Ibáñez, C. F., T. Ebendal, and H. Persson. 1991. *EMBO J.* 10:2105–2110.

Ibáñez, C. F., T. Ebendal, G. Barbany, J. Murray-Rust, T. L. Blundell, and H. Persson. 1992. *Cell* 69:329–341.

Ibáñez, C. F., L. Ilag, J. Murray-Rust, and H. Persson. 1993. *EMBO J.* 12:2281–2293.

Ibáñez, C. F. 1994. *J. Neurobiol.* 25:1349–1361.

Ibáñez, C. F. 1995. *Trends Biotech.* 13:217–227.

Ilag, L. L., P. Lönnerberg, H. Persson, and C. F. Ibáñez. 1994. *J. Biol. Chem.* 269:19941–19946.

IUPAC-IUB Commission on Biochemical Nomenclature. 1970. *Biochemistry* 9:3471–3479.

Jing, S. Q., P. Tapley, and M. Barbacid. 1992. *Neuron* 9:1067–1079.

Johnson, D., A. Lanahan, C. R. Buck, A. Sehgal, C. Morgan, E. Mercer, M. Bothwell, and M. Chao. 1986. *Cell* 47:545–554.

Judson, R. S.; Jaeger, E. P.; Treasurywala, A. M. 1994. *J. Mol. Struct. (Theochem)* 308: 191–206.

Kahle, P., L. E. Burton, C. H. Schmeizer, and C. Hertel. 1992. *J Biol. Chem.* 267:22707–22710.

Kaplan, D. R.; Hempstead, B. L.; Martin-Zanca, D.; Chao, M. V.; Parada, L. F. 1991. *Science* 252: 554–558.

Kaplan, D. R., and R. M. Stephens. 1994. *J. Neurobiol.* 25:1404–1417.

Kincaid, R. H.; Scheraga, H. A. 1982. *J. Comput. Chem.* 3: 525–547.

Kirkpatrick, S., C. D. Gelatt, Jr., and M. P. Vecchi. 1983. *Science* 220:671–680.

Klein, R.; Jing, S.; Nanduri, V.; O'Rourke, E.; Barbacid, M. 1991. *Cell* 65: 189–197.

Klein, R.; Lamballe, F.; Bryant, S.; Barbacid, M. 1992. *Neuron* 8: 947–956.

Kobe, B., and J. Deisenhofer. 1993. *Nature* 366:751–756.

Kobe, B., and J. Deisenhofer. 1994. *Trends Biochem. Sci.* 19:415–421.

Kobe, B., and J. Deisenhofer. 1995. *Nature* 374:183–186.

Korsching, S. 1993. *J. Neurosci.* 13:2739–2748.

Krüttgen, A., J. V. Heymach, P. Kahle, and E. M. Shooter. 1996. *Soc. Neurosci. Abs.* 22:557.

Kullander, K., and T. Ebendal. 1994. *J Neurosci. Res.* 39:195–210.

Kullander, K., and T. Ebendal. 1996. *Soc. Neurosci. Abs.* 22:557.

Kushner, H. J. 1987. *SIAM J. Appl. Math.* 47: 169–185.

Lai, K.-O., D. J. Glass, D. Geis, G. D. Yancopoulos, and N. Y. Ip. 1996. *J. Neurosci. Res.* 46:618–629.

Lamballe, F.; Klein, R.; Barbacid, M. 1991. *Cell* 66: 967–970.

Landreth, G. E., and E. M. Shooter. 1980. *Proc. Natl. Acad. Sci. U.S.A.* 77: 4751–4755.

Large, T. H., G. Weskamp, J. C. Helder, M. J. Radeke, T. P. Misko, E. M. Shooter, and L. F. Reichardt. 1989. *Neuron* 2:1123–1134.

Leibrock, J.; Lottspeich, A. H.; Hohn, A.; Hofer, M.; Hengerer, B.; Masiakowski, P.; Thoenen, H.; Barde, Y.-A. 1989. *Nature* 341: 149–152.

Lelj, F.; Grimaldi, P.; Cristianziano, P. L. 1991. *Biopolymers* 31: 663–670.

Leven, G. R.; Mendel, L. M. 1993. *TINS* 16: 353–359.

Levi-Montalcini, R. 1987. *EMBO J.* 6:1145–1154.

Li, Z.; Scheraga, H. A. 1988. *J. Mol Struct.* (*Theochem*) 179: 333–352.

Livnah, O., E. A. Stura, D. L. Johnson, S. A. Middleton, L. S. Mulcahy, N. C. Wrighton, W. J. Dower, L. K. Jolliffe, and I. A. Wilson. 1996. *Science* 273:464–471.

Loeb, D. M.; Maragos, J.; Martin-Zanca, D.; Chao, M. V.; Parada, L. F.; Greene, L. A. 1991. *Cell* 66: 961–966.

Luo, Y., and K. E. Neet. 1992. *J. Biol. Chem.* 267:12275–12283.

MacDonald, J. I. S., and S. O. Meakin. 1996. *Mol. Cell. Neurosci.* 7:371–390.

Mahadeo, D., L. Kaplan, M. V. Chao, and B. L. Hempstead. 1994. *J. Biol. Chem.* 269:6884–6891.

Maisopierre, P. C.; Belluscio, L. S. S.; Squinto, S.; Ip, N.Y.; Furth, M. E.; Lindsay, R. M.; Yancopoulos, G. D. 1990. *Science* 247: 1446–1451.

Maness, L. M., A. J. Kastin, J. T. Weber, W. A. Banks, B. S. Beckman, and J. E. Zadina. 1994. *Neurosci. Biobehav. Rev.* 18:143–159.

Marchetti, D., McQuillan, D. J., W. C. Spohn, D. D. Carson, and G. L. Nicolson. 1996. *Cancer Res.* 56:2856–2863.

Matsumoto, K., R. K. Wada, J. M. Yamashiro, D. R. Kaplan, and C. J. Thiele. 1995. *Cancer Res.* 55:1798–1806.

McDonald, N. Q., R. Lapatto, J. Murray-Rust, J. Gunning, A. Wlodawer, and T. L. Blundell. 1991. *Nature* 354:411–414.

McKee, A. C.; Kosik, K. S.; Kowal, N. W. 1991. *Ann. Neurol.* 30:156.

McMahon, S. B.; Bennett, D. L. H.; Priestley, J. V.; Shelton, D. L. 1995. *Nature Med.* 1: 774–780.

Meakin, S. O., and E. M. Shooter. 1992. *Trends Neurosci.* 15:323–331.

Merrell, R., M. W. Pulliam, L. Randono, L. F. Boyd, R. A. Bradshaw, and L. Glaser. 1975. *Proc. Natl. Acad. Sci. U.S.A.* 72:4270–4274.

Metropolis, N.; Rosenbluth, A. W.; Rosenbluth, M. N.; Teller, A. H.; Teller, E. 1953. *J. Chem. Phys.* 21: 1087–1092.

Moore, J. B., and E. M. Shooter. 1975. *Neurobiology* 5:369–381.

Morgan et al. 1989. In Annual Reports in Medicinal Chemistry. Ed.: Vinick, F. J. Academic Press, San Diego, Calif., pp.243–252.

Nayeem, A.; Vila, J.; Scheraga, H. A. 1991. *J. Comput. Chem.* 12: 594–605.

Nilges, M.; G. M. Clore, and A. M. Gronenborn. 1988. *FEBS Lett.* 229:317–324.

Paine, G. H.; Scheraga, H. A. 1985. *Biopolymers* 24:1391–1436.

Pérez, P., P. M. Coll, B. L. Hempstead, D. Martin-Zanca, and M. V. Chao. 1995. *Mol. Cell. Neurosci.* 6:97–105.

Persson, H., and C. F. Ibáñez. 1993. *Curr. Opin. Neurol. Neurosurg.* 6:11–18.

Piela, L.; Kostrowicki, J.; Scheraga, H. A. 1989. *J. Phys. Chem.* 93: 3339–3346.

Piela, L.; Olszewski, K. A.; Pillardy, J. 1994. *J. Mol. Struct.* (*Theochem*) 308: 229–239.

Ponnuswamy, P. K., and P. Manavalan. 1976. *J. Theor. Biol.* 60:481–486.

Purves, D. 1988. Body and Brain. A Trophic Theory of Neural Connectors. Cambridge, Mass.: Harvard University Press, pp. 1–1231.

Radeke, M. J., T. P. Misko, C. Hsu, L. A. Herzenberg, and E. M. Shooter. 1987. *Nature* 325:593–597.

Radziejewski, C., and R. C. Robinson. 1993. *Biochemistry* 32:13350–13356.

Radziejewski, C.; Robinson, R. C.; DiStefano, P. S.; Taylor, J. W. 1992. *Biochemistry* 31: 4431–4436.

Raj, N.; Morley, S. D.; Jackson, D. E. 1994. *J. Mol. Struct.* (*Theochem*) 308: 175–190.

Rao, M.; Pangali, C.; Berne, B. J. 1979. *Mol. Phys.* 37: 1773–1798.

Rashid, K.; van der Zee, C. E. E. M.; Ross, G. M.; Chapman, C. A.; Stanisz, J.; Riopelle, R. J.;

Racine, R. J.; Fahnestock, M. 1995. *Proc. Natl. Acad. Sci. U.S.A.* 92: 9495–9499.

Ripoll, D. R.; Scheraga, H. A. 1988. *Biopolymers* 27: 283–1303.

Robinson, R. C., C. Radziejewski, D. I. Stuart, and E. Y. Jones. 1995. *Biochemistry* 34:4139–4146.

Rodrigues-Tébar, A., G. Dechant, and Y.-A. Barde. 1990. *Neuron* 4:487–492.

Rodnigues-Tébar, A., G. Dechant, R. Gotz, and Y.-A. Barde. 1992. *EMBO J.* 11:917–922.

Rosenthal, A.; Goeddel, D. V.; Nguyen, T.; Lewis, M.; Shih, A.; Laramee, G. R.; Nikolics, K.; Winslow, J. W. 1990. *Neuron* 4: 767–773.

Ross, A. H., M.-C. Daou, C. A. McKinnon, P. J. Condon, M. B. Lachyankar, R. M. Stephens, D. R. Kaplan, and D. E. Wolf. 1996. *J. Cell Biol.* 132:945–953.

Ross, G. M., I. L. Shamovsky, G. Lawrance, M. Solc, S. M. Dostaler, S. L. Jimmo, D. F. Weaver, and R. J. Riopelle. 1997. *Nature Med.* 3:872–878.

Rossky, P. J.; Doll, J. D.; Friedman, H. L. 1978. *J. Chem. Phys.* 69: 4628–4633.

Rovelli, G.; Heller, R. A.; Canossa, M.; Shooter, E. M. 1993. *Proc. Natl. Acad. Sci. USA* 90:8717–8721.

Ryckaert, J.-P., Ciccotti, G.; Berendsen, H. J. C. 1977. *J. Comput. Phys.* 23:327–341.

Rydén, M., J. Murray-Rust, D. Glass, L. L. Ilag, M. Trupp, G. D. Yancopoulos, N. Q. McDonald, and C. F. Ibáñez. 1995. *EMBO J.* 14:1979–1990.

Rydén, M., and C. F. Ibáñez, C. F. 1996. *J. Biol. Chem.* 271:5623–5627.

Schauer, M., and E. R. Bernstein. 1985. *J. Chem. Phys.* 82:3722–3727.

Schechter, A. L., and M. A. Bothwell. 1981. *Cell* 24:867–874.

Scheraga, H. A. 1989. *Prog. Clin. Biol. Res.* 289: 3–18.

Scheraga, H. A. 1994. *Pol. J. Chem.* 68: 889–891.

Schmelzer, C. H., L. E. Burton, W.-P. Chan, E. Martin, C. Gorman, E. Canova-Davis, V. T. Ling, M. B. Sliwkowski, G. McCray, J. A. Briggs, T. H. Nguyen, and G. Polastri. 1992. *J. Neurochem.* 59:1675–1683.

Schneider, R., E. Schneider-Scherzer, M. Thurnher, B. Auer, and M. Schweiger. 1988. *EMBO J.* 7:4151–4156.

Schneider, R., and M. Schweiger. 1991. *Oncogene* 6:1807–1811.

Shamovsky, I. L.; Yarovskaya, I. Yu.; Khrapova, N. G.; Burlakova, E. B. 1992. *J. Mol. Struct. (Theochem)* 253: 149–159.

Shamovsky, I. L., G. M. Ross, R. J. Riopelle, and D. F. Weaver. 1996. *J. Am. Chem. Soc.* 118:9743–9749.

Shih, A., G. R. Laramee, C. H. Schmeizer, L. E. Burton, and J. W. Winslow. 1994. *J. Biol. Chem.* 269:27679–27686.

Simon, I.; Nemethy, G.; Scheraga, H. A. 1978. *Macromolecules* 11: 797–804.

Snider, W. D., and E. M. Johnson. 1989. *Ann. Neurol.* 26:489–506.

Snow, M. E. 1992. *J. Comput. Chem.* 13: 579–584.

Soppet, D.; Escandon, E.; Maragos, J.; Middlemas, D. S.; Reid, S. W.; Blair, J.; Burton, L. E.;

Stanton, B.; Kaplan, D. R.; Hunter, T.; Nikolics, K.; Parada, L. F. 1991. *Cell* 65: 895–903.

Squinto, S. P.; Stitt, T. N.; Aldrich, T. H.; Davis, S.; Bianco, S. M.; Radziejewski, C.; Glass, D. J.; Masiakowski, P.; Furth, M. E.; Valenzuela, D. M.; DiStefano, P. S.; Yancopoulos, G. D. 1991. *Cell* 65: 885–893.

Suter, U., C. Angst, C.-L. Tien, C. C. Drinkwater, R. M. Lindsay, and E. M. Shooter. 1992. *J. Neurosci.* 12:306–318.

Sutter, A., R. J. Riopelle, R. M. Harris-Warrick, and E. M. Shooter. 1979. *J. Bio. Chem.* 254:5972–5982.

Szentpsly, L. V.; Shamovsky, I. L.; Nefedova, V. V.; Zubkus, V. E. 1994. *J. Mol. Struct. (Theochem)* 308: 125–140.

Taylor, R. A. V., J. F. Kerrigan, F. M. Longo, M. deBoisblanc, and W. C. Mobley. 1991. *Soc. Neurosci. Abs.* 17: 712.

Thoenen, H. 1991. *Trends Neurosci.* 14: 165–170.

Treanor, J. J. S., C. Schmeizer, B. Knusel, J. W. Winslow, D. L. Shelton, F. Hefti, K. Nikolics, and L. E. Burton. 1995. *J. Biol. Chem.* 270: 23104–23110.

Ullrich, A., and J. Schlessinger. 1990. *Cell* 61: 203–212.

Urfer, R., P. Tsoulfas, D. Soppet, E. Escandón, L. F. Parada, and L. G. Presta. 1994. *EMBO J.* 13:5896–5909.

Urfer, R., P. Tsoulfas, L. O'Connell, D. L. Shelton, L. F. Parada, and L. G. Presta. 1995. *EMBO J.* 14:2795–2805.

Vale, R. D.; Shooter, E. M. 1985. *Methods Enzymol.* 109: 21–39.

Vanderbilt, D., and S. G. Louie. 1984. *J. Comput. Phys.* 56:259–271.

Van der Zee, C. E. E., G. M. Ross, R. J. Riopelle, and T. Hagg. 1996. *Science* 274: 1729–1732.

Villani, V.; Tamburro, A. M. 1994. *J. Mol. Struct. (Theochem)* 308: 141–157.

Warme, P. K., and R. S. Morgan. 1978. *J. Mol. Biol.* 118: 289–304.

Washiyama, K., Y. Muragaki, L. B. Rorke, V. M.-Y. Lee, S. C. Feinstein, M. J. Radeke, D. Blumberg, D. R. Kaplan, and J. Q. Trojanowski. 1996. *Amer. J. Path.* 148:929–940.

Weiner, S. J., P. A. Kollman, D. A. Case, U. C. Singh, C. Ghio, G. Alagona, S. Profeta Jr., and P. Weiner. 1984. *J. Am. Chem. Soc.* 106:765–784.

Weskamp, G.; Reichardt, L. F. 1991. *Neuron* 6: 649–663.

Wilson, C., and S. Doniach. 1989. *Proteins* 6:193–209.

Wilson, S. R., W. Cui, J. W. Moscowitz, and K. E. Schmidt. 1988. *Tetrahedron Lett.* 29:4373–4376.

Windisch, J. M., B. Auer, R. Marksteiner, M. E. Lang, and R. Schneider. 1995a. *FEBS Lett.* 374:125–129.

Windisch, J. M., R. Marksteiner, and R. Schneider. 1995b. *J. Biol. Chem.* 270: 28133–28138.

Windisch, J. M., R. Marksteiner, M. E. Lang, B. Auer, and R. Schneider. 1995c. *Biochemistry* 34:11256–11263.

Wolf, D. E., C. A. McKinnon, M.-C. Daou, R. M. Stephens, D. R. Kaplan, and A. H. Ross. 1995. *J. Biol. Chem.* 270:2133–2138.

Woo, S. B., D. E. Timm, and K. E. Neet. 1995. *J Biol. Chem.* 270:6278–6285.

Woo, S. B., and K. E. Neet. 1996. *J Biol. Chem.* 271:24433–24441.

Woolf, C. J.; Doubell, T. A. 1994. *Current Opinions in Neurobiol.* 4: 525–534.

Yan, H., and M. V. Chao. 1991. *J. Biol. Chem.* 266:12099–12104.

Yoder, M. D.; Keen, N. T.; Jurnak, F. 1993. *Science* 260: 1503–1507.

Appendix 1. Geometry of the LRM-2A in PDB format.*

REMARK 1 The bioactive conformation of the second LRM of TrkA.
REMARK 2    HSC stands for charged HIS
REMARK 3
ATOM      1 N   LEU S  93      19.399 -23.034 -15.306  1.00 -0.45
ATOM      2 CA  LEU S  93      18.757 -22.140 -14.332  1.00 -0.07
ATOM      3 C   LEU S  93      19.555 -20.869 -14.130  1.00  0.53
ATOM      4 O   LEU S  93      20.777 -20.864 -14.044  1.00 -0.50
ATOM      5 CB  LEU S  93      18.635 -22.886 -13.002  1.00  0.02
ATOM      6 CG  LEU S  93      17.661 -22.206 -12.037  1.00  0.05
ATOM      7 CD1 LEU S  93      16.251 -22.083 -12.617  1.00 -0.01
ATOM      8 CD2 LEU S  93      17.517 -22.968 -10.718  1.00 -0.01
ATOM      9 1H  LEU S  93      19.651 -23.930 -14.841  1.00  0.15
ATOM     10 2H  LEU S  93      18.742 -23.223 -16.089  1.00  0.15
ATOM     11 3H  LEU S  93      20.260 -22.582 -15.677  1.00  0.15
ATOM     12 N   ARG S  94      18.551 -20.159 -13.624  1.00 -0.52
ATOM     13 CA  ARG S  94      18.777 -19.044 -12.708  1.00  0.24
ATOM     14 C   ARG S  94      17.460 -18.800 -12.010  1.00  0.53
ATOM     15 O   ARG S  94      17.364 -18.941 -10.781  1.00 -0.50
ATOM     16 CB  ARG S  94      19.316 -17.812 -13.451  1.00  0.05
ATOM     17 CG  ARG S  94      19.818 -16.700 -12.515  1.00  0.06
ATOM     18 CD  ARG S  94      20.009 -15.345 -13.215  1.00  0.11
ATOM     19 NE  ARG S  94      18.720 -14.803 -13.642  1.00 -0.49
ATOM     20 CZ  ARG S  94      18.631 -13.550 -14.138  1.00  0.81
ATOM     21 NH1 ARG S  94      19.703 -12.767 -14.256  1.00 -0.63
ATOM     22 NH2 ARG S  94      17.444 -13.087 -14.518  1.00 -0.63
ATOM     23 H   ARG S  94      17.611 -20.389 -13.873  1.00  0.25
ATOM     24 HE  ARG S  94      17.892 -15.358 -13.571  1.00  0.29
ATOM     25 1HH1 ARG S  94     19.604 -11.843 -14.627  1.00  0.36
ATOM     26 2HH1 ARG S  94     20.606 -13.094 -13.977  1.00  0.36
ATOM     27 1HH2 ARG S  94     17.363 -12.161 -14.887  1.00  0.36
ATOM     28 2HH2 ARG S  94     16.633 -13.666 -14.434  1.00  0.36
ATOM     29 N   ASN S  95      16.446 -18.435 -12.789  1.00 -0.52

| | | | | | | |
|---|---|---|---|---|---|---|
| ATOM | 30 | CA ASN S 95 | 15.116 | -18.165 | -12.251 | 1.00 0.22 |
| ATOM | 31 | C ASN S 95 | 14.111 | -19.178 | -12.745 | 1.00 0.53 |
| ATOM | 32 | O ASN S 95 | 14.047 | -19.466 | -13.950 | 1.00 -0.50 |
| ATOM | 33 | CB ASN S 95 | 14.629 | -16.742 | -12.566 | 1.00 0.00 |
| ATOM | 34 | CG ASN S 95 | 15.171 | -16.300 | -13.911 | 1.00 0.68 |
| ATOM | 35 | OD1 ASN S 95 | 16.007 | -15.410 | -13.997 | 1.00 -0.47 |
| ATOM | 36 | ND2 ASN S 95 | 14.657 | -16.965 | -14.959 | 1.00 -0.87 |
| ATOM | 37 | H ASN S 95 | 16.591 | -18.340 | -13.774 | 1.00 0.25 |
| ATOM | 38 | 1HD2 ASN S 95 | 14.948 | -16.750 | -15.892 | 1.00 0.34 |
| ATOM | 39 | 2HD2 ASN S 95 | 13.976 | -17.684 | -14.820 | 1.00 0.34 |
| ATOM | 40 | N LEU S 96 | 13.325 | -19.720 | -11.819 | 1.00 -0.52 |
| ATOM | 41 | CA LEU S 96 | 12.308 | -20.713 | -12.151 | 1.00 0.20 |
| ATOM | 42 | C LEU S 96 | 11.023 | -20.296 | -11.479 | 1.00 0.53 |
| ATOM | 43 | O LEU S 96 | 10.934 | -20.287 | -10.242 | 1.00 -0.50 |
| ATOM | 44 | CB LEU S 96 | 12.767 | -22.109 | -11.701 | 1.00 0.02 |
| ATOM | 45 | CG LEU S 96 | 12.022 | -23.268 | -12.383 | 1.00 0.05 |
| ATOM | 46 | CD1 LEU S 96 | 12.921 | -24.464 | -12.732 | 1.00 -0.01 |
| ATOM | 47 | CD2 LEU S 96 | 10.797 | -23.704 | -11.562 | 1.00 -0.01 |
| ATOM | 48 | H LEU S 96 | 13.428 | -19.444 | -10.863 | 1.00 0.25 |
| ATOM | 49 | N THR S 97 | 10.026 | -19.951 | -12.289 | 1.00 -0.52 |
| ATOM | 50 | CA THR S 97 | 8.726 | -19.526 | -11.778 | 1.00 0.27 |
| ATOM | 51 | C THR S 97 | 7.604 | -19.988 | -12.678 | 1.00 0.53 |
| ATOM | 52 | O THR S 97 | 7.607 | -19.702 | -13.884 | 1.00 -0.50 |
| ATOM | 53 | CB THR S 97 | 8.692 | -18.000 | -11.598 | 1.00 0.21 |
| ATOM | 54 | OG1 THR S 97 | 7.420 | -17.594 | -11.097 | 1.00 -0.55 |
| ATOM | 55 | CG2 THR S 97 | 9.014 | -17.248 | -12.899 | 1.00 0.01 |
| ATOM | 56 | H THR S 97 | 10.163 | -19.980 | -13.279 | 1.00 0.25 |
| ATOM | 57 | HG1 THR S 97 | 7.431 | -16.635 | -11.053 | 1.00 0.31 |
| ATOM | 58 | N ILE S 98 | 6.645 | -20.701 | -12.095 | 1.00 -0.52 |
| ATOM | 59 | CA ILE S 98 | 5.499 | -21.213 | -12.841 | 1.00 0.20 |
| ATOM | 60 | C ILE S 98 | 4.166 | -20.765 | -12.292 | 1.00 0.53 |
| ATOM | 61 | O ILE S 98 | 3.134 | -21.406 | -12.544 | 1.00 -0.50 |
| ATOM | 62 | CB ILE S 98 | 5.633 | -22.735 | -13.006 | 1.00 0.03 |
| ATOM | 63 | CG1 ILE S 98 | 5.655 | -23.480 | -11.662 | 1.00 0.02 |

| | | | | |
|---|---|---|---|---|
| ATOM | 64 | CG2 ILE S 98 | 6.841 -23.109 -13.880 | 1.00 0.00 |
| ATOM | 65 | CD1 ILE S 98 | 4.338 -24.216 -11.369 | 1.00 0.00 |
| ATOM | 66 | H ILE S 98 | 6.703 -20.897 -11.116 | 1.00 0.25 |
| ATOM | 67 | N VAL S 99 | 4.183 -19.667 -11.541 | 1.00 -0.52 |
| ATOM | 68 | CA VAL S 99 | 2.969 -19.119 -10.945 | 1.00 0.20 |
| ATOM | 69 | C VAL S 99 | 1.976 -18.727 -12.013 | 1.00 0.53 |
| ATOM | 70 | O VAL S 99 | 2.172 -17.725 -12.717 | 1.00 -0.50 |
| ATOM | 71 | CB VAL S 99 | 3.389 -17.945 -10.045 | 1.00 0.03 |
| ATOM | 72 | CG1 VAL S 99 | 2.188 -17.207 -9.432 | 1.00 0.01 |
| ATOM | 73 | CG2 VAL S 99 | 4.444 -18.324 -8.993 | 1.00 0.01 |
| ATOM | 74 | H VAL S 99 | 5.050 -19.197 -11.376 | 1.00 0.25 |
| ATOM | 75 | N LYS S 100 | 0.911 -19.514 -12.136 | 1.00 -0.52 |
| ATOM | 76 | CA LYS S 100 | -0.131 -19.257 -13.126 | 1.00 0.23 |
| ATOM | 77 | C LYS S 100 | 0.517 -19.154 -14.486 | 1.00 0.53 |
| ATOM | 78 | O LYS S 100 | 0.146 -18.291 -15.296 | 1.00 -0.50 |
| ATOM | 79 | CB LYS S 100 | -0.916 -17.989 -12.753 | 1.00 0.04 |
| ATOM | 80 | CG LYS S 100 | -1.911 -18.178 -11.597 | 1.00 0.05 |
| ATOM | 81 | CD LYS S 100 | -2.337 -16.845 -10.961 | 1.00 0.05 |
| ATOM | 82 | CE LYS S 100 | -3.230 -17.043 -9.726 | 1.00 0.22 |
| ATOM | 83 | NZ LYS S 100 | -3.328 -15.780 -8.983 | 1.00 -0.27 |
| ATOM | 84 | H LYS S 100 | 0.814 -20.308 -11.536 | 1.00 0.25 |
| ATOM | 85 | 1HZ LYS S 100 | -2.395 -15.321 -8.953 | 1.00 0.31 |
| ATOM | 86 | 2HZ LYS S 100 | -3.649 -15.972 -8.012 | 1.00 0.31 |
| ATOM | 87 | 3HZ LYS S 100 | -4.008 -15.150 -9.454 | 1.00 0.31 |
| ATOM | 88 | N SER S 101 | 1.485 -20.030 -14.739 | 1.00 -0.52 |
| ATOM | 89 | CA SER S 101 | 2.199 -20.048 -16.012 | 1.00 0.36 |
| ATOM | 90 | C SER S 101 | 1.652 -21.075 -16.974 | 1.00 0.53 |
| ATOM | 91 | O SER S 101 | 1.546 -20.813 -18.182 | 1.00 -0.50 |
| ATOM | 92 | CB SER S 101 | 3.695 -20.297 -15.758 | 1.00 0.19 |
| ATOM | 93 | OG SER S 101 | 4.426 -20.237 -16.981 | 1.00 -0.55 |
| ATOM | 94 | H SER S 101 | 1.736 -20.701 -14.041 | 1.00 0.25 |
| ATOM | 95 | HG SER S 101 | 5.354 -20.203 -16.738 | 1.00 0.31 |
| ATOM | 96 | N GLY S 102 | 1.302 -22.243 -16.444 | 1.00 -0.52 |
| ATOM | 97 | CA GLY S 102 | 0.758 -23.329 -17.254 | 1.00 0.25 |

| | | | | | |
|---|---|---|---|---|---|
| ATOM | 98 | C | GLY S 102 | 1.148 -24.732 -16.854 | 1.00 0.53 |
| ATOM | 99 | O | GLY S 102 | 1.526 -25.548 -17.708 | 1.00 -0.50 |
| ATOM | 100 | H | GLY S 102 | 1.413 -22.390 -15.461 | 1.00 0.25 |
| ATOM | 101 | N | LEU S 103 | 1.058 -25.015 -15.558 | 1.00 -0.52 |
| ATOM | 102 | CA | LEU S 103 | 1.402 -26.331 -15.027 | 1.00 0.20 |
| ATOM | 103 | C | LEU S 103 | 0.326 -26.726 -14.045 | 1.00 0.53 |
| ATOM | 104 | O | LEU S 103 | -0.356 -25.860 -13.476 | 1.00 -0.50 |
| ATOM | 105 | CB | LEU S 103 | 2.792 -26.289 -14.372 | 1.00 0.02 |
| ATOM | 106 | CG | LEU S 103 | 3.957 -26.492 -15.354 | 1.00 0.05 |
| ATOM | 107 | CD1 | LEU S 103 | 4.502 -25.183 -15.949 | 1.00 -0.01 |
| ATOM | 108 | CD2 | LEU S 103 | 5.078 -27.333 -14.723 | 1.00 -0.01 |
| ATOM | 109 | H | LEU S 103 | 0.745 -24.311 -14.920 | 1.00 0.25 |
| ATOM | 110 | N | ARG S 104 | 0.170 -28.031 -13.843 | 1.00 -0.52 |
| ATOM | 111 | CA | ARG S 104 | -0.832 -28.558 -12.921 | 1.00 0.24 |
| ATOM | 112 | C | ARG S 104 | -0.225 -28.464 -11.541 | 1.00 0.53 |
| ATOM | 113 | O | ARG S 104 | 0.920 -28.016 -11.387 | 1.00 -0.50 |
| ATOM | 114 | CB | ARG S 104 | -1.253 -29.984 -13.311 | 1.00 0.05 |
| ATOM | 115 | CG | ARG S 104 | -1.250 -30.233 -14.827 | 1.00 0.06 |
| ATOM | 116 | CD | ARG S 104 | -1.308 -31.721 -15.207 | 1.00 0.11 |
| ATOM | 117 | NE | ARG S 104 | -0.254 -32.467 -14.521 | 1.00 -0.49 |
| ATOM | 118 | CZ | ARG S 104 | 0.365 -33.502 -15.129 | 1.00 0.81 |
| ATOM | 119 | NH1 | ARG S 104 | 0.042 -33.880 -16.366 | 1.00 -0.63 |
| ATOM | 120 | NH2 | ARG S 104 | 1.319 -34.159 -14.478 | 1.00 -0.63 |
| ATOM | 121 | H | ARG S 104 | 0.754 -28.678 -14.334 | 1.00 0.25 |
| ATOM | 122 | HE | ARG S 104 | 0.018 -32.215 -13.592 | 1.00 0.29 |
| ATOM | 123 | 1HH1 | ARG S 104 | 0.519 -34.651 -16.789 | 1.00 0.36 |
| ATOM | 124 | 2HH1 | ARG S 104 | -0.672 -33.401 -16.875 | 1.00 0.36 |
| ATOM | 125 | 1HH2 | ARG S 104 | 1.786 -34.927 -14.915 | 1.00 0.36 |
| ATOM | 126 | 2HH2 | ARG S 104 | 1.569 -33.884 -13.549 | 1.00 0.36 |
| ATOM | 127 | N | PHE S 105 | -0.990 -28.886 -10.538 | 1.00 -0.52 |
| ATOM | 128 | CA | PHE S 105 | -0.535 -28.854 -9.152 | 1.00 0.21 |
| ATOM | 129 | C | PHE S 105 | 0.558 -29.894 -9.090 | 1.00 0.53 |
| ATOM | 130 | O | PHE S 105 | 1.596 -29.679 -8.447 | 1.00 -0.50 |
| ATOM | 131 | CB | PHE S 105 | -1.656 -29.230 -8.170 | 1.00 0.04 |

| | | | | | |
|---|---|---|---|---|---|
| ATOM | 132 | CG PHE S 105 | -1.354 -28.726 -6.778 | 1.00 | 0.01 |
| ATOM | 133 | CD1 PHE S 105 | -1.851 -27.471 -6.366 | 1.00 | -0.01 |
| ATOM | 134 | CD2 PHE S 105 | -0.575 -29.526 -5.913 | 1.00 | -0.01 |
| ATOM | 135 | CE1 PHE S 105 | -1.566 -27.007 -5.067 | 1.00 | 0.00 |
| ATOM | 136 | CE2 PHE S 105 | -0.290 -29.063 -4.616 | 1.00 | 0.00 |
| ATOM | 137 | CZ PHE S 105 | -0.788 -27.809 -4.206 | 1.00 | 0.00 |
| ATOM | 138 | H PHE S 105 | -1.906 -29.236 -10.732 | 1.00 | 0.25 |
| ATOM | 139 | N VAL S 106 | 0.329 -31.021 -9.758 | 1.00 | -0.52 |
| ATOM | 140 | CA VAL S 106 | 1.297 -32.114 -9.787 | 1.00 | 0.20 |
| ATOM | 141 | C VAL S 106 | 1.984 -32.186 -11.130 | 1.00 | 0.53 |
| ATOM | 142 | O VAL S 106 | 1.469 -32.815 -12.067 | 1.00 | -0.50 |
| ATOM | 143 | CB VAL S 106 | 0.545 -33.403 -9.418 | 1.00 | 0.03 |
| ATOM | 144 | CG1 VAL S 106 | 1.433 -34.654 -9.506 | 1.00 | 0.01 |
| ATOM | 145 | CG2 VAL S 106 | -0.212 -33.313 -8.084 | 1.00 | 0.01 |
| ATOM | 146 | H VAL S 106 | -0.530 -31.131 -10.258 | 1.00 | 0.25 |
| ATOM | 147 | N ALA S 107 | 3.145 -31.545 -11.226 | 1.00 | -0.52 |
| ATOM | 148 | CA ALA S 107 | 3.920 -31.529 -12.463 | 1.00 | 0.22 |
| ATOM | 149 | C ALA S 107 | 5.237 -30.854 -12.163 | 1.00 | 0.53 |
| ATOM | 150 | O ALA S 107 | 6.308 -31.425 -12.415 | 1.00 | -0.50 |
| ATOM | 151 | CB ALA S 107 | 3.199 -30.751 -13.576 | 1.00 | 0.03 |
| ATOM | 152 | H ALA S 107 | 3.504 -31.056 -10.432 | 1.00 | 0.25 |
| ATOM | 153 | N PRO S 108 | 5.161 -29.640 -11.625 | 1.00 | -0.26 |
| ATOM | 154 | CA PRO S 108 | 6.351 -28.871 -11.283 | 1.00 | 0.11 |
| ATOM | 155 | C PRO S 108 | 7.264 -29.638 -10.357 | 1.00 | 0.53 |
| ATOM | 156 | O PRO S 108 | 8.481 -29.403 -10.336 | 1.00 | -0.50 |
| ATOM | 157 | CB PRO S 108 | 5.782 -27.574 -10.686 | 1.00 | 0.00 |
| ATOM | 158 | CG PRO S 108 | 4.356 -27.900 -10.256 | 1.00 | 0.04 |
| ATOM | 159 | CD PRO S 108 | 3.932 -28.917 -11.305 | 1.00 | 0.08 |
| ATOM | 160 | N ASP S 109 | 6.680 -30.556 -9.591 | 1.00 | -0.52 |
| ATOM | 161 | CA ASP S 109 | 7.439 -31.374 -8.649 | 1.00 | 0.25 |
| ATOM | 162 | C ASP S 109 | 7.956 -32.544 -9.451 | 1.00 | 0.53 |
| ATOM | 163 | O ASP S 109 | 7.574 -33.697 -9.200 | 1.00 | -0.50 |
| ATOM | 164 | CB ASP S 109 | 6.510 -31.884 -7.536 | 1.00 | -0.21 |
| ATOM | 165 | CG ASP S 109 | 6.933 -31.318 -6.195 | 1.00 | 0.62 |

| | ATOM | 166 | OD1 | ASP S 109 | 6.290 -30.391 -5.711 1.00 -0.71 |
|---|---|---|---|---|---|
| | ATOM | 167 | OD2 | ASP S 109 | 7.907 -31.800 -5.626 1.00 -0.71 |
| | ATOM | 168 | H | ASP S 109 | 5.692 -30.697 -9.657 1.00 0.25 |
| | ATOM | 169 | N | ALA S 110 | 8.824 -32.252 -10.416 1.00 -0.52 |
| 5 | ATOM | 170 | CA | ALA S 110 | 9.406 -33.282 -11.270 1.00 0.22 |
| | ATOM | 171 | C | ALA S 110 | 10.898 -33.275 -11.034 1.00 0.53 |
| | ATOM | 172 | O | ALA S 110 | 11.481 -34.304 -10.662 1.00 -0.50 |
| | ATOM | 173 | CB | ALA S 110 | 9.132 -33.009 -12.758 1.00 0.03 |
| | ATOM | 174 | H | ALA S 110 | 9.090 -31.300 -10.566 1.00 0.25 |
| 10 | ATOM | 175 | N | PHE S 111 | 11.517 -32.118 -11.249 1.00 -0.52 |
| | ATOM | 176 | CA | PHE S 111 | 12.956 -31.964 -11.061 1.00 0.21 |
| | ATOM | 177 | C | PHE S 111 | 13.127 -31.810 -9.568 1.00 0.53 |
| | ATOM | 178 | O | PHE S 111 | 12.376 -31.064 -8.923 1.00 -0.50 |
| | ATOM | 179 | CB | PHE S 111 | 13.497 -30.712 -11.770 1.00 0.04 |
| 15 | ATOM | 180 | CG | PHE S 111 | 12.526 -29.559 -11.656 1.00 0.01 |
| | ATOM | 181 | CD1 | PHE S 111 | 12.618 -28.673 -10.561 1.00 -0.01 |
| | ATOM | 182 | CD2 | PHE S 111 | 11.542 -29.391 -12.654 1.00 -0.01 |
| | ATOM | 183 | CE1 | PHE S 111 | 11.710 -27.601 -10.462 1.00 0.00 |
| | ATOM | 184 | CE2 | PHE S 111 | 10.634 -28.321 -12.556 1.00 0.00 |
| 20 | ATOM | 185 | CZ | PHE S 111 | 10.727 -27.436 -11.461 1.00 0.00 |
| | ATOM | 186 | H | PHE S 111 | 10.987 -31.324 -11.549 1.00 0.25 |
| | ATOM | 187 | N | HSC S 112 | 14.112 -32.515 -9.019 1.00 -0.52 |
| | ATOM | 188 | H | HSC S 112 | 14.681 -33.099 -9.597 1.00 0.25 |
| | ATOM | 189 | CA | HSC S 112 | 14.393 -32.465 -7.587 1.00 0.19 |
| 25 | ATOM | 190 | CB | HSC S 112 | 13.775 -33.685 -6.885 1.00 0.21 |
| | ATOM | 191 | CG | HSC S 112 | 12.263 -33.637 -6.920 1.00 0.10 |
| | ATOM | 192 | CD2 | HSC S 112 | 11.396 -33.062 -5.986 1.00 0.35 |
| | ATOM | 193 | ND1 | HSC S 112 | 11.533 -34.176 -7.915 1.00 -0.61 |
| | ATOM | 194 | HD1 | HSC S 112 | 11.881 -34.643 -8.703 1.00 0.48 |
| 30 | ATOM | 195 | CE1 | HSC S 112 | 10.215 -33.947 -7.619 1.00 0.72 |
| | ATOM | 196 | NE2 | HSC S 112 | 10.132 -33.262 -6.434 1.00 -0.69 |
| | ATOM | 197 | HE2 | HSC S 112 | 9.308 -32.971 -5.991 1.00 0.49 |
| | ATOM | 198 | C | HSC S 112 | 15.841 -32.262 -7.208 1.00 0.53 |
| | ATOM | 199 | O | HSC S 112 | 16.534 -33.221 -6.836 1.00 -0.50 |

| | | | | | | |
|---|---|---|---|---|---|---|
| | ATOM | 200 | N | PHE S 113 | 16.299 -31.017 -7.301 | 1.00 -0.52 |
| | ATOM | 201 | CA | PHE S 113 | 17.678 -30.673 -6.967 | 1.00 0.21 |
| | ATOM | 202 | C | PHE S 113 | 17.554 -29.654 -5.860 | 1.00 0.53 |
| | ATOM | 203 | O | PHE S 113 | 18.444 -29.545 -5.003 | 1.00 -0.50 |
| 5 | ATOM | 204 | CB | PHE S 113 | 18.418 -30.047 -8.160 | 1.00 0.04 |
| | ATOM | 205 | CG | PHE S 113 | 17.666 -28.854 -8.702 | 1.00 0.01 |
| | ATOM | 206 | CD1 | PHE S 113 | 18.011 -27.554 -8.270 | 1.00 -0.01 |
| | ATOM | 207 | CD2 | PHE S 113 | 16.627 -29.064 -9.635 | 1.00 -0.01 |
| | ATOM | 208 | CE1 | PHE S 113 | 17.306 -26.447 -8.780 | 1.00 0.00 |
| 10 | ATOM | 209 | CE2 | PHE S 113 | 15.922 -27.959 -10.145 | 1.00 0.00 |
| | ATOM | 210 | CZ | PHE S 113 | 16.268 -26.661 -9.712 | 1.00 0.00 |
| | ATOM | 211 | H | PHE S 113 | 15.686 -30.289 -7.608 | 1.00 0.25 |
| | ATOM | 212 | N | THR S 114 | 16.454 -28.908 -5.874 | 1.00 -0.52 |
| | ATOM | 213 | CA | THR S 114 | 16.200 -27.883 -4.866 | 1.00 0.27 |
| 15 | ATOM | 214 | C | THR S 114 | 16.150 -28.477 -3.478 | 1.00 0.53 |
| | ATOM | 215 | O | THR S 114 | 16.898 -28.053 -2.585 | 1.00 -0.50 |
| | ATOM | 216 | CB | THR S 114 | 14.903 -27.124 -5.185 | 1.00 0.21 |
| | ATOM | 217 | OG1 | THR S 114 | 14.606 -27.224 -6.576 | 1.00 -0.55 |
| | ATOM | 218 | CG2 | THR S 114 | 14.967 -25.648 -4.762 | 1.00 0.01 |
| 20 | ATOM | 219 | H | THR S 114 | 15.774 -29.046 -6.595 | 1.00 0.25 |
| | ATOM | 220 | HG1 | THR S 114 | 13.824 -26.691 -6.734 | 1.00 0.31 |
| | ATOM | 221 | N | PRO S 115 | 15.270 -29.457 -3.296 | 1.00 -0.26 |
| | ATOM | 222 | CA | PRO S 115 | 15.113 -30.124 -2.008 | 1.00 0.11 |
| | ATOM | 223 | C | PRO S 115 | 16.420 -30.691 -1.510 | 1.00 0.53 |
| 25 | ATOM | 224 | O | PRO S 115 | 16.789 -30.490 -0.343 | 1.00 -0.50 |
| | ATOM | 225 | CB | PRO S 115 | 14.024 -31.174 -2.277 | 1.00 0.00 |
| | ATOM | 226 | CG | PRO S 115 | 14.008 -31.384 -3.788 | 1.00 0.04 |
| | ATOM | 227 | CD | PRO S 115 | 14.364 -29.999 -4.305 | 1.00 0.08 |
| | ATOM | 228 | N | ARG S 116 | 17.122 -31.399 -2.390 | 1.00 -0.52 |
| 30 | ATOM | 229 | CA | ARG S 116 | 18.405 -32.006 -2.048 | 1.00 0.24 |
| | ATOM | 230 | C | ARG S 116 | 19.201 -32.059 -3.330 | 1.00 0.53 |
| | ATOM | 231 | O | ARG S 116 | 18.642 -32.307 -4.408 | 1.00 -0.50 |
| | ATOM | 232 | CB | ARG S 116 | 18.212 -33.381 -1.388 | 1.00 0.05 |
| | ATOM | 233 | CG | ARG S 116 | 17.213 -34.284 -2.128 | 1.00 0.06 |

```
ATOM    234  CD   ARG S 116      17.881 -35.312  -3.055  1.00  0.11
ATOM    235  NE   ARG S 116      17.832 -34.856  -4.444  1.00 -0.49
ATOM    236  CZ   ARG S 116      18.735 -35.300  -5.346  1.00  0.81
ATOM    237  NH1  ARG S 116      19.694 -36.161  -5.009  1.00 -0.63
ATOM    238  NH2  ARG S 116      18.663 -34.866  -6.600  1.00 -0.63
ATOM    239  H    ARG S 116      16.767 -31.523  -3.317  1.00  0.25
ATOM    240  HE   ARG S 116      17.128 -34.209  -4.737  1.00  0.29
ATOM    241 1HH1  ARG S 116      20.347 -36.471  -5.701  1.00  0.36
ATOM    242 2HH1  ARG S 116      19.767 -36.501  -4.072  1.00  0.36
ATOM    243 1HH2  ARG S 116      19.324 -35.186  -7.279  1.00  0.36
ATOM    244 2HH2  ARG S 116      17.947 -34.219  -6.864  1.00  0.36
ATOM    245  N    LEU S 117      20.506 -31.828  -3.216  1.00 -0.52
ATOM    246  CA   LEU S 117      21.399 -31.846  -4.370  1.00  0.23
ATOM    247  C    LEU S 117      21.643 -33.299  -4.741  1.00  0.50
ATOM    248  O    LEU S 117      21.687 -33.594  -5.933  1.00 -0.25
ATOM    249  CB   LEU S 117      22.706 -31.110  -4.038  1.00  0.02
ATOM    250  CG   LEU S 117      23.454 -31.672  -2.818  1.00  0.05
ATOM    251  CD1  LEU S 117      24.851 -32.222  -3.147  1.00 -0.01
ATOM    252  CD2  LEU S 117      23.506 -30.647  -1.674  1.00 -0.01
ATOM    253  OXT  LEU S 117      21.785 -34.114  -3.834  1.00 -0.25
ATOM    254  H    LEU S 117      20.894 -31.634  -2.315  1.00  0.25
END
```

*Principal residues are bolded.

Appendix 2. Geometry of the LRM-2B in PDB format.*
REMARK 1 The bioactive conformation of the second LRM of TrkB.
REMARK 2

```
ATOM    1 N    LEU S 93   -32.287 14.723 17.944 1.00 -0.45
ATOM    2 CA   LEU S 93   -33.186 15.831 17.679 1.00 -0.07
ATOM    3 C    LEU S 93   -32.411 17.027 17.215 1.00  0.53
ATOM    4 O    LEU S 93   -31.203 17.150 17.385 1.00 -0.50
ATOM    5 CB   LEU S 93   -33.996 16.167 18.941 1.00  0.02
ATOM    6 CG   LEU S 93   -35.339 15.426 19.042 1.00  0.05
ATOM    7 CD1  LEU S 93   -36.286 15.694 17.861 1.00 -0.01
ATOM    8 CD2  LEU S 93   -35.131 13.920 19.266 1.00 -0.01
ATOM    9 1H   LEU S 93   -31.777 14.490 17.116 1.00  0.15
ATOM   10 2H   LEU S 93   -32.810 13.922 18.239 1.00  0.15
ATOM   11 3H   LEU S 93   -31.641 14.971 18.665 1.00  0.15
ATOM   12 N    ARG S 94   -33.510 17.650 16.801 1.00 -0.52
ATOM   13 CA   ARG S 94   -33.484 19.028 16.320 1.00  0.24
ATOM   14 C    ARG S 94   -34.175 19.857 17.377 1.00  0.53
ATOM   15 O    ARG S 94   -33.609 20.841 17.874 1.00 -0.50
ATOM   16 CB   ARG S 94   -34.128 19.146 14.929 1.00  0.05
ATOM   17 CG   ARG S 94   -33.300 18.494 13.811 1.00  0.06
ATOM   18 CD   ARG S 94   -34.051 18.379 12.475 1.00  0.11
ATOM   19 NE   ARG S 94   -33.282 17.579 11.523 1.00 -0.49
ATOM   20 CZ   ARG S 94   -33.792 16.435 11.016 1.00  0.81
ATOM   21 NH1  ARG S 94   -35.003 15.996 11.360 1.00 -0.63
ATOM   22 NH2  ARG S 94   -33.068 15.730 10.153 1.00 -0.63
ATOM   23 H    ARG S 94   -34.386 17.167 16.817 1.00  0.25
ATOM   24 HE   ARG S 94   -32.370 17.873 11.238 1.00  0.29
ATOM   25 1HH1 ARG S 94   -35.352 15.145 10.968 1.00  0.36
ATOM   26 2HH1 ARG S 94   -35.565 16.510 12.008 1.00  0.36
ATOM   27 1HH2 ARG S 94   -33.433 14.882  9.769 1.00  0.36
ATOM   28 2HH2 ARG S 94   -32.159 16.050  9.887 1.00  0.36
ATOM   29 N    ASN S 95   -35.397 19.461 17.721 1.00 -0.52
ATOM   30 CA   ASN S 95   -36.183 20.166 18.729 1.00  0.22
ATOM   31 C    ASN S 95   -37.332 19.318 19.219 1.00  0.53
```

```
ATOM   32 O   ASN S  95     -37.969 18.605 18.430 1.00 -0.50
ATOM   33 CB  ASN S  95     -36.706 21.522 18.229 1.00  0.00
ATOM   34 CG  ASN S  95     -36.363 22.606 19.233 1.00  0.68
ATOM   35 OD1 ASN S  95     -37.231 23.137 19.913 1.00 -0.47
ATOM   36 ND2 ASN S  95     -35.056 22.909 19.294 1.00 -0.87
ATOM   37 H   ASN S  95     -35.797 18.657 17.281 1.00  0.25
ATOM   38 1HD2 ASN S  95    -34.725 23.610 19.925 1.00  0.34
ATOM   39 2HD2 ASN S  95    -34.397 22.435 18.709 1.00  0.34
ATOM   40 N   LEU S  96     -37.598 19.391 20.520 1.00 -0.52
ATOM   41 CA  LEU S  96     -38.679 18.626 21.134 1.00  0.20
ATOM   42 C   LEU S  96     -39.965 19.383 20.901 1.00  0.53
ATOM   43 O   LEU S  96     -40.388 20.181 21.751 1.00 -0.50
ATOM   44 CB  LEU S  96     -38.396 18.419 22.630 1.00  0.02
ATOM   45 CG  LEU S  96     -37.665 17.107 22.956 1.00  0.05
ATOM   46 CD1 LEU S  96     -38.413 15.848 22.489 1.00 -0.01
ATOM   47 CD2 LEU S  96     -36.219 17.129 22.436 1.00 -0.01
ATOM   48 H   LEU S  96     -37.044 19.987 21.103 1.00  0.25
ATOM   49 N   THR S  97     -40.588 19.136 19.753 1.00 -0.52
ATOM   50 CA  THR S  97     -41.840 19.794 19.394 1.00  0.27
ATOM   51 C   THR S  97     -42.809 18.826 18.759 1.00  0.53
ATOM   52 O   THR S  97     -42.400 17.929 18.007 1.00 -0.50
ATOM   53 CB  THR S  97     -41.572 20.990 18.466 1.00  0.21
ATOM   54 OG1 THR S  97     -42.795 21.657 18.160 1.00 -0.55
ATOM   55 CG2 THR S  97     -40.854 20.578 17.171 1.00  0.01
ATOM   56 H   THR S  97     -40.193 18.480 19.110 1.00  0.25
ATOM   57 HG1 THR S  97     -42.562 22.479 17.722 1.00  0.31
ATOM   58 N   ILE S  98     -44.093 19.003 19.059 1.00 -0.52
ATOM   59 CA  ILE S  98     -45.140 18.142 18.518 1.00  0.20
ATOM   60 C   ILE S  98     -46.361 18.894 18.043 1.00  0.53
ATOM   61 O   ILE S  98     -46.834 19.818 18.721 1.00 -0.50
ATOM   62 CB  ILE S  98     -45.444 17.014 19.516 1.00  0.03
ATOM   63 CG1 ILE S  98     -46.244 15.862 18.888 1.00  0.02
ATOM   64 CG2 ILE S  98     -46.123 17.547 20.788 1.00  0.00
ATOM   65 CD1 ILE S  98     -45.346 14.810 18.219 1.00  0.00
```

| | | | | | | | |
|---|---|---|---|---|---|---|---|
| ATOM | 66 | H | ILE S 98 | -44.356 | 19.747 | 19.673 | 1.00 0.25 |
| ATOM | 67 | N | VAL S 99 | -46.872 | 18.500 | 16.880 | 1.00 -0.52 |
| ATOM | 68 | CA | VAL S 99 | -48.051 | 19.135 | 16.298 | 1.00 0.20 |
| ATOM | 69 | C | VAL S 99 | -49.253 | 18.226 | 16.395 | 1.00 0.53 |
| ATOM | 70 | O | VAL S 99 | -49.110 | 16.994 | 16.408 | 1.00 -0.50 |
| ATOM | 71 | CB | VAL S 99 | -47.698 | 19.525 | 14.854 | 1.00 0.03 |
| ATOM | 72 | CG1 | VAL S 99 | -46.688 | 20.681 | 14.780 | 1.00 0.01 |
| ATOM | 73 | CG2 | VAL S 99 | -47.287 | 18.331 | 13.978 | 1.00 0.01 |
| ATOM | 74 | H | VAL S 99 | -46.441 | 17.747 | 16.383 | 1.00 0.25 |
| ATOM | 75 | N | ASP S 100 | -50.436 | 18.829 | 16.461 | 1.00 -0.52 |
| ATOM | 76 | CA | ASP S 100 | -51.684 | 18.077 | 16.557 | 1.00 0.25 |
| ATOM | 77 | C | ASP S 100 | -51.849 | 17.392 | 15.222 | 1.00 0.53 |
| ATOM | 78 | O | ASP S 100 | -51.673 | 16.169 | 15.115 | 1.00 -0.50 |
| ATOM | 79 | CB | ASP S 100 | -52.858 | 19.041 | 16.789 | 1.00 -0.21 |
| ATOM | 80 | CG | ASP S 100 | -52.508 | 20.428 | 16.287 | 1.00 0.62 |
| ATOM | 81 | OD1 | ASP S 100 | -52.854 | 20.755 | 15.156 | 1.00 -0.71 |
| ATOM | 82 | OD2 | ASP S 100 | -51.889 | 21.189 | 17.023 | 1.00 -0.71 |
| ATOM | 83 | H | ASP S 100 | -50.481 | 19.828 | 16.445 | 1.00 0.25 |
| ATOM | 84 | N | SER S 101 | -52.187 | 18.177 | 14.202 | 1.00 -0.52 |
| ATOM | 85 | CA | SER S 101 | -52.382 | 17.652 | 12.854 | 1.00 0.29 |
| ATOM | 86 | C | SER S 101 | -53.017 | 16.282 | 12.846 | 1.00 0.53 |
| ATOM | 87 | O | SER S 101 | -52.684 | 15.439 | 12.000 | 1.00 -0.50 |
| ATOM | 88 | CB | SER S 101 | -51.034 | 17.621 | 12.116 | 1.00 0.19 |
| ATOM | 89 | OG | SER S 101 | -51.236 | 17.656 | 10.705 | 1.00 -0.55 |
| ATOM | 90 | H | SER S 101 | -52.314 | 19.157 | 14.356 | 1.00 0.25 |
| ATOM | 91 | HG | SER S 101 | -50.419 | 17.987 | 10.324 | 1.00 0.31 |
| ATOM | 92 | N | GLY S 102 | -53.930 | 16.058 | 13.786 | 1.00 -0.52 |
| ATOM | 93 | CA | GLY S 102 | -54.626 | 14.779 | 13.900 | 1.00 0.25 |
| ATOM | 94 | C | GLY S 102 | -53.788 | 13.536 | 13.720 | 1.00 0.53 |
| ATOM | 95 | O | GLY S 102 | -54.199 | 12.596 | 13.024 | 1.00 -0.50 |
| ATOM | 96 | H | GLY S 102 | -54.153 | 16.782 | 14.439 | 1.00 0.25 |
| ATOM | 97 | N | LEU S 103 | -52.615 | 13.527 | 14.347 | 1.00 -0.52 |
| ATOM | 98 | CA | LEU S 103 | -51.701 | 12.392 | 14.263 | 1.00 0.20 |
| ATOM | 99 | C | LEU S 103 | -51.521 | 11.844 | 15.658 | 1.00 0.53 |

| | | | | | | | | |
|---|---|---|---|---|---|---|---|---|
| | ATOM | 100 | O | LEU S 103 | -51.586 | 12.596 | 16.643 | 1.00 -0.50 |
| | ATOM | 101 | CB | LEU S 103 | -50.367 | 12.833 | 13.641 | 1.00 0.02 |
| | ATOM | 102 | CG | LEU S 103 | -49.757 | 14.089 | 14.284 | 1.00 0.05 |
| | ATOM | 103 | CD1 | LEU S 103 | -48.873 | 13.793 | 15.505 | 1.00 -0.01 |
| 5 | ATOM | 104 | CD2 | LEU S 103 | -49.015 | 14.944 | 13.244 | 1.00 -0.01 |
| | ATOM | 105 | H | LEU S 103 | -52.343 | 14.319 | 14.894 | 1.00 0.25 |
| | ATOM | 106 | N | LYS S 104 | -51.296 | 10.536 | 15.747 | 1.00 -0.52 |
| | ATOM | 107 | CA | LYS S 104 | -51.102 | 9.870 | 17.032 | 1.00 0.23 |
| | ATOM | 108 | C | LYS S 104 | -49.623 | 9.824 | 17.329 | 1.00 0.53 |
| 10 | ATOM | 109 | O | LYS S 104 | -49.013 | 8.744 | 17.326 | 1.00 -0.50 |
| | ATOM | 110 | CB | LYS S 104 | -51.738 | 8.471 | 17.005 | 1.00 0.04 |
| | ATOM | 111 | CG | LYS S 104 | -52.308 | 8.008 | 18.355 | 1.00 0.05 |
| | ATOM | 112 | CD | LYS S 104 | -53.074 | 6.679 | 18.249 | 1.00 0.05 |
| | ATOM | 113 | CE | LYS S 104 | -52.171 | 5.461 | 18.503 | 1.00 0.22 |
| 15 | ATOM | 114 | NZ | LYS S 104 | -52.891 | 4.233 | 18.143 | 1.00 -0.27 |
| | ATOM | 115 | H | LYS S 104 | -51.256 | 9.986 | 14.913 | 1.00 0.25 |
| | ATOM | 116 | 1HZ | LYS S 104 | -53.368 | 4.364 | 17.227 | 1.00 0.31 |
| | ATOM | 117 | 2HZ | LYS S 104 | -53.600 | 4.018 | 18.873 | 1.00 0.31 |
| | ATOM | 118 | 3HZ | LYS S 104 | -52.219 | 3.443 | 18.071 | 1.00 0.31 |
| 20 | ATOM | 119 | N | PHE S 105 | -49.043 | 10.993 | 17.585 | 1.00 -0.52 |
| | ATOM | 120 | CA | PHE S 105 | -47.619 | 11.101 | 17.889 | 1.00 0.21 |
| | ATOM | 121 | C | PHE S 105 | -46.933 | 10.882 | 16.562 | 1.00 0.53 |
| | ATOM | 122 | O | PHE S 105 | -46.495 | 11.844 | 15.914 | 1.00 -0.50 |
| | ATOM | 123 | CB | PHE S 105 | -47.162 | 10.024 | 18.886 | 1.00 0.04 |
| 25 | ATOM | 124 | CG | PHE S 105 | -45.861 | 10.412 | 19.549 | 1.00 0.01 |
| | ATOM | 125 | CD1 | PHE S 105 | -44.683 | 9.692 | 19.251 | 1.00 -0.01 |
| | ATOM | 126 | CD2 | PHE S 105 | -45.849 | 11.493 | 20.457 | 1.00 -0.01 |
| | ATOM | 127 | CE1 | PHE S 105 | -43.474 | 10.058 | 19.873 | 1.00 0.00 |
| | ATOM | 128 | CE2 | PHE S 105 | -44.641 | 11.860 | 21.078 | 1.00 0.00 |
| 30 | ATOM | 129 | CZ | PHE S 105 | -43.466 | 11.139 | 20.780 | 1.00 0.00 |
| | ATOM | 130 | H | PHE S 105 | -49.592 | 11.829 | 17.571 | 1.00 0.25 |
| | ATOM | 131 | N | VAL S 106 | -46.838 | 9.619 | 16.156 | 1.00 -0.52 |
| | ATOM | 132 | CA | VAL S 106 | -46.200 | 9.259 | 14.893 | 1.00 0.20 |
| | ATOM | 133 | C | VAL S 106 | -44.818 | 9.859 | 14.800 | 1.00 0.53 |

| | | | | | | | | | |
|---|---|---|---|---|---|---|---|---|---|
| | ATOM | 134 | O | VAL S 106 | -44.261 | 9.989 | 13.699 | 1.00 | -0.50 |
| | ATOM | 135 | CB | VAL S 106 | -47.136 | 9.709 | 13.760 | 1.00 | 0.03 |
| | ATOM | 136 | CG1 | VAL S 106 | -46.649 | 9.261 | 12.372 | 1.00 | 0.01 |
| | ATOM | 137 | CG2 | VAL S 106 | -48.612 | 9.356 | 14.005 | 1.00 | 0.01 |
| 5 | ATOM | 138 | H | VAL S 106 | -47.213 | 8.889 | 16.726 | 1.00 | 0.25 |
| | ATOM | 139 | N | ALA S 107 | -44.263 | 10.225 | 15.951 | 1.00 | -0.52 |
| | ATOM | 140 | CA | ALA S 107 | -42.930 | 10.820 | 16.013 | 1.00 | 0.22 |
| | ATOM | 141 | C | ALA S 107 | -42.034 | 9.846 | 16.740 | 1.00 | 0.53 |
| | ATOM | 142 | O | ALA S 107 | -41.035 | 10.247 | 17.354 | 1.00 | -0.50 |
| 10 | ATOM | 143 | CB | ALA S 107 | -42.939 | 12.156 | 16.772 | 1.00 | 0.03 |
| | ATOM | 144 | H | ALA S 107 | -44.766 | 10.093 | 16.805 | 1.00 | 0.25 |
| | ATOM | 145 | N | TYR S 108 | -42.388 | 8.565 | 16.671 | 1.00 | -0.52 |
| | ATOM | 146 | CA | TYR S 108 | -41.616 | 7.513 | 17.325 | 1.00 | 0.25 |
| | ATOM | 147 | C | TYR S 108 | -40.181 | 7.445 | 16.861 | 1.00 | 0.53 |
| 15 | ATOM | 148 | O | TYR S 108 | -39.320 | 6.888 | 17.557 | 1.00 | -0.50 |
| | ATOM | 149 | CB | TYR S 108 | -42.269 | 6.142 | 17.090 | 1.00 | 0.02 |
| | ATOM | 150 | CG | TYR S 108 | -43.761 | 6.173 | 17.332 | 1.00 | 0.00 |
| | ATOM | 151 | CD1 | TYR S 108 | -44.625 | 6.208 | 16.220 | 1.00 | -0.04 |
| | ATOM | 152 | CD2 | TYR S 108 | -44.248 | 6.166 | 18.656 | 1.00 | -0.04 |
| 20 | ATOM | 153 | CE1 | TYR S 108 | -46.012 | 6.237 | 16.436 | 1.00 | 0.10 |
| | ATOM | 154 | CE2 | TYR S 108 | -45.636 | 6.196 | 18.871 | 1.00 | 0.10 |
| | ATOM | 155 | CZ | TYR S 108 | -46.500 | 6.231 | 17.759 | 1.00 | -0.12 |
| | ATOM | 156 | OH | TYR S 108 | -47.863 | 6.259 | 17.970 | 1.00 | -0.37 |
| | ATOM | 157 | H | TYR S 108 | -43.207 | 8.308 | 16.159 | 1.00 | 0.25 |
| 25 | ATOM | 158 | HH | TYR S 108 | -48.199 | 7.127 | 17.791 | 1.00 | 0.34 |
| | ATOM | 159 | N | LYS S 109 | -39.921 | 8.011 | 15.685 | 1.00 | -0.52 |
| | ATOM | 160 | CA | LYS S 109 | -38.579 | 8.021 | 15.112 | 1.00 | 0.23 |
| | ATOM | 161 | C | LYS S 109 | -37.724 | 8.976 | 15.910 | 1.00 | 0.53 |
| | ATOM | 162 | O | LYS S 109 | -36.497 | 8.811 | 15.985 | 1.00 | -0.50 |
| 30 | ATOM | 163 | CB | LYS S 109 | -38.641 | 8.396 | 13.622 | 1.00 | 0.04 |
| | ATOM | 164 | CG | LYS S 109 | -39.200 | 9.801 | 13.345 | 1.00 | 0.05 |
| | ATOM | 165 | CD | LYS S 109 | -40.553 | 9.764 | 12.617 | 1.00 | 0.05 |
| | ATOM | 166 | CE | LYS S 109 | -41.148 | 11.167 | 12.416 | 1.00 | 0.22 |
| | ATOM | 167 | NZ | LYS S 109 | -42.394 | 11.066 | 11.645 | 1.00 | -0.27 |

|    |      |     |     |       |        |         |        |        |      |       |
|----|------|-----|-----|-------|--------|---------|--------|--------|------|-------|
|    | ATOM | 168 | H   | LYS S | 109    | -40.662 | 8.444  | 15.173 | 1.00 | 0.25  |
|    | ATOM | 169 | 1HZ | LYS S | 109    | -42.761 | 12.020 | 11.449 | 1.00 | 0.31  |
|    | ATOM | 170 | 2HZ | LYS S | 109    | -43.099 | 10.531 | 12.191 | 1.00 | 0.31  |
|    | ATOM | 171 | 3HZ | LYS S | 109    | -42.209 | 10.576 | 10.746 | 1.00 | 0.31  |
| 5  | ATOM | 172 | N   | ALA S | 110    | -38.368 | 9.974  | 16.509 | 1.00 | -0.52 |
|    | ATOM | 173 | CA  | ALA S | 110    | -37.671 | 10.972 | 17.314 | 1.00 | 0.22  |
|    | ATOM | 174 | C   | ALA S | 110    | -37.673 | 10.482 | 18.742 | 1.00 | 0.53  |
|    | ATOM | 175 | O   | ALA S | 110    | -36.724 | 10.741 | 19.497 | 1.00 | -0.50 |
|    | ATOM | 176 | CB  | ALA S | 110    | -38.368 | 12.341 | 17.251 | 1.00 | 0.03  |
| 10 | ATOM | 177 | H   | ALA S | 110    | -39.360 | 10.050 | 16.409 | 1.00 | 0.25  |
|    | ATOM | 178 | N   | PHE S | 111    | -38.736 | 9.775  | 19.114 | 1.00 | -0.52 |
|    | ATOM | 179 | CA  | PHE S | 111    | -38.873 | 9.238  | 20.465 | 1.00 | 0.21  |
|    | ATOM | 180 | C   | PHE S | 111    | -37.731 | 8.259  | 20.599 | 1.00 | 0.53  |
|    | ATOM | 181 | O   | PHE S | 111    | -37.123 | 8.144  | 21.673 | 1.00 | -0.50 |
| 15 | ATOM | 182 | CB  | PHE S | 111    | -40.207 | 8.499  | 20.656 | 1.00 | 0.04  |
|    | ATOM | 183 | CG  | PHE S | 111    | -40.461 | 8.200  | 22.115 | 1.00 | 0.01  |
|    | ATOM | 184 | CD1 | PHE S | 111    | -41.035 | 9.191  | 22.942 | 1.00 | -0.01 |
|    | ATOM | 185 | CD2 | PHE S | 111    | -40.116 | 6.930  | 22.626 | 1.00 | -0.01 |
|    | ATOM | 186 | CE1 | PHE S | 111    | -41.269 | 8.906  | 24.301 | 1.00 | 0.00  |
| 20 | ATOM | 187 | CE2 | PHE S | 111    | -40.349 | 6.645  | 23.983 | 1.00 | 0.00  |
|    | ATOM | 188 | CZ  | PHE S | 111    | -40.924 | 7.636  | 24.807 | 1.00 | 0.00  |
|    | ATOM | 189 | H   | PHE S | 111    | -39.467 | 9.602  | 18.455 | 1.00 | 0.25  |
|    | ATOM | 190 | N   | LEU S | 112    | -37.439 | 7.552  | 19.511 | 1.00 | -0.52 |
|    | ATOM | 191 | CA  | LEU S | 112    | -36.360 | 6.568  | 19.494 | 1.00 | 0.20  |
| 25 | ATOM | 192 | C   | LEU S | 112    | -35.074 | 7.293  | 19.811 | 1.00 | 0.53  |
|    | ATOM | 193 | O   | LEU S | 112    | -34.249 | 6.798  | 20.594 | 1.00 | -0.50 |
|    | ATOM | 194 | CB  | LEU S | 112    | -36.305 | 5.868  | 18.127 | 1.00 | 0.02  |
|    | ATOM | 195 | CG  | LEU S | 112    | -35.374 | 4.646  | 18.082 | 1.00 | 0.05  |
|    | ATOM | 196 | CD1 | LEU S | 112    | -36.074 | 3.321  | 18.421 | 1.00 | -0.01 |
| 30 | ATOM | 197 | CD2 | LEU S | 112    | -34.628 | 4.563  | 16.740 | 1.00 | -0.01 |
|    | ATOM | 198 | H   | LEU S | 112    | -37.970 | 7.692  | 18.675 | 1.00 | 0.25  |
|    | ATOM | 199 | N   | LYS S | 113    | -34.900 | 8.464  | 19.205 | 1.00 | -0.52 |
|    | ATOM | 200 | CA  | LYS S | 113    | -33.705 | 9.275  | 19.417 | 1.00 | 0.23  |
|    | ATOM | 201 | C   | LYS S | 113    | -33.633 | 9.650  | 20.878 | 1.00 | 0.53  |

| | | | | | | | |
|---|---|---|---|---|---|---|---|
| ATOM | 202 | O | LYS S 113 | -32.578 | 9.508 | 21.513 | 1.00 -0.50 |
| ATOM | 203 | CB | LYS S 113 | -33.728 | 10.505 | 18.496 | 1.00 0.04 |
| ATOM | 204 | CG | LYS S 113 | -33.318 | 10.217 | 17.043 | 1.00 0.05 |
| ATOM | 205 | CD | LYS S 113 | -33.954 | 11.198 | 16.045 | 1.00 0.05 |
| ATOM | 206 | CE | LYS S 113 | -33.790 | 10.739 | 14.587 | 1.00 0.22 |
| ATOM | 207 | NZ | LYS S 113 | -34.498 | 9.467 | 14.390 | 1.00 -0.27 |
| ATOM | 208 | H | LYS S 113 | -35.605 | 8.807 | 18.585 | 1.00 0.25 |
| ATOM | 209 | 1HZ | LYS S 113 | -35.239 | 9.365 | 15.113 | 1.00 0.31 |
| ATOM | 210 | 2HZ | LYS S 113 | -33.826 | 8.678 | 14.472 | 1.00 0.31 |
| ATOM | 211 | 3HZ | LYS S 113 | -34.933 | 9.453 | 13.446 | 1.00 0.31 |
| ATOM | 212 | N | ASN S 114 | -34.754 | 10.128 | 21.412 | 1.00 -0.52 |
| ATOM | 213 | CA | ASN S 114 | -34.832 | 10.531 | 22.813 | 1.00 0.22 |
| ATOM | 214 | C | ASN S 114 | -34.508 | 9.379 | 23.733 | 1.00 0.53 |
| ATOM | 215 | O | ASN S 114 | -33.878 | 9.570 | 24.784 | 1.00 -0.50 |
| ATOM | 216 | CB | ASN S 114 | -36.198 | 11.131 | 23.180 | 1.00 0.00 |
| ATOM | 217 | CG | ASN S 114 | -36.349 | 12.495 | 22.535 | 1.00 0.68 |
| ATOM | 218 | OD1 | ASN S 114 | -37.101 | 12.669 | 21.585 | 1.00 -0.47 |
| ATOM | 219 | ND2 | ASN S 114 | -35.597 | 13.457 | 23.097 | 1.00 -0.87 |
| ATOM | 220 | H | ASN S 114 | -35.572 | 10.217 | 20.844 | 1.00 0.25 |
| ATOM | 221 | 1HD2 | ASN S 114 | -35.623 | 14.393 | 22.746 | 1.00 0.34 |
| ATOM | 222 | 2HD2 | ASN S 114 | -35.002 | 13.248 | 23.873 | 1.00 0.34 |
| ATOM | 223 | N | SER S 115 | -34.937 | 8.182 | 23.342 | 1.00 -0.52 |
| ATOM | 224 | CA | SER S 115 | -34.696 | 6.977 | 24.131 | 1.00 0.29 |
| ATOM | 225 | C | SER S 115 | -33.240 | 6.580 | 24.160 | 1.00 0.53 |
| ATOM | 226 | O | SER S 115 | -32.755 | 6.037 | 25.165 | 1.00 -0.50 |
| ATOM | 227 | CB | SER S 115 | -35.553 | 5.825 | 23.584 | 1.00 0.19 |
| ATOM | 228 | OG | SER S 115 | -36.939 | 6.156 | 23.655 | 1.00 -0.55 |
| ATOM | 229 | H | SER S 115 | -35.440 | 8.096 | 22.482 | 1.00 0.25 |
| ATOM | 230 | HG | SER S 115 | -37.081 | 6.859 | 23.017 | 1.00 0.31 |
| ATOM | 231 | N | ASN S 116 | -32.540 | 6.850 | 23.062 | 1.00 -0.52 |
| ATOM | 232 | CA | ASN S 116 | -31.121 | 6.522 | 22.949 | 1.00 0.22 |
| ATOM | 233 | C | ASN S 116 | -30.264 | 7.559 | 23.632 | 1.00 0.53 |
| ATOM | 234 | O | ASN S 116 | -29.329 | 7.216 | 24.372 | 1.00 -0.50 |
| ATOM | 235 | CB | ASN S 116 | -30.671 | 6.343 | 21.490 | 1.00 0.00 |

| | ATOM | 236 | CG | ASN S 116 | -30.988 | 4.935 | 21.025 | 1.00 | 0.68 |
|---|---|---|---|---|---|---|---|---|---|
| | ATOM | 237 | OD1 | ASN S 116 | -30.139 | 4.053 | 21.046 | 1.00 | -0.47 |
| | ATOM | 238 | ND2 | ASN S 116 | -32.252 | 4.764 | 20.603 | 1.00 | -0.87 |
| | ATOM | 239 | H | ASN S 116 | -32.991 | 7.290 | 22.286 | 1.00 | 0.25 |
| 5 | ATOM | 240 | 1HD2 | ASN S 116 | -32.564 | 3.872 | 20.275 | 1.00 | 0.34 |
| | ATOM | 241 | 2HD2 | ASN S 116 | -32.898 | 5.528 | 20.611 | 1.00 | 0.34 |
| | ATOM | 242 | N | LEU S 117 | -30.578 | 8.828 | 23.387 | 1.00 | -0.52 |
| | ATOM | 243 | CA | LEU S 117 | -29.835 | 9.937 | 23.980 | 1.00 | 0.23 |
| | ATOM | 244 | C | LEU S 117 | -30.840 | 10.862 | 24.645 | 1.00 | 0.50 |
| 10 | ATOM | 245 | O | LEU S 117 | -31.725 | 11.354 | 23.951 | 1.00 | -0.25 |
| | ATOM | 246 | CB | LEU S 117 | -29.015 | 10.660 | 22.900 | 1.00 | 0.02 |
| | ATOM | 247 | CG | LEU S 117 | -27.751 | 9.905 | 22.458 | 1.00 | 0.05 |
| | ATOM | 248 | CD1 | LEU S 117 | -27.875 | 9.246 | 21.075 | 1.00 | -0.01 |
| | ATOM | 249 | CD2 | LEU S 117 | -26.506 | 10.802 | 22.546 | 1.00 | -0.01 |
| 15 | ATOM | 250 | OXT | LEU S 117 | -30.723 | 11.077 | 25.849 | 1.00 | -0.25 |
| | ATOM | 251 | H | LEU S 117 | -31.344 | 9.038 | 22.780 | 1.00 | 0.25 |

END

*Principal residues are bolded.

Appendix 3. Geometry of the p75$^{NTR}$ binding site for neurotrophins in PDB format.*

```
REMARK  1  Second CRD of p75NTR, bound to NGF.
REMARK  2
ATOM    1  N   CYS R  39    -32.488 -11.161  6.915  1.00  0.00
ATOM    2  CA  CYS R  39    -33.024  -9.817  7.111  1.00  0.00
ATOM    3  C   CYS R  39    -33.595  -9.148  5.878  1.00  0.00
ATOM    4  O   CYS R  39    -34.221  -8.095  5.967  1.00  0.00
ATOM    5  CB  CYS R  39    -31.991  -8.907  7.780  1.00  0.00
ATOM    6  SG  CYS R  39    -30.272  -9.354  7.401  1.00  0.00
ATOM    7  1H  CYS R  39    -31.698 -11.178  6.287  1.00  0.00
ATOM    8  2H  CYS R  39    -32.170 -11.586  7.775  1.00  0.00
ATOM    9  3H  CYS R  39    -33.166 -11.799  6.523  1.00  0.00
ATOM   10  N   LEU R  40    -33.398  -9.779  4.707  1.00  0.00
ATOM   11  CA  LEU R  40    -34.095  -9.260  3.530  1.00  0.00
ATOM   12  C   LEU R  40    -35.322 -10.097  3.220  1.00  0.00
ATOM   13  O   LEU R  40    -36.442  -9.632  3.041  1.00  0.00
ATOM   14  CB  LEU R  40    -33.148  -9.230  2.327  1.00  0.00
ATOM   15  CG  LEU R  40    -31.880  -8.404  2.561  1.00  0.00
ATOM   16  CD1 LEU R  40    -30.862  -8.604  1.438  1.00  0.00
ATOM   17  CD2 LEU R  40    -32.184  -6.924  2.806  1.00  0.00
ATOM   18  H   LEU R  40    -32.867 -10.625  4.675  1.00  0.00
ATOM   19  N   ASP R  41    -35.034 -11.407  3.188  1.00  0.00
ATOM   20  CA  ASP R  41    -36.070 -12.408  2.947  1.00  0.00
ATOM   21  C   ASP R  41    -35.822 -13.609  3.848  1.00  0.00
ATOM   22  O   ASP R  41    -34.792 -13.673  4.525  1.00  0.00
ATOM   23  CB  ASP R  41    -36.054 -12.772  1.449  1.00  0.00
ATOM   24  CG  ASP R  41    -37.195 -13.703  1.074  1.00  0.00
ATOM   25  OD1 ASP R  41    -38.299 -13.520  1.568  1.00  0.00
ATOM   26  OD2 ASP R  41    -36.979 -14.633  0.314  1.00  0.00
ATOM   27  H   ASP R  41    -34.111 -11.739  3.385  1.00  0.00
ATOM   28  N   SER R  42    -36.757 -14.563  3.825  1.00  0.00
ATOM   29  CA  SER R  42    -36.565 -15.812  4.545  1.00  0.00
```

```
ATOM  30 C   SER R 42   -35.305 -16.572  4.150 1.00 0.00
ATOM  31 O   SER R 42   -34.755 -17.350  4.918 1.00 0.00
ATOM  32 CB  SER R 42   -37.816 -16.678  4.398 1.00 0.00
ATOM  33 OG  SER R 42   -38.988 -15.930  4.780 1.00 0.00
ATOM  34 H   SER R 42   -37.497 -14.449  3.168 1.00 0.00
ATOM  35 HG  SER R 42   -39.404 -15.604  3.984 1.00 0.00
ATOM  36 N   VAL R 43   -34.794 -16.284  2.940 1.00 0.00
ATOM  37 CA  VAL R 43   -33.503 -16.883  2.574 1.00 0.00
ATOM  38 C   VAL R 43   -32.270 -16.339  3.305 1.00 0.00
ATOM  39 O   VAL R 43   -31.128 -16.743  3.081 1.00 0.00
ATOM  40 CB  VAL R 43   -33.300 -16.823  1.054 1.00 0.00
ATOM  41 CG1 VAL R 43   -34.389 -17.623  0.337 1.00 0.00
ATOM  42 CG2 VAL R 43   -33.208 -15.383  0.537 1.00 0.00
ATOM  43 H   VAL R 43   -35.321 -15.679  2.336 1.00 0.00
ATOM  44 N   THR R 44   -32.539 -15.360  4.166 1.00 0.00
ATOM  45 CA  THR R 44   -31.443 -14.732  4.879 1.00 0.00
ATOM  46 C   THR R 44   -31.701 -14.680  6.367 1.00 0.00
ATOM  47 O   THR R 44   -32.659 -14.063  6.830 1.00 0.00
ATOM  48 CB  THR R 44   -31.171 -13.339  4.300 1.00 0.00
ATOM  49 OG1 THR R 44   -32.382 -12.578  4.130 1.00 0.00
ATOM  50 CG2 THR R 44   -30.430 -13.431  2.962 1.00 0.00
ATOM  51 H   THR R 44   -33.481 -15.090  4.359 1.00 0.00
ATOM  52 HG1 THR R 44   -33.031 -12.981  4.718 1.00 0.00
ATOM  53 N   PHE R 45   -30.805 -15.368  7.080 1.00 0.00
ATOM  54 CA  PHE R 45   -30.829 -15.256  8.526 1.00 0.00
ATOM  55 C   PHE R 45   -30.085 -13.996  8.932 1.00 0.00
ATOM  56 O   PHE R 45   -29.293 -13.430  8.175 1.00 0.00
ATOM  57 CB  PHE R 45   -30.243 -16.531  9.157 1.00 0.00
ATOM  58 CG  PHE R 45   -30.514 -16.587 10.647 1.00 0.00
ATOM  59 CD1 PHE R 45   -31.844 -16.581 11.126 1.00 0.00
ATOM  60 CD2 PHE R 45   -29.423 -16.628 11.539 1.00 0.00
ATOM  61 CE1 PHE R 45   -32.085 -16.592 12.512 1.00 0.00
ATOM  62 CE2 PHE R 45   -29.661 -16.637 12.927 1.00 0.00
ATOM  63 CZ  PHE R 45   -30.989 -16.611 13.400 1.00 0.00
```

| | | | | | | | |
|---|---|---|---|---|---|---|---|
| | ATOM | 64 | H   PHE R 45 | -30.025 | -15.788 | 6.623 | 1.00 0.00 |
| | ATOM | 65 | N   SER R 46 | -30.382 | -13.575 | 10.161 | 1.00 0.00 |
| | ATOM | 66 | CA  SER R 46 | -29.961 | -12.259 | 10.626 | 1.00 0.00 |
| | ATOM | 67 | C   SER R 46 | -28.732 | -12.274 | 11.517 | 1.00 0.00 |
| 5 | ATOM | 68 | O   SER R 46 | -28.497 | -11.407 | 12.346 | 1.00 0.00 |
| | ATOM | 69 | CB  SER R 46 | -31.156 | -11.630 | 11.337 | 1.00 0.00 |
| | ATOM | 70 | OG  SER R 46 | -31.890 | -12.664 | 12.026 | 1.00 0.00 |
| | ATOM | 71 | H   SER R 46 | -31.046 | -14.080 | 10.714 | 1.00 0.00 |
| | ATOM | 72 | HG  SER R 46 | -32.811 | -12.512 | 11.820 | 1.00 0.00 |
| 10 | ATOM | 73 | N   ASP R 47 | -27.906 | -13.314 | 11.317 | 1.00 0.00 |
| | ATOM | 74 | CA  ASP R 47 | -26.772 | -13.543 | 12.226 | 1.00 0.00 |
| | ATOM | 75 | C   ASP R 47 | -25.567 | -12.610 | 12.077 | 1.00 0.00 |
| | ATOM | 76 | O   ASP R 47 | -24.410 | -13.027 | 12.086 | 1.00 0.00 |
| | ATOM | 77 | CB  ASP R 47 | -26.337 | -15.025 | 12.168 | 1.00 0.00 |
| 15 | ATOM | 78 | CG  ASP R 47 | -25.807 | -15.429 | 10.794 | 1.00 0.00 |
| | ATOM | 79 | OD1 ASP R 47 | -26.456 | -15.180 | 9.790 | 1.00 0.00 |
| | ATOM | 80 | OD2 ASP R 47 | -24.712 | -15.961 | 10.694 | 1.00 0.00 |
| | ATOM | 81 | H   ASP R 47 | -28.048 | -13.919 | 10.531 | 1.00 0.00 |
| | ATOM | 82 | N   VAL R 48 | -25.857 | -11.312 | 11.875 | 1.00 0.00 |
| 20 | ATOM | 83 | CA  VAL R 48 | -24.733 | -10.395 | 11.691 | 1.00 0.00 |
| | ATOM | 84 | C   VAL R 48 | -24.130 | -9.906 | 13.003 | 1.00 0.00 |
| | ATOM | 85 | O   VAL R 48 | -22.914 | -9.763 | 13.131 | 1.00 0.00 |
| | ATOM | 86 | CB  VAL R 48 | -25.108 | -9.258 | 10.720 | 1.00 0.00 |
| | ATOM | 87 | CG1 VAL R 48 | -26.299 | -8.421 | 11.194 | 1.00 0.00 |
| 25 | ATOM | 88 | CG2 VAL R 48 | -23.886 | -8.416 | 10.349 | 1.00 0.00 |
| | ATOM | 89 | H   VAL R 48 | -26.767 | -10.954 | 12.073 | 1.00 0.00 |
| | ATOM | 90 | N   VAL R 49 | -25.034 | -9.713 | 13.984 | 1.00 0.00 |
| | ATOM | 91 | CA  VAL R 49 | -24.767 | -9.685 | 15.431 | 1.00 0.00 |
| | ATOM | 92 | C   VAL R 49 | -23.506 | -9.045 | 16.022 | 1.00 0.00 |
| 30 | ATOM | 93 | O   VAL R 49 | -23.103 | -9.361 | 17.142 | 1.00 0.00 |
| | ATOM | 94 | CB  VAL R 49 | -25.003 | -11.080 | 16.043 | 1.00 0.00 |
| | ATOM | 95 | CG1 VAL R 49 | -26.440 | -11.541 | 15.783 | 1.00 0.00 |
| | ATOM | 96 | CG2 VAL R 49 | -23.973 | -12.125 | 15.594 | 1.00 0.00 |
| | ATOM | 97 | H   VAL R 49 | -25.987 | -9.707 | 13.681 | 1.00 0.00 |

```
ATOM   98 N   SER R 50    -22.912 -8.118 15.261 1.00 0.00
ATOM   99 CA  SER R 50    -21.729 -7.376 15.719 1.00 0.00
ATOM  100 C   SER R 50    -21.546 -6.123 14.873 1.00 0.00
ATOM  101 O   SER R 50    -21.505 -4.977 15.336 1.00 0.00
ATOM  102 CB  SER R 50    -20.431 -8.205 15.623 1.00 0.00
ATOM  103 OG  SER R 50    -20.525 -9.489 16.273 1.00 0.00
ATOM  104 H   SER R 50    -23.312 -7.897 14.372 1.00 0.00
ATOM  105 HG  SER R 50    -21.302 -9.403 16.827 1.00 0.00
ATOM  106 N   ALA R 51    -21.454 -6.446 13.572 1.00 0.00
ATOM  107 CA  ALA R 51    -21.546 -5.403 12.562 1.00 0.00
ATOM  108 C   ALA R 51    -23.013 -5.196 12.263 1.00 0.00
ATOM  109 O   ALA R 51    -23.862 -5.866 12.848 1.00 0.00
ATOM  110 CB  ALA R 51    -20.808 -5.825 11.288 1.00 0.00
ATOM  111 H   ALA R 51    -21.633 -7.392 13.330 1.00 0.00
ATOM  112 N   THR R 52    -23.266 -4.259 11.348 1.00 0.00
ATOM  113 CA  THR R 52    -24.606 -3.698 11.228 1.00 0.00
ATOM  114 C   THR R 52    -25.679 -4.557 10.579 1.00 0.00
ATOM  115 O   THR R 52    -26.564 -5.091 11.239 1.00 0.00
ATOM  116 CB  THR R 52    -24.481 -2.344 10.532 1.00 0.00
ATOM  117 OG1 THR R 52    -23.205 -1.766 10.845 1.00 0.00
ATOM  118 CG2 THR R 52    -25.624 -1.389 10.891 1.00 0.00
ATOM  119 H   THR R 52    -22.533 -3.835 10.820 1.00 0.00
ATOM  120 HG1 THR R 52    -23.136 -0.977 10.314 1.00 0.00
ATOM  121 N   GLU R 53    -25.602 -4.625  9.241 1.00 0.00
ATOM  122 CA  GLU R 53    -26.765 -5.151  8.526 1.00 0.00
ATOM  123 C   GLU R 53    -26.656 -6.149  7.362 1.00 0.00
ATOM  124 O   GLU R 53    -27.702 -6.492  6.808 1.00 0.00
ATOM  125 CB  GLU R 53    -27.678 -3.966  8.146 1.00 0.00
ATOM  126 CG  GLU R 53    -27.452 -3.289  6.779 1.00 0.00
ATOM  127 CD  GLU R 53    -25.983 -3.036  6.488 1.00 0.00
ATOM  128 OE1 GLU R 53    -25.530 -3.408  5.413 1.00 0.00
ATOM  129 OE2 GLU R 53    -25.284 -2.484  7.329 1.00 0.00
ATOM  130 H   GLU R 53    -24.901 -4.146  8.704 1.00 0.00
ATOM  131 N   PRO R 54    -25.448 -6.634  6.953 1.00 0.00
```

| | ATOM | 132 | CA | PRO R 54 | -25.503 | -7.661 | 5.912 | 1.00 | 0.00 |
|---|---|---|---|---|---|---|---|---|---|
| | ATOM | 133 | C | PRO R 54 | -26.227 | -8.929 | 6.351 | 1.00 | 0.00 |
| | ATOM | 134 | O | PRO R 54 | -26.254 | -9.343 | 7.509 | 1.00 | 0.00 |
| | ATOM | 135 | CB | PRO R 54 | -24.032 | -7.892 | 5.550 | 1.00 | 0.00 |
| 5 | ATOM | 136 | CG | PRO R 54 | -23.286 | -6.653 | 6.033 | 1.00 | 0.00 |
| | ATOM | 137 | CD | PRO R 54 | -24.070 | -6.275 | 7.278 | 1.00 | 0.00 |
| | ATOM | 138 | N | CYS R 55 | -26.841 | -9.564 | 5.355 | 1.00 | 0.00 |
| | ATOM | 139 | CA | CYS R 55 | -27.561 | -10.782 | 5.715 | 1.00 | 0.00 |
| | ATOM | 140 | C | CYS R 55 | -26.758 | -12.020 | 5.403 | 1.00 | 0.00 |
| 10 | ATOM | 141 | O | CYS R 55 | -25.722 | -11.942 | 4.747 | 1.00 | 0.00 |
| | ATOM | 142 | CB | CYS R 55 | -28.884 | -10.816 | 4.980 | 1.00 | 0.00 |
| | ATOM | 143 | SG | CYS R 55 | -29.966 | -9.423 | 5.373 | 1.00 | 0.00 |
| | ATOM | 144 | H | CYS R 55 | -26.798 | -9.206 | 4.422 | 1.00 | 0.00 |
| | ATOM | 145 | N | LYS R 56 | -27.264 | -13.165 | 5.871 | 1.00 | 0.00 |
| 15 | ATOM | 146 | CA | LYS R 56 | -26.589 | -14.362 | 5.398 | 1.00 | 0.00 |
| | ATOM | 147 | C | LYS R 56 | -27.549 | -15.386 | 4.837 | 1.00 | 0.00 |
| | ATOM | 148 | O | LYS R 56 | -28.519 | -15.789 | 5.477 | 1.00 | 0.00 |
| | ATOM | 149 | CB | LYS R 56 | -25.714 | -14.916 | 6.522 | 1.00 | 0.00 |
| | ATOM | 150 | CG | LYS R 56 | -24.805 | -16.085 | 6.153 | 1.00 | 0.00 |
| 20 | ATOM | 151 | CD | LYS R 56 | -23.591 | -16.147 | 7.077 | 1.00 | 0.00 |
| | ATOM | 152 | CE | LYS R 56 | -23.022 | -17.552 | 7.202 | 1.00 | 0.00 |
| | ATOM | 153 | NZ | LYS R 56 | -23.951 | -18.331 | 8.015 | 1.00 | 0.00 |
| | ATOM | 154 | H | LYS R 56 | -28.051 | -13.262 | 6.482 | 1.00 | 0.00 |
| | ATOM | 155 | 1HZ | LYS R 56 | -23.881 | -18.006 | 8.995 | 1.00 | 0.00 |
| 25 | ATOM | 156 | 2HZ | LYS R 56 | -23.728 | -19.338 | 7.946 | 1.00 | 0.00 |
| | ATOM | 157 | 3HZ | LYS R 56 | -24.928 | -18.196 | 7.691 | 1.00 | 0.00 |
| | ATOM | 158 | N | PRO R 57 | -27.236 | -15.830 | 3.598 | 1.00 | 0.00 |
| | ATOM | 159 | CA | PRO R 57 | -27.952 | -16.989 | 3.057 | 1.00 | 0.00 |
| | ATOM | 160 | C | PRO R 57 | -27.718 | -18.237 | 3.898 | 1.00 | 0.00 |
| 30 | ATOM | 161 | O | PRO R 57 | -26.590 | -18.524 | 4.312 | 1.00 | 0.00 |
| | ATOM | 162 | CB | PRO R 57 | -27.397 | -17.079 | 1.631 | 1.00 | 0.00 |
| | ATOM | 163 | CG | PRO R 57 | -26.018 | -16.418 | 1.682 | 1.00 | 0.00 |
| | ATOM | 164 | CD | PRO R 57 | -26.218 | -15.301 | 2.698 | 1.00 | 0.00 |
| | ATOM | 165 | N | CYS R 58 | -28.842 | -18.939 | 4.129 | 1.00 | 0.00 |

| | ATOM | 166 | CA | CYS R 58 | -28.833 | -20.145 | 4.956 | 1.00 | 0.00 |
|---|---|---|---|---|---|---|---|---|---|
| | ATOM | 167 | C | CYS R 58 | -28.246 | -21.406 | 4.309 | 1.00 | 0.00 |
| | ATOM | 168 | O | CYS R 58 | -27.067 | -21.414 | 3.958 | 1.00 | 0.00 |
| | ATOM | 169 | CB | CYS R 58 | -30.219 | -20.336 | 5.550 | 1.00 | 0.00 |
| 5 | ATOM | 170 | SG | CYS R 58 | -31.446 | -20.570 | 4.242 | 1.00 | 0.00 |
| | ATOM | 171 | H | CYS R 58 | -29.694 | -18.544 | 3.776 | 1.00 | 0.00 |
| | ATOM | 172 | N | THR R 59 | -29.040 | -22.485 | 4.171 | 1.00 | 0.00 |
| | ATOM | 173 | CA | THR R 59 | -28.405 | -23.777 | 3.884 | 1.00 | 0.00 |
| | ATOM | 174 | C | THR R 59 | -29.331 | -24.758 | 3.170 | 1.00 | 0.00 |
| 10 | ATOM | 175 | O | THR R 59 | -30.560 | -24.647 | 3.205 | 1.00 | 0.00 |
| | ATOM | 176 | CB | THR R 59 | -27.872 | -24.385 | 5.190 | 1.00 | 0.00 |
| | ATOM | 177 | OG1 | THR R 59 | -27.853 | -23.393 | 6.235 | 1.00 | 0.00 |
| | ATOM | 178 | CG2 | THR R 59 | -26.489 | -25.021 | 5.023 | 1.00 | 0.00 |
| | ATOM | 179 | H | THR R 59 | -30.024 | -22.480 | 4.346 | 1.00 | 0.00 |
| 15 | ATOM | 180 | HG1 | THR R 59 | -27.610 | -23.881 | 7.025 | 1.00 | 0.00 |
| | ATOM | 181 | N | GLU R 60 | -28.701 | -25.728 | 2.496 | 1.00 | 0.00 |
| | ATOM | 182 | CA | GLU R 60 | -29.419 | -26.674 | 1.647 | 1.00 | 0.00 |
| | ATOM | 183 | C | GLU R 60 | -30.161 | -27.753 | 2.390 | 1.00 | 0.00 |
| | ATOM | 184 | O | GLU R 60 | -29.788 | -28.927 | 2.459 | 1.00 | 0.00 |
| 20 | ATOM | 185 | CB | GLU R 60 | -28.473 | -27.229 | 0.578 | 1.00 | 0.00 |
| | ATOM | 186 | CG | GLU R 60 | -28.436 | -26.362 | -0.692 | 1.00 | 0.00 |
| | ATOM | 187 | CD | GLU R 60 | -28.332 | -24.886 | -0.343 | 1.00 | 0.00 |
| | ATOM | 188 | OE1 | GLU R 60 | -29.269 | -24.151 | -0.619 | 1.00 | 0.00 |
| | ATOM | 189 | OE2 | GLU R 60 | -27.340 | -24.471 | 0.243 | 1.00 | 0.00 |
| 25 | ATOM | 190 | H | GLU R 60 | -27.701 | -25.728 | 2.526 | 1.00 | 0.00 |
| | ATOM | 191 | N | CYS R 61 | -31.270 | -27.273 | 2.945 | 1.00 | 0.00 |
| | ATOM | 192 | CA | CYS R 61 | -32.170 | -28.156 | 3.661 | 1.00 | 0.00 |
| | ATOM | 193 | C | CYS R 61 | -33.085 | -28.944 | 2.755 | 1.00 | 0.00 |
| | ATOM | 194 | O | CYS R 61 | -34.299 | -28.751 | 2.709 | 1.00 | 0.00 |
| 30 | ATOM | 195 | CB | CYS R 61 | -32.910 | -27.347 | 4.714 | 1.00 | 0.00 |
| | ATOM | 196 | SG | CYS R 61 | -31.740 | -26.942 | 6.031 | 1.00 | 0.00 |
| | ATOM | 197 | H | CYS R 61 | -31.509 | -26.320 | 2.772 | 1.00 | 0.00 |
| | ATOM | 198 | N | VAL R 62 | -32.425 | -29.827 | 1.999 | 1.00 | 0.00 |
| | ATOM | 199 | CA | VAL R 62 | -33.134 | -30.711 | 1.091 | 1.00 | 0.00 |

| | | | | | | | |
|---|---|---|---|---|---|---|---|
| ATOM | 200 | C | VAL R 62 | -32.620 | -32.122 | 1.268 | 1.00 0.00 |
| ATOM | 201 | O | VAL R 62 | -31.507 | -32.351 | 1.744 | 1.00 0.00 |
| ATOM | 202 | CB | VAL R 62 | -32.966 | -30.257 | -0.371 | 1.00 0.00 |
| ATOM | 203 | CG1 | VAL R 62 | -33.771 | -28.988 | -0.662 | 1.00 0.00 |
| ATOM | 204 | CG2 | VAL R 62 | -31.491 | -30.099 | -0.762 | 1.00 0.00 |
| ATOM | 205 | H | VAL R 62 | -31.439 | -29.935 | 2.116 | 1.00 0.00 |
| ATOM | 206 | N | GLY R 63 | -33.482 | -33.057 | 0.831 | 1.00 0.00 |
| ATOM | 207 | CA | GLY R 63 | -33.115 | -34.472 | 0.773 | 1.00 0.00 |
| ATOM | 208 | C | GLY R 63 | -32.332 | -34.987 | 1.965 | 1.00 0.00 |
| ATOM | 209 | O | GLY R 63 | -32.817 | -35.076 | 3.086 | 1.00 0.00 |
| ATOM | 210 | H | GLY R 63 | -34.346 | -32.742 | 0.449 | 1.00 0.00 |
| ATOM | 211 | N | LEU R 64 | -31.064 | -35.302 | 1.662 | 1.00 0.00 |
| ATOM | 212 | CA | LEU R 64 | -30.174 | -35.897 | 2.660 | 1.00 0.00 |
| ATOM | 213 | C | LEU R 64 | -29.939 | -35.063 | 3.905 | 1.00 0.00 |
| ATOM | 214 | O | LEU R 64 | -29.748 | -35.602 | 4.993 | 1.00 0.00 |
| ATOM | 215 | CB | LEU R 64 | -28.818 | -36.268 | 2.047 | 1.00 0.00 |
| ATOM | 216 | CG | LEU R 64 | -28.759 | -37.594 | 1.273 | 1.00 0.00 |
| ATOM | 217 | CD1 | LEU R 64 | -29.223 | -38.770 | 2.135 | 1.00 0.00 |
| ATOM | 218 | CD2 | LEU R 64 | -29.458 | -37.548 | -0.089 | 1.00 0.00 |
| ATOM | 219 | H | LEU R 64 | -30.789 | -35.155 | 0.715 | 1.00 0.00 |
| ATOM | 220 | N | GLN R 65 | -29.920 | -33.749 | 3.667 | 1.00 0.00 |
| ATOM | 221 | CA | GLN R 65 | -29.848 | -32.806 | 4.767 | 1.00 0.00 |
| ATOM | 222 | C | GLN R 65 | -31.138 | -32.025 | 4.898 | 1.00 0.00 |
| ATOM | 223 | O | GLN R 65 | -31.327 | -30.896 | 4.444 | 1.00 0.00 |
| ATOM | 224 | CB | GLN R 65 | -28.607 | -31.923 | 4.628 | 1.00 0.00 |
| ATOM | 225 | CG | GLN R 65 | -27.300 | -32.698 | 4.852 | 1.00 0.00 |
| ATOM | 226 | CD | GLN R 65 | -27.227 | -33.242 | 6.271 | 1.00 0.00 |
| ATOM | 227 | OE1 | GLN R 65 | -28.016 | -32.916 | 7.148 | 1.00 0.00 |
| ATOM | 228 | NE2 | GLN R 65 | -26.211 | -34.066 | 6.484 | 1.00 0.00 |
| ATOM | 229 | H | GLN R 65 | -30.093 | -33.389 | 2.753 | 1.00 0.00 |
| ATOM | 230 | 1HE2 | GLN R 65 | -26.039 | -34.449 | 7.390 | 1.00 0.00 |
| ATOM | 231 | 2HE2 | GLN R 65 | -25.596 | -34.408 | 5.773 | 1.00 0.00 |
| ATOM | 232 | N | SER R 66 | -32.061 | -32.731 | 5.554 | 1.00 0.00 |
| ATOM | 233 | CA | SER R 66 | -33.390 | -32.190 | 5.816 | 1.00 0.00 |

```
ATOM  234  C   SER R  66    -33.405 -31.182  6.954 1.00 0.00
ATOM  235  O   SER R  66    -32.729 -31.340  7.966 1.00 0.00
ATOM  236  CB  SER R  66    -34.355 -33.332  6.140 1.00 0.00
ATOM  237  OG  SER R  66    -34.545 -34.205  5.013 1.00 0.00
ATOM  238  H   SER R  66    -31.773 -33.614  5.922 1.00 0.00
ATOM  239  HG  SER R  66    -33.695 -34.243  4.566 1.00 0.00
ATOM  240  N   MET R  67    -34.238 -30.147  6.731 1.00 0.00
ATOM  241  CA  MET R  67    -34.452 -29.049  7.683 1.00 0.00
ATOM  242  C   MET R  67    -34.580 -29.454  9.146 1.00 0.00
ATOM  243  O   MET R  67    -35.591 -30.030  9.547 1.00 0.00
ATOM  244  CB  MET R  67    -35.701 -28.290  7.216 1.00 0.00
ATOM  245  CG  MET R  67    -36.123 -27.081  8.053 1.00 0.00
ATOM  246  SD  MET R  67    -37.648 -26.329  7.454 1.00 0.00
ATOM  247  CE  MET R  67    -37.010 -25.683  5.898 1.00 0.00
ATOM  248  H   MET R  67    -34.671 -30.083  5.833 1.00 0.00
ATOM  249  N   SER R  68    -33.535 -29.137  9.905 1.00 0.00
ATOM  250  CA  SER R  68    -33.655 -29.183 11.360 1.00 0.00
ATOM  251  C   SER R  68    -34.023 -27.827 11.919 1.00 0.00
ATOM  252  O   SER R  68    -34.862 -27.691 12.800 1.00 0.00
ATOM  253  CB  SER R  68    -32.358 -29.637 12.009 1.00 0.00
ATOM  254  OG  SER R  68    -31.643 -30.509 11.115 1.00 0.00
ATOM  255  H   SER R  68    -32.761 -28.695  9.455 1.00 0.00
ATOM  256  HG  SER R  68    -31.558 -30.009 10.294 1.00 0.00
ATOM  257  N   ALA R  69    -33.375 -26.830 11.302 1.00 0.00
ATOM  258  CA  ALA R  69    -33.917 -25.487 11.420 1.00 0.00
ATOM  259  C   ALA R  69    -34.131 -24.964 10.022 1.00 0.00
ATOM  260  O   ALA R  69    -33.406 -25.351  9.101 1.00 0.00
ATOM  261  CB  ALA R  69    -32.949 -24.567 12.163 1.00 0.00
ATOM  262  H   ALA R  69    -32.643 -27.065 10.660 1.00 0.00
ATOM  263  N   PRO R  70    -35.166 -24.103  9.901 1.00 0.00
ATOM  264  CA  PRO R  70    -35.349 -23.341  8.665 1.00 0.00
ATOM  265  C   PRO R  70    -34.275 -22.271  8.587 1.00 0.00
ATOM  266  O   PRO R  70    -33.227 -22.350  9.229 1.00 0.00
ATOM  267  CB  PRO R  70    -36.770 -22.793  8.852 1.00 0.00
```

```
ATOM  268 CG  PRO R 70    -36.928 -22.604 10.359 1.00 0.00
ATOM  269 CD  PRO R 70    -36.166 -23.793 10.921 1.00 0.00
ATOM  270 N   CYS R 71    -34.550 -21.233  7.785 1.00 0.00
ATOM  271 CA  CYS R 71    -33.601 -20.119  7.809 1.00 0.00
ATOM  272 C   CYS R 71    -33.970 -19.007  8.772 1.00 0.00
ATOM  273 O   CYS R 71    -33.266 -18.019  8.957 1.00 0.00
ATOM  274 CB  CYS R 71    -33.418 -19.571  6.407 1.00 0.00
ATOM  275 SG  CYS R 71    -33.225 -20.894  5.186 1.00 0.00
ATOM  276 H   CYS R 71    -35.393 -21.195  7.252 1.00 0.00
ATOM  277 N   VAL R 72    -35.153 -19.212  9.378 1.00 0.00
ATOM  278 CA  VAL R 72    -35.518 -18.365 10.505 1.00 0.00
ATOM  279 C   VAL R 72    -35.220 -19.134 11.781 1.00 0.00
ATOM  280 O   VAL R 72    -34.442 -20.088 11.731 1.00 0.00
ATOM  281 CB  VAL R 72    -36.968 -17.871 10.369 1.00 0.00
ATOM  282 CG1 VAL R 72    -37.035 -16.768  9.311 1.00 0.00
ATOM  283 CG2 VAL R 72    -37.963 -18.992 10.064 1.00 0.00
ATOM  284 H   VAL R 72    -35.684 -20.042  9.226 1.00 0.00
ATOM  285 N   GLU R 73    -35.790 -18.668 12.904 1.00 0.00
ATOM  286 CA  GLU R 73    -35.488 -19.248 14.217 1.00 0.00
ATOM  287 C   GLU R 73    -34.000 -19.471 14.515 1.00 0.00
ATOM  288 O   GLU R 73    -33.279 -18.511 14.794 1.00 0.00
ATOM  289 CB  GLU R 73    -36.399 -20.461 14.483 1.00 0.00
ATOM  290 CG  GLU R 73    -37.842 -20.111 14.899 1.00 0.00
ATOM  291 CD  GLU R 73    -38.628 -19.399 13.805 1.00 0.00
ATOM  292 OE1 GLU R 73    -39.196 -20.066 12.948 1.00 0.00
ATOM  293 OE2 GLU R 73    -38.693 -18.173 13.816 1.00 0.00
ATOM  294 H   GLU R 73    -36.613 -18.100 12.819 1.00 0.00
ATOM  295 N   ALA R 74    -33.549 -20.733 14.428 1.00 0.00
ATOM  296 CA  ALA R 74    -32.139 -20.969 14.723 1.00 0.00
ATOM  297 C   ALA R 74    -31.209 -20.464 13.628 1.00 0.00
ATOM  298 O   ALA R 74    -31.627 -19.858 12.643 1.00 0.00
ATOM  299 CB  ALA R 74    -31.896 -22.456 14.994 1.00 0.00
ATOM  300 H   ALA R 74    -34.142 -21.443 14.054 1.00 0.00
ATOM  301 N   ASP R 75    -29.901 -20.717 13.841 1.00 0.00
```

| | | | | | | | | | |
|---|---|---|---|---|---|---|---|---|---|
| | ATOM | 302 | CA | ASP R | 75 | -28.988 | -20.165 | 12.838 | 1.00 0.00 |
| | ATOM | 303 | C | ASP R | 75 | -28.978 | -20.946 | 11.540 | 1.00 0.00 |
| | ATOM | 304 | O | ASP R | 75 | -28.907 | -22.175 | 11.568 | 1.00 0.00 |
| | ATOM | 305 | CB | ASP R | 75 | -27.570 | -19.881 | 13.412 | 1.00 0.00 |
| 5 | ATOM | 306 | CG | ASP R | 75 | -26.502 | -20.949 | 13.148 | 1.00 0.00 |
| | ATOM | 307 | OD1 | ASP R | 75 | -25.764 | -20.841 | 12.170 | 1.00 0.00 |
| | ATOM | 308 | OD2 | ASP R | 75 | -26.375 | -21.893 | 13.918 | 1.00 0.00 |
| | ATOM | 309 | H | ASP R | 75 | -29.610 | -21.308 | 14.596 | 1.00 0.00 |
| | ATOM | 310 | N | ASP R | 76 | -29.031 | -20.167 | 10.438 | 1.00 0.00 |
| 10 | ATOM | 311 | CA | ASP R | 76 | -28.563 | -20.650 | 9.133 | 1.00 0.00 |
| | ATOM | 312 | C | ASP R | 76 | -28.887 | -22.099 | 8.799 | 1.00 0.00 |
| | ATOM | 313 | O | ASP R | 76 | -28.004 | -22.960 | 8.851 | 1.00 0.00 |
| | ATOM | 314 | CB | ASP R | 76 | -27.048 | -20.433 | 9.048 | 1.00 0.00 |
| | ATOM | 315 | CG | ASP R | 76 | -26.651 | -19.628 | 7.832 | 1.00 0.00 |
| 15 | ATOM | 316 | OD1 | ASP R | 76 | -26.280 | -20.197 | 6.821 | 1.00 0.00 |
| | ATOM | 317 | OD2 | ASP R | 76 | -26.657 | -18.412 | 7.895 | 1.00 0.00 |
| | ATOM | 318 | H | ASP R | 76 | -29.310 | -19.218 | 10.546 | 1.00 0.00 |
| | ATOM | 319 | N | ALA R | 77 | -30.181 | -22.342 | 8.504 | 1.00 0.00 |
| | ATOM | 320 | CA | ALA R | 77 | -30.727 | -23.675 | 8.210 | 1.00 0.00 |
| 20 | ATOM | 321 | C | ALA R | 77 | -29.903 | -24.882 | 8.622 | 1.00 0.00 |
| | ATOM | 322 | O | ALA R | 77 | -28.947 | -25.313 | 7.977 | 1.00 0.00 |
| | ATOM | 323 | CB | ALA R | 77 | -31.146 | -23.786 | 6.745 | 1.00 0.00 |
| | ATOM | 324 | H | ALA R | 77 | -30.762 | -21.532 | 8.486 | 1.00 0.00 |
| | ATOM | 325 | N | VAL R | 78 | -30.293 | -25.370 | 9.804 | 1.00 0.00 |
| 25 | ATOM | 326 | CA | VAL R | 78 | -29.473 | -26.437 | 10.365 | 1.00 0.00 |
| | ATOM | 327 | C | VAL R | 78 | -29.674 | -27.730 | 9.608 | 1.00 0.00 |
| | ATOM | 328 | O | VAL R | 78 | -30.689 | -28.419 | 9.719 | 1.00 0.00 |
| | ATOM | 329 | CB | VAL R | 78 | -29.705 | -26.621 | 11.875 | 1.00 0.00 |
| | ATOM | 330 | CG1 | VAL R | 78 | -28.824 | -27.731 | 12.461 | 1.00 0.00 |
| 30 | ATOM | 331 | CG2 | VAL R | 78 | -29.474 | -25.311 | 12.630 | 1.00 0.00 |
| | ATOM | 332 | H | VAL R | 78 | -31.196 | -25.121 | 10.147 | 1.00 0.00 |
| | ATOM | 333 | N | CYS R | 79 | -28.632 | -28.038 | 8.838 | 1.00 0.00 |
| | ATOM | 334 | CA | CYS R | 79 | -28.713 | -29.247 | 8.033 | 1.00 0.00 |
| | ATOM | 335 | C | CYS R | 79 | -27.339 | -29.828 | 7.920 | 1.00 0.00 |

| | | | | | | | |
|---|---|---|---|---|---|---|---|
| | ATOM | 336 | O | CYS R 79 | -26.525 | -29.376 | 7.119 1.00 0.00 |
| | ATOM | 337 | CB | CYS R 79 | -29.320 | -28.928 | 6.669 1.00 0.00 |
| | ATOM | 338 | SG | CYS R 79 | -31.114 | -28.721 | 6.825 1.00 0.00 |
| | ATOM | 339 | H | CYS R 79 | -27.953 | -27.324 | 8.640 1.00 0.00 |
| 5 | ATOM | 340 | N | ARG R 80 | -27.136 | -30.778 | 8.851 1.00 0.00 |
| | ATOM | 341 | CA | ARG R 80 | -25.874 | -31.473 | 9.118 1.00 0.00 |
| | ATOM | 342 | C | ARG R 80 | -26.145 | -32.410 | 10.286 1.00 0.00 |
| | ATOM | 343 | O | ARG R 80 | -27.174 | -32.258 | 10.947 1.00 0.00 |
| | ATOM | 344 | CB | ARG R 80 | -24.794 | -30.457 | 9.480 1.00 0.00 |
| 10 | ATOM | 345 | CG | ARG R 80 | -23.510 | -30.612 | 8.671 1.00 0.00 |
| | ATOM | 346 | CD | ARG R 80 | -23.609 | -30.483 | 7.144 1.00 0.00 |
| | ATOM | 347 | NE | ARG R 80 | -22.248 | -30.464 | 6.602 1.00 0.00 |
| | ATOM | 348 | CZ | ARG R 80 | -21.752 | -29.350 | 6.025 1.00 0.00 |
| | ATOM | 349 | NH1 | ARG R 80 | -20.446 | -29.201 | 5.899 1.00 0.00 |
| 15 | ATOM | 350 | NH2 | ARG R 80 | -22.565 | -28.390 | 5.605 1.00 0.00 |
| | ATOM | 351 | H | ARG R 80 | -27.930 | -31.029 | 9.408 1.00 0.00 |
| | ATOM | 352 | HE | ARG R 80 | -21.632 | -31.222 | 6.850 1.00 0.00 |
| | ATOM | 353 | 1HH1 | ARG R 80 | -20.066 | -28.349 | 5.510 1.00 0.00 |
| | ATOM | 354 | 2HH1 | ARG R 80 | -19.803 | -29.904 | 6.220 1.00 0.00 |
| 20 | ATOM | 355 | 1HH2 | ARG R 80 | -22.163 | -27.510 | 5.312 1.00 0.00 |
| | ATOM | 356 | 2HH2 | ARG R 80 | -23.555 | -28.546 | 5.585 1.00 0.00 |
| | ATOM | 357 | N | CYS R 81 | -25.254 | -33.378 | 10.546 1.00 0.00 |
| | ATOM | 358 | CA | CYS R 81 | -25.630 | -34.302 | 11.618 1.00 0.00 |
| | ATOM | 359 | C | CYS R 81 | -24.657 | -34.425 | 12.779 1.00 0.00 |
| 25 | ATOM | 360 | O | CYS R 81 | -23.437 | -34.482 | 12.654 1.00 0.00 |
| | ATOM | 361 | CB | CYS R 81 | -25.971 | -35.691 | 11.060 1.00 0.00 |
| | ATOM | 362 | SG | CYS R 81 | -27.286 | -35.685 | 9.805 1.00 0.00 |
| | ATOM | 363 | H | CYS R 81 | -24.383 | -33.437 | 10.057 1.00 0.00 |
| | ATOM | 364 | N | ALA R 82 | -25.276 | -34.521 | 13.965 1.00 0.00 |
| 30 | ATOM | 365 | CA | ALA R 82 | -24.515 | -34.749 | 15.194 1.00 0.00 |
| | ATOM | 366 | C | ALA R 82 | -25.304 | -35.664 | 16.121 1.00 0.00 |
| | ATOM | 367 | O | ALA R 82 | -26.298 | -36.259 | 15.706 1.00 0.00 |
| | ATOM | 368 | CB | ALA R 82 | -24.220 | -33.410 | 15.880 1.00 0.00 |
| | ATOM | 369 | H | ALA R 82 | -26.275 | -34.483 | 13.959 1.00 0.00 |

| | | | | | | | |
|---|---|---|---|---|---|---|---|
| | ATOM | 370 | N | TYR R 83 | -24.873 | -35.700 | 17.401 1.00 0.00 |
| | ATOM | 371 | CA | TYR R 83 | -25.613 | -36.307 | 18.519 1.00 0.00 |
| | ATOM | 372 | C | TYR R 83 | -25.565 | -37.827 | 18.584 1.00 0.00 |
| | ATOM | 373 | O | TYR R 83 | -24.974 | -38.412 | 19.487 1.00 0.00 |
| 5 | ATOM | 374 | CB | TYR R 83 | -27.078 | -35.829 | 18.634 1.00 0.00 |
| | ATOM | 375 | CG | TYR R 83 | -27.226 | -34.328 | 18.781 1.00 0.00 |
| | ATOM | 376 | CD1 | TYR R 83 | -26.962 | -33.725 | 20.028 1.00 0.00 |
| | ATOM | 377 | CD2 | TYR R 83 | -27.670 | -33.574 | 17.674 1.00 0.00 |
| | ATOM | 378 | CE1 | TYR R 83 | -27.210 | -32.351 | 20.189 1.00 0.00 |
| 10 | ATOM | 379 | CE2 | TYR R 83 | -27.914 | -32.198 | 17.834 1.00 0.00 |
| | ATOM | 380 | CZ | TYR R 83 | -27.710 | -31.608 | 19.099 1.00 0.00 |
| | ATOM | 381 | OH | TYR R 83 | -28.024 | -30.273 | 19.294 1.00 0.00 |
| | ATOM | 382 | H | TYR R 83 | -23.940 | -35.374 | 17.555 1.00 0.00 |
| | ATOM | 383 | HH | TYR R 83 | -28.217 | -29.854 | 18.456 1.00 0.00 |
| 15 | ATOM | 384 | N | GLY R 84 | -26.236 | -38.425 | 17.591 1.00 0.00 |
| | ATOM | 385 | CA | GLY R 84 | -26.228 | -39.880 | 17.476 1.00 0.00 |
| | ATOM | 386 | C | GLY R 84 | -25.429 | -40.269 | 16.256 1.00 0.00 |
| | ATOM | 387 | O | GLY R 84 | -24.379 | -40.900 | 16.321 1.00 0.00 |
| | ATOM | 388 | H | GLY R 84 | -26.647 | -37.841 | 16.890 1.00 0.00 |
| 20 | ATOM | 389 | N | TYR R 85 | -25.951 | -39.784 | 15.120 1.00 0.00 |
| | ATOM | 390 | CA | TYR R 85 | -25.110 | -39.752 | 13.923 1.00 0.00 |
| | ATOM | 391 | C | TYR R 85 | -24.142 | -38.590 | 13.997 1.00 0.00 |
| | ATOM | 392 | O | TYR R 85 | -24.434 | -37.463 | 13.597 1.00 0.00 |
| | ATOM | 393 | CB | TYR R 85 | -25.941 | -39.668 | 12.637 1.00 0.00 |
| 25 | ATOM | 394 | CG | TYR R 85 | -26.885 | -40.843 | 12.509 1.00 0.00 |
| | ATOM | 395 | CD1 | TYR R 85 | -26.367 | -42.140 | 12.304 1.00 0.00 |
| | ATOM | 396 | CD2 | TYR R 85 | -28.271 | -40.602 | 12.591 1.00 0.00 |
| | ATOM | 397 | CE1 | TYR R 85 | -27.258 | -43.221 | 12.185 1.00 0.00 |
| | ATOM | 398 | CE2 | TYR R 85 | -29.161 | -41.681 | 12.467 1.00 0.00 |
| 30 | ATOM | 399 | CZ | TYR R 85 | -28.645 | -42.978 | 12.269 1.00 0.00 |
| | ATOM | 400 | OH | TYR R 85 | -29.528 | -44.039 | 12.161 1.00 0.00 |
| | ATOM | 401 | H | TYR R 85 | -26.801 | -39.267 | 15.189 1.00 0.00 |
| | ATOM | 402 | HH | TYR R 85 | -30.392 | -43.682 | 11.979 1.00 0.00 |
| | ATOM | 403 | N | TYR R 86 | -23.001 | -38.941 | 14.593 1.00 0.00 |

|    | ATOM | 404 | CA   | TYR R 86 | -21.996 -37.958 14.983 1.00 0.00 |
|----|------|-----|------|----------|----------------------------------|
|    | ATOM | 405 | C    | TYR R 86 | -21.418 -37.177 13.824 1.00 0.00 |
|    | ATOM | 406 | O    | TYR R 86 | -21.126 -35.992 13.937 1.00 0.00 |
|    | ATOM | 407 | CB   | TYR R 86 | -20.809 -38.602 15.710 1.00 0.00 |
| 5  | ATOM | 408 | CG   | TYR R 86 | -21.207 -39.697 16.673 1.00 0.00 |
|    | ATOM | 409 | CD1  | TYR R 86 | -20.850 -41.023 16.352 1.00 0.00 |
|    | ATOM | 410 | CD2  | TYR R 86 | -21.890 -39.374 17.863 1.00 0.00 |
|    | ATOM | 411 | CE1  | TYR R 86 | -21.141 -42.050 17.264 1.00 0.00 |
|    | ATOM | 412 | CE2  | TYR R 86 | -22.184 -40.403 18.774 1.00 0.00 |
| 10 | ATOM | 413 | CZ   | TYR R 86 | -21.785 -41.722 18.473 1.00 0.00 |
|    | ATOM | 414 | OH   | TYR R 86 | -22.023 -42.711 19.413 1.00 0.00 |
|    | ATOM | 415 | H    | TYR R 86 | -22.958 -39.890 14.897 1.00 0.00 |
|    | ATOM | 416 | HH   | TYR R 86 | -21.495 -43.480 19.212 1.00 0.00 |
|    | ATOM | 417 | N    | GLN R 87 | -21.218 -37.946 12.732 1.00 0.00 |
| 15 | ATOM | 418 | CA   | GLN R 87 | -20.570 -37.470 11.510 1.00 0.00 |
|    | ATOM | 419 | C    | GLN R 87 | -19.097 -37.109 11.556 1.00 0.00 |
|    | ATOM | 420 | O    | GLN R 87 | -18.514 -36.712 12.563 1.00 0.00 |
|    | ATOM | 421 | CB   | GLN R 87 | -21.334 -36.316 10.855 1.00 0.00 |
|    | ATOM | 422 | CG   | GLN R 87 | -22.628 -36.720 10.170 1.00 0.00 |
| 20 | ATOM | 423 | CD   | GLN R 87 | -22.807 -35.859 8.937 1.00 0.00  |
|    | ATOM | 424 | OE1  | GLN R 87 | -23.553 -34.880 8.908 1.00 0.00  |
|    | ATOM | 425 | NE2  | GLN R 87 | -22.130 -36.305 7.879 1.00 0.00  |
|    | ATOM | 426 | H    | GLN R 87 | -21.584 -38.879 12.734 1.00 0.00 |
|    | ATOM | 427 | 1HE2 | GLN R 87 | -22.399 -35.962 6.979 1.00 0.00  |
| 25 | ATOM | 428 | 2HE2 | GLN R 87 | -21.431 -37.016 7.960 1.00 0.00  |
|    | ATOM | 429 | N    | ASP R 88 | -18.536 -37.210 10.345 1.00 0.00 |
|    | ATOM | 430 | CA   | ASP R 88 | -17.727 -36.069 9.929 1.00 0.00  |
|    | ATOM | 431 | C    | ASP R 88 | -18.634 -35.318 8.978 1.00 0.00  |
|    | ATOM | 432 | O    | ASP R 88 | -19.200 -35.901 8.064 1.00 0.00  |
| 30 | ATOM | 433 | CB   | ASP R 88 | -16.408 -36.490 9.269 1.00 0.00  |
|    | ATOM | 434 | CG   | ASP R 88 | -15.384 -35.376 9.431 1.00 0.00  |
|    | ATOM | 435 | OD1  | ASP R 88 | -14.915 -34.822 8.442 1.00 0.00  |
|    | ATOM | 436 | OD2  | ASP R 88 | -15.051 -35.032 10.560 1.00 0.00 |
|    | ATOM | 437 | H    | ASP R 88 | -19.040 -37.751 9.666 1.00 0.00  |

```
ATOM    438  N   GLU R  89     -18.883 -34.048  9.301  1.00  0.00
ATOM    439  CA  GLU R  89     -20.163 -33.427  8.949  1.00  0.00
ATOM    440  C   GLU R  89     -20.666 -33.353  7.500  1.00  0.00
ATOM    441  O   GLU R  89     -21.862 -33.159  7.271  1.00  0.00
ATOM    442  CB  GLU R  89     -20.252 -32.098  9.722  1.00  0.00
ATOM    443  CG  GLU R  89     -19.934 -30.765  9.024  1.00  0.00
ATOM    444  CD  GLU R  89     -18.588 -30.734  8.336  1.00  0.00
ATOM    445  OE1 GLU R  89     -18.494 -31.092  7.174  1.00  0.00
ATOM    446  OE2 GLU R  89     -17.616 -30.321  8.940  1.00  0.00
ATOM    447  H   GLU R  89     -18.289 -33.640  9.988  1.00  0.00
ATOM    448  N   THR R  90     -19.709 -33.499  6.555  1.00  0.00
ATOM    449  CA  THR R  90     -19.933 -32.941  5.217  1.00  0.00
ATOM    450  C   THR R  90     -21.285 -33.118  4.552  1.00  0.00
ATOM    451  O   THR R  90     -21.938 -34.160  4.600  1.00  0.00
ATOM    452  CB  THR R  90     -18.810 -33.347  4.255  1.00  0.00
ATOM    453  OG1 THR R  90     -17.674 -33.836  4.984  1.00  0.00
ATOM    454  CG2 THR R  90     -18.392 -32.204  3.324  1.00  0.00
ATOM    455  H   THR R  90     -18.784 -33.648  6.889  1.00  0.00
ATOM    456  HG1 THR R  90     -17.327 -33.064  5.444  1.00  0.00
ATOM    457  N   THR R  91     -21.647 -32.017  3.895  1.00  0.00
ATOM    458  CA  THR R  91     -22.860 -31.897  3.097  1.00  0.00
ATOM    459  C   THR R  91     -23.258 -33.149  2.323  1.00  0.00
ATOM    460  O   THR R  91     -22.484 -33.676  1.526  1.00  0.00
ATOM    461  CB  THR R  91     -22.647 -30.720  2.141  1.00  0.00
ATOM    462  OG1 THR R  91     -21.666 -29.793  2.666  1.00  0.00
ATOM    463  CG2 THR R  91     -23.964 -30.007  1.827  1.00  0.00
ATOM    464  H   THR R  91     -20.984 -31.271  3.860  1.00  0.00
ATOM    465  HG1 THR R  91     -20.894 -29.846  2.096  1.00  0.00
ATOM    466  N   GLY R  92     -24.499 -33.584  2.577  1.00  0.00
ATOM    467  CA  GLY R  92     -24.978 -34.710  1.781  1.00  0.00
ATOM    468  C   GLY R  92     -24.860 -36.093  2.409  1.00  0.00
ATOM    469  O   GLY R  92     -25.335 -37.085  1.850  1.00  0.00
ATOM    470  H   GLY R  92     -25.022 -33.210  3.337  1.00  0.00
ATOM    471  N   ARG R  93     -24.236 -36.138  3.595  1.00  0.00
```

```
ATOM    472  CA  ARG R  93     -24.173 -37.427  4.280 1.00 0.00
ATOM    473  C   ARG R  93     -24.418 -37.314  5.777 1.00 0.00
ATOM    474  O   ARG R  93     -24.453 -36.210  6.315 1.00 0.00
ATOM    475  CB  ARG R  93     -22.867 -38.152  3.925 1.00 0.00
ATOM    476  CG  ARG R  93     -21.604 -37.313  4.120 1.00 0.00
ATOM    477  CD  ARG R  93     -20.324 -38.083  3.779 1.00 0.00
ATOM    478  NE  ARG R  93     -19.135 -37.298  4.115 1.00 0.00
ATOM    479  CZ  ARG R  93     -18.683 -37.255  5.391 1.00 0.00
ATOM    480  NH1 ARG R  93     -17.741 -36.386  5.728 1.00 0.00
ATOM    481  NH2 ARG R  93     -19.200 -38.034  6.329 1.00 0.00
ATOM    482  H   ARG R  93     -23.801 -35.328  3.987 1.00 0.00
ATOM    483  HE  ARG R  93     -18.726 -36.705  3.421 1.00 0.00
ATOM    484 1HH1 ARG R  93     -17.400 -36.385  6.666 1.00 0.00
ATOM    485 2HH1 ARG R  93     -17.378 -35.697  5.095 1.00 0.00
ATOM    486 1HH2 ARG R  93     -18.999 -37.871  7.294 1.00 0.00
ATOM    487 2HH2 ARG R  93     -19.832 -38.785  6.135 1.00 0.00
ATOM    488  N   CYS R  94     -24.653 -38.506  6.371 1.00 0.00
ATOM    489  CA  CYS R  94     -24.768 -38.726  7.818 1.00 0.00
ATOM    490  C   CYS R  94     -24.488 -40.182  8.172 1.00 0.00
ATOM    491  O   CYS R  94     -25.041 -41.119  7.594 1.00 0.00
ATOM    492  CB  CYS R  94     -26.138 -38.358  8.397 1.00 0.00
ATOM    493  SG  CYS R  94     -26.692 -36.659  8.083 1.00 0.00
ATOM    494  H   CYS R  94     -24.611 -39.336  5.816 1.00 0.00
ATOM    495  N   GLU R  95     -23.572 -40.320  9.142 1.00 0.00
ATOM    496  CA  GLU R  95     -22.945 -41.588  9.514 1.00 0.00
ATOM    497  C   GLU R  95     -22.224 -41.383 10.836 1.00 0.00
ATOM    498  O   GLU R  95     -22.258 -40.278 11.382 1.00 0.00
ATOM    499  CB  GLU R  95     -21.981 -42.075  8.412 1.00 0.00
ATOM    500  CG  GLU R  95     -20.721 -41.229  8.154 1.00 0.00
ATOM    501  CD  GLU R  95     -21.085 -39.811  7.761 1.00 0.00
ATOM    502  OE1 GLU R  95     -21.467 -39.570  6.627 1.00 0.00
ATOM    503  OE2 GLU R  95     -20.997 -38.922  8.591 1.00 0.00
ATOM    504  H   GLU R  95     -23.203 -39.480  9.540 1.00 0.00
ATOM    505  N   ALA R  96     -21.599 -42.462 11.332 1.00 0.00
```

| | | | | | | | |
|---|---|---|---|---|---|---|---|
| | ATOM | 506 | CA  | ALA R 96 | -20.851 | -42.305 | 12.578 1.00 0.00 |
| | ATOM | 507 | C   | ALA R 96 | -19.527 | -41.574 | 12.413 1.00 0.00 |
| | ATOM | 508 | O   | ALA R 96 | -18.742 | -41.952 | 11.544 1.00 0.00 |
| | ATOM | 509 | CB  | ALA R 96 | -20.605 | -43.668 | 13.231 1.00 0.00 |
| 5 | ATOM | 510 | OXT | ALA R 96 | -19.293 | -40.619 | 13.151 1.00 0.00 |
| | ATOM | 511 | H   | ALA R 96 | -21.711 | -43.344 | 10.871 1.00 0.00 |
| | END | | | | | | |

| | | | | | | | |
|---|---|---|---|---|---|---|---|
| | REMARK | 1 | Second CRD of p75$^{NTR}$, bound to BDNF. | | | | |
| 10 | REMARK | 2 | | | | | |
| | ATOM | 1 | N | CYS R 39 | -28.731 | -23.425 | 17.186 1.00 0.00 |
| | ATOM | 2 | CA | CYS R 39 | -29.491 | -22.215 | 17.484 1.00 0.00 |
| | ATOM | 3 | C | CYS R 39 | -30.988 | -22.434 | 17.523 1.00 0.00 |
| | ATOM | 4 | O | CYS R 39 | -31.773 | -21.495 | 17.660 1.00 0.00 |
| 15 | ATOM | 5 | CB | CYS R 39 | -29.203 | -21.102 | 16.474 1.00 0.00 |
| | ATOM | 6 | SG | CYS R 39 | -27.698 | -21.312 | 15.471 1.00 0.00 |
| | ATOM | 7 | 1H | CYS R 39 | -27.735 | -23.264 | 17.148 1.00 0.00 |
| | ATOM | 8 | 2H | CYS R 39 | -28.868 | -24.153 | 17.874 1.00 0.00 |
| | ATOM | 9 | 3H | CYS R 39 | -28.982 | -23.835 | 16.298 1.00 0.00 |
| 20 | ATOM | 10 | N | LEU R 40 | -31.381 | -23.704 | 17.336 1.00 0.00 |
| | ATOM | 11 | CA | LEU R 40 | -32.802 | -24.005 | 17.397 1.00 0.00 |
| | ATOM | 12 | C | LEU R 40 | -33.098 | -24.788 | 18.662 1.00 0.00 |
| | ATOM | 13 | O | LEU R 40 | -32.371 | -24.712 | 19.645 1.00 0.00 |
| | ATOM | 14 | CB | LEU R 40 | -33.224 | -24.736 | 16.114 1.00 0.00 |
| 25 | ATOM | 15 | CG | LEU R 40 | -33.141 | -23.868 | 14.854 1.00 0.00 |
| | ATOM | 16 | CD1 | LEU R 40 | -33.498 | -24.664 | 13.599 1.00 0.00 |
| | ATOM | 17 | CD2 | LEU R 40 | -33.987 | -22.598 | 14.968 1.00 0.00 |
| | ATOM | 18 | H | LEU R 40 | -30.734 | -24.467 | 17.314 1.00 0.00 |
| | ATOM | 19 | N | ASP R 41 | -34.194 | -25.545 | 18.604 1.00 0.00 |
| 30 | ATOM | 20 | CA | ASP R 41 | -34.394 | -26.559 | 19.630 1.00 0.00 |
| | ATOM | 21 | C | ASP R 41 | -33.510 | -27.762 | 19.326 1.00 0.00 |
| | ATOM | 22 | O | ASP R 41 | -32.569 | -27.678 | 18.542 1.00 0.00 |
| | ATOM | 23 | CB | ASP R 41 | -35.888 | -26.923 | 19.676 1.00 0.00 |
| | ATOM | 24 | CG | ASP R 41 | -36.282 | -27.631 | 18.391 1.00 0.00 |

| | | | | | | |
|---|---|---|---|---|---|---|
| | ATOM | 25 | OD1 ASP R 41 | -36.462 | -28.842 | 18.426 1.00 0.00 |
| | ATOM | 26 | OD2 ASP R 41 | -36.364 | -26.975 | 17.359 1.00 0.00 |
| | ATOM | 27 | H ASP R 41 | -34.766 | -25.640 | 17.790 1.00 0.00 |
| | ATOM | 28 | N SER R 42 | -33.860 | -28.892 | 19.945 1.00 0.00 |
| 5 | ATOM | 29 | CA SER R 42 | -33.192 | -30.156 | 19.648 1.00 0.00 |
| | ATOM | 30 | C SER R 42 | -32.956 | -30.499 | 18.173 1.00 0.00 |
| | ATOM | 31 | O SER R 42 | -31.967 | -31.144 | 17.816 1.00 0.00 |
| | ATOM | 32 | CB SER R 42 | -33.975 | -31.256 | 20.359 1.00 0.00 |
| | ATOM | 33 | OG SER R 42 | -34.507 | -30.738 | 21.597 1.00 0.00 |
| 10 | ATOM | 34 | H SER R 42 | -34.638 | -28.916 | 20.568 1.00 0.00 |
| | ATOM | 35 | HG SER R 42 | -35.328 | -31.194 | 21.757 1.00 0.00 |
| | ATOM | 36 | N VAL R 43 | -33.884 | -30.042 | 17.310 1.00 0.00 |
| | ATOM | 37 | CA VAL R 43 | -33.712 | -30.372 | 15.895 1.00 0.00 |
| | ATOM | 38 | C VAL R 43 | -32.454 | -29.826 | 15.235 1.00 0.00 |
| 15 | ATOM | 39 | O VAL R 43 | -31.932 | -30.402 | 14.281 1.00 0.00 |
| | ATOM | 40 | CB VAL R 43 | -34.955 | -30.058 | 15.044 1.00 0.00 |
| | ATOM | 41 | CG1 VAL R 43 | -36.186 | -30.773 | 15.604 1.00 0.00 |
| | ATOM | 42 | CG2 VAL R 43 | -35.182 | -28.560 | 14.824 1.00 0.00 |
| | ATOM | 43 | H VAL R 43 | -34.615 | -29.433 | 17.633 1.00 0.00 |
| 20 | ATOM | 44 | N THR R 44 | -31.938 | -28.722 | 15.786 1.00 0.00 |
| | ATOM | 45 | CA THR R 44 | -30.651 | -28.248 | 15.283 1.00 0.00 |
| | ATOM | 46 | C THR R 44 | -29.869 | -27.538 | 16.372 1.00 0.00 |
| | ATOM | 47 | O THR R 44 | -30.165 | -26.391 | 16.716 1.00 0.00 |
| | ATOM | 48 | CB THR R 44 | -30.833 | -27.333 | 14.062 1.00 0.00 |
| 25 | ATOM | 49 | OG1 THR R 44 | -31.913 | -27.770 | 13.215 1.00 0.00 |
| | ATOM | 50 | CG2 THR R 44 | -29.538 | -27.231 | 13.256 1.00 0.00 |
| | ATOM | 51 | H THR R 44 | -32.435 | -28.226 | 16.507 1.00 0.00 |
| | ATOM | 52 | HG1 THR R 44 | -31.927 | -28.725 | 13.271 1.00 0.00 |
| | ATOM | 53 | N PHE R 45 | -28.911 | -28.291 | 16.916 1.00 0.00 |
| 30 | ATOM | 54 | CA PHE R 45 | -28.186 | -27.770 | 18.069 1.00 0.00 |
| | ATOM | 55 | C PHE R 45 | -26.993 | -26.926 | 17.656 1.00 0.00 |
| | ATOM | 56 | O PHE R 45 | -26.806 | -26.646 | 16.478 1.00 0.00 |
| | ATOM | 57 | CB PHE R 45 | -27.822 | -28.924 | 19.006 1.00 0.00 |
| | ATOM | 58 | CG PHE R 45 | -26.899 | -29.937 | 18.362 1.00 0.00 |

| | | | | | | | | | |
|---|---|---|---|---|---|---|---|---|---|
| | ATOM | 59 | CD1 | PHE R | 45 | -27.449 | -31.094 | 17.770 | 1.00 0.00 |
| | ATOM | 60 | CD2 | PHE R | 45 | -25.503 | -29.718 | 18.376 | 1.00 0.00 |
| | ATOM | 61 | CE1 | PHE R | 45 | -26.592 | -32.040 | 17.179 | 1.00 0.00 |
| | ATOM | 62 | CE2 | PHE R | 45 | -24.646 | -30.663 | 17.785 | 1.00 0.00 |
| 5 | ATOM | 63 | CZ | PHE R | 45 | -25.200 | -31.813 | 17.186 | 1.00 0.00 |
| | ATOM | 64 | H | PHE R | 45 | -28.575 | -29.099 | 16.440 | 1.00 0.00 |
| | ATOM | 65 | N | SER R | 46 | -26.169 | -26.504 | 18.621 | 1.00 0.00 |
| | ATOM | 66 | CA | SER R | 46 | -25.321 | -25.406 | 18.156 | 1.00 0.00 |
| | ATOM | 67 | C | SER R | 46 | -23.805 | -25.596 | 18.062 | 1.00 0.00 |
| 10 | ATOM | 68 | O | SER R | 46 | -23.139 | -25.015 | 17.205 | 1.00 0.00 |
| | ATOM | 69 | CB | SER R | 46 | -25.722 | -24.118 | 18.887 | 1.00 0.00 |
| | ATOM | 70 | OG | SER R | 46 | -27.050 | -24.244 | 19.441 | 1.00 0.00 |
| | ATOM | 71 | H | SER R | 46 | -26.281 | -26.700 | 19.596 | 1.00 0.00 |
| | ATOM | 72 | HG | SER R | 46 | -26.881 | -24.590 | 20.319 | 1.00 0.00 |
| 15 | ATOM | 73 | N | ASP R | 47 | -23.284 | -26.424 | 18.982 | 1.00 0.00 |
| | ATOM | 74 | CA | ASP R | 47 | -21.847 | -26.704 | 19.149 | 1.00 0.00 |
| | ATOM | 75 | C | ASP R | 47 | -20.914 | -25.513 | 19.394 | 1.00 0.00 |
| | ATOM | 76 | O | ASP R | 47 | -19.707 | -25.533 | 19.159 | 1.00 0.00 |
| | ATOM | 77 | CB | ASP R | 47 | -21.313 | -27.830 | 18.204 | 1.00 0.00 |
| 20 | ATOM | 78 | CG | ASP R | 47 | -20.687 | -27.453 | 16.853 | 1.00 0.00 |
| | ATOM | 79 | OD1 | ASP R | 47 | -20.787 | -28.220 | 15.898 | 1.00 0.00 |
| | ATOM | 80 | OD2 | ASP R | 47 | -20.046 | -26.421 | 16.716 | 1.00 0.00 |
| | ATOM | 81 | H | ASP R | 47 | -23.930 | -26.730 | 19.679 | 1.00 0.00 |
| | ATOM | 82 | N | VAL R | 48 | -21.525 | -24.456 | 19.953 | 1.00 0.00 |
| 25 | ATOM | 83 | CA | VAL R | 48 | -20.791 | -23.190 | 20.089 | 1.00 0.00 |
| | ATOM | 84 | C | VAL R | 48 | -19.752 | -23.030 | 21.212 | 1.00 0.00 |
| | ATOM | 85 | O | VAL R | 48 | -19.796 | -22.163 | 22.083 | 1.00 0.00 |
| | ATOM | 86 | CB | VAL R | 48 | -21.762 | -22.000 | 20.041 | 1.00 0.00 |
| | ATOM | 87 | CG1 | VAL R | 48 | -22.331 | -21.847 | 18.628 | 1.00 0.00 |
| 30 | ATOM | 88 | CG2 | VAL R | 48 | -22.865 | -22.095 | 21.103 | 1.00 0.00 |
| | ATOM | 89 | H | VAL R | 48 | -22.434 | -24.585 | 20.351 | 1.00 0.00 |
| | ATOM | 90 | N | VAL R | 49 | -18.722 | -23.884 | 21.116 | 1.00 0.00 |
| | ATOM | 91 | CA | VAL R | 49 | -17.548 | -23.718 | 21.974 | 1.00 0.00 |
| | ATOM | 92 | C | VAL R | 49 | -16.827 | -22.386 | 21.754 | 1.00 0.00 |

| | | | | | | |
|---|---|---|---|---|---|---|
| | ATOM | 93 | O VAL R 49 | -16.199 | -21.808 | 22.647 1.00 0.00 |
| | ATOM | 94 | CB VAL R 49 | -16.621 | -24.942 | 21.815 1.00 0.00 |
| | ATOM | 95 | CG1 VAL R 49 | -16.113 | -25.126 | 20.379 1.00 0.00 |
| | ATOM | 96 | CG2 VAL R 49 | -15.490 | -24.948 | 22.848 1.00 0.00 |
| 5 | ATOM | 97 | H VAL R 49 | -18.738 | -24.575 | 20.398 1.00 0.00 |
| | ATOM | 98 | N SER R 50 | -16.984 | -21.895 | 20.512 1.00 0.00 |
| | ATOM | 99 | CA SER R 50 | -16.545 | -20.542 | 20.170 1.00 0.00 |
| | ATOM | 100 | C SER R 50 | -17.478 | -20.015 | 19.099 1.00 0.00 |
| | ATOM | 101 | O SER R 50 | -18.142 | -20.822 | 18.450 1.00 0.00 |
| 10 | ATOM | 102 | CB SER R 50 | -15.104 | -20.582 | 19.665 1.00 0.00 |
| | ATOM | 103 | OG SER R 50 | -14.388 | -21.603 | 20.381 1.00 0.00 |
| | ATOM | 104 | H SER R 50 | -17.472 | -22.447 | 19.837 1.00 0.00 |
| | ATOM | 105 | HG SER R 50 | -14.702 | -21.503 | 21.280 1.00 0.00 |
| | ATOM | 106 | N ALA R 51 | -17.535 | -18.689 | 18.939 1.00 0.00 |
| 15 | ATOM | 107 | CA ALA R 51 | -18.444 | -18.111 | 17.945 1.00 0.00 |
| | ATOM | 108 | C ALA R 51 | -18.009 | -18.327 | 16.502 1.00 0.00 |
| | ATOM | 109 | O ALA R 51 | -17.384 | -17.480 | 15.860 1.00 0.00 |
| | ATOM | 110 | CB ALA R 51 | -18.633 | -16.614 | 18.202 1.00 0.00 |
| | ATOM | 111 | H ALA R 51 | -16.914 | -18.119 | 19.470 1.00 0.00 |
| 20 | ATOM | 112 | N THR R 52 | -18.362 | -19.542 | 16.034 1.00 0.00 |
| | ATOM | 113 | CA THR R 52 | -17.855 | -20.040 | 14.756 1.00 0.00 |
| | ATOM | 114 | C THR R 52 | -18.740 | -21.103 | 14.084 1.00 0.00 |
| | ATOM | 115 | O THR R 52 | -18.814 | -22.264 | 14.488 1.00 0.00 |
| | ATOM | 116 | CB THR R 52 | -16.422 | -20.581 | 14.935 1.00 0.00 |
| 25 | ATOM | 117 | OG1 THR R 52 | -15.633 | -19.712 | 15.770 1.00 0.00 |
| | ATOM | 118 | CG2 THR R 52 | -15.723 | -20.802 | 13.589 1.00 0.00 |
| | ATOM | 119 | H THR R 52 | -18.809 | -20.200 | 16.644 1.00 0.00 |
| | ATOM | 120 | HG1 THR R 52 | -15.985 | -18.832 | 15.634 1.00 0.00 |
| | ATOM | 121 | N GLU R 53 | -19.349 | -20.674 | 12.968 1.00 0.00 |
| 30 | ATOM | 122 | CA GLU R 53 | -20.398 | -19.674 | 13.115 1.00 0.00 |
| | ATOM | 123 | C GLU R 53 | -21.732 | -20.164 | 13.692 1.00 0.00 |
| | ATOM | 124 | O GLU R 53 | -22.195 | -19.586 | 14.668 1.00 0.00 |
| | ATOM | 125 | CB GLU R 53 | -20.639 | -18.835 | 11.840 1.00 0.00 |
| | ATOM | 126 | CG GLU R 53 | -19.550 | -18.814 | 10.755 1.00 0.00 |

| | | | | | | | | |
|---|---|---|---|---|---|---|---|---|
| | ATOM | 127 | CD | GLU R 53 | -19.530 | -20.110 | 9.955 | 1.00 0.00 |
| | ATOM | 128 | OE1 | GLU R 53 | -20.581 | -20.583 | 9.522 | 1.00 0.00 |
| | ATOM | 129 | OE2 | GLU R 53 | -18.455 | -20.666 | 9.758 | 1.00 0.00 |
| | ATOM | 130 | H | GLU R 53 | -19.314 | -21.243 | 12.150 | 1.00 0.00 |
| 5 | ATOM | 131 | N | PRO R 54 | -22.382 | -21.186 | 13.062 | 1.00 0.00 |
| | ATOM | 132 | CA | PRO R 54 | -23.801 | -21.374 | 13.363 | 1.00 0.00 |
| | ATOM | 133 | C | PRO R 54 | -24.087 | -22.600 | 14.224 | 1.00 0.00 |
| | ATOM | 134 | O | PRO R 54 | -23.206 | -23.245 | 14.790 | 1.00 0.00 |
| | ATOM | 135 | CB | PRO R 54 | -24.322 | -21.543 | 11.933 | 1.00 0.00 |
| 10 | ATOM | 136 | CG | PRO R 54 | -23.279 | -22.449 | 11.267 | 1.00 0.00 |
| | ATOM | 137 | CD | PRO R 54 | -21.973 | -22.056 | 11.958 | 1.00 0.00 |
| | ATOM | 138 | N | CYS R 55 | -25.389 | -22.945 | 14.169 | 1.00 0.00 |
| | ATOM | 139 | CA | CYS R 55 | -25.953 | -24.243 | 14.552 | 1.00 0.00 |
| | ATOM | 140 | C | CYS R 55 | -25.269 | -25.446 | 13.903 | 1.00 0.00 |
| 15 | ATOM | 141 | O | CYS R 55 | -24.242 | -25.300 | 13.245 | 1.00 0.00 |
| | ATOM | 142 | CB | CYS R 55 | -27.451 | -24.242 | 14.222 | 1.00 0.00 |
| | ATOM | 143 | SG | CYS R 55 | -28.150 | -22.588 | 13.922 | 1.00 0.00 |
| | ATOM | 144 | H | CYS R 55 | -26.029 | -22.260 | 13.834 | 1.00 0.00 |
| | ATOM | 145 | N | LYS R 56 | -25.873 | -26.628 | 14.098 | 1.00 0.00 |
| 20 | ATOM | 146 | CA | LYS R 56 | -25.241 | -27.917 | 13.821 | 1.00 0.00 |
| | ATOM | 147 | C | LYS R 56 | -26.256 | -29.045 | 13.957 | 1.00 0.00 |
| | ATOM | 148 | O | LYS R 56 | -26.703 | -29.417 | 15.037 | 1.00 0.00 |
| | ATOM | 149 | CB | LYS R 56 | -24.073 | -28.150 | 14.789 | 1.00 0.00 |
| | ATOM | 150 | CG | LYS R 56 | -23.350 | -29.501 | 14.702 | 1.00 0.00 |
| 25 | ATOM | 151 | CD | LYS R 56 | -22.658 | -29.801 | 13.373 | 1.00 0.00 |
| | ATOM | 152 | CE | LYS R 56 | -21.673 | -30.966 | 13.503 | 1.00 0.00 |
| | ATOM | 153 | NZ | LYS R 56 | -20.454 | -30.524 | 14.191 | 1.00 0.00 |
| | ATOM | 154 | H | LYS R 56 | -26.725 | -26.673 | 14.623 | 1.00 0.00 |
| | ATOM | 155 | 1HZ | LYS R 56 | -19.887 | -31.370 | 14.402 | 1.00 0.00 |
| 30 | ATOM | 156 | 2HZ | LYS R 56 | -20.632 | -30.000 | 15.073 | 1.00 0.00 |
| | ATOM | 157 | 3HZ | LYS R 56 | -19.886 | -29.946 | 13.544 | 1.00 0.00 |
| | ATOM | 158 | N | PRO R 57 | -26.633 | -29.599 | 12.787 | 1.00 0.00 |
| | ATOM | 159 | CA | PRO R 57 | -27.416 | -30.837 | 12.811 | 1.00 0.00 |
| | ATOM | 160 | C | PRO R 57 | -26.644 | -31.966 | 13.476 | 1.00 0.00 |

| | | | | | | |
|---|---|---|---|---|---|---|
| | ATOM | 161 O PRO R 57 | -25.420 | -31.911 | 13.609 | 1.00 0.00 |
| | ATOM | 162 CB PRO R 57 | -27.665 | -31.109 | 11.323 | 1.00 0.00 |
| | ATOM | 163 CG PRO R 57 | -27.447 | -29.776 | 10.607 | 1.00 0.00 |
| | ATOM | 164 CD PRO R 57 | -26.356 | -29.119 | 11.441 | 1.00 0.00 |
| 5 | ATOM | 165 N CYS R 58 | -27.418 | -32.994 | 13.860 | 1.00 0.00 |
| | ATOM | 166 CA CYS R 58 | -26.761 | -34.217 | 14.319 | 1.00 0.00 |
| | ATOM | 167 C CYS R 58 | -26.309 | -35.070 | 13.141 | 1.00 0.00 |
| | ATOM | 168 O CYS R 58 | -26.576 | -34.743 | 11.987 | 1.00 0.00 |
| | ATOM | 169 CB CYS R 58 | -27.709 | -34.963 | 15.259 | 1.00 0.00 |
| 10 | ATOM | 170 SG CYS R 58 | -27.015 | -36.478 | 15.973 | 1.00 0.00 |
| | ATOM | 171 H CYS R 58 | -28.408 | -32.886 | 13.776 | 1.00 0.00 |
| | ATOM | 172 N THR R 59 | -25.623 | -36.173 | 13.459 | 1.00 0.00 |
| | ATOM | 173 CA THR R 59 | -25.066 | -37.074 | 12.445 | 1.00 0.00 |
| | ATOM | 174 C THR R 59 | -26.048 | -38.160 | 11.949 | 1.00 0.00 |
| 15 | ATOM | 175 O THR R 59 | -27.196 | -38.234 | 12.397 | 1.00 0.00 |
| | ATOM | 176 CB THR R 59 | -23.767 | -37.636 | 13.055 | 1.00 0.00 |
| | ATOM | 177 OG1 THR R 59 | -23.270 | -36.723 | 14.052 | 1.00 0.00 |
| | ATOM | 178 CG2 THR R 59 | -22.667 | -37.924 | 12.029 | 1.00 0.00 |
| | ATOM | 179 H THR R 59 | -25.398 | -36.368 | 14.415 | 1.00 0.00 |
| 20 | ATOM | 180 HG1 THR R 59 | -22.729 | -37.252 | 14.644 | 1.00 0.00 |
| | ATOM | 181 N GLU R 60 | -25.578 | -38.985 | 10.999 | 1.00 0.00 |
| | ATOM | 182 CA GLU R 60 | -26.467 | -40.006 | 10.445 | 1.00 0.00 |
| | ATOM | 183 C GLU R 60 | -26.899 | -41.149 | 11.355 | 1.00 0.00 |
| | ATOM | 184 O GLU R 60 | -26.152 | -42.083 | 11.672 | 1.00 0.00 |
| 25 | ATOM | 185 CB GLU R 60 | -25.943 | -40.541 | 9.111 | 1.00 0.00 |
| | ATOM | 186 CG GLU R 60 | -27.011 | -40.494 | 8.010 | 1.00 0.00 |
| | ATOM | 187 CD GLU R 60 | -28.263 | -41.228 | 8.450 | 1.00 0.00 |
| | ATOM | 188 OE1 GLU R 60 | -28.349 | -42.428 | 8.253 | 1.00 0.00 |
| | ATOM | 189 OE2 GLU R 60 | -29.161 | -40.605 | 9.003 | 1.00 0.00 |
| 30 | ATOM | 190 H GLU R 60 | -24.642 | -38.859 | 10.693 | 1.00 0.00 |
| | ATOM | 191 N CYS R 61 | -28.169 | -41.001 | 11.750 | 1.00 0.00 |
| | ATOM | 192 CA CYS R 61 | -28.775 | -41.881 | 12.742 | 1.00 0.00 |
| | ATOM | 193 C CYS R 61 | -29.712 | -42.937 | 12.185 | 1.00 0.00 |
| | ATOM | 194 O CYS R 61 | -30.148 | -43.845 | 12.890 | 1.00 0.00 |

```
ATOM  195 CB  CYS R 61    -29.564 -41.086 13.782 1.00 0.00
ATOM  196 SG  CYS R 61    -28.791 -39.568 14.416 1.00 0.00
ATOM  197 H   CYS R 61    -28.690 -40.307 11.255 1.00 0.00
ATOM  198 N   VAL R 62    -30.069 -42.806 10.908 1.00 0.00
ATOM  199 CA  VAL R 62    -31.084 -43.768 10.496 1.00 0.00
ATOM  200 C   VAL R 62    -30.571 -44.884  9.598 1.00 0.00
ATOM  201 O   VAL R 62    -30.480 -46.055  9.964 1.00 0.00
ATOM  202 CB  VAL R 62    -32.301 -43.050  9.878 1.00 0.00
ATOM  203 CG1 VAL R 62    -33.489 -44.005  9.713 1.00 0.00
ATOM  204 CG2 VAL R 62    -32.705 -41.812 10.685 1.00 0.00
ATOM  205 H   VAL R 62    -29.584 -42.202 10.268 1.00 0.00
ATOM  206 N   GLY R 63    -30.336 -44.466  8.349 1.00 0.00
ATOM  207 CA  GLY R 63    -30.443 -45.442  7.270 1.00 0.00
ATOM  208 C   GLY R 63    -29.148 -45.809  6.584 1.00 0.00
ATOM  209 O   GLY R 63    -29.004 -46.882  6.009 1.00 0.00
ATOM  210 H   GLY R 63    -30.082 -43.508  8.197 1.00 0.00
ATOM  211 N   LEU R 64    -28.206 -44.867  6.628 1.00 0.00
ATOM  212 CA  LEU R 64    -26.859 -45.283  6.260 1.00 0.00
ATOM  213 C   LEU R 64    -26.145 -45.795  7.489 1.00 0.00
ATOM  214 O   LEU R 64    -25.525 -46.855  7.545 1.00 0.00
ATOM  215 CB  LEU R 64    -26.088 -44.113  5.644 1.00 0.00
ATOM  216 CG  LEU R 64    -26.754 -43.525  4.397 1.00 0.00
ATOM  217 CD1 LEU R 64    -26.073 -42.229  3.958 1.00 0.00
ATOM  218 CD2 LEU R 64    -26.848 -44.540  3.255 1.00 0.00
ATOM  219 H   LEU R 64    -28.391 -43.992  7.076 1.00 0.00
ATOM  220 N   GLN R 65    -26.262 -44.951  8.515 1.00 0.00
ATOM  221 CA  GLN R 65    -25.639 -45.245  9.796 1.00 0.00
ATOM  222 C   GLN R 65    -26.708 -45.080 10.851 1.00 0.00
ATOM  223 O   GLN R 65    -27.738 -44.460 10.612 1.00 0.00
ATOM  224 CB  GLN R 65    -24.456 -44.300 10.006 1.00 0.00
ATOM  225 CG  GLN R 65    -23.336 -44.444  8.965 1.00 0.00
ATOM  226 CD  GLN R 65    -22.421 -45.624  9.253 1.00 0.00
ATOM  227 OE1 GLN R 65    -21.315 -45.443  9.762 1.00 0.00
ATOM  228 NE2 GLN R 65    -22.857 -46.816  8.833 1.00 0.00
```

| | | | | | | | |
|---|---|---|---|---|---|---|---|
| | ATOM | 229 | H GLN R 65 | -26.850 | -44.141 | 8.449 | 1.00 0.00 |
| | ATOM | 230 | 1HE2 GLN R 65 | -22.292 | -47.635 | 8.846 | 1.00 0.00 |
| | ATOM | 231 | 2HE2 GLN R 65 | -23.800 | -46.898 | 8.500 | 1.00 0.00 |
| | ATOM | 232 | N SER R 66 | -26.473 | -45.715 | 12.001 | 1.00 0.00 |
| 5 | ATOM | 233 | CA SER R 66 | -27.657 | -45.886 | 12.838 | 1.00 0.00 |
| | ATOM | 234 | C SER R 66 | -27.604 | -45.224 | 14.204 | 1.00 0.00 |
| | ATOM | 235 | O SER R 66 | -26.542 | -44.815 | 14.682 | 1.00 0.00 |
| | ATOM | 236 | CB SER R 66 | -28.013 | -47.373 | 12.884 | 1.00 0.00 |
| | ATOM | 237 | OG SER R 66 | -27.869 | -47.927 | 11.565 | 1.00 0.00 |
| 10 | ATOM | 238 | H SER R 66 | -25.586 | -46.141 | 12.173 | 1.00 0.00 |
| | ATOM | 239 | HG SER R 66 | -28.474 | -47.423 | 11.013 | 1.00 0.00 |
| | ATOM | 240 | N MET R 67 | -28.808 | -45.110 | 14.779 | 1.00 0.00 |
| | ATOM | 241 | CA MET R 67 | -29.048 | -44.257 | 15.939 | 1.00 0.00 |
| | ATOM | 242 | C MET R 67 | -28.294 | -44.575 | 17.212 | 1.00 0.00 |
| 15 | ATOM | 243 | O MET R 67 | -28.404 | -45.649 | 17.800 | 1.00 0.00 |
| | ATOM | 244 | CB MET R 67 | -30.556 | -44.203 | 16.197 | 1.00 0.00 |
| | ATOM | 245 | CG MET R 67 | -31.008 | -42.933 | 16.916 | 1.00 0.00 |
| | ATOM | 246 | SD MET R 67 | -32.793 | -42.833 | 17.123 | 1.00 0.00 |
| | ATOM | 247 | CE MET R 67 | -33.244 | -42.903 | 15.380 | 1.00 0.00 |
| 20 | ATOM | 248 | H MET R 67 | -29.573 | -45.360 | 14.189 | 1.00 0.00 |
| | ATOM | 249 | N SER R 68 | -27.557 | -43.553 | 17.633 | 1.00 0.00 |
| | ATOM | 250 | CA SER R 68 | -26.992 | -43.620 | 18.977 | 1.00 0.00 |
| | ATOM | 251 | C SER R 68 | -27.868 | -42.986 | 20.035 | 1.00 0.00 |
| | ATOM | 252 | O SER R 68 | -27.813 | -43.326 | 21.215 | 1.00 0.00 |
| 25 | ATOM | 253 | CB SER R 68 | -25.615 | -42.989 | 18.978 | 1.00 0.00 |
| | ATOM | 254 | OG SER R 68 | -25.029 | -43.228 | 17.693 | 1.00 0.00 |
| | ATOM | 255 | H SER R 68 | -27.423 | -42.756 | 17.044 | 1.00 0.00 |
| | ATOM | 256 | HG SER R 68 | -24.083 | -43.177 | 17.834 | 1.00 0.00 |
| | ATOM | 257 | N ALA R 69 | -28.706 | -42.060 | 19.521 | 1.00 0.00 |
| 30 | ATOM | 258 | CA ALA R 69 | -29.837 | -41.437 | 20.214 | 1.00 0.00 |
| | ATOM | 259 | C ALA R 69 | -30.311 | -40.307 | 19.312 | 1.00 0.00 |
| | ATOM | 260 | O ALA R 69 | -29.592 | -39.924 | 18.387 | 1.00 0.00 |
| | ATOM | 261 | CB ALA R 69 | -29.406 | -40.835 | 21.565 | 1.00 0.00 |
| | ATOM | 262 | H ALA R 69 | -28.493 | -41.701 | 18.610 | 1.00 0.00 |

| | | | | | | |
|---|---|---|---|---|---|---|
| ATOM | 263 | N   PRO R 70 | -31.506 | -39.724 | 19.607 | 1.00 0.00 |
| ATOM | 264 | CA  PRO R 70 | -31.722 | -38.322 | 19.207 | 1.00 0.00 |
| ATOM | 265 | C   PRO R 70 | -30.580 | -37.436 | 19.699 | 1.00 0.00 |
| ATOM | 266 | O   PRO R 70 | -29.722 | -37.895 | 20.456 | 1.00 0.00 |
| ATOM | 267 | CB  PRO R 70 | -33.063 | -37.990 | 19.869 | 1.00 0.00 |
| ATOM | 268 | CG  PRO R 70 | -33.779 | -39.331 | 20.022 | 1.00 0.00 |
| ATOM | 269 | CD  PRO R 70 | -32.637 | -40.289 | 20.334 | 1.00 0.00 |
| ATOM | 270 | N   CYS R 71 | -30.549 | -36.191 | 19.227 | 1.00 0.00 |
| ATOM | 271 | CA  CYS R 71 | -29.381 | -35.417 | 19.642 | 1.00 0.00 |
| ATOM | 272 | C   CYS R 71 | -29.730 | -34.124 | 20.337 | 1.00 0.00 |
| ATOM | 273 | O   CYS R 71 | -30.848 | -33.618 | 20.262 | 1.00 0.00 |
| ATOM | 274 | CB  CYS R 71 | -28.418 | -35.200 | 18.474 | 1.00 0.00 |
| ATOM | 275 | SG  CYS R 71 | -27.801 | -36.785 | 17.835 | 1.00 0.00 |
| ATOM | 276 | H   CYS R 71 | -31.299 | -35.781 | 18.711 | 1.00 0.00 |
| ATOM | 277 | N   VAL R 72 | -28.733 | -33.641 | 21.079 | 1.00 0.00 |
| ATOM | 278 | CA  VAL R 72 | -28.793 | -32.337 | 21.739 | 1.00 0.00 |
| ATOM | 279 | C   VAL R 72 | -27.441 | -31.695 | 21.515 | 1.00 0.00 |
| ATOM | 280 | O   VAL R 72 | -26.587 | -32.323 | 20.897 | 1.00 0.00 |
| ATOM | 281 | CB  VAL R 72 | -29.087 | -32.477 | 23.244 | 1.00 0.00 |
| ATOM | 282 | CG1 VAL R 72 | -30.554 | -32.827 | 23.502 | 1.00 0.00 |
| ATOM | 283 | CG2 VAL R 72 | -28.125 | -33.455 | 23.932 | 1.00 0.00 |
| ATOM | 284 | H   VAL R 72 | -27.860 | -34.132 | 21.089 | 1.00 0.00 |
| ATOM | 285 | N   GLU R 73 | -27.282 | -30.465 | 22.038 | 1.00 0.00 |
| ATOM | 286 | CA  GLU R 73 | -25.992 | -29.787 | 21.908 | 1.00 0.00 |
| ATOM | 287 | C   GLU R 73 | -24.848 | -30.522 | 22.569 | 1.00 0.00 |
| ATOM | 288 | O   GLU R 73 | -24.610 | -30.447 | 23.773 | 1.00 0.00 |
| ATOM | 289 | CB  GLU R 73 | -26.073 | -28.328 | 22.365 | 1.00 0.00 |
| ATOM | 290 | CG  GLU R 73 | -24.825 | -27.556 | 21.923 | 1.00 0.00 |
| ATOM | 291 | CD  GLU R 73 | -24.974 | -26.067 | 22.159 | 1.00 0.00 |
| ATOM | 292 | OE1 GLU R 73 | -25.947 | -25.478 | 21.698 | 1.00 0.00 |
| ATOM | 293 | OE2 GLU R 73 | -24.103 | -25.484 | 22.793 | 1.00 0.00 |
| ATOM | 294 | H   GLU R 73 | -28.030 | -30.065 | 22.564 | 1.00 0.00 |
| ATOM | 295 | N   ALA R 74 | -24.183 | -31.276 | 21.690 | 1.00 0.00 |
| ATOM | 296 | CA  ALA R 74 | -22.982 | -32.030 | 22.006 | 1.00 0.00 |

```
     ATOM  297  C   ALA R  74    -22.211 -32.099  20.717  1.00  0.00
     ATOM  298  O   ALA R  74    -22.796 -32.213  19.640  1.00  0.00
     ATOM  299  CB  ALA R  74    -23.328 -33.451  22.455  1.00  0.00
     ATOM  300  H   ALA R  74    -24.600 -31.329  20.777  1.00  0.00
 5   ATOM  301  N   ASP R  75    -20.889 -31.945  20.853  1.00  0.00
     ATOM  302  CA  ASP R  75    -20.105 -31.837  19.633  1.00  0.00
     ATOM  303  C   ASP R  75    -20.167 -33.101  18.799  1.00  0.00
     ATOM  304  O   ASP R  75    -20.254 -34.213  19.326  1.00  0.00
     ATOM  305  CB  ASP R  75    -18.676 -31.418  19.976  1.00  0.00
 10  ATOM  306  CG  ASP R  75    -18.194 -30.327  19.038  1.00  0.00
     ATOM  307  OD1 ASP R  75    -17.534 -29.398  19.470  1.00  0.00
     ATOM  308  OD2 ASP R  75    -18.410 -30.388  17.841  1.00  0.00
     ATOM  309  H   ASP R  75    -20.452 -31.968  21.747  1.00  0.00
     ATOM  310  N   ASP R  76    -20.194 -32.858  17.466  1.00  0.00
 15  ATOM  311  CA  ASP R  76    -20.556 -33.842  16.433  1.00  0.00
     ATOM  312  C   ASP R  76    -21.294 -35.063  16.965  1.00  0.00
     ATOM  313  O   ASP R  76    -20.725 -36.140  17.153  1.00  0.00
     ATOM  314  CB  ASP R  76    -19.324 -34.222  15.591  1.00  0.00
     ATOM  315  CG  ASP R  76    -18.850 -33.033  14.765  1.00  0.00
 20  ATOM  316  OD1 ASP R  76    -18.213 -32.134  15.285  1.00  0.00
     ATOM  317  OD2 ASP R  76    -19.132 -32.953  13.580  1.00  0.00
     ATOM  318  H   ASP R  76    -19.875 -31.943  17.215  1.00  0.00
     ATOM  319  N   ALA R  77    -22.571 -34.806  17.303  1.00  0.00
     ATOM  320  CA  ALA R  77    -23.290 -35.694  18.218  1.00  0.00
 25  ATOM  321  C   ALA R  77    -23.531 -37.073  17.651  1.00  0.00
     ATOM  322  O   ALA R  77    -23.725 -37.259  16.456  1.00  0.00
     ATOM  323  CB  ALA R  77    -24.619 -35.075  18.644  1.00  0.00
     ATOM  324  H   ALA R  77    -23.001 -34.012  16.881  1.00  0.00
     ATOM  325  N   VAL R  78    -23.455 -38.052  18.556  1.00  0.00
 30  ATOM  326  CA  VAL R  78    -22.704 -39.281  18.232  1.00  0.00
     ATOM  327  C   VAL R  78    -23.295 -40.388  17.344  1.00  0.00
     ATOM  328  O   VAL R  78    -23.041 -41.583  17.543  1.00  0.00
     ATOM  329  CB  VAL R  78    -22.160 -39.877  19.542  1.00  0.00
     ATOM  330  CG1 VAL R  78    -21.189 -38.911  20.224  1.00  0.00
```

```
ATOM  331 CG2 VAL R  78   -23.287 -40.288  20.497  1.00  0.00
ATOM  332 H   VAL R  78   -23.598 -37.743  19.493  1.00  0.00
ATOM  333 N   CYS R  79   -24.111 -40.011  16.349  1.00  0.00
ATOM  334 CA  CYS R  79   -24.667 -41.058  15.490  1.00  0.00
ATOM  335 C   CYS R  79   -23.639 -41.706  14.569  1.00  0.00
ATOM  336 O   CYS R  79   -23.161 -41.097  13.611  1.00  0.00
ATOM  337 CB  CYS R  79   -25.854 -40.535  14.695  1.00  0.00
ATOM  338 SG  CYS R  79   -27.265 -40.010  15.706  1.00  0.00
ATOM  339 H   CYS R  79   -24.146 -39.049  16.105  1.00  0.00
ATOM  340 N   ARG R  80   -23.326 -42.955  14.966  1.00  0.00
ATOM  341 CA  ARG R  80   -22.220 -43.688  14.354  1.00  0.00
ATOM  342 C   ARG R  80   -22.617 -45.027  13.739  1.00  0.00
ATOM  343 O   ARG R  80   -22.898 -45.120  12.547  1.00  0.00
ATOM  344 CB  ARG R  80   -21.047 -43.866  15.333  1.00  0.00
ATOM  345 CG  ARG R  80   -19.958 -42.787  15.285  1.00  0.00
ATOM  346 CD  ARG R  80   -19.283 -42.600  13.916  1.00  0.00
ATOM  347 NE  ARG R  80   -18.739 -43.844  13.361  1.00  0.00
ATOM  348 CZ  ARG R  80   -19.343 -44.423  12.298  1.00  0.00
ATOM  349 NH1 ARG R  80   -18.915 -45.588  11.814  1.00  0.00
ATOM  350 NH2 ARG R  80   -20.397 -43.844  11.740  1.00  0.00
ATOM  351 H   ARG R  80   -23.849 -43.366  15.715  1.00  0.00
ATOM  352 HE  ARG R  80   -17.952 -44.277  13.804  1.00  0.00
ATOM  353 1HH1 ARG R  80   -19.409 -46.064  11.082  1.00  0.00
ATOM  354 2HH1 ARG R  80   -18.080 -46.022  12.174  1.00  0.00
ATOM  355 1HH2 ARG R  80   -20.880 -44.269  10.976  1.00  0.00
ATOM  356 2HH2 ARG R  80   -20.749 -42.984  12.102  1.00  0.00
ATOM  357 N   CYS R  81   -22.630 -46.086  14.566  1.00  0.00
ATOM  358 CA  CYS R  81   -22.946 -47.400  14.002  1.00  0.00
ATOM  359 C   CYS R  81   -23.527 -48.331  15.049  1.00  0.00
ATOM  360 O   CYS R  81   -22.830 -49.080  15.728  1.00  0.00
ATOM  361 CB  CYS R  81   -21.732 -48.025  13.284  1.00  0.00
ATOM  362 SG  CYS R  81   -22.046 -48.494  11.547  1.00  0.00
ATOM  363 H   CYS R  81   -22.342 -45.997  15.517  1.00  0.00
ATOM  364 N   ALA R  82   -24.869 -48.212  15.160  1.00  0.00
```

| | ATOM | 365 | CA | ALA R 82 | -25.712 -49.047 16.033 1.00 0.00 |
|---|---|---|---|---|---|
| | ATOM | 366 | C | ALA R 82 | -25.041 -49.677 17.246 1.00 0.00 |
| | ATOM | 367 | O | ALA R 82 | -24.801 -50.881 17.310 1.00 0.00 |
| | ATOM | 368 | CB | ALA R 82 | -26.390 -50.148 15.212 1.00 0.00 |
| 5 | ATOM | 369 | H | ALA R 82 | -25.322 -47.577 14.537 1.00 0.00 |
| | ATOM | 370 | N | TYR R 83 | -24.697 -48.786 18.189 1.00 0.00 |
| | ATOM | 371 | CA | TYR R 83 | -23.809 -49.240 19.256 1.00 0.00 |
| | ATOM | 372 | C | TYR R 83 | -24.319 -50.384 20.116 1.00 0.00 |
| | ATOM | 373 | O | TYR R 83 | -25.492 -50.522 20.451 1.00 0.00 |
| 10 | ATOM | 374 | CB | TYR R 83 | -23.268 -48.059 20.087 1.00 0.00 |
| | ATOM | 375 | CG | TYR R 83 | -24.247 -47.511 21.108 1.00 0.00 |
| | ATOM | 376 | CD1 | TYR R 83 | -25.207 -46.556 20.715 1.00 0.00 |
| | ATOM | 377 | CD2 | TYR R 83 | -24.147 -47.951 22.445 1.00 0.00 |
| | ATOM | 378 | CE1 | TYR R 83 | -26.058 -46.003 21.688 1.00 0.00 |
| 15 | ATOM | 379 | CE2 | TYR R 83 | -25.001 -47.400 23.417 1.00 0.00 |
| | ATOM | 380 | CZ | TYR R 83 | -25.937 -46.419 23.031 1.00 0.00 |
| | ATOM | 381 | OH | TYR R 83 | -26.753 -45.849 23.995 1.00 0.00 |
| | ATOM | 382 | H | TYR R 83 | -25.061 -47.858 18.145 1.00 0.00 |
| | ATOM | 383 | HH | TYR R 83 | -27.139 -45.055 23.619 1.00 0.00 |
| 20 | ATOM | 384 | N | GLY R 84 | -23.359 -51.236 20.478 1.00 0.00 |
| | ATOM | 385 | CA | GLY R 84 | -23.783 -52.411 21.232 1.00 0.00 |
| | ATOM | 386 | C | GLY R 84 | -23.284 -53.694 20.609 1.00 0.00 |
| | ATOM | 387 | O | GLY R 84 | -23.189 -54.732 21.259 1.00 0.00 |
| | ATOM | 388 | H | GLY R 84 | -22.420 -51.099 20.167 1.00 0.00 |
| 25 | ATOM | 389 | N | TYR R 85 | -22.925 -53.551 19.317 1.00 0.00 |
| | ATOM | 390 | CA | TYR R 85 | -21.764 -54.346 18.941 1.00 0.00 |
| | ATOM | 391 | C | TYR R 85 | -20.520 -53.484 19.090 1.00 0.00 |
| | ATOM | 392 | O | TYR R 85 | -20.632 -52.266 19.248 1.00 0.00 |
| | ATOM | 393 | CB | TYR R 85 | -21.930 -54.959 17.539 1.00 0.00 |
| 30 | ATOM | 394 | CG | TYR R 85 | -21.890 -53.946 16.413 1.00 0.00 |
| | ATOM | 395 | CD1 | TYR R 85 | -23.084 -53.333 15.975 1.00 0.00 |
| | ATOM | 396 | CD2 | TYR R 85 | -20.649 -53.671 15.805 1.00 0.00 |
| | ATOM | 397 | CE1 | TYR R 85 | -23.042 -52.477 14.860 1.00 0.00 |
| | ATOM | 398 | CE2 | TYR R 85 | -20.609 -52.814 14.697 1.00 0.00 |

| | | ATOM | 399 | CZ | TYR R 85 | -21.808 -52.257 14.215 1.00 0.00 |
|---|---|---|---|---|---|---|
| | | ATOM | 400 | OH | TYR R 85 | -21.760 -51.493 13.062 1.00 0.00 |
| | | ATOM | 401 | H | TYR R 85 | -23.172 -52.734 18.790 1.00 0.00 |
| | | ATOM | 402 | HH | TYR R 85 | -20.964 -51.753 12.596 1.00 0.00 |
| 5 | | ATOM | 403 | N | TYR R 86 | -19.354 -54.143 19.022 1.00 0.00 |
| | | ATOM | 404 | CA | TYR R 86 | -18.070 -53.498 19.330 1.00 0.00 |
| | | ATOM | 405 | C | TYR R 86 | -17.547 -52.466 18.319 1.00 0.00 |
| | | ATOM | 406 | O | TYR R 86 | -16.457 -52.635 17.784 1.00 0.00 |
| | | ATOM | 407 | CB | TYR R 86 | -17.072 -54.652 19.552 1.00 0.00 |
| 10 | | ATOM | 408 | CG | TYR R 86 | -15.786 -54.368 20.316 1.00 0.00 |
| | | ATOM | 409 | CD1 | TYR R 86 | -15.322 -53.061 20.597 1.00 0.00 |
| | | ATOM | 410 | CD2 | TYR R 86 | -15.053 -55.502 20.719 1.00 0.00 |
| | | ATOM | 411 | CE1 | TYR R 86 | -14.087 -52.896 21.255 1.00 0.00 |
| | | ATOM | 412 | CE2 | TYR R 86 | -13.825 -55.340 21.380 1.00 0.00 |
| 15 | | ATOM | 413 | CZ | TYR R 86 | -13.346 -54.040 21.627 1.00 0.00 |
| | | ATOM | 414 | OH | TYR R 86 | -12.110 -53.911 22.244 1.00 0.00 |
| | | ATOM | 415 | H | TYR R 86 | -19.425 -55.102 18.757 1.00 0.00 |
| | | ATOM | 416 | HH | TYR R 86 | -11.829 -53.003 22.149 1.00 0.00 |
| | | ATOM | 417 | N | GLN R 87 | -18.334 -51.399 18.081 1.00 0.00 |
| 20 | | ATOM | 418 | CA | GLN R 87 | -17.800 -50.310 17.258 1.00 0.00 |
| | | ATOM | 419 | C | GLN R 87 | -17.117 -49.255 18.112 1.00 0.00 |
| | | ATOM | 420 | O | GLN R 87 | -17.704 -48.681 19.022 1.00 0.00 |
| | | ATOM | 421 | CB | GLN R 87 | -18.910 -49.706 16.371 1.00 0.00 |
| | | ATOM | 422 | CG | GLN R 87 | -18.725 -48.273 15.812 1.00 0.00 |
| 25 | | ATOM | 423 | CD | GLN R 87 | -17.729 -48.089 14.663 1.00 0.00 |
| | | ATOM | 424 | OE1 | GLN R 87 | -17.701 -47.027 14.040 1.00 0.00 |
| | | ATOM | 425 | NE2 | GLN R 87 | -16.936 -49.120 14.374 1.00 0.00 |
| | | ATOM | 426 | H | GLN R 87 | -19.143 -51.256 18.647 1.00 0.00 |
| | | ATOM | 427 | 1HE2 | GLN R 87 | -16.239 -49.104 13.659 1.00 0.00 |
| 30 | | ATOM | 428 | 2HE2 | GLN R 87 | -16.869 -50.003 14.846 1.00 0.00 |
| | | ATOM | 429 | N | ASP R 88 | -15.845 -49.028 17.759 1.00 0.00 |
| | | ATOM | 430 | CA | ASP R 88 | -15.041 -48.001 18.429 1.00 0.00 |
| | | ATOM | 431 | C | ASP R 88 | -14.442 -47.101 17.361 1.00 0.00 |
| | | ATOM | 432 | O | ASP R 88 | -14.123 -47.592 16.276 1.00 0.00 |

| | | | | | | | | |
|---|---|---|---|---|---|---|---|---|
| | ATOM | 433 | CB | ASP R 88 | -13.968 | -48.725 | 19.273 | 1.00 0.00 |
| | ATOM | 434 | CG | ASP R 88 | -12.942 | -47.819 | 19.953 | 1.00 0.00 |
| | ATOM | 435 | OD1 | ASP R 88 | -11.758 | -48.104 | 19.876 | 1.00 0.00 |
| | ATOM | 436 | OD2 | ASP R 88 | -13.294 | -46.831 | 20.580 | 1.00 0.00 |
| 5 | ATOM | 437 | H | ASP R 88 | -15.429 | -49.592 | 17.039 | 1.00 0.00 |
| | ATOM | 438 | N | GLU R 89 | -14.306 | -45.805 | 17.710 | 1.00 0.00 |
| | ATOM | 439 | CA | GLU R 89 | -13.680 | -44.795 | 16.839 | 1.00 0.00 |
| | ATOM | 440 | C | GLU R 89 | -14.515 | -44.403 | 15.614 | 1.00 0.00 |
| | ATOM | 441 | O | GLU R 89 | -15.309 | -43.460 | 15.616 | 1.00 0.00 |
| 10 | ATOM | 442 | CB | GLU R 89 | -12.257 | -45.283 | 16.493 | 1.00 0.00 |
| | ATOM | 443 | CG | GLU R 89 | -11.293 | -44.524 | 15.571 | 1.00 0.00 |
| | ATOM | 444 | CD | GLU R 89 | -10.219 | -45.518 | 15.145 | 1.00 0.00 |
| | ATOM | 445 | OE1 | GLU R 89 | -9.962 | -45.681 | 13.957 | 1.00 0.00 |
| | ATOM | 446 | OE2 | GLU R 89 | -9.644 | -46.177 | 15.998 | 1.00 0.00 |
| 15 | ATOM | 447 | H | GLU R 89 | -14.511 | -45.638 | 18.676 | 1.00 0.00 |
| | ATOM | 448 | N | THR R 90 | -14.293 | -45.184 | 14.553 | 1.00 0.00 |
| | ATOM | 449 | CA | THR R 90 | -14.096 | -44.591 | 13.232 | 1.00 0.00 |
| | ATOM | 450 | C | THR R 90 | -15.313 | -44.151 | 12.444 | 1.00 0.00 |
| | ATOM | 451 | O | THR R 90 | -16.239 | -44.933 | 12.212 | 1.00 0.00 |
| 20 | ATOM | 452 | CB | THR R 90 | -13.307 | -45.598 | 12.397 | 1.00 0.00 |
| | ATOM | 453 | OG1 | THR R 90 | -12.719 | -46.613 | 13.229 | 1.00 0.00 |
| | ATOM | 454 | CG2 | THR R 90 | -12.269 | -44.936 | 11.490 | 1.00 0.00 |
| | ATOM | 455 | H | THR R 90 | -14.031 | -46.141 | 14.672 | 1.00 0.00 |
| | ATOM | 456 | HG1 | THR R 90 | -11.932 | -46.206 | 13.613 | 1.00 0.00 |
| 25 | ATOM | 457 | N | THR R 91 | -15.264 | -42.906 | 11.946 | 1.00 0.00 |
| | ATOM | 458 | CA | THR R 91 | -16.086 | -42.598 | 10.774 | 1.00 0.00 |
| | ATOM | 459 | C | THR R 91 | -15.551 | -43.214 | 9.474 | 1.00 0.00 |
| | ATOM | 460 | O | THR R 91 | -15.041 | -42.576 | 8.553 | 1.00 0.00 |
| | ATOM | 461 | CB | THR R 91 | -16.263 | -41.089 | 10.611 | 1.00 0.00 |
| 30 | ATOM | 462 | OG1 | THR R 91 | -15.526 | -40.320 | 11.595 | 1.00 0.00 |
| | ATOM | 463 | CG2 | THR R 91 | -17.753 | -40.737 | 10.608 | 1.00 0.00 |
| | ATOM | 464 | H | THR R 91 | -14.546 | -42.271 | 12.218 | 1.00 0.00 |
| | ATOM | 465 | HG1 | THR R 91 | -16.170 | -40.159 | 12.292 | 1.00 0.00 |
| | ATOM | 466 | N | GLY R 92 | -15.638 | -44.548 | 9.437 | 1.00 0.00 |

|    |      |     |       |         |                      |
|----|------|-----|-------|---------|----------------------|
|    | ATOM | 467 | CA    | GLY R 92 | -14.952 -45.240 8.341 1.00 0.00 |
|    | ATOM | 468 | C     | GLY R 92 | -14.947 -46.747 8.485 1.00 0.00 |
|    | ATOM | 469 | O     | GLY R 92 | -15.038 -47.506 7.517 1.00 0.00 |
|    | ATOM | 470 | H     | GLY R 92 | -16.190 -45.008 10.134 1.00 0.00 |
| 5  | ATOM | 471 | N     | ARG R 93 | -14.906 -47.132 9.766 1.00 0.00 |
|    | ATOM | 472 | CA    | ARG R 93 | -15.165 -48.526 10.101 1.00 0.00 |
|    | ATOM | 473 | C     | ARG R 93 | -16.597 -48.659 10.561 1.00 0.00 |
|    | ATOM | 474 | O     | ARG R 93 | -17.179 -47.725 11.108 1.00 0.00 |
|    | ATOM | 475 | CB    | ARG R 93 | -14.257 -49.027 11.231 1.00 0.00 |
| 10 | ATOM | 476 | CG    | ARG R 93 | -12.866 -49.498 10.801 1.00 0.00 |
|    | ATOM | 477 | CD    | ARG R 93 | -12.088 -50.205 11.924 1.00 0.00 |
|    | ATOM | 478 | NE    | ARG R 93 | -11.530 -49.278 12.906 1.00 0.00 |
|    | ATOM | 479 | CZ    | ARG R 93 | -11.885 -49.270 14.210 1.00 0.00 |
|    | ATOM | 480 | NH1   | ARG R 93 | -11.321 -48.407 15.046 1.00 0.00 |
| 15 | ATOM | 481 | NH2   | ARG R 93 | -12.806 -50.108 14.666 1.00 0.00 |
|    | ATOM | 482 | H     | ARG R 93 | -14.866 -46.429 10.469 1.00 0.00 |
|    | ATOM | 483 | HE    | ARG R 93 | -10.826 -48.644 12.583 1.00 0.00 |
|    | ATOM | 484 | 1HH1  | ARG R 93 | -11.678 -48.273 15.969 1.00 0.00 |
|    | ATOM | 485 | 2HH1  | ARG R 93 | -10.552 -47.825 14.774 1.00 0.00 |
| 20 | ATOM | 486 | 1HH2  | ARG R 93 | -13.112 -50.146 15.616 1.00 0.00 |
|    | ATOM | 487 | 2HH2  | ARG R 93 | -13.266 -50.761 14.058 1.00 0.00 |
|    | ATOM | 488 | N     | CYS R 94 | -17.121 -49.864 10.349 1.00 0.00 |
|    | ATOM | 489 | CA    | CYS R 94 | -18.327 -50.307 11.053 1.00 0.00 |
|    | ATOM | 490 | C     | CYS R 94 | -18.187 -51.790 11.280 1.00 0.00 |
| 25 | ATOM | 491 | O     | CYS R 94 | -18.340 -52.598 10.361 1.00 0.00 |
|    | ATOM | 492 | CB    | CYS R 94 | -19.611 -50.063 10.264 1.00 0.00 |
|    | ATOM | 493 | SG    | CYS R 94 | -20.314 -48.399 10.429 1.00 0.00 |
|    | ATOM | 494 | H     | CYS R 94 | -16.640 -50.508 9.754 1.00 0.00 |
|    | ATOM | 495 | N     | GLU R 95 | -17.798 -52.106 12.524 1.00 0.00 |
| 30 | ATOM | 496 | CA    | GLU R 95 | -17.382 -53.477 12.826 1.00 0.00 |
|    | ATOM | 497 | C     | GLU R 95 | -18.334 -54.564 12.388 1.00 0.00 |
|    | ATOM | 498 | O     | GLU R 95 | -19.545 -54.380 12.270 1.00 0.00 |
|    | ATOM | 499 | CB    | GLU R 95 | -17.063 -53.650 14.313 1.00 0.00 |
|    | ATOM | 500 | CG    | GLU R 95 | -15.587 -53.436 14.658 1.00 0.00 |

```
ATOM  501 CD  GLU R 95   -15.185 -51.998 14.416 1.00 0.00
ATOM  502 OE1 GLU R 95   -14.757 -51.672 13.318 1.00 0.00
ATOM  503 OE2 GLU R 95   -15.280 -51.193 15.328 1.00 0.00
ATOM  504 H   GLU R 95   -17.570 -51.381 13.172 1.00 0.00
ATOM  505 N   ALA R 96   -17.715 -55.723 12.129 1.00 0.00
ATOM  506 CA  ALA R 96   -18.517 -56.877 11.727 1.00 0.00
ATOM  507 C   ALA R 96   -18.962 -57.733 12.900 1.00 0.00
ATOM  508 O   ALA R 96   -20.158 -57.994 13.010 1.00 0.00
ATOM  509 CB  ALA R 96   -17.748 -57.740 10.723 1.00 0.00
ATOM  510 OXT ALA R 96   -18.116 -58.127 13.704 1.00 0.00
ATOM  511 H   ALA R 96   -16.728 -55.754 12.290 1.00 0.00
END
```

*Principal residues are bolded.

Appendix 4. The Fortran-77 source code of the VBMC algorithm.*

```
        SUBROUTINE MONTE(XMIN,N,S0)
     C*
 5   C*   Variable Basis Monte Carlo simulated annealing:
     C*   XMIN - initial configurational variables and
     C*          final variables for subsequent local energy
     C*          refinement.
     C*   N - the number of configurational variables.
10   C*   S0 - initial energy.
     C*   FUN - potential energy function.
     C*
        IMPLICIT REAL*8(A-H,O-Z)
        DIMENSION XX(250),X(250),XMIN(1)
15      DIMENSION Y(500,250),C(250,250),E(250),V(250,250)
        IYES=0
        ITEST=0
        READ(5,1)N1,N4,N5,NG1,ITE,IPR1,N33
        IF(N1.EQ.0)RETURN
20      WRITE(6,3000)ITE,S0
        TT=ITE
     3000 FORMAT(/10X,'INITIAL TEMPERATURE',I7,
        1    '  INITIAL ENERGY ',F15.6/)
        PR1=IPR1
25      PR2=PR1*2.D0
        WRITE(6,210)PR1,PR1
      210 FORMAT(' RANDOM TORSIONAL INCREMENT -'
        2    ,F5.2,' TO +',F5.2,' GRAD')
        WRITE(6,302)
30      302 FORMAT(10X,'*VARIABLE BASIS MC SIMULATED ANNEALING*'/)
     C*   Boltzmann factor.
        T=-1./(0.001987*TT)
     C   *** TEMPERATURE T=ITE ***
      1 FORMAT(15I5)
```

140

```
            N1=N*N1
            N3=N
            K=N
       C*   Cooling schedule.
  5         DT=(ITE-120)/(N5*N3)
            NG=NG1
            IF(NG.EQ.0)NG=1
       C*   Initial set of random number generator.
            CALL SRAND(NG)
 10         WRITE(6,2)N1,N3,N4,N5,NG
          2 FORMAT(/5X,'MONTE-CARLO PARAMETERS:'/
           *5X,'BLIND CUT',I10/
           *5X,'BYPASS',I10/
           *5X,'FREQUENCY OF CONTROL OUTPUT',I10/
 15        *5X,'LENGTH OF ANNEALING REGION',I10/
           *5X,'INITIAL SET OF THE RANDOM GENERATOR ',I10/)
            IBEGIN=0
            MNCARL=0
            LQ=0
 20         I7=0
            L1=0
            EMIN=1.D37
            S3=0.
            S4=0.
 25    C*   Initial set of basis of independent variables.
            DO 88 I=1,N
            DO 88 J=1,N
            V(I,J)=0.D0
            IF(I.EQ.J)V(I,J)=1.D0
 30      88 CONTINUE
            DO 2005 I=1,N
       2005 X(I)=XMIN(I)
        264 S1=0.
            S2=0.
```

```
        L=0
C*      Method Monte Carlo.
        IYES=0
        KG=0
        L2=0
        I=0
     26 I=I+1
C*      Random choice of a variable to move.
        H=RAND()
        IK=IDINT(H*N)+1
        RA=RAND()
        D=RA*PR2-PR1
C*      Variable Basis Markov chain: move along basis vectors.
        DO 513 II=1,N
    513 XX(II)=X(II)+V(II,IK)*D
        CALL FUN(N,XX,SS)
C*      SS - potential energy of the configuration XX.
        S=SS-S0
        BI=S*T
        IF(BI.GT.50.D0) GOTO 263
C*      CALCULATION OF TRANSITION PROBABILITY
        IF(BI.LT.-50.D0) GOTO 262
        B=DEXP(BI)
        W7=B/(B+1.D0)
C*      DOES TRANSITION TAKE PLACE ?
        Z=RAND()
        IF(W7-Z)262,263,263
C*      ** NO **
    262 CONTINUE
        GOTO 274
C*      ** YES ! **
    263 S0=SS
        IYES=IYES+1
        DO 1314 II=1,N
```

```
      1314 X(II)=XX(II)
       C*    Blind cut off
       274 IF(IBEGIN.EQ.1) GOTO 266
           MNCARL=MNCARL+1
 5         IF(MNCARL-N1)26,1264,265
       1264 WRITE(6,1265)MNCARL,S0
       1265 FORMAT('Initial point has been cut off',I10,1PD17.9)
       C*    Cut off upon criteria.
           GOTO 264
10      265 S1=S1+S0
           S2=S2+S0*S0
           L=L+1
           IF(L.NE.20*N) GOTO 26
           L=0
15         SR1=S1/I
           DISP1=S2/I-SR1**2
           IF(DABS(SR1-S0)-DSQRT(DISP1))270,270,271
       271 ITEST=0
           GOTO 272
20      270 ITEST=ITEST+1
       272 YES=(1.D2*IYES)/I
           WRITE(6,268)I,S0,SR1,DISP1,ITEST,YES
       268 FORMAT('Cut off',I8,3D14.7,I3,2PF7.1)
           IF(I.GE.50000)GOTO 267
25         IF(ITEST-3) 26,267,267
       267 IBEGIN=1
           WRITE(6,1265)MNCARL,S0
           WRITE(6,269)
       269 FORMAT(//45X,'Equilibrium has been reached '/)
30         GOTO 264
       C*    N3 - parameter of bypassing.
       C*    DT - cooling schedule.
       266 L=L+1
           IF(TT.LE.120.D0)GOTO 3333
```

143

```
          C*      Slow cooling.
              TT=TT-DT
          C*      Boltzmann factor.
              T=-1.D0/(1.987D-3*TT)
     5        IF(L.LT.N3)GOTO 26
              L=0
              KG=KG+1
          C*      Accumulating N33 sequential points of the Markov chain.
              DO 1992 J=1,N
    10     1992 Y(KG,J)=X(J)
              L1=L1+1
              L2=L2+1
              IF(S0.GE.EMIN)GOTO 1957
              EMIN=S0
    15        DO 1961 IJ=1,N
           1961 XMIN(IJ)=X(IJ)
              LQ=LQ+1
              WRITE(6,100)LQ,I,EMIN,TT,(XMIN(J),J=1,N)
           100  FORMAT(/' LQ',2I7,D17.9,F7.1/(1X,10F12.3))
    20     447  FORMAT(/' CR',2I7,D17.9,F7.1/(1X,10F12.3))
           1957 IF(KG.LT.N33)GOTO 45
          C*      Computing covariant matrix of the distribution of
          C*      the N33 accumulated points in the configurational
          C*      space.
    25        KG=0
              DO 71 II=1,K
              YYY=0.0
              DO 82 J=1,N33
           82 YYY=YYY+Y(J,II)
    30        YYY=YYY/N
              DO 54 J=1,N33
           54 Y(J,II)=Y(J,II)-YYY
           71 CONTINUE
              DO 710 II=1,K
```

```
            DO 710 J=1,K
            S=0.0
            DO 711 LL=1,N33
        711 S=S+Y(LL,II)*Y(LL,J)
        710 C(II,J)=S
      C*    Covariant matrix is ready.
      C*    Roration of basis V:
            CALL SDIAG2(250,K,C,E,V)
         45 IF(L2.LT.N4) GOTO 26
            L2=0
            YES=(1.D2*IYES)/I
            WRITE(6,72)I,L1,EMIN,S0,TT,YES
         72 FORMAT(' CO',2I10,2D15.6,F7.1,2PF7.1)
            IF(L1.LT.N5) GOTO 26
       3333 WRITE(6,1111)
       1111 FORMAT(//10X,'END OF MONTE CARLO STAGE')
            RETURN
            END
            SUBROUTINE SDIAG2(M,N,A,D,X)
      C*
      C*    Diagonalization of symmetric matrix A (NxN).
      C*    Results: D - eigenvalues; X - eigenvectors.
      C*
            IMPLICIT REAL*8(A-H,O-Z)
            DIMENSION A(M,M),D(M),X(M,M)
            DIMENSION E(250)
            EPS=1.0D-14
            TOL=1.0D-30
            IF(N.EQ.1)GOTO 400
            DO 10 I=1,N
            DO 10 J=1,I
         10 X(I,J)=A(I,J)
            DO 150 NI=2,N
            II=N+2-NI
```

```
        DO 150 I=II,II
        L=I-2
        H=.0D0
        G=X(I,I-1)
 5      IF(L)140,140,20
     20 DO 30 K=1,L
     30 H=H+X(I,K)**2
        S=H+G*G
        IF(S.GE.TOL)GOTO 50
10      H=.0D0
        GOTO 140
     50 IF(H)140,140,60
     60 L=L+1
        F=G
15      G=DSQRT(S)
        IF(F)75,75,70
     70 G=-G
     75 H=S-F*G
        X(I,I-1)=F-G
20      F=.0D0
        DO 110 J=1,L
        X(J,I)=X(I,J)/H
        S=.0D0
        DO 80 K=1,J
25   80 S=S+X(J,K)*X(I,K)
        J1=J+1
        IF(J1.GT.L)GOTO 100
        DO 90 K=J1,L
     90 S=S+X(K,J)*X(I,K)
30  100 E(J)=S/H
    110 F=F+S*X(J,I)
        F=F/(H+H)
        DO 120 J=1,L
    120 E(J)=E(J)-F*X(I,J)
```

```
        DO 130 J=1,L
        F=X(I,J)
        S=E(J)
        DO 130 K=1,J
 130    X(J,K)=X(J,K)-F*E(K)-X(I,K)*S
 140    D(I)=H
 150    E(I-1)=G
 160    D(1)=X(1,1)
        X(1,1)=1.D0
        DO 220 I=2,N
        L=I-1
        IF(D(I))200,200,170
 170 DO 190 J=1,L
        S=.0D0
        DO 180 K=1,L
 180    S=S+X(I,K)*X(K,J)
        DO 190 K=1,L
 190    X(K,J)=X(K,J)-S*X(K,I)
 200    D(I)=X(I,I)
        X(I,I)=1.D0
 210    DO 220 J=1,L
        X(I,J)=.0D0
 220    X(J,I)=.0D0
        B=.0D0
        F=.0D0
        E(N)=.0D0
        DO 340 L=1,N
        H=EPS*(DABS(D(L))+DABS(E(L)))
        IF(H.LE.B)GOTO 235
        B=H
 235 DO 240 J=L,N
        IF(DABS(E(J)).LE.B)GOTO 250
 240 CONTINUE
 250 IF(J.EQ.L)GOTO 340
```

```
260 P=(D(L+1)-D(L))*.5D0/E(L)
    R=DSQRT(P*P+1.D0)
    IF(P)270,280,280
270 P=P-R
    GOTO 290
280 P=P+R
290 H=D(L)-E(L)/P
    DO 300 I=L,N
300 D(I)=D(I)-H
    F=F+H
    P=D(J)
    C=1.D0
    S=0.D0
    J1=J-1
    DO 330 NI=L,J1
    II=L+J1-NI
    DO 330 I=II,II
    G=C*E(I)
    H=C*P
    IF(DABS(P).LT.DABS(E(I)))GOTO 310
    C=E(I)/P
    R=DSQRT(C*C+1.D0)
    E(I+1)=S*P*R
    S=C/R
    C=1.D0/R
    GOTO 320
310 C=P/E(I)
    R=DSQRT(C*C+1.D0)
    E(I+1)=S*E(I)*R
    S=1.D0/R
    C=C/R
320 P=C*D(I)-S*G
    D(I+1)=H+S*(C*G+S*D(I))
    DO 330 K=1,N
```

```
         H=X(K,I+1)
         X(K,I+1)=X(K,I)*S+H*C
     330 X(K,I)=X(K,I)*C-H*S
         E(L)=S*P
  5      D(L)=C*P
         IF(DABS(E(L)).GT.B)GOTO 260
     340 D(L)=D(L)+F
         NI=N-1
     350 DO 380 I=1,NI
 10      K=I
         P=D(I)
         J1=I+1
         DO 360 J=J1,N
         IF(D(J).GE.P)GOTO 360
 15      K=J
         P=D(J)
     360 CONTINUE
         IF(K.EQ.I)GOTO 380
         D(K)=D(I)
 20      D(I)=P
         DO 370 J=1,N
         P=X(J,I)
         X(J,I)=X(J,K)
     370 X(J,K)=P
 25  380 CONTINUE
         RETURN
     400 D(1)=A(1,1)
         X(1,1)=1.D0
         RETURN
 30      END
```

*The essential places of the VBMC algorithm (different from conventional Monte Carlo technique) are bolded.

What is claimed is:

1. A method of designing a ligand for binding with common neurotrophin receptor p75$^{NTR}$, wherein p75$^{NTR}$ comprises a binding site including amino acid residues Cys$^{39p}$ to Cys$^{94p}$ inclusive, said residues of said binding site having spatial coordinates given in Appendix 3 when in a complex with a neurotrophin, said binding site having three binding areas including binding loop 2A comprising region Cys$^{39p}$ to Cy$^{58p}$ capable of attractive electrostatic interaction, binding loop 2B comprising region Cys$^{68p}$ to Cys$^{79p}$ capable of attractive electrostatic interaction, and binding loop 3A comprising region Cys$^{79p}$ to Cys$^{94p}$ capable of attractive electrostatic interaction, the method comprising:

computationally evolving a ligand using an effective algorithm so that said evolved ligand comprises at least two effective moieties located relative to each other in the ligand so that a first moiety can bind to a first of said three binding areas and a second moiety can bind to a second of said three binding areas, wherein a representation of said computationally evolved ligand is output.

2. A method of identifying a ligand to bind with common neurotrophin receptor p75$^{NTR}$, comprising:

providing a three dimensional conformation for the common neurotrophin receptor p75$^{NTR}$, wherein p75$^{NTR}$ comprises a binding site including amino acid residues Cys$^{30p}$ to Cys$^{94p}$ inclusive, said residues of said binding site having spatial coordinates given in Appendix 3 when in a complex with a neurotrophin, said binding site having three binding areas including binding loop 2A comprising region $Cys^{39p}$ to $Cys^{58p}$ capable of attractive electrostatic interaction, binding loop 2B comprising region $Cys^{58p}$ to $Cys^{78p}$ capable of attractive electrostatic interaction, and binding loop 3A comprising region $Cys^{79p}$ to $Cys^{94p}$ capable of attractive electrostatic interaction;

providing a data base containing molecules coded for spatial occupancy, relative atomic position, bond type and/or charge; and screening said data base to select a ligand comprising moieties that can bind with at least two of said three binding loops, wherein a representation of said selected ligand is output.

3. The method according to claim 2 wherein said ligand is an agonist, and wherein one of said at least two moieties binds to loop 2B.

4. The method according to claim 2 further comprising a third moiety wherein said first moiety binds to loop 2A, said second moiety binds to loop 2B and said third moiety binds to loop 3A.

5. The method according to claim 2 wherein said first moiety binds to any two of $Asp^{47p}$, $Lys^{56p}$ and $Glu^{53p}$.

6. The method according to claim 2 wherein said binding loop 2A includes amino acid residues $Asp^{47p}$ and $Lys^{56p}$ and said first moiety ionically binds to said residues $Asp^{47p}$ and $Lys^{56p}$.

7. The method according to claim 2 wherein said binding loop 2B includes amino acid residues $Asp^{75p}$ and $Asp^{76p}$ and said second moiety ionically binds to said residues $Asp^{75p}$ and $Asp^{76p}$.

8. The method according to claim 4 wherein said binding loop 3A includes amino acid residues $Asp^{88p}$ and $Glu^{89p}$ and said third moiety ionically binds to said residues $Asp^{88p}$ and $Glu^{89p}$.

9. The method according to claim 4 wherein said third moiety binds to any two of $Asp^{88p}$, $Glu^{89p}$ and $Arg^{80p}$.

10. The method according to claim 1 wherein said ligand is an agonist, and wherein one of said at least two moieties binds to loop 2B.

11. The method according to claim 1 further comprising a third moiety wherein said first moiety binds to loop 2A, said second moiety binds to loop 2B and said third moiety binds to loop 3A.

12. The method according to claim 1 wherein said first moiety binds to any two of $Asp^{47p}$, $Lys^{56p}$ and $Glu^{53p}$.

13. The method according to claim 1 wherein said binding loop 2A includes amino acid residues $Asp^{47p}$ and $Lys^{56p}$ and said first moiety ionically binds to said residues $Asp^{47p}$ and $Lys^{56p}$.

14. The method according to claim 1 wherein said binding loop 2B includes amino acid residues $Asp^{75p}$ and $Asp^{76p}$ and said second moiety ionically binds to said residues $Asp^{75p}$ and $Asp^{76p}$.

15. The method according to claim 11 wherein said binding loop 3A includes amino acid residues $Asp^{88p}$ and $Glu^{89p}$ and said third moiety ionically binds to said residues $Asp^{88p}$ and $Glu^{89p}$.

16. The method according to claim 11 wherein said third moiety binds to any two of $Asp^{88p}$, $Glu^{89p}$ and $Arg^{80p}$.

17. The method according to claim 1, wherein said ligand is bifunctional, such that a first portion of the ligand binds to at least two of said three binding areas of a first receptor monomer and a second portion of the ligand binds to at least two of said three binding areas of a second receptor monomer.

18. The method according to claim 2, wherein said ligand is bifunctional, such that a first portion of the ligand binds to at least two of said three binding loops of a first receptor monomer and a second portion of the ligand binds to at least two of said three binding loops of a second receptor monomer.

* * * * *

UNITED STATES PATENT AND TRADEMARK OFFICE
CERTIFICATE OF CORRECTION

PATENT NO. : 6,029,114
DATED : February 22, 2000
INVENTOR(S) : Igor L. Shamovsky, Gregory M. Ross, Richard Riopelle and Donald F. Weaver It is certified that error appears in the above-identified patent and that said Letters Patent is hereby corrected as shown below:

Abstract,
Line 20, "$Cys^{78P}$" should read -- $Cys^{79P}$ --;

Figure 2:
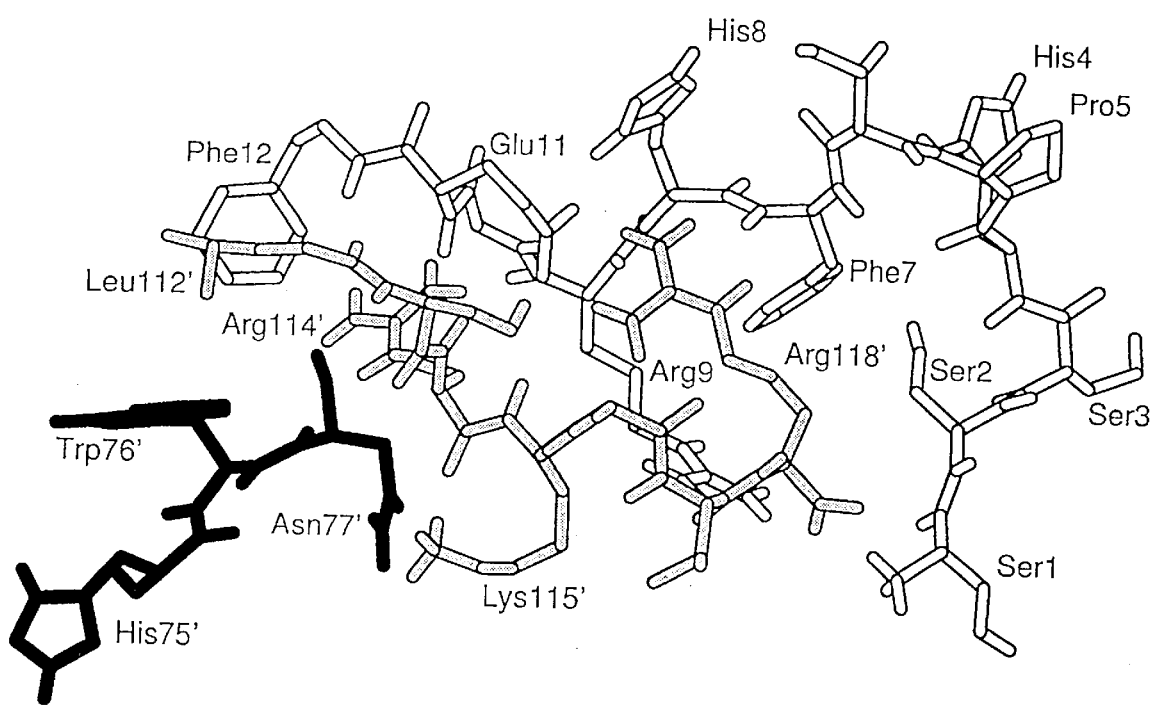
Figure 3:
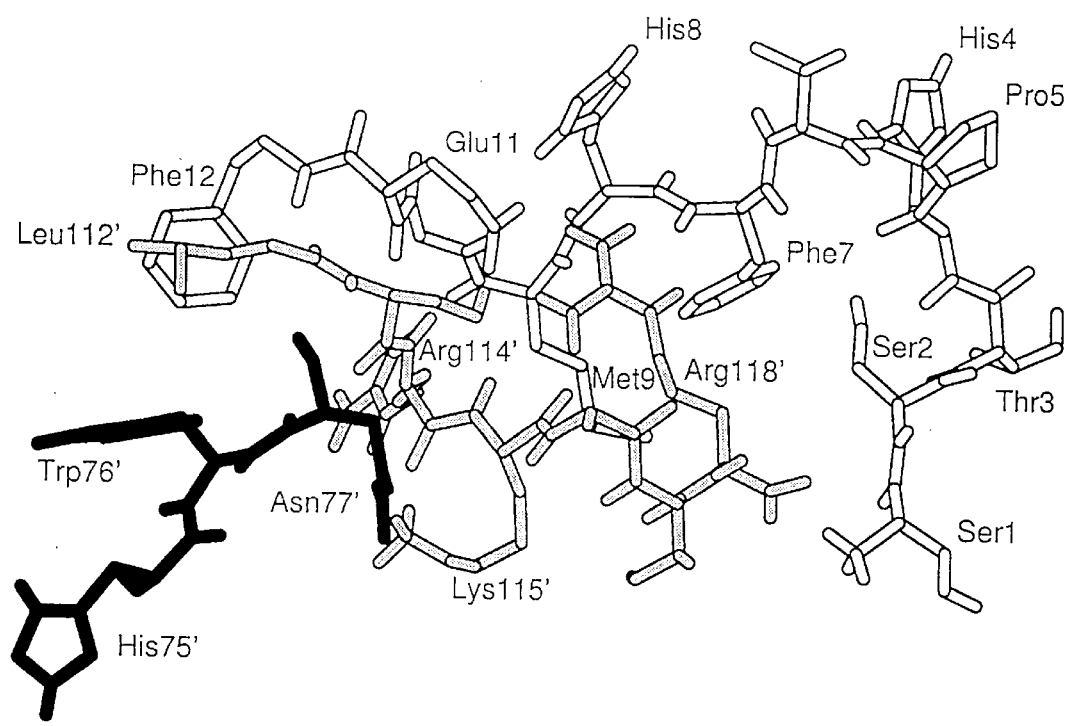
Figure 4:
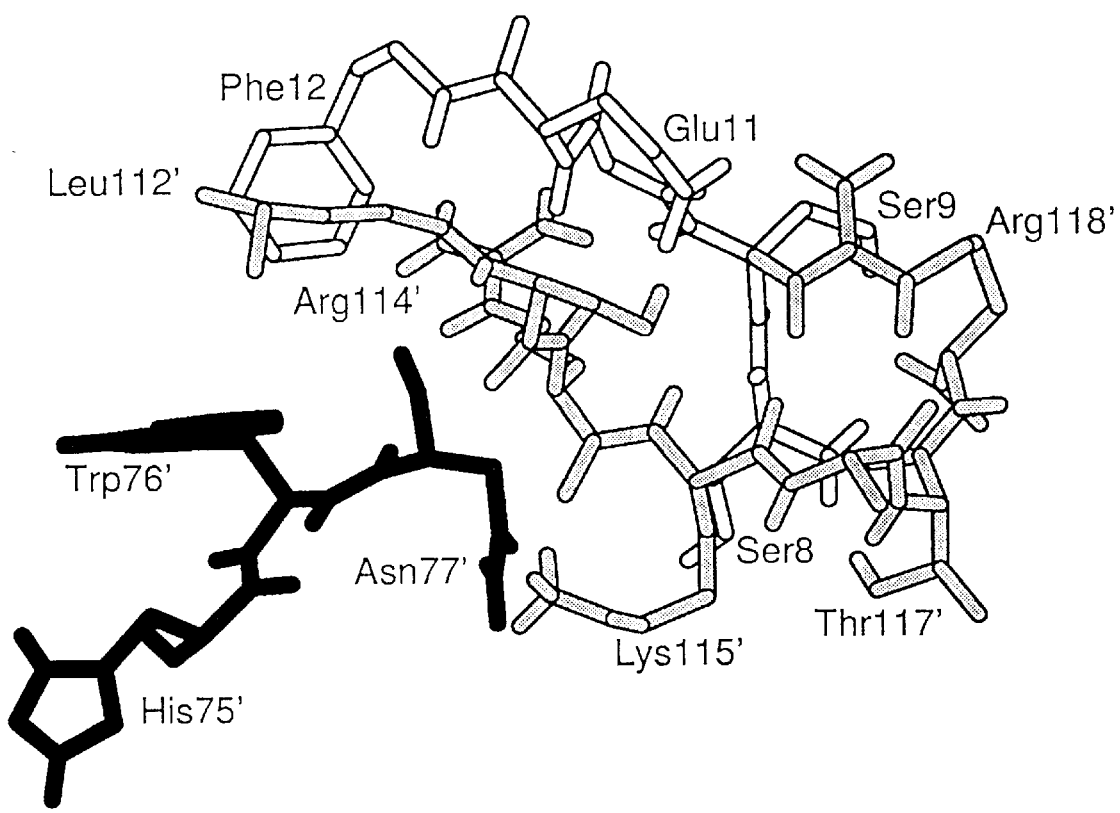
Figure 5:
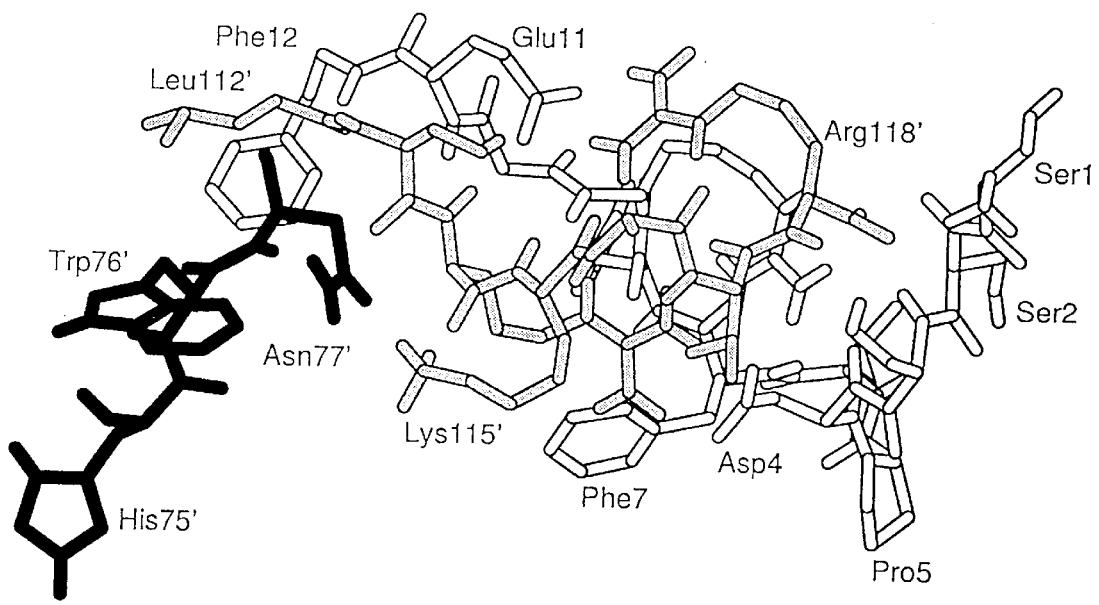
Figure 6:
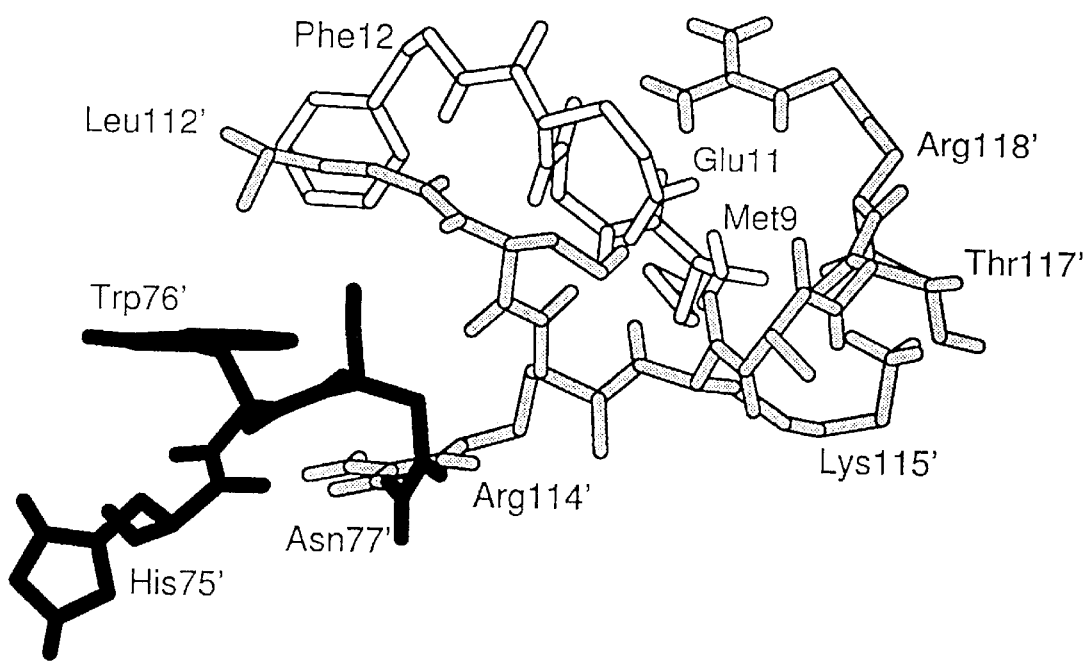
Figure 7:
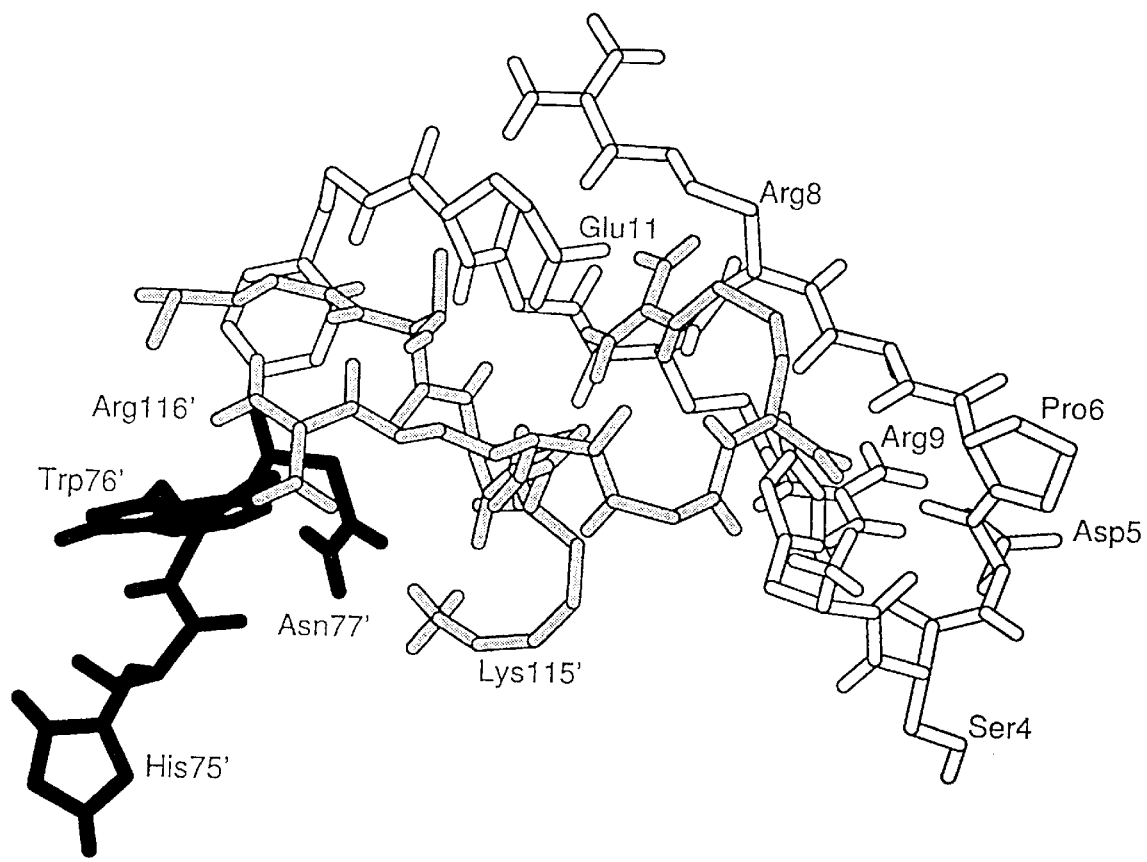
Figure 10A:
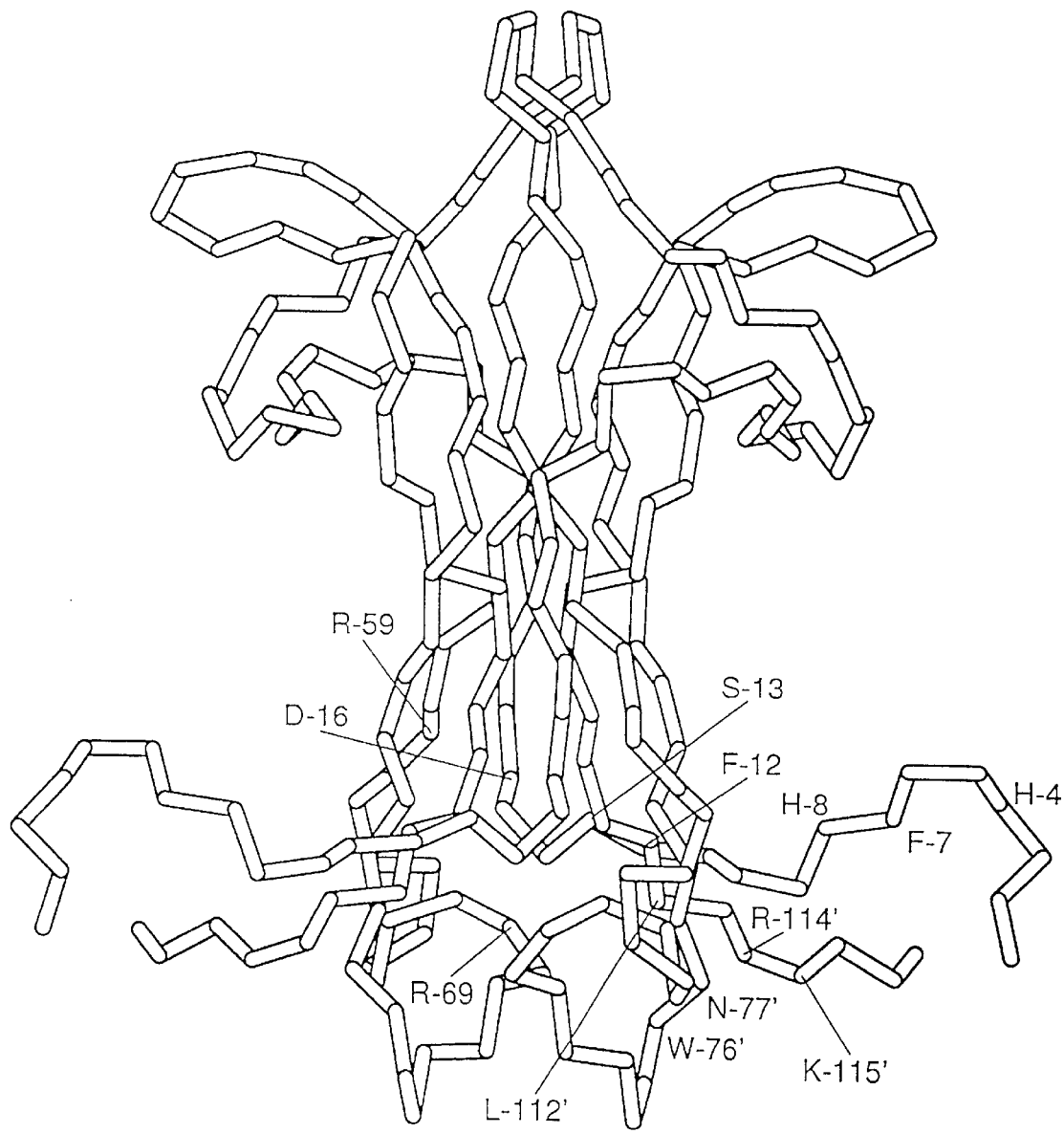
Figure 10B:
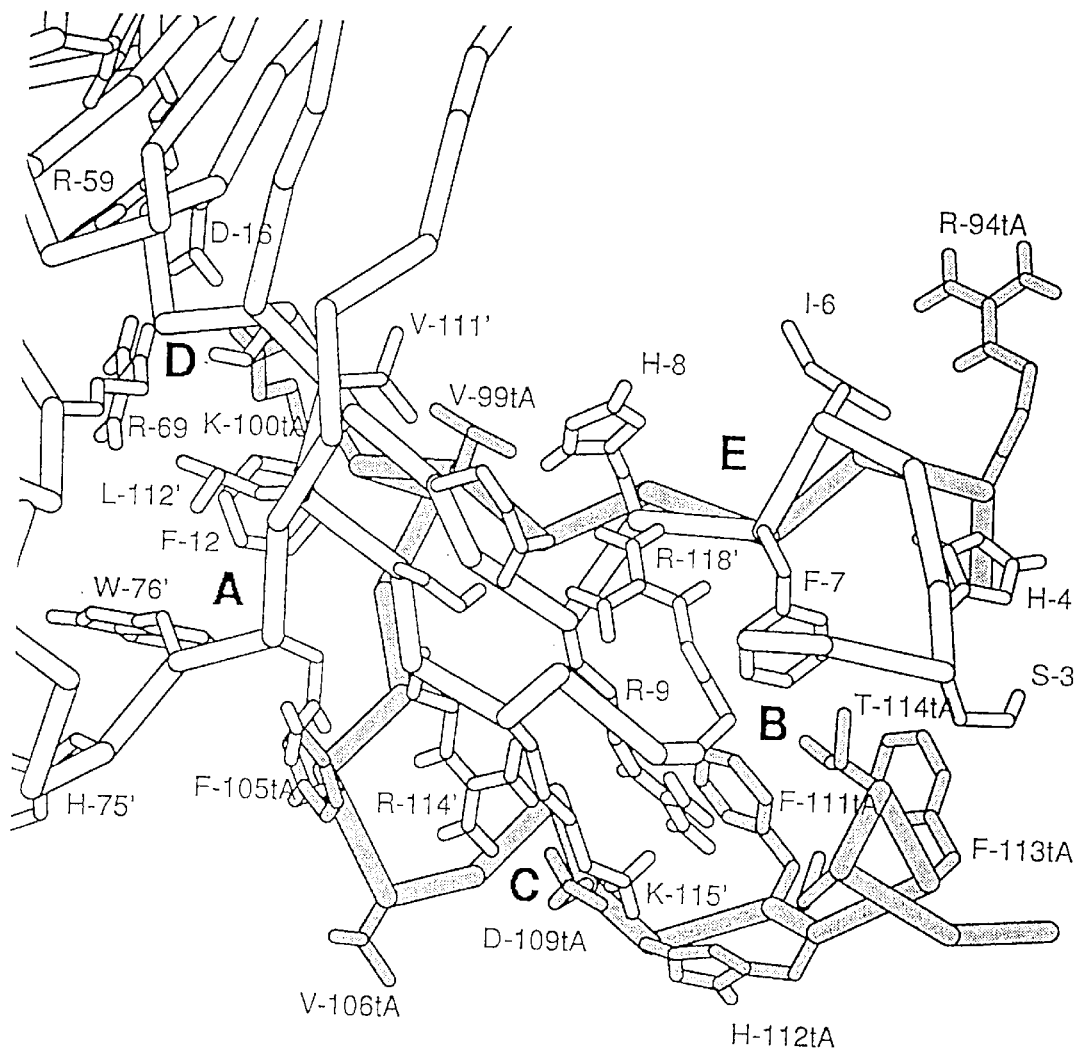
Figure 10C:
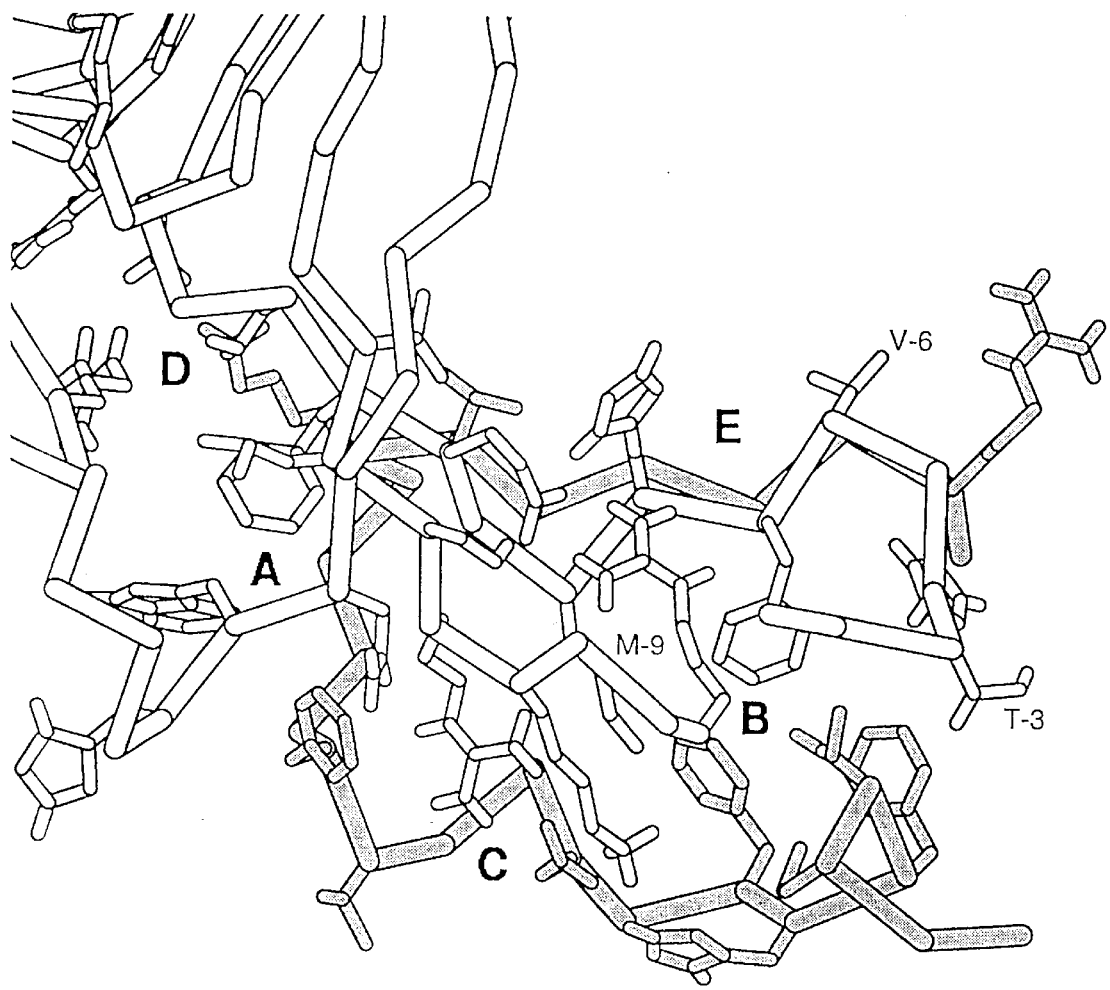
Figure 10D:
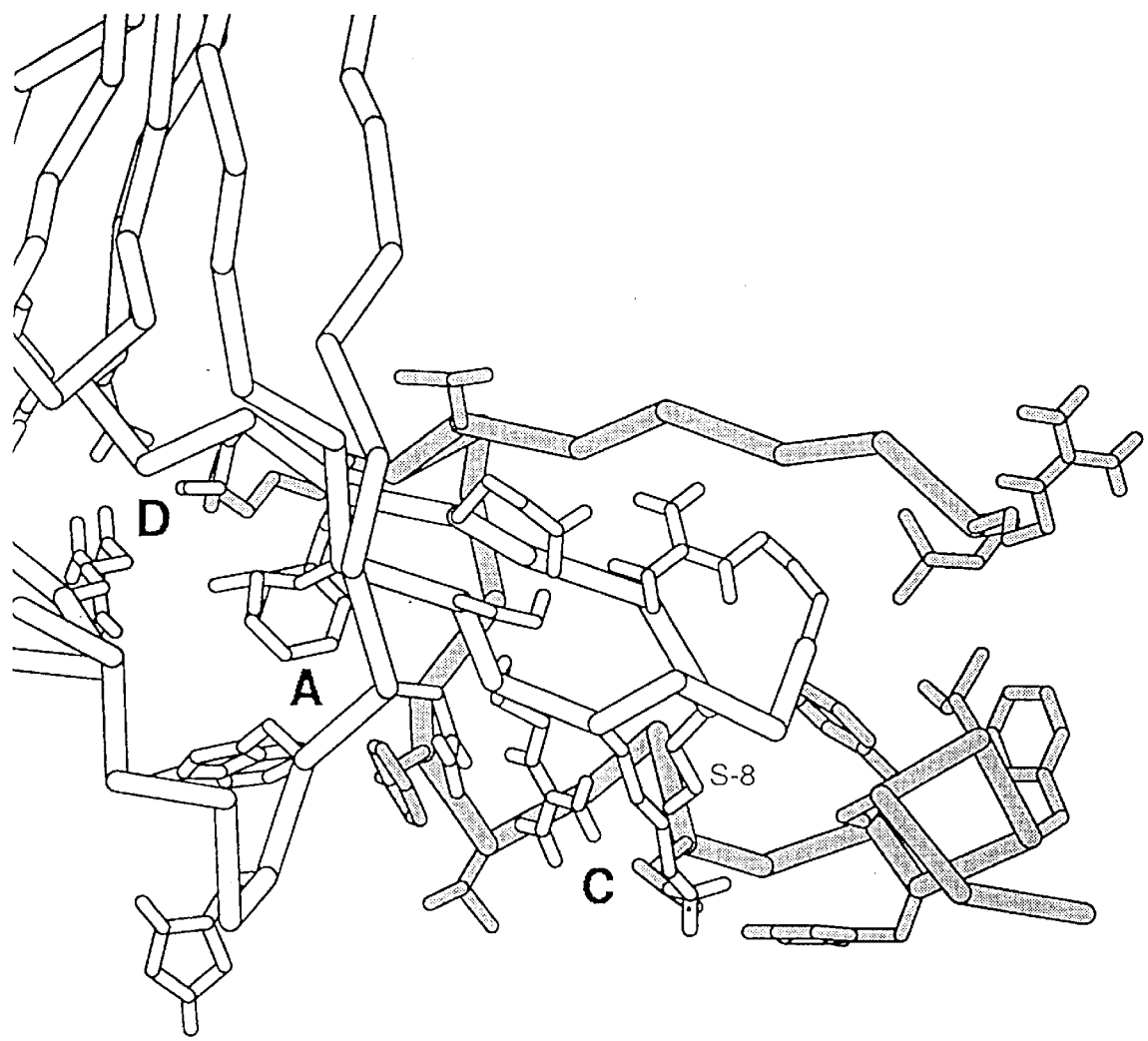
Figure 10E:
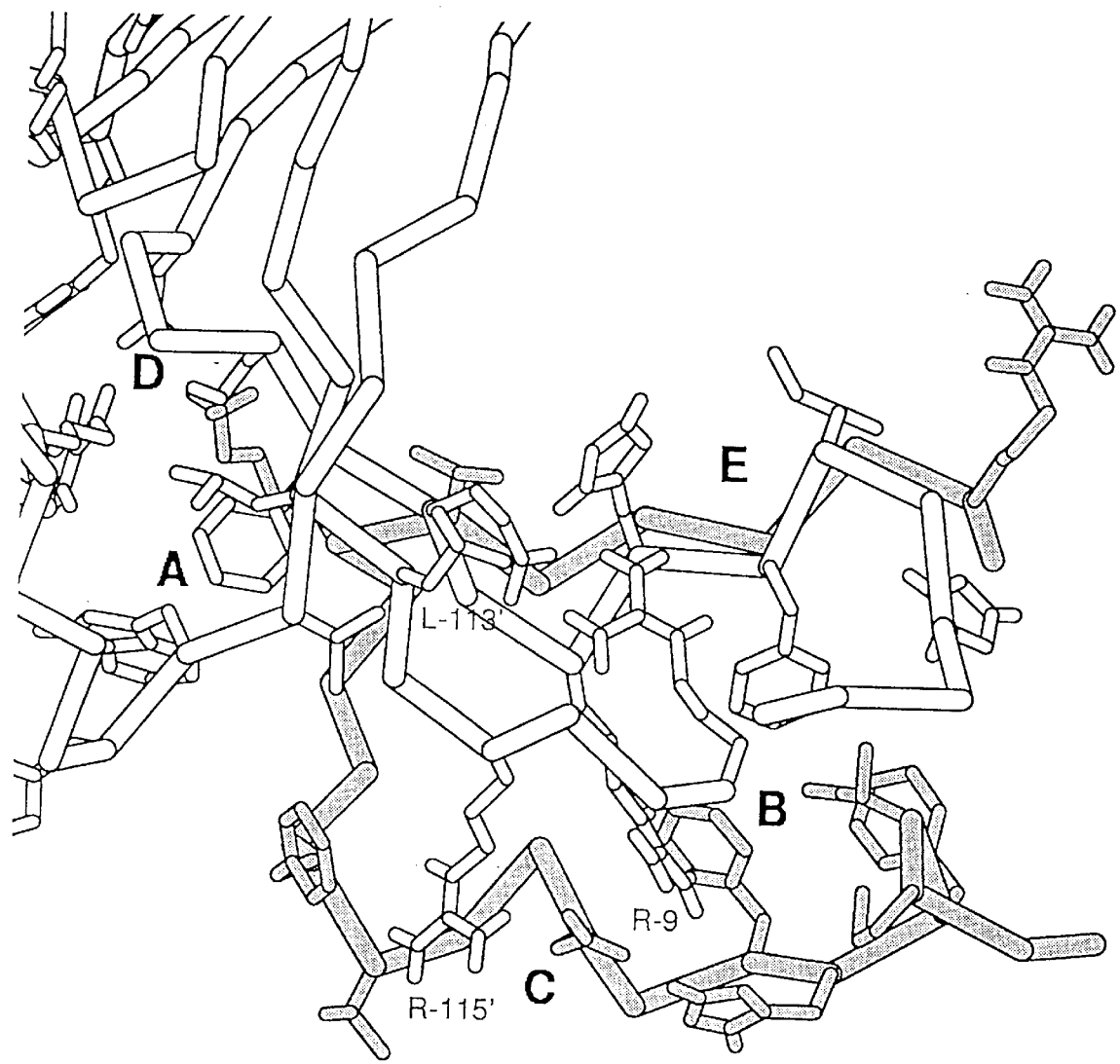
Figure 11A:
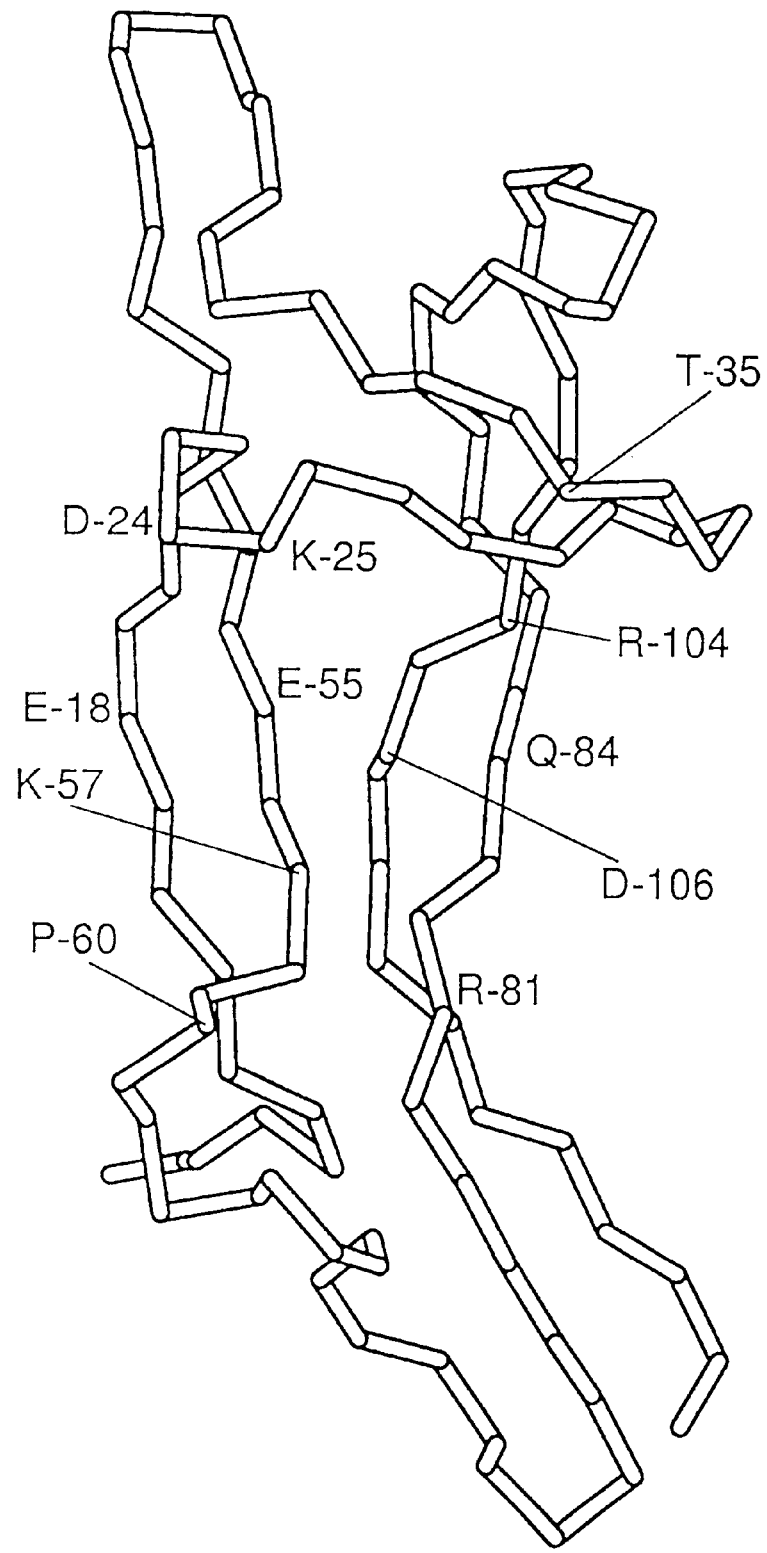
Figure 11B:
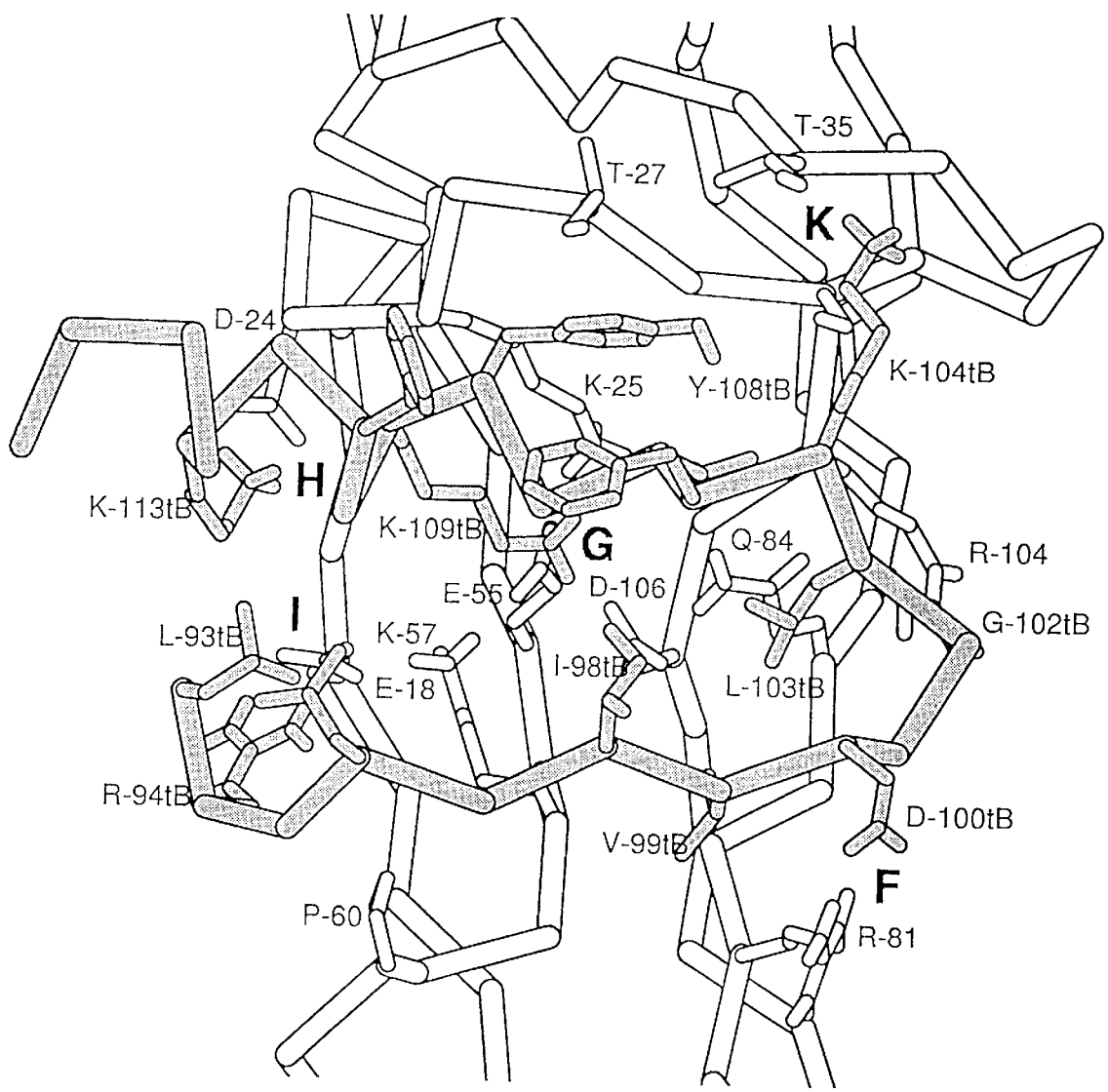
Figure 11C:
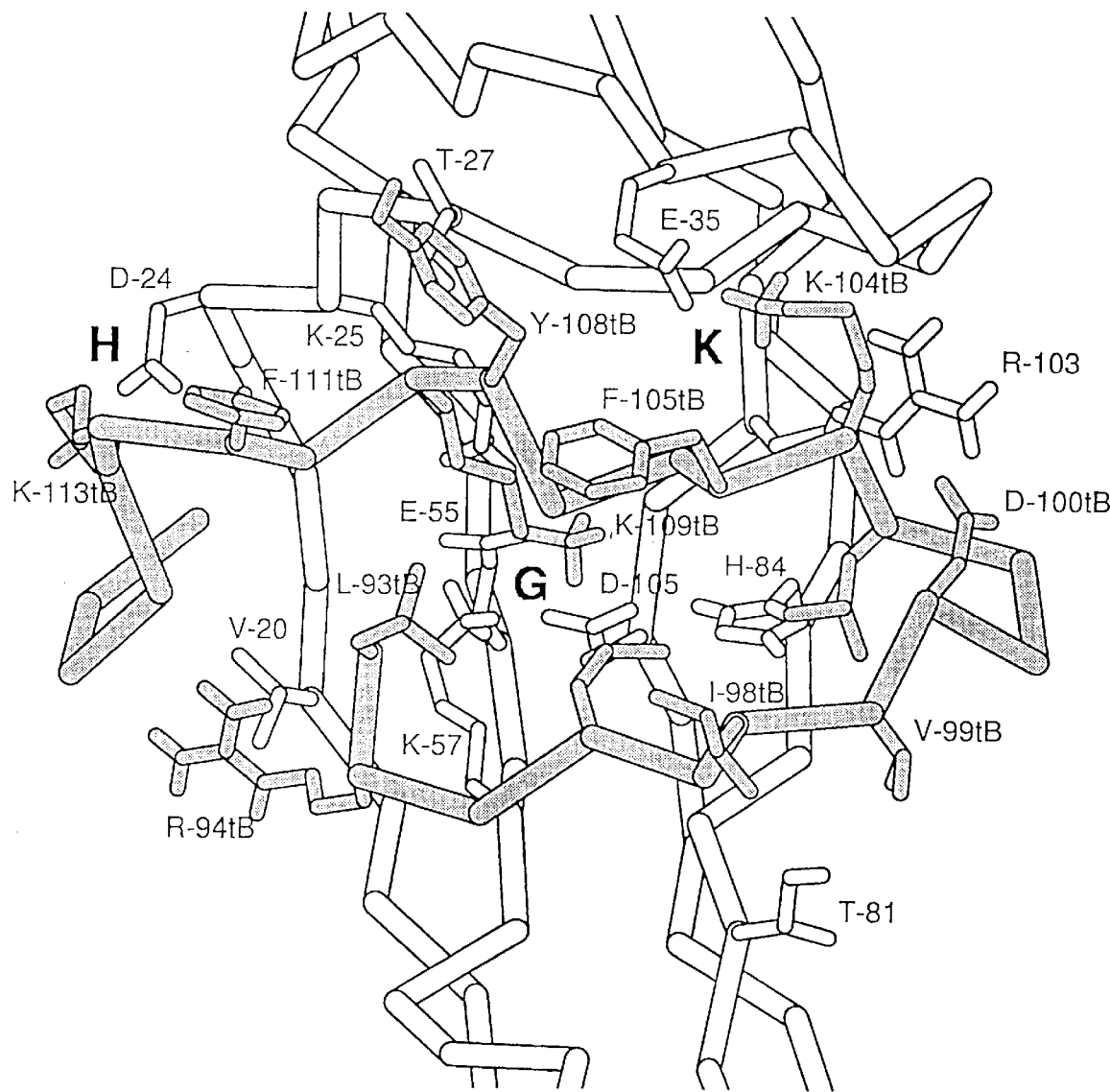
Figure 12:
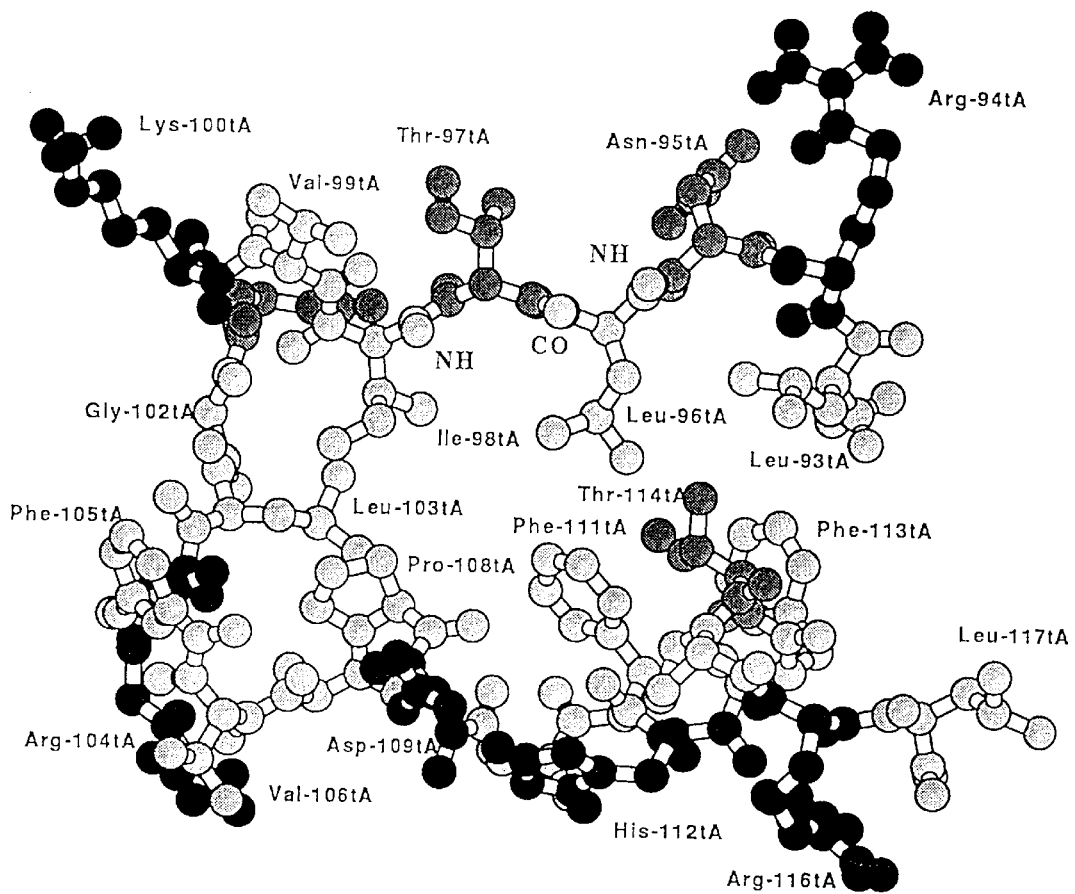
Figure 15:
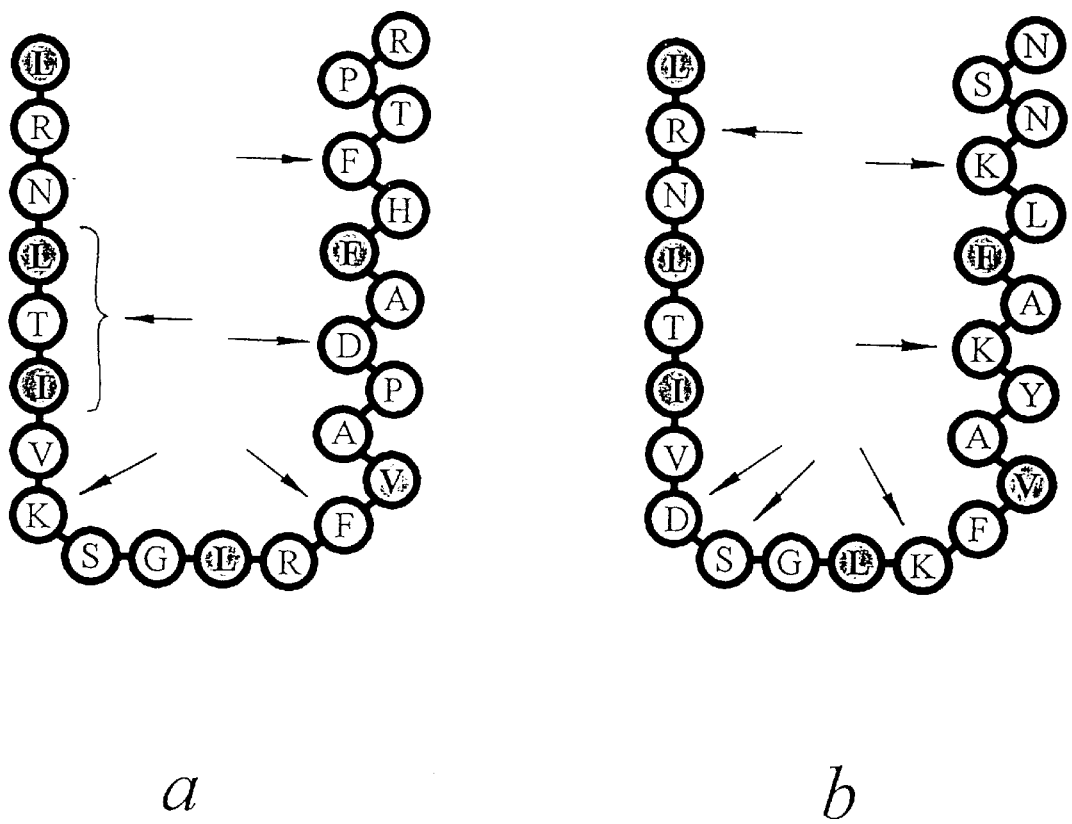
Figure 16:
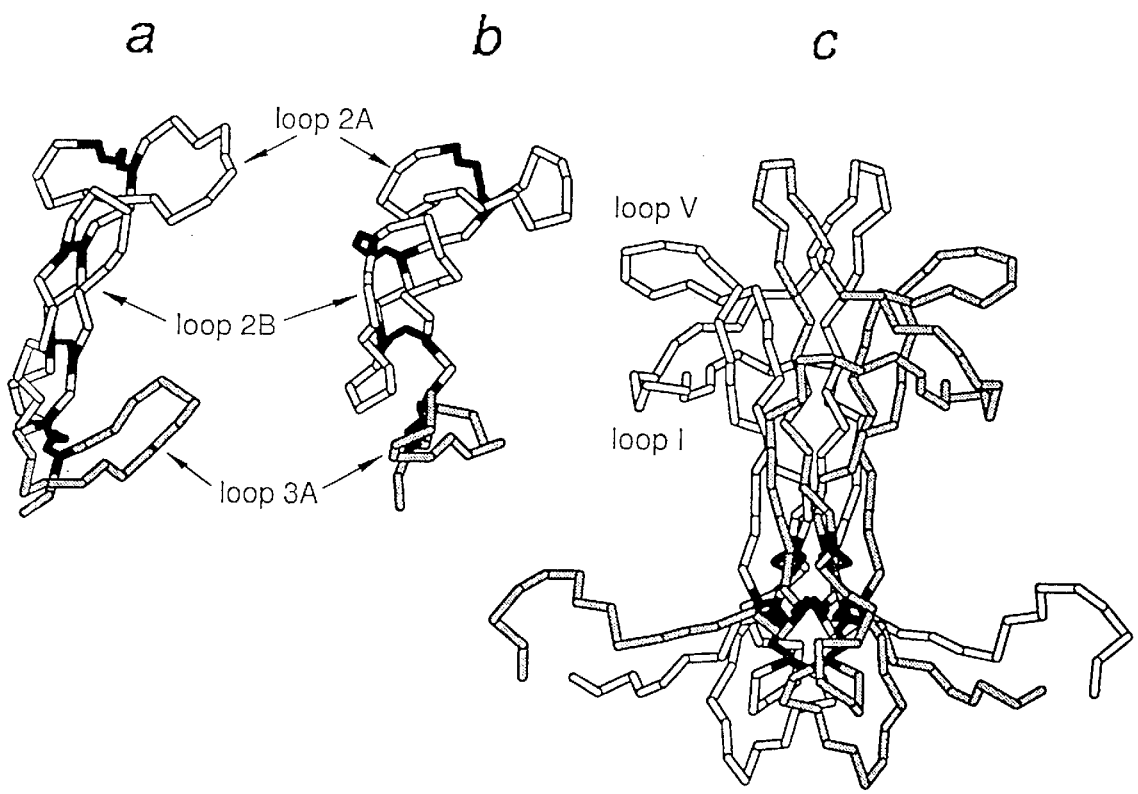
Figure 18A:
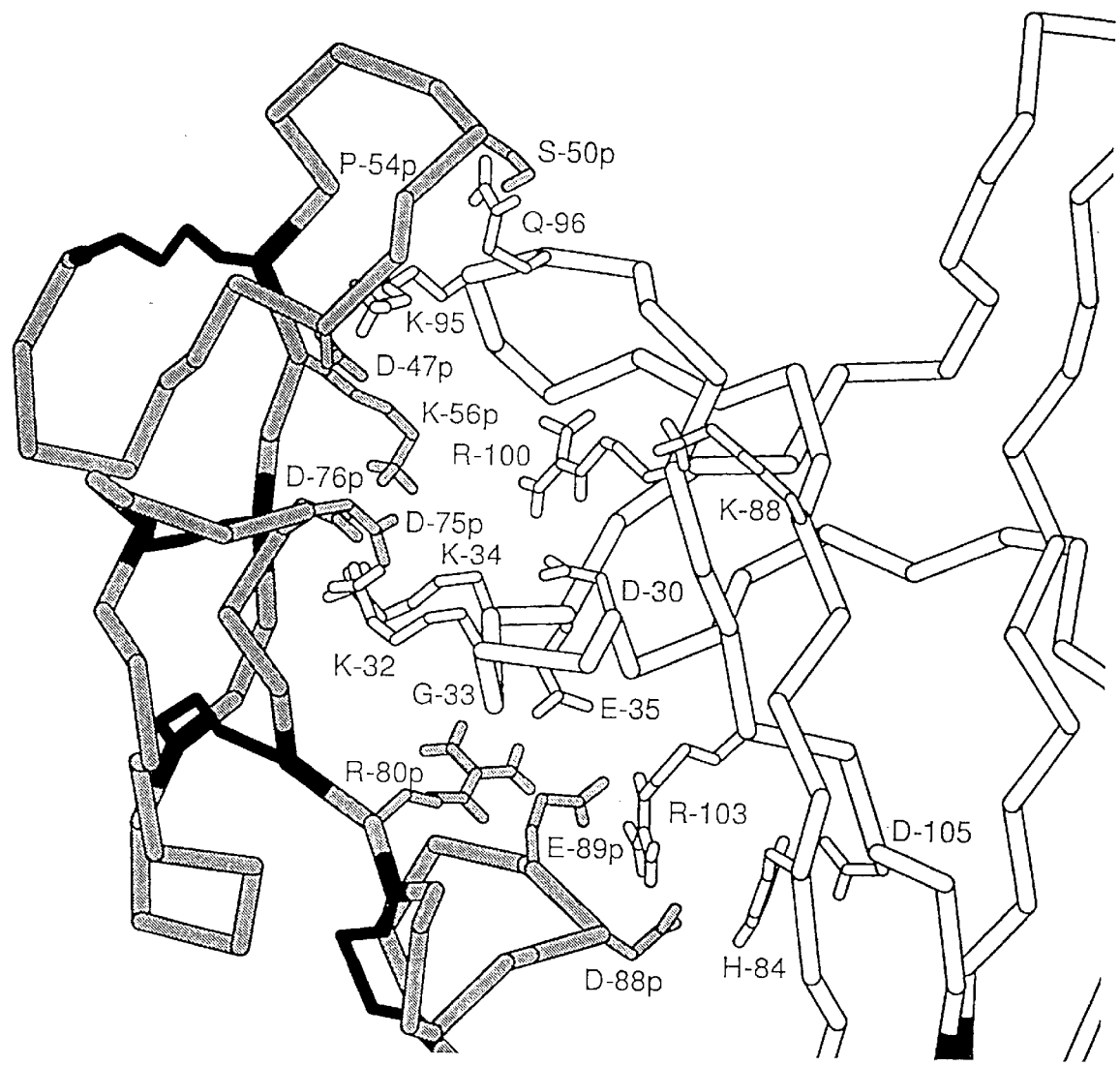
Figure 18B:
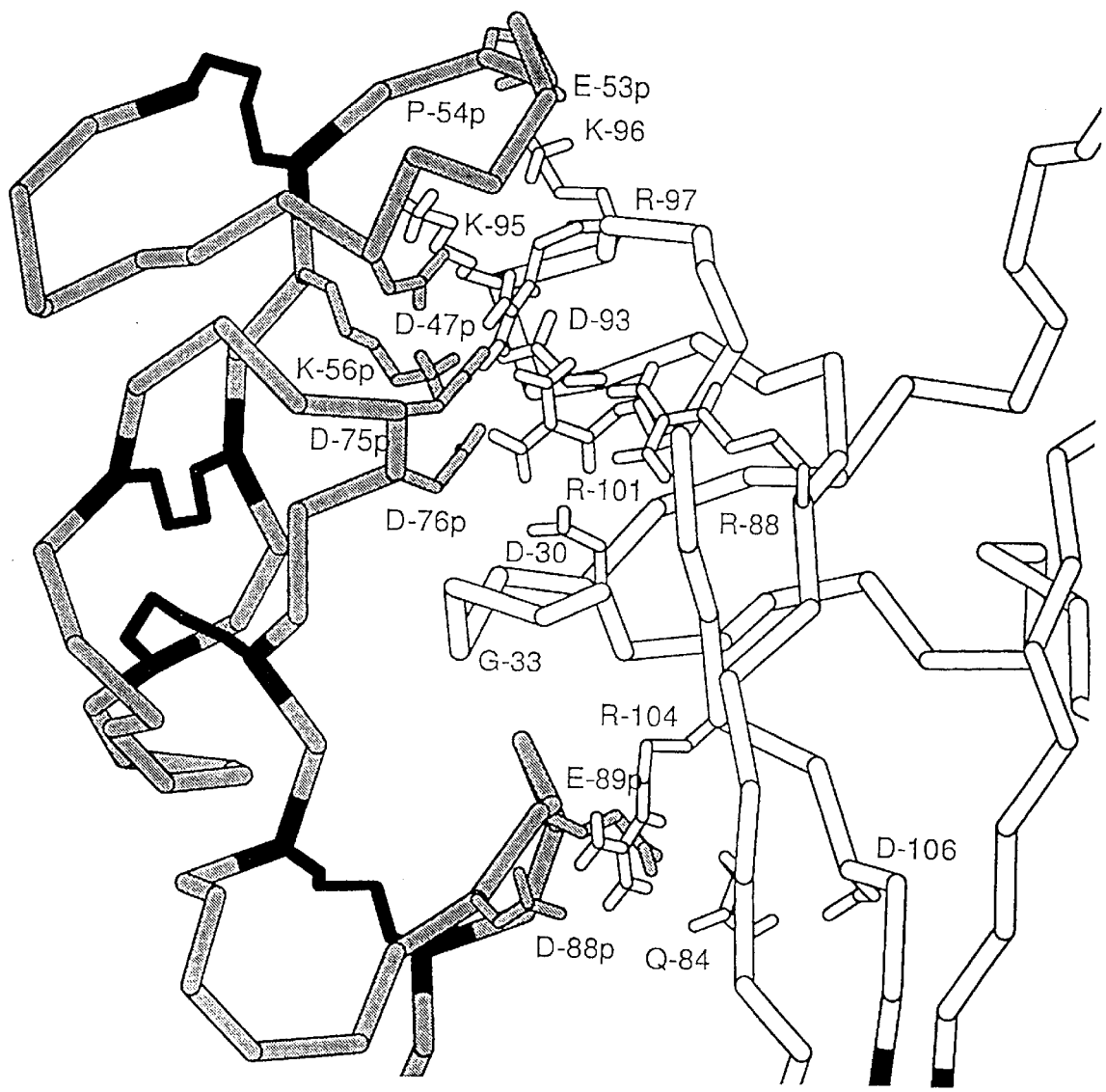
Figure 18C:
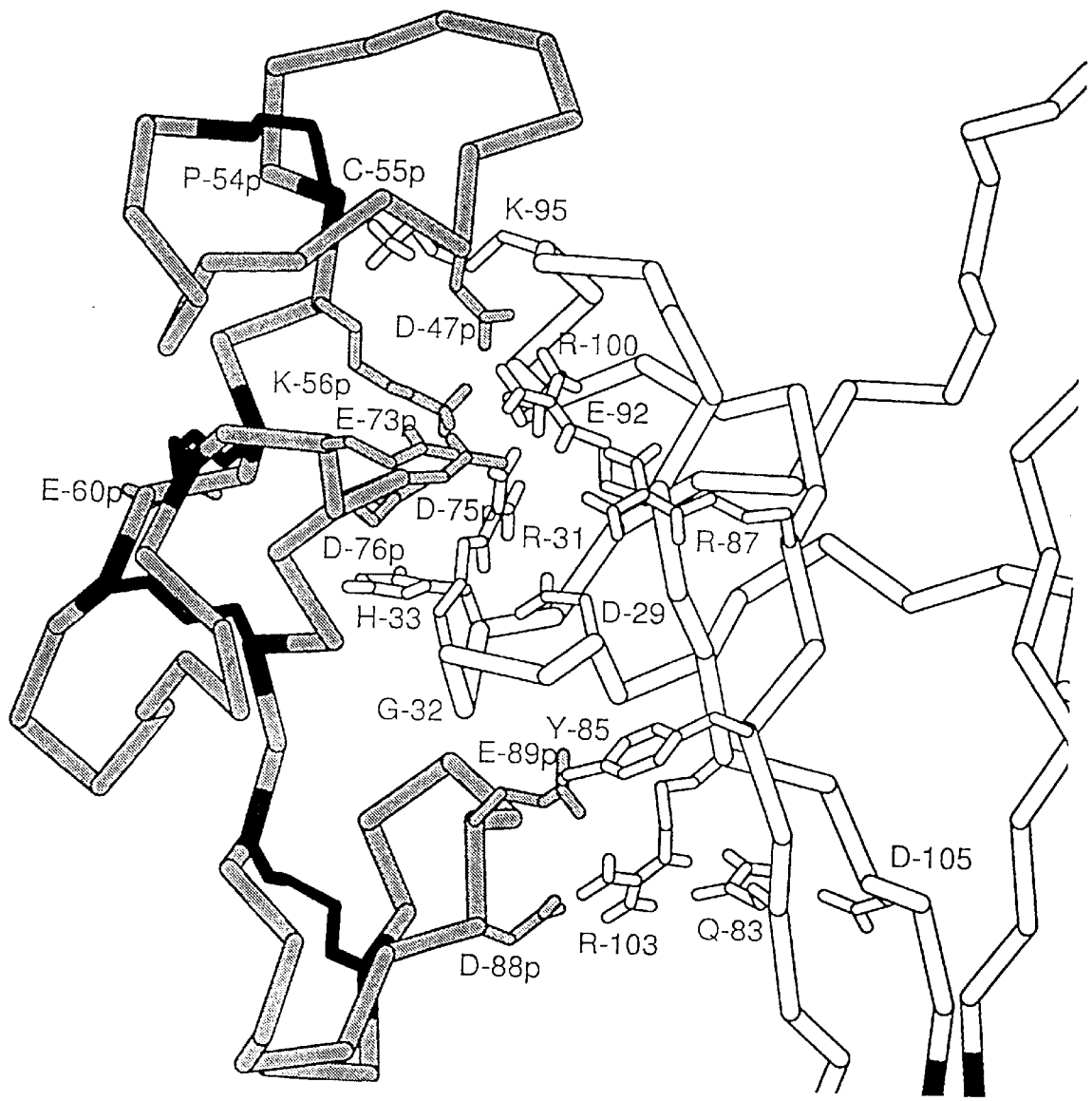
Figure 18D:
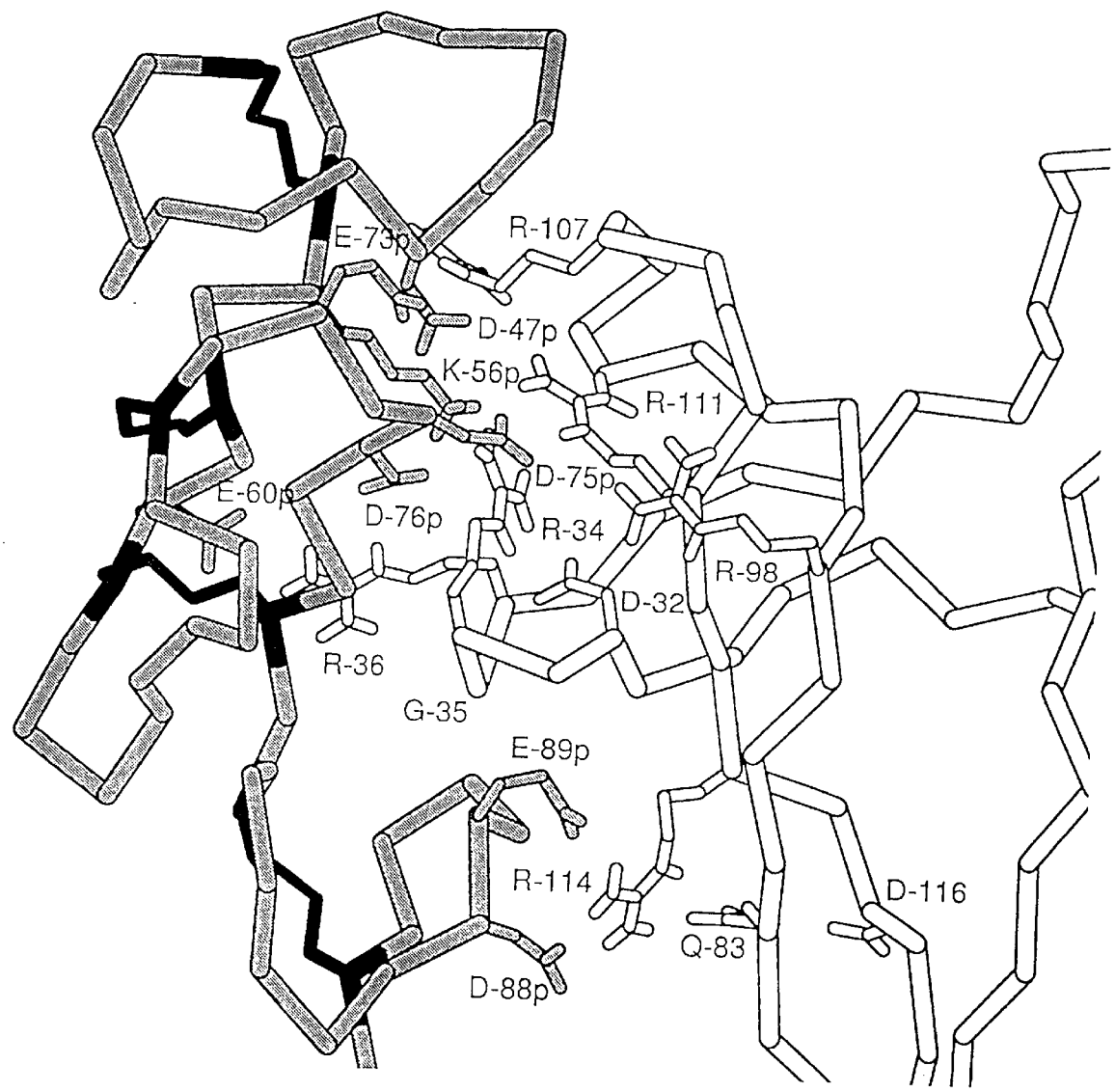
Figure 19:
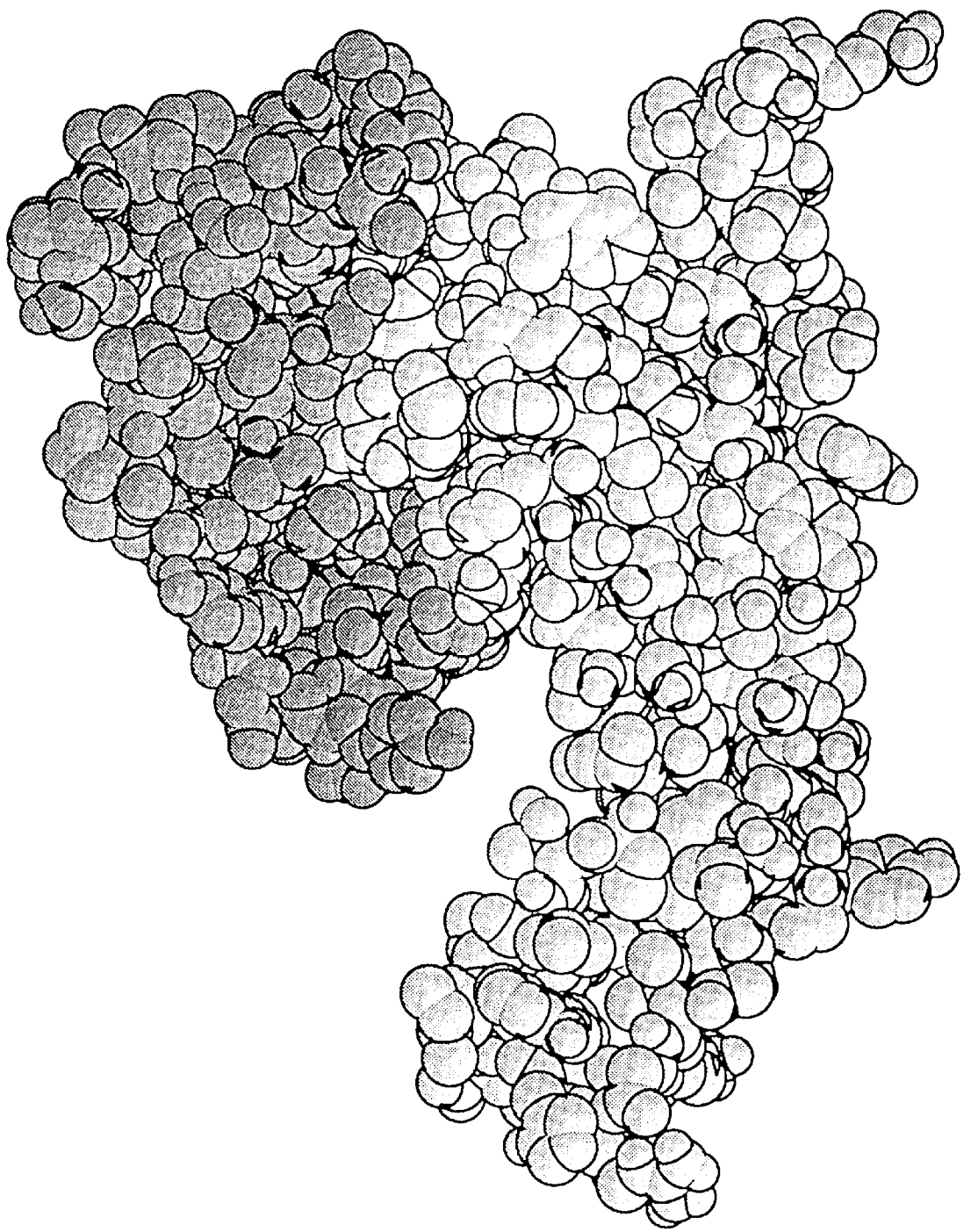
Figure 20:
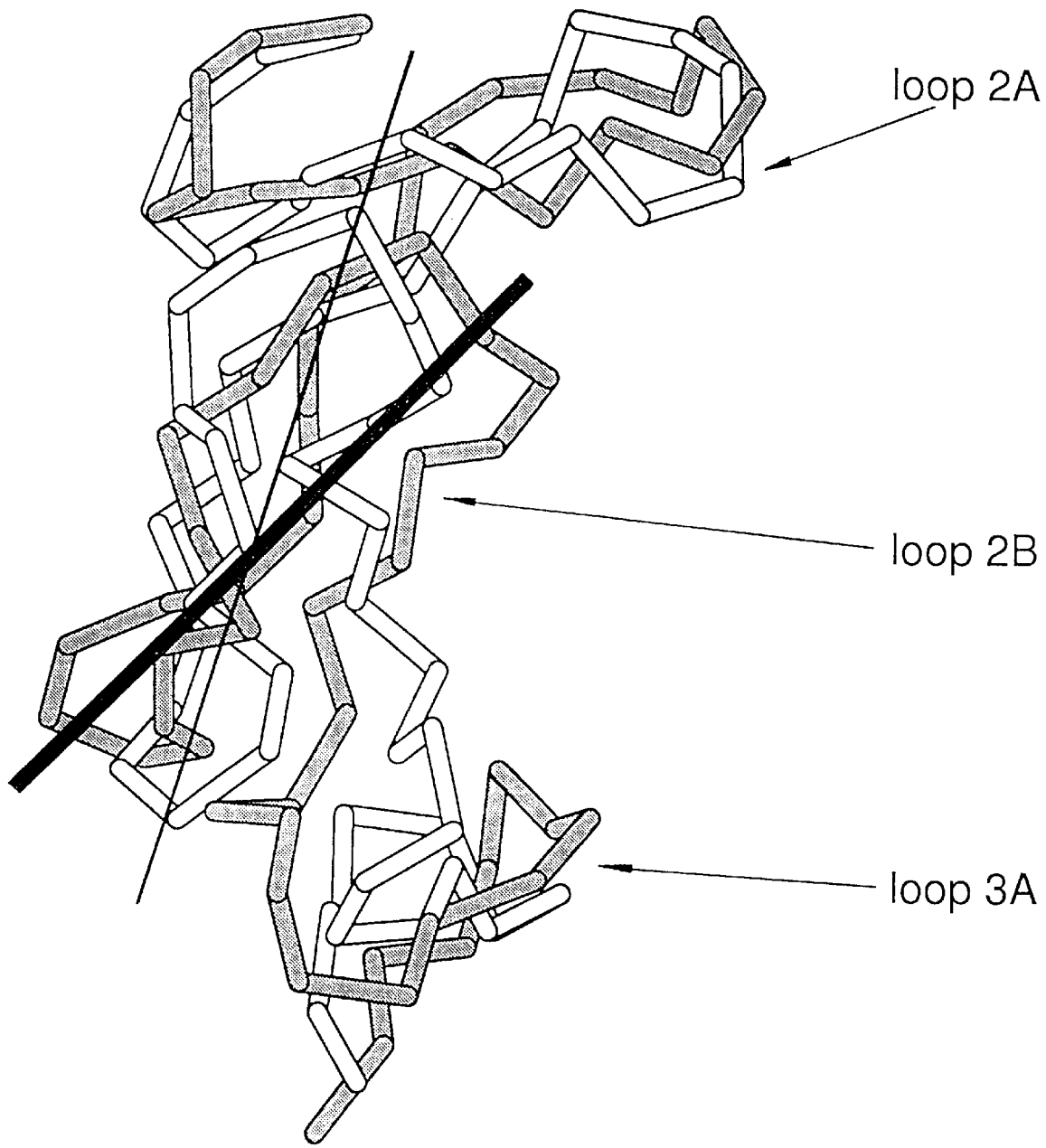

Column 4,
Line 38, "$p55^{NTR}$" should read -- $p75^{NTR}$ --;

Column 6,
Line 39, "N-strand" should read -- β-strand --;
Line 58, "tonically" should read -- ionically --;

Column 7,
Line 2, "area comprises" should read -- area C comprises --;
Line 2, "$His^{121A}$" should read -- $His^{112A}$ --;
Line 13, "tonically" should read -- ionically --;

Column 10,
Line 57, "BDNFILRM" should read -- BDNF/LRM --;
Line 64, "N-strand" should read -- β-strand --;

Column 11,
Line 21, "SEQ ID NO:12" should read -- SEQ ID NO:13 --;
Line 67, "a.-carbon" should read -- α-carbon --;

Column 14,
Lines 15-20, between $^{\Delta}d_r$ and "(1/M)" insert the equal sign (=);
Line 23, "$x_\eta^1$" should read -- $x_\eta^1$ --;

Column 15,
Line 44, "mNGF&1-8" should read -- mNGFΔ1-B --;

Column 18,
Line 61, "$Lys^{118'}$" should read -- $Lys^{115'}$ --;

Column 23,
Line 48, "N-strand" should read -- β-strand --;
Line 57, "P-strands" should read -- β-strands --;
Line 59, "P-strand" should read -- β-strand --;

UNITED STATES PATENT AND TRADEMARK OFFICE
CERTIFICATE OF CORRECTION

PATENT NO. : 6,029,114
DATED : February 22, 2000
INVENTOR(S) : Igor L. Shamovsky, Gregory M. Ross, Richard Riopelle and Donald F. Weaver It is certified that error appears in the above-identified patent and that said Letters Patent is hereby corrected as shown below:

Column 26,
Line 45, "A 30 and" should read -- A and --;

Column 27,
Line 41, "$Val^{o11A}$" should read -- $Val^{o91A}$ --;
Line 44, "salvation" should read -- solvation --;

Column 28,
Line 2, "N-strand" should read -- β-strand --;

Column 32,
Line 57, "R1 18Q" should read -- R118Q --;

Column 33,
Line 19, "NGFILRM" should read -- NGF/LRM --;
Line 22, "$ASp^{190A}$" should read -- $Asp^{109A}$ --;
Line 24, "$Phe^{131}$" should read -- $Phe^{113A}$ --;
Line 33, "$Lys^{113}$" should read -- $Lys^{113A}$ --;

Column 35,
Line 16, "NGFILRM" should read -- NGF/LRM --;
Line 17, "(1-1 17)" should read -- 1-117) --;

Column 41,
Line 7, "a-carbon" should read -- α-carbon --;

Column 42,
Line 25, "a-carbon" should read -- α-carbon --;
Line 51, "tonically" should read -- ionically --;
Line 63, "tonically" should read -- ionically --;
Line 66, "tonically" should read -- ionically --; and Column 52, table 8,
Line 23, "$Gln^{51}$", prior to "1.2", should read -- $Gln^{54}$ --.

UNITED STATES PATENT AND TRADEMARK OFFICE
CERTIFICATE OF CORRECTION

PATENT NO.    : 6,029,114
DATED         : February 22, 2000
INVENTOR(S)   : Igor L. Shamovsky, Gregory M. Ross, Richard Riopelle and Donald F. Weaver It is certified that error appears in the above-identified patent and that said Letters Patent is hereby corrected as shown below:

Claim 1,
Line 8, "$Cy^{58\rho}$" should read -- $Cys^{58\rho}$ --;
Line 9, the superscript of Cys, "$68\rho$" should read -- $58\rho$ --;

Claim 2, column 190,
Line 6, the superscript of Cys, "$30\rho$" should read -- $39\rho$ --;

Claim 2, column 191,
Line 6, the superscript of Cys, "$78\rho$" should read -- $79\rho$ --.

Signed and Sealed this

Twenty-seventh Day of November, 2001

Attest:

*Nicholas P. Godici*

NICHOLAS P. GODICI
*Attesting Officer*   Acting Director of the United States Patent and Trademark Office

UNITED STATES PATENT AND TRADEMARK OFFICE
CERTIFICATE OF CORRECTION

PATENT NO.    : 6,029,114
DATED         : February 22, 2000
INVENTOR(S)   : Igor L. Shamovsky, Gregory M. Ross, Richard Riopelle and Donald F. Weaver It is certified that error appears in the above-identified patent and that said Letters Patent is hereby corrected as shown below:

Abstract,
Line 20, "$Cys^{78\rho}$" should read -- $Cys^{79\rho}$ --;

Column 4,
Line 38, "$p55^{NTR}$" should read -- $p75^{NTR}$ --;

Column 6,
Line 39, "N-strand" should read -- β-strand --;
Line 58, "tonically" should read -- ionically --;

Column 7,
Line 2, "area comprises" should read -- area C comprises --;
Line 2, "$His^{121tA}$" should read -- $His^{M2tA}$ --;
Line 13, "tonically" should read -- ionically --;

Column 10,
Line 57, "BDNFILRM" should read -- BDNF/LRM --;
Line 64, "N-strand" should read -- β-strand --;

Column 11,
Line 21, "SEQ ID NO:12" should read -- SEQ ID NO:13 --;
Line 67, "a.-carbon" should read -- α-carbon --;

Column 14,
Lines 15-20, between "$^{\Delta}d_{ij}$" and "(1/M)" insert the equal sign (=);
Line 23, "$x_n^1$" should read -- $x_n^i$ --;

Column 15,
Line 44, "mNGF&1-8" should read -- mNGFΔ1-8 --;

Column 18,
Line 61, "$Lys^{118'}$" should read -- $Lys^{115'}$ --;

Column 23,
Line 48, "N-strand" should read -- β-strand --;
Line 57, "P-strands" should read -- β-strands --;
Line 59, "P-strand" should read -- β-strand --;

UNITED STATES PATENT AND TRADEMARK OFFICE
CERTIFICATE OF CORRECTION

PATENT NO.    : 6,029,114
DATED         : February 22, 2000
INVENTOR(S)   : Igor L. Shamovsky, Gregory M. Ross, Richard Riopelle and Donald F. Weaver It is certified that error appears in the above-identified patent and that said Letters Patent is hereby corrected as shown below:

Column 26,
Line 45, "A 30 and" should read -- A and --;

Column 27,
Line 41, "Val$^{911tA}$" should read -- Val$^{99tA}$ --;
Line 44, "salvation" should read -- solvation --;

Column 28,
Line 2, "N-strand" should read -- β-strand --;

Column 32,
Line 57, "R1 18Q" should read -- R118Q --;

Column 33,
Line 19, "NGFILRM" should read -- NGF/LRM --;
Line 22, "ASp$^{109tA}$" should read -- Asp$^{109tA}$ --;
Line 24, "Phe$^{131tA}$" should read -- Phe$^{113tA}$ --;
Line 33, "Lys$^{113'}$" should read -- Lys$^{113tA}$ --;

Column 35,
Line 16, "NGFILRM" should read -- NGF/LRM --;
Line 17, "(1-1 17)" should read -- 1-117) --;

Column 41,
Line 7, "a-carbon" should read --α-carbon --;

Column 42,
Line 25, "a-carbon" should read -- α-carbon --;
Line 51, "tonically" should read -- ionically --;
Line 63, "tonically" should read -- ionically --;
Line 66, "tonically" should read -- ionically --; and Column 52, table 8,
Line 23, "Gln$^{81}$", prior to "1.2", should read -- Gln$^{84}$ --.

UNITED STATES PATENT AND TRADEMARK OFFICE
CERTIFICATE OF CORRECTION

PATENT NO. : 6,029,114
DATED : February 22, 2000
INVENTOR(S) : Igor L. Shamovsky, Gregory M. Ross, Richard Riopelle and Donald F. Weaver It is certified that error appears in the above-identified patent and that said Letters Patent is hereby corrected as shown below:

Claim 1,
Line 8, "$Cy^{58\rho}$" should read -- $Cys^{58\rho}$ --;
Line 9, the superscript of Cys, "$68\rho$" should read -- $58\rho$ --;

Claim 2, column 190,
Line 6, the superscript of Cys, "$30\rho$" should read -- $39\rho$ --;

Claim 2, column 191,
Line 6, the superscript of Cys, "$78\rho$" should read -- $79\rho$ --.

This certificate supersedes Certificate of Correction issued November 27, 2001.

Signed and Sealed this

Nineteenth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,029,114
DATED         : February 22, 2000
INVENTOR(S)   : Igor L. Shamovsky et al.

It is certified that error appears in the above-identified patent and that said Letters Patent is hereby corrected as shown below:

Abstract,
Line 20, "$Cys^{78\rho}$" should read -- $Cys^{79\rho}$ --;

Column 4,
Line 38, "$p55^{NTR}$" should read -- $p75^{NTR}$ --;

Column 6,
Line 39, "N-strand" should read -- β-strand --;
Line 58, "tonically" should read -- ionically --;

Column 7,
Line 2, "area comprises" should read -- area C comprises --;
Line 2, "$His^{121tA}$" should read -- $His^{112tA}$ --;
Line 13, "tonically" should read -- ionically --;

Column 10,
Line 57, "BDNFILRM" should read -- BDNF/LRM --;
Line 64, "N-strand" should read -- β-strand --;

Column 11,
Line 21, "SEQ ID NO:12" should read -- SEQ ID NO:13 --;
Line 67, "a.-carbon" should read -- α-carbon --;

Column 14,
Lines 15-20, between "$^{\Delta}d_{ij}$" and "(1/M)" insert the equal sign -- = --;
Line 23, "$x_n^1$" should read -- $x_n^i$ --;

Column 15,
Line 44, "mNGF&1-8" should read -- mNGFΔ1-8 --;

Column 18,
Line 61, "$Lys^{118'}$" should read -- $Lys^{115'}$ --;

Column 23,
Line 48, "N-strand" should read -- β-strand --;
Line 57, "P-strands" should read -- β-strands --;
Line 59, "P-strand" should read -- β-strand --;

UNITED STATES PATENT AND TRADEMARK OFFICE
CERTIFICATE OF CORRECTION

PATENT NO. : 6,029,114
DATED : February 22, 2000
INVENTOR(S) : Igor L. Shamovsky et al.

It is certified that error appears in the above-identified patent and that said Letters Patent is hereby corrected as shown below:

Column 26,
Line 45, "A 30 and" should read -- A and --;

Column 27,
Line 41, "Val$^{911tA}$" should read -- Val$^{99tA}$ --;
Line 44, "salvation" should read -- solvation --;

Column 28,
Line 2, "N-strand" should read -- β-strand --;

Column 32,
Line 57, "R1 18Q" should read -- R118Q --;

Column 33,
Line 19, "NGFILRM" should read -- NGF/LRM --;
Line 22, "ASp$^{109tA}$" should read -- Asp$^{109tA}$ --;
Line 24, "Phe$^{131tA}$" should read -- Phe$^{113tA}$ --;
Line 33, "Lys$^{113}$" should read -- Lys$^{113tA}$ --;

Column 35,
Line 16, "NGFILRM" should read -- NGF/LRM --;
Line 17, "(1-1 17)" should read -- 1-117) --;

Column 41,
Line 7, "a-carbon" should read --α-carbon --;

Column 42,
Line 25, "a-carbon" should read -- α-carbon --;
Line 51, "tonically" should read -- ionically --;
Line 63, "tonically" should read -- ionically --;
Line 66, "tonically" should read -- ionically --; and Column 52, table 8,
Line 23, "Gln$^{81}$", prior to "1.2", should read -- Gln$^{84}$ --.

UNITED STATES PATENT AND TRADEMARK OFFICE
CERTIFICATE OF CORRECTION

PATENT NO.    : 6,029,114
DATED         : February 22, 2000
INVENTOR(S)   : Igor L. Shamovsky et al.

It is certified that error appears in the above-identified patent and that said Letters Patent is hereby corrected as shown below:

Claim 1,
Line 8, "$Cy^{58\rho}$" should read -- $Cys^{58\rho}$ --;
Line 9, the superscript of Cys, "$68\rho$" should read -- $58\rho$ --;

Claim 2, column 190,
Line 6, the superscript of Cys, "$30\rho$" should read -- $39\rho$ --;

Claim 2, column 191,
Line 6, the superscript of Cys, "$78\rho$" should read -- $79\rho$ --.

This certificate supersedes Certificate of Correction issued August 19, 2003.

Signed and Sealed this

Third Day of August, 2004

JON W. DUDAS
*Acting Director of the United States Patent and Trademark Office*